(12) United States Patent
Zhang et al.

(10) Patent No.: US 8,207,172 B2
(45) Date of Patent: *Jun. 26, 2012

(54) PYRIMIDINOTHIENOINDAZOLES USEFUL FOR THE TREATMENT OF HYPERPROLIFERATIVE DISORDERS

(75) Inventors: Chengzhi Zhang, Orange, CT (US); Jacques Dumas, Bethany, CT (US); Qingming Zhu, Malden, MA (US); Roger Smith, Madison, CT (US); Qingjie Liu, Orange, CT (US); Sharad Verma, New Haven, CT (US); Jason Duquette, San Mateo, CA (US); Qian Zhao, Wallingford, CT (US); Dongping Fan, North Haven, CT (US); Georgiy Bondar, West Haven, CT (US); Philip Coish, North Haven, CT (US)

(73) Assignee: Bayer Intellectual Property GmbH, Monheim (DE)

( * ) Notice: Subject to any disclaimer, the term of this patent is extended or adjusted under 35 U.S.C. 154(b) by 1273 days.

This patent is subject to a terminal disclaimer.

(21) Appl. No.: 11/662,416

(22) PCT Filed: Aug. 19, 2005

(86) PCT No.: PCT/US2005/029764
§ 371 (c)(1),
(2), (4) Date: Mar. 8, 2007

(87) PCT Pub. No.: WO2006/023843
PCT Pub. Date: Mar. 2, 2006

(65) Prior Publication Data
US 2011/0172224 A1 Jul. 14, 2011

Related U.S. Application Data

(60) Provisional application No. 60/603,398, filed on Aug. 20, 2004, provisional application No. 60/607,281, filed on Sep. 2, 2004.

(51) Int. Cl.
*C07D 471/04* (2006.01)

(52) U.S. Cl. ........ 514/257; 514/256; 514/248; 514/247; 514/183; 544/247; 544/246; 544/245; 544/242; 544/224

(58) Field of Classification Search .................. None
See application file for complete search history.

(56) References Cited

U.S. PATENT DOCUMENTS

| 5,679,683 | A | 10/1997 | Bridges et al. ........... 514/267 |
| 6,495,557 | B1* | 12/2002 | Jonas et al. ............. 514/267 |
| 7,511,048 | B2* | 3/2009 | Zhang et al. ............. 514/257 |
| 2003/0144529 | A1* | 7/2003 | Hanson et al. ............ 548/364.1 |

FOREIGN PATENT DOCUMENTS
WO 2006055268 5/2006

OTHER PUBLICATIONS

"Cellular and Molecular Basis of Cancer" in The Merck Manual, by Chabner et al. (2008).*
"Contemporary pre-clinical development of anticancer agents—What are the optimal preclinical models?" by Damia et al., Eur. J. Cancer 45, 2768-81 (2009).*
"Cancer Drug Design and Discovery" by Neidle (Ed.), Academic Press, pp. 427-431 (2008).*
"In Vitro Sensitivity Assays in Cancer: A Review, Analysis, and Prognosis" by Hoffman, J. Clin. Lab. Anal. 5, 133-43 (1991).*
"Lack of in vitro—in vivo correlation of a novel investigational anticancer agent, SH 30" by Poondru et al., Invest. New Drugs 20, 23-33 (2002).*
"Flow Cytometric Identification of Preliferative Subpopulations within Normal Human Epidermis and Localization of the Primary Hyperproliferative Population in Psoriasis" by Bata-Csorgo et al., J. Exp. Med. 178, 1271-81 (1993).*
"Hyperproliferation markers in ear canal epidermis" by Gurgel et al., Braz. J. Otorhinolaryngol. 76, 667-71 (2010).*
"Upragulation of integrin expression in benign vulvar warts" by Williams et al., J. Pathol. 175, 311-17 (1995) (PubMed Abstract 7538163).*
"Hyperproliferative apoptosis-resistant endothelial cells in idiopathic pulmonary arterial hypertension" by Masri et al., Am. J. Physiol. Lung Cell Mol. Physiol. 293, L548-54 (2007).*
"Human Immunodeficiency Virus-1 Tat Induces Hyperproliferation and Dysregulation of Renal Glomerular Epithelial cells" by Conaldi et al., Am. J. Pathol. 161, 53-61 (2002).*

* cited by examiner

*Primary Examiner* — Anish Gupta
*Assistant Examiner* — Theodore R West

(57) ABSTRACT

The invention relates to novel heterocycles of formula (I) processes for their preparation and their use for preparing medicaments for the treatment or prophylaxis of disorders, especially of hyperproliferative disorders.

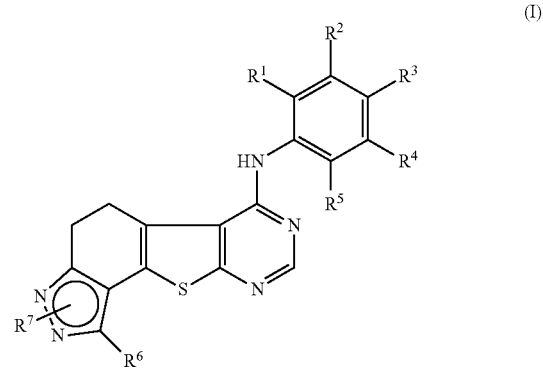

13 Claims, No Drawings

PYRIMIDINOTHIENOINDAZOLES USEFUL FOR THE TREATMENT OF HYPERPROLIFERATIVE DISORDERS

This application claims benefit of U.S. Provisional Application Ser. No. 60/603,398; filed on Aug. 20, 2004, and U.S. Provisional Application Ser. No. 60/607,281; filed on Sep. 2, 2004, the contents of which are incorporated herein by reference in their entirety.

This invention relates to novel heterocycles, processes for their preparation and their use for preparing medicaments for the treatment or prophylaxis of disorders, especially of hyperproliferative disorders.

U.S. Pat. No. 5,679,683 (Pfizer) and WO 97/13760 (Glaxo Wellcome) describe tricyclic compounds capable of inhibiting tyrosine kinases of the epidermal growth factor receptor family.

U.S. Pat. No. 6,482,948 (Nippon Soda), U.S. Pat. No. 6,130,223, U.S. Pat. No. 6,495,557, WO 00/78767, WO 01/019369, WO 01/021620, US 2003/153585, US 2003/022906, US 2004/058940, US 2004/077664 and WO 02/072100 (Merck GmbH) disclose tricyclic compounds as PDE inhibitors.

WO 03/057149 (Bayer) describes heteropyrimidines and hetero-4-pyrimidones for the treatment of $PDE7_B$-mediated diseases.

The present invention relates to a compound of formula

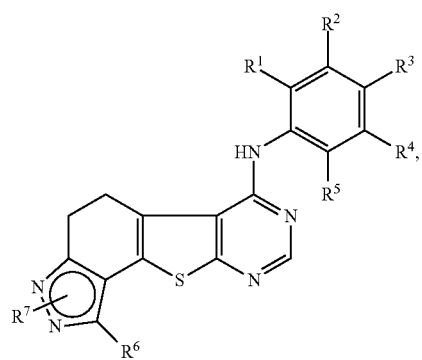

(I)

wherein
$R^1$ is selected from the group consisting of hydrogen, alkyl, and halo;
$R^2$ is selected from the group consisting of hydrogen, alkyl, hydroxy, cyano, and halo;
$R^3$ is selected from the group consisting of hydrogen, alkyl, halo, hydroxy, alkoxy, trifluoromethoxy, benzyloxy, pyridoxy, pyridylmethyl, pyridylmethoxy, pyridylmethylthio, thiazolylmethoxy, and N-morpholinyl, wherein benzyloxy, pyridoxy and pyridylmethoxy can optionally be substituted with 0, 1 or 2 substituents independently selected from the group consisting of halo, alkyl, alkoxy, and trifluoromethyl or
$R^2$ and $R^3$, together with the carbon atoms to which they are attached, form a pyrazole ring, wherein said pyrazole ring can optionally be substituted with 0, 1 or 2 substituents independently selected from the group consisting of alkyl, benzyl, halogenated benzyl, pyridylmethyl, pyridylmethoxy, and halogenated pyridylmethoxy;
$R^4$ is selected from the group consisting of hydrogen, alkyl, hydroxy, cyano, and halo;
$R^5$ is selected from the group consisting of hydrogen, alkyl, and halo;
$R^6$ is selected from the group consisting of hydrogen, and alkyl;
$R^7$ is selected from the group consisting of hydrogen, and alkyl, or
$R^7$ is a heterocycle selected from the group consisting of pyrrolidinyl, morpholinyl, piperidinyl, and piperazinyl, or
$R^7$ is piperidinyl, wherein said piperidinyl is substituted with 1, 2 or 3 independently selected substituents $R^{7-3}$, wherein
$R^{7-3}$ is alkyl, wherein said alkyl can optionally be substituted with 0, 1, or 2 substituents independently selected from the group consisting of halo, oxo, amino, alkylamino, piperazinyl, N-methylpiperazinyl, morpholinyl, and alkylaminopyrrolidinyl, or
$R^7$ is alkyl selected from the group consisting of methyl, ethyl, n-propyl, i-propyl, n-butyl, i-butyl and t-butyl, wherein said alkyl is substituted with 1, 2 or 3 independently selected substituents $R^{7-1}$,
wherein $R^{7-1}$ is selected from the group consisting of halo, oxo, hydroxy, alkoxy, hydroxycarbonyl, alkoxycarbonyl, pyridylaminocarbonyl, alkylsulfonyloxy, aminosulfonyloxy, aminoalkylcarbonyloxy, alkyl-C(O)NHCH$_2$C(O)O—*, and amino, or
$R^{7-1}$ is alkylamino, wherein said alkylamino can optionally be substituted with 0, 1 or 2 substituents independently selected from the group consisting of hydroxy, alkoxy, amino, alkylamino, alkylsulfonyl, alkylsulfenyl, pyrrolidinyl, morpholinyl, piperidinyl, and piperazinyl, or
$R^{7-1}$ is alkenylamino, wherein said alkenylamino can optionally be substituted with 0, 1 or 2 substituents independently selected from the group consisting of oxo, hydroxy, alkoxy, amino, alkylamino, alkylsulfonyl, N-pyrrolidinyl, N-morpholinyl, N-piperidinyl, and N-piperazinyl, or
$R^{7-1}$ is a heterocycle selected from the group consisting of pyrrolidinyl, imidazolidinyl, imidazolyl, pyrazolyl, morpholinyl, piperidinyl, piperazinyl, and thiomorpholinyl, wherein said heterocycle can optionally be substituted with 0, 1 or 2 substituents independently selected from the group consisting of halo, hydroxy, alkoxy, amino, alkylamino, hydroxyalkyl, alkoxyalkyl, carboxyl, alkoxycarbonyl, N-pyrrolidinyl, N-piperidinyl, N-piperazinyl, pyrazinyl, benzyl, and pyridylmethyl, or
$R^{7-1}$ is a heterocycle selected from the group consisting of piperidinyl, wherein said heterocycle is substituted with 1 alkyl, wherein said alkyl can optionally be substituted with 0, 1 or 2 substituents independently selected from the group consisting of halo, hydroxy, oxo, alkylamino, hydroxyalkylamino, pyrrolidinyl, alkylaminopyrrolidinyl, piperazinyl, N-methylpiperazinyl, morpholinyl, furyl, or
$R^7$ is alkenyl selected from the group consisting of allyl, prop-1-enyl, 2-methyl-prop-1-enyl, but-1-enyl, but-2-enyl, but-3-enyl, pent-1-enyl, pent-2-enyl, pent-3-enyl, pent-4-enyl, wherein said alkenyl is substituted with 1, 2 or 3 independently selected substituents $R^{7-2}$,
wherein $R^{7-2}$ is oxo, or
wherein $R^{7-2}$ is alkylamino, wherein said alkylamino can optionally be substituted with 0, 1 or 2 substituents independently selected from the group consisting of oxo, hydroxy, alkoxy, amino, and alkylamino;
or a pharmaceutically acceptable salt thereof.

Depending on their structure, the compounds according to the invention can exist in stereoisomeric forms (enantiomers, diastereomers). The invention therefore relates to the enantiomers or diastereomers and to their respective mixtures. Such mixtures of enantiomers and/or diastereomers can be separated into stereoisomerically unitary constituents in a known manner. For example, Examples 28 and 31 represent related R- and S-stereoisomers.

The invention also relates to tautomers of the compounds, depending on the structure of the compounds.

Salts for the purposes of the invention are preferably pharmacologically acceptable salts of the compounds according to the invention.

Pharmacologically acceptable salts of the compounds (I) include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, malic acid, citric acid, fumaric acid, maleic acid and benzoic acid. For example, Example 147 represents the trifluoroacetate salt of Example 146.

Pharmacologically acceptable salts of the compounds (I) also include salts of customary bases, such as for example and preferably alkali metal salts (for example sodium and potassium salts, alkaline earth metal salts (for example calcium and magnesium salts) and ammonium salts derived from ammonia or organic amines having 1 to 16 carbon atoms, such as illustratively and preferably ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, dihydroabietyamine, arginine, lysine, ethylenediamine and methylpiperidine.

Solvates for the purposes of the invention are those forms of the compounds that coordinate with solvent molecules to form a complex in the solid or liquid state. Hydrates are a specific form of solvates, where the coordination is with water.

For the purposes of the present invention, the substituents have the following meanings, unless otherwise specified:

Alkyl per se and "alk" and "alkyl" in other radicals represent a linear or branched alkyl radical having generally 1 to 6, 1 to 4 or 1 to 3 carbon atoms, representing illustratively methyl, ethyl, n-propyl, isopropyl, tert-butyl, n-pentyl and n-hexyl.

Alkenyl represents a linear or branched alkyl radical having one or more double bonds and generally 2 to 6, 2 to 4 or 2 to 3 carbon atoms, representing illustratively allyl.

Alkoxy represents a straight-chain or branched hydrocarbon radical having 1 to 6 carbon atoms and bound via an oxygen atom. Non-limiting examples include methoxy, ethoxy, propoxy, isopropoxy, butoxy, isobutoxy, pentoxy, isopentoxy, hexoxy, isohexoxy. The terms "alkoxy" and "alkyloxy" can be used synonymously.

Alkylamino represents an amino radical having one or two (independently selected) alkyl substituents, illustratively representing methylamino, ethylamino, n-propylamino, isopropylamino, tert-butylamino, n-pentylamino, n-hexylamino, N,N-dimethylamino, N,N-diethylamino, N-ethyl-N-methylamino, N-methyl-N-n-propylamino, N-isopropyl-N-n-propylamino, N-t-butyl-N-methylamino, N-ethyl-N-n-pentylamino and N-n-hexyl-N-methylamino.

Hydroxyalkylamino represents an amino radical having one or two (independently selected) alkyl substituents, wherein at least one of said alkyl substituents is substituted with hydroxy, illustratively representing hydroxyethylamino.

Alkenylamino represents an amino radical having one or two (independently selected) alkenyl substituents, illustratively representing allylamino.

Aminoalkylcarbonyloxy represents a carbonyloxy group (alkC(O)O—*) substituted with an amino group.

Alkylsulfonyloxy represents *—OS(O)$_2$alkyl.
Aminosulfonyloxy represents *—OS(O)$_2$NH$_2$.
Alkylsulfonyl represents *—S(O)$_2$alkyl.
Alkylsulfenyl represents *—S(O)alkyl.
Chloroacetyl represents *—C(O)CH$_2$Cl.

Alkoxycarbonyl represents an alkoxy radical bound via a carbonyl group, e.g. methoxycarbonyl, ethoxycarbonyl, n-propoxycarbonyl, isopropoxycarbonyl, tert-butoxycarbonyl, n-pentoxycarbonyl and n-hexoxycarbonyl.

Aryl represents a mono- to tricyclic carbocyclic radical, which is aromatic at least in one ring and bound via an oxygen atom, having generally 6 to 14 carbon atoms, illustratively representing phenyl, naphthyl and phenanthrenyl.

Heteroaryl represents an mono- or bicyclic radical having generally 5 to 10 and preferably 5 or 6 ring atoms and up to 5 and preferably up to 4 hetero atoms selected from the group consisting of nitrogen, oxygen and sulfur, which is aromatic at least in one ring. It can be attached via a ring carbon atom or a ring nitrogen atom. If it represents a bicycle, wherein one ring is aromatic and the other one is not, it can be attached at both rings. Illustrative examples are thienyl, furyl, pyrrolyl, thiazolyl, oxazolyl, imidazolyl, pyridyl, pyrimidyl, pyridazinyl, indolyl, indazolyl, benzofuranyl, benzothiophenyl, quinolinyl, isoquinolinyl.

Heterocyclyl represents a mono- or polycyclic, preferably mono- or bicyclic, nonaromatic heterocyclic radical having generally 4 to 10 and preferably 5 to 8 ring atoms and up to 3 or up to 2 hetero atoms and/or hetero groups selected from the group consisting of nitrogen, oxygen and sulfur, SO and SO$_2$. It can be attached via a ring carbon atom or a ring nitrogen atom. Illustrative examples are tetrahydrofuran-2-yl, pyrrolidin-2-yl, pyrrolidin-3-yl, pyrrolinyl, piperidinyl, morpholinyl, perhydroazepinyl.

Pyridylmethoxy represents a pyridyl substituent attached to the carbon atom of a methoxy group, e.g. 2-pyridylmethoxy.

Pyridylmethyl represents a methyl group substituted with a pyridyl ring (*—CH$_2$Pyr).

Pyridylmethylthio represents a thiomethyl group substituted with a pyridyl ring (*—SCH$_2$Pyr).

Pyridylaminocarbonyl represents a carbonyl group substituted with aminopyridyl (*—C(O)NHPyr).

Thiazolylmethoxy represents a methoxy group substituted with a thiazolyl ring.

Halogen represents fluorine, chlorine, bromine and iodine.

An asterist (*) symbol next to a bond denotes the point of attachment in the molecule.

The depiction of R$^7$ in formula (I) with a bond directed into the aromatic pyrazole ring means that one R$^7$ can be attached to one of the two nitrogen atoms in said aromatic pyrazole ring, i.e. either to the nitrogen atom next to the carbon atom substituted with R$^6$ or to the other one.

When the conjunction "or" connects two part sentences of a claim defining alternative definitions for a substituent which can be present in a number larger than one, said "or" may also be interpreted as an "and".

If radicals in the compounds according to the invention are substituted, the radicals, unless otherwise specified, can be substituted by one or more identical or different substituents. A substitution with up to three identical or different substituents is preferred. Substitution with 2 or 3 substituents can be on the same or on different atoms. For example, in the expression "$R^7$ is piperidinyl, wherein said piperidinyl is substituted with 2 or 3 independently selected substituents $R^{7-3}$" the two substituents $R^{7-3}$ can be on the same atom or on different atoms of said piperidinyl ring. Very particular preference, unless otherwise specified, is given to substitution with one substituent. When a nitrogen-containing molecule is further substituted, the substitution preferably does not take place on the nitrogen atom, if such substitution leads to quaternization of said nitrogen atom, e.g. in the case of alkylation.

Except for intermediates, chemically unstable compounds are less preferred in the context of the present invention. For example, a chemically unstable compound would be one where two nitrogen or oxygen substituents are bonded to a single aliphatic carbon atom. Another example of a chemically unstable compound would be one where an alkoxy group is bonded to the unsaturated carbon of an alkene to form an enol ether. Furthermore, an aliphatic carbon atom attached to oxygen may not also bear a chloro, bromo or iodo substituent, and when any alkyl group is attached to O, S, or N, and bears a hydroxyl substituent, then the hydroxyl substituent is separated by at least two carbon atoms from the O, S, or N to which the alkyl group is attached.

In another embodiment, the present invention provides a compound of formula (I), wherein
  $R^1$ is hydrogen;
  $R^2$ is selected from the group consisting of hydrogen, and halo;
  $R^3$ is selected from the group consisting of halo, benzyloxy, and pyridylmethoxy, wherein benzyloxy, and pyridylmethoxy can optionally be substituted with 0, 1 or 2 substituents independently selected from the group consisting of halo, and alkyl, or
  $R^2$ and $R^3$, together with the carbon atoms to which they are attached, form a pyrazole ring, wherein said pyrazole ring can optionally be substituted with 0, 1 or 2 substituents independently selected from the group consisting of benzyl, and halogenated benzyl;
  $R^4$ is selected from the group consisting of hydrogen, and halo;
  $R^5$ is hydrogen;
  $R^6$ is hydrogen;
  $R^7$ is hydrogen, or
  $R^7$ is piperidinyl, wherein said piperidinyl is substituted with 1, 2 or 3 independently selected substituents $R^{7-3}$, wherein
    $R^{7-3}$ is alkyl, wherein said alkyl can optionally be substituted with 0, 1, or 2 substituents independently selected from the group consisting of halo, oxo, amino, alkylamino, piperazinyl, N-methylpiperazinyl, morpholinyl, and alkylaminopyrrolidinyl, or
  $R^7$ is alkyl selected from the group consisting of methyl, ethyl, n-propyl, and i-propyl, wherein said alkyl is substituted with 1, 2 or 3 independently selected substituents $R^{7-1}$,
    wherein $R^{7-1}$ is selected from the group consisting of oxo, hydroxy, alkoxy, hydroxycarbonyl, alkoxycarbonyl, alkylsulfonyloxy, aminosulfonyloxy, aminoalkylcarbonyloxy, alkyl-C(O)NHCH$_2$C(O)O—*, and amino, or
    $R^{7-1}$ is alkylamino, wherein said alkylamino can optionally be substituted with 0, 1 or 2 substituents independently selected from the group consisting of hydroxy, alkoxy, amino, alkylamino, alkylsulfonyl, pyrrolidinyl, morpholinyl, piperidinyl, and piperazinyl, or
    $R^{7-1}$ is a heterocycle selected from the group consisting of pyrrolidinyl, imidazolidinyl, imidazolyl, pyrazolyl, morpholinyl, piperidinyl, and piperazinyl, wherein said heterocycle can optionally be substituted with 0, 1 or 2 substituents independently selected from the group consisting of hydroxy, alkoxy, amino, alkylamino, hydroxyalkyl, alkoxyalkyl, carboxyl, and alkoxycarbonyl, or
    $R^{7-1}$ is a heterocycle selected from the group consisting of piperidinyl, wherein said heterocycle is substituted with 1 alkyl, wherein said alkyl can optionally be substituted with 0, 1 or 2 substituents independently selected from the group consisting of hydroxy, oxo, alkylamino, or hydroxyalkylamino,
or a pharmaceutically acceptable salt thereof.

In another embodiment, the present invention provides a compound of formula (I), wherein
  $R^1$ is hydrogen;
  $R^2$ is selected from the group consisting of hydrogen, and halo;
  $R^3$ is selected from the group consisting of benzyloxy, and pyridylmethoxy, wherein benzyloxy, and pyridylmethoxy can optionally be substituted with 0, 1 or 2 substituents independently selected from the group consisting of halo, and alkyl, or
  $R^2$ and $R^3$, together with the carbon atoms to which they are attached, form a pyrazole ring, wherein said pyrazole ring can optionally be substituted with 0, 1 or 2 substituents independently selected from the group consisting of benzyl, and halogenated benzyl;
  $R^4$ is hydrogen;
  $R^5$ is hydrogen;
  $R^6$ is hydrogen;
  $R^7$ is hydrogen, or
  $R^7$ is alkyl selected from the group consisting of methyl, ethyl, n-propyl, and i-propyl, wherein said alkyl is substituted with 1, 2 or 3 independently selected substituents $R^{7-1}$,
    wherein $R^{7-1}$ is selected from the group consisting of oxo, hydroxy, alkoxy, hydroxycarbonyl, alkoxycarbonyl, alkylsulfonyloxy, aminosulfonyloxy, aminoalkylcarbonyloxy, alkyl-C(O)NHCH$_2$C(O)O—*, and amino, or
    $R^{7-1}$ is alkylamino, wherein said alkylamino can optionally be substituted with 0, 1 or 2 substituents independently selected from the group consisting of hydroxy, alkoxy, amino, alkylamino, alkylsulfonyl, pyrrolidinyl, morpholinyl, piperidinyl, and piperazinyl, or
    $R^{7-1}$ is a heterocycle selected from the group consisting of morpholinyl, piperidinyl, and piperazinyl, wherein said heterocycle can optionally be substituted with 0, 1 or 2 substituents independently selected from the group consisting of hydroxy, alkoxy, amino, alkylamino, hydroxyalkyl, alkoxyalkyl, carboxyl, and alkoxycarbonyl, or
    $R^{7-1}$ is a heterocycle selected from the group consisting of piperidinyl, wherein said heterocycle is substituted with 1 alkyl, wherein said alkyl can optionally be substituted with 0, 1 or 2 substituents independently selected from the group consisting of hydroxy, oxo, alkylamino, or hydroxyalkylamino,
or pharmaceutically acceptable salt thereof.

In another embodiment, the present invention provides a compound of formula (I), wherein $R^2$ and $R^3$, together with the carbon atoms to which they are attached, form a pyrazole ring, wherein said pyrazole ring is substituted with 1 substituent m-fluorobenzyl or m-chlorobenzyl.

In another embodiment, the present invention provides a compound of formula (I), wherein $R^1$, $R^2$, and $R^5$ are hydrogen, $R^3$ is fluoro and $R^4$ is chloro.

In another embodiment, the present invention provides a compound of formula (I), wherein $R^1$, $R^2$, $R^4$, and $R^5$ are hydrogen, and $R^3$ is 3-fluorobenzyloxy.

In yet another embodiment, the present invention relates to a compound of formula (I), wherein
$R^1$ is selected from the group consisting of hydrogen, methyl, ethyl, and halo;
$R^2$ is selected from the group consisting of hydrogen, methyl, ethyl, and halo;
$R^3$ is selected from the group consisting of hydrogen, alkyl, halo, hydroxy, alkoxy, trifluoromethoxy, benzyloxy, halogenated benzyloxy, alkylated benzyloxy, pyridoxy, alkylated pyridoxy, halogenated pyridoxy, pyridylmethoxy, halogenated pyridylmethoxy, and N-morpholinyl, or
$R^2$ and $R^3$, together with the carbon atoms to which they are attached, form an pyrazole ring, wherein said pyrazole ring can optionally be substituted with 0, 1 or 2 substituents independently selected from the group consisting of alkyl, benzyl, halogenated benzyl, pyridylmethoxy, and halogenated pyridylmethoxy;
$R^4$ is selected from the group consisting of hydrogen, alkyl, cyano, and halo;
$R^5$ is selected from the group consisting of hydrogen, alkyl, and halo;
$R^6$ is selected from the group consisting of hydrogen, and alkyl;
$R^7$ is selected from the group consisting of hydrogen, and alkyl, or
$R^7$ is a heterocycle selected from the group consisting of pyrrolidinyl, morpholinyl, piperidinyl, and piperazinyl, or
$R^7$ is alkyl selected from the group consisting of methyl, ethyl, n-propyl, i-propyl, n-butyl, i-butyl and t-butyl, wherein said alkyl is substituted with 1, 2 or 3 independently selected substituents $R^{7-1}$,
wherein $R^{7-1}$ is selected from the group consisting of halo, hydroxy, alkoxy, alkylsulfonyloxy, and amino, or
$R^{7-1}$ is alkylamino, wherein said alkylamino can optionally be substituted with 0, 1 or 2 substituents independently selected from the group consisting of hydroxy, alkoxy, amino, alkylamino, alkylsulfonyl, pyrrolidinyl, morpholinyl, piperidinyl, and piperazinyl, or
$R^{7-1}$ is alkenylamino, wherein said alkenylamino can optionally be substituted with 0, 1 or 2 substituents independently selected from the group consisting of oxo, hydroxy, alkoxy, amino, alkylamino, alkylsulfonyl, N-pyrrolidinyl, N-morpholinyl, N-piperidinyl, and N-piperazinyl, or
$R^{7-1}$ is a heterocycle selected from the group consisting of pyrrolidinyl, imidazolidinyl, imidazolyl, pyrazolyl, morpholinyl, piperidinyl, piperazinyl, and thiomorpholinyl, wherein said heterocycle can optionally be substituted with 0, 1 or 2 substituents independently selected from the group consisting of alkyl, halo, hydroxy, alkoxy, amino, alkylamino, hydroxyalkyl, alkoxyalkyl, carboxyl, alkoxycarbonyl, N-pyrrolidinyl, N-piperidinyl, N-piperazinyl, pyrazinyl, benzyl, and pyridylmethyl, or
$R^7$ is alkenyl selected from the group consisting of allyl, prop-1-enyl, 2-methyl-prop-1-enyl, but-1-enyl, but-2-enyl, but-3-enyl, pent-1-enyl, pent-2-enyl, pent-3-enyl, pent-4-enyl, wherein said alkenyl is substituted with 1, 2 or 3 independently selected substituents $R^{7-2}$,
wherein $R^{7-2}$ is oxo, or
wherein $R^{7-2}$ is alkylamino, wherein said alkylamino can optionally be substituted with 0, 1 or 2 substituents independently selected from the group consisting of oxo, hydroxy, alkoxy, amino, and alkylamino;
or its salt, solvate or solvate of the salt.

In yet another embodiment, the present invention relates to a compound of formula (I), wherein
$R^1$ is hydrogen;
$R^2$ is hydrogen;
$R^3$ is selected from the group consisting of hydrogen, halo, hydroxy, methoxy, ethoxy, n-propyloxy, i-propyloxy, trifluoromethoxy, benzyloxy, halogenated benzyloxy, pyridoxy, methylated pyridoxy, ethylated pyridoxy, halogenated pyridoxy, pyridylmethoxy, halogenated pyridylmethoxy, and N-morpholinyl, or
$R^2$ and $R^3$, together with the carbon atoms to which they are attached, form an pyrazole ring, wherein said pyrazole ring can optionally be substituted with 0 or 1 substituents benzyl;
$R^4$ is selected from the group consisting of hydrogen, methyl, ethyl, n-propyl, i-propyl, cyano, and halo;
$R^5$ is hydrogen;
$R^6$ is hydrogen;
$R^7$ is selected from the group consisting of hydrogen, methyl, ethyl, n-propyl, i-propyl, n-butyl, i-butyl, t-butyl, and amino, or
$R^7$ is alkyl selected from the group consisting of methyl, ethyl, and n-propyl, wherein said alkyl is substituted with 1 or 2 independently selected substituents $R^{7-1}$,
wherein $R^{7-1}$ is selected from the group consisting of halo, hydroxy, methoxy, ethoxy, n-propyloxy, i-propyloxy, methylsulfonyloxy, amino, or
$R^{7-1}$ is alkylamino, wherein said alkylamino can optionally be substituted with 0, 1 or 2 substituents independently selected from the group consisting of hydroxy, methoxy, ethoxy, n-propyloxy, i-propyloxy, amino, methylamino, ethylamino, dimethylamino, diethylamino, methylethylamino, methylsulfonyl, N-pyrrolidinyl, and N-morpholinyl, or
$R^{7-1}$ is a heterocycle selected from the group consisting of N-pyrrolidinyl, N-imidazolyl, N-morpholinyl, N-piperidinyl, N-piperazinyl, and N-thiomorpholinyl, wherein said heterocycle can optionally be substituted with 0 or 1 substituents independently selected from the group consisting of methyl, ethyl, n-propyl, i-propyl, halo, hydroxy, methoxy, ethoxy, n-propyloxy, i-propyloxy, amino, methylamino, ethylamino, dimethylamino, diethylamino, methylethylamino, hydroxymethyl, hydroxyethyl, methoxymethyl, methoxyethyl, carboxyl, methoxycarbonyl, ethoxycarbonyl, n-propyloxycarbonyl, i-propyloxycarbonyl, n-butyloxycarbonyl, i-butyloxycarbonyl, t-butyloxycarbonyl, N-pyrrolidinyl, N-piperidinyl, N-piperazinyl, pyrazinyl, benzyl, and pyridylmethyl;
or its salt, solvate or solvate of the salt.

In yet another embodiment, the present invention provides compounds of the formula (I), wherein $R^1$, $R^2$, and $R^5$ are hydrogen, $R^3$ is 2-pyridylmethoxy and $R^4$ is chloro.

In another embodiment, the present invention provides a process for preparing the compounds of the formula (I), wherein a compound of formula (8)

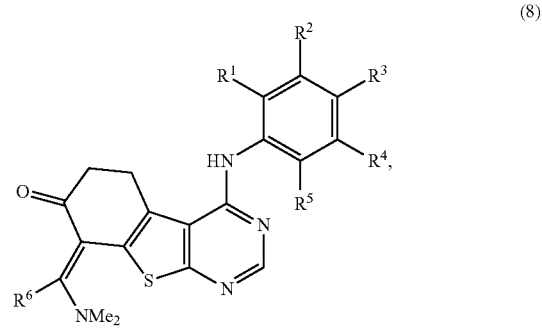

(8)

wherein R¹ to R⁶ have the meaning indicated above, is reacted with a compound of formula

wherein R⁷ has the meaning indicated above.

In another embodiment, the present invention provides a process for preparing the compounds of the formula (I), wherein a compound of formula

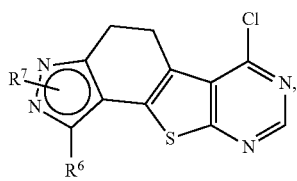

wherein R⁶ and R⁷ have the meaning indicated above, is reacted with a compound of formula (20)

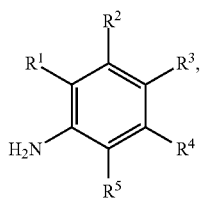
(20)

wherein R¹ to R⁵ have the meaning indicated above.

Accordingly, a compound of formula (8)

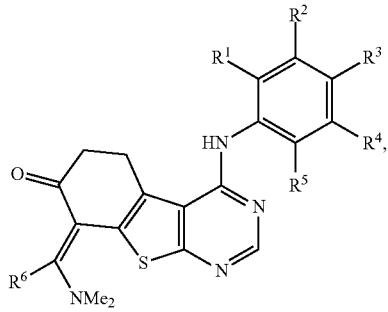
(8)

wherein R¹ to R⁶ have the meaning indicated above, as well as a compound of formula

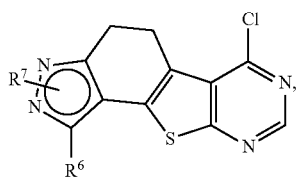

wherein R⁶ and R⁷ have the meaning indicated above, are valuable precursors for making a compound of the present invention, and are as such also part of the present invention.

The preparation of the compounds according to the invention can be illustrated by means of the following synthetic schemes. In these schemes, unless specifically designated otherwise, R¹-R⁷ are as defined for formula (I) above.

In general, compounds of formula (I) can be prepared from the route outlined in Reaction Scheme 1. In this scheme, a mono-protected cyclohexane-1-4-dione of formula (1) is allowed to react with a cyanoacetic acid ester of formula (2) in the presence of sulfur and a base, to form the bicyclic aminothiophene carboxylic acid ester of formula (3). Reaction of this compound with either formamidine or formamide gives the tricyclic thiopyrimidone of formula (4). Reaction of the formula (4) compound with a halogenating agent such as POCl₃ gives the chloro derivative of formula (5). The tricyclic compound of formula (5) is allowed to react with a substituted aniline of formula (20) in the presence of a base and a polar solvent such as ethanol to give the intermediate of formula (6). Hydrolysis of (6) under aqueous acidic conditions provides the ketone of formula (7). Reaction of (7) with a N,N-dimethylamide dimethyl acetal, such as DMF dimethylacetal, gives an enaminone intermediate of formula (8). This intermediate is then condensed with a hydrazine of general formula R⁷—NHNH₂, to give the compound of formula (I).

Reaction Scheme 1

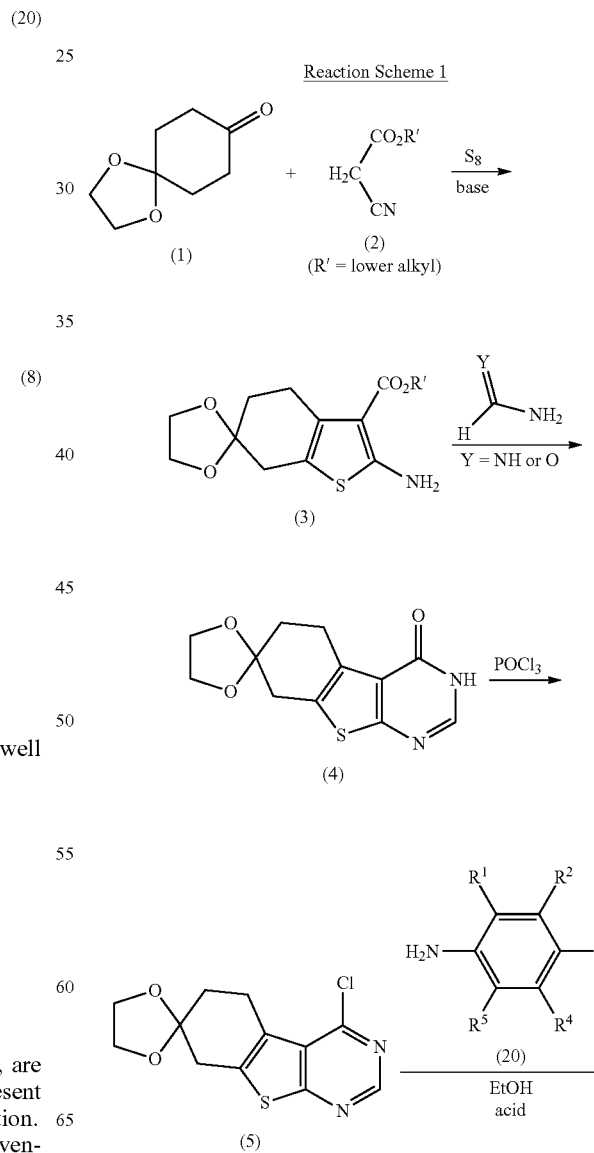

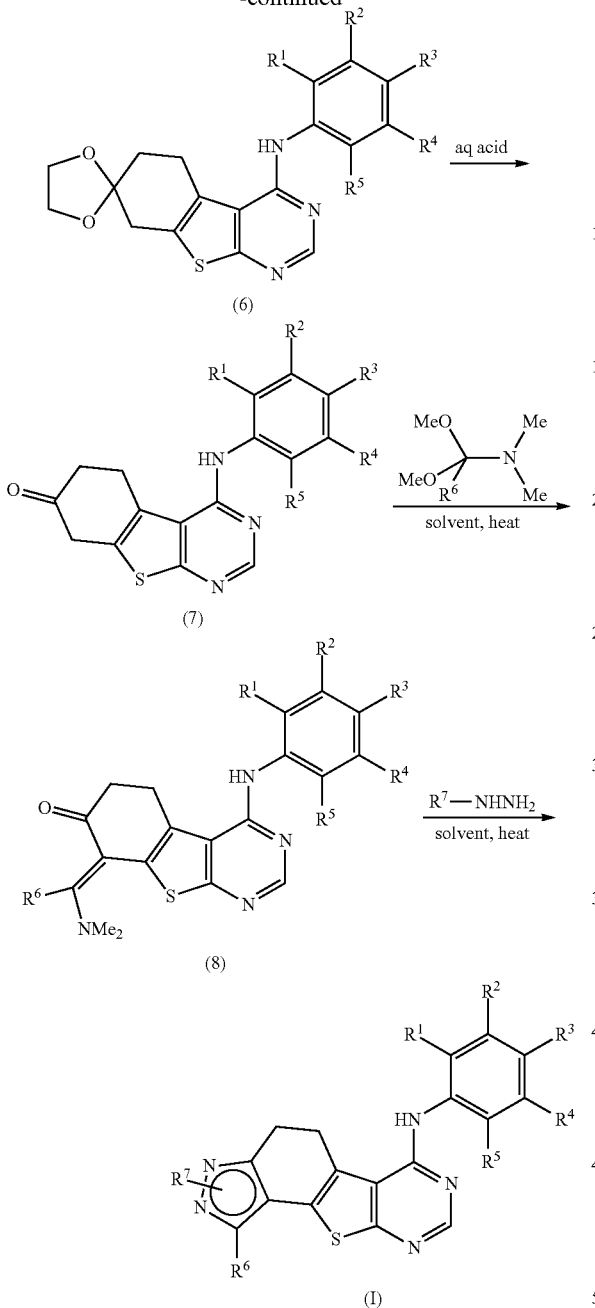

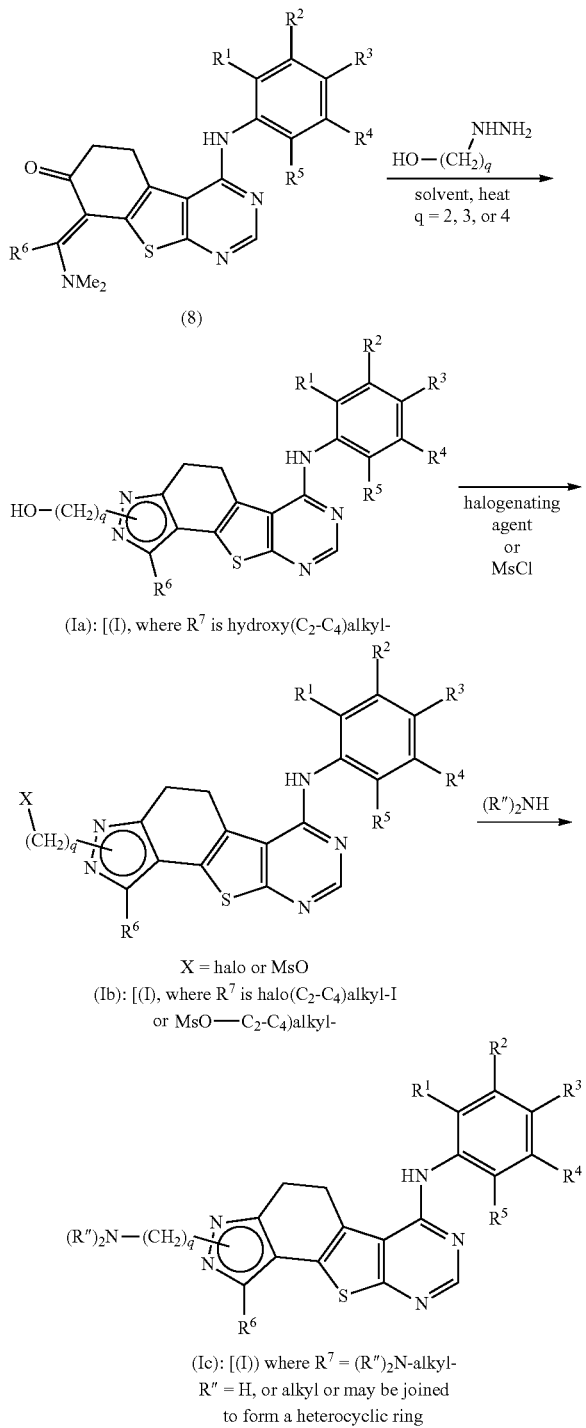

The general preparation of compounds of formula (I), in which $R^7$ is $C_2$-$C_4$ alkyl substituted by halo, alkylsulfonyloxy, amino or a N-heterocyclic group, is shown in Reaction Scheme 2. In this scheme, the hydrazine used in the pyrazole ring-forming step is a hydroxy-substituted alkyl hydrazine such as 2-hydroxyethylhydrazine, which provides the compound of formula (Ia) where $R^7$ is a hydroxy-substituted alkyl group. This formula (Ia) compound can be converted to the corresponding formula (Ib) compound in which $R^7$ is haloalkyl or alkylsulfonyloxyalkyl, by reaction of (Ia) with a halogenating agent such as $SOBr_2$ or with an alkanesulfonyl chloride such as methanesulfonyl chloride. The compound of formula (Ib) may be converted to the compound of formula (Ic) by allowing it to react with a secondary or primary amine, such as diethylamine, or with an optionally substituted nitrogen heterocycle, such as a pyrrolidine, a piperidine, or a morpholine, provided the N-atom of the heterocycle remains unsubstituted.

The methods generally described in Reaction Schemes 1 and 2 may provide regioisomeric mixtures in which the location of the $R^7$ group may be on either nitrogen atom of the fused pyrazole ring. These regioisomers may be separated, as desired by standard chromatographic methods. However, Reaction Schemes 3a-3b illustrate general methods to prepare the individual regioisomers of formula (I).

In Reaction Scheme 3a, the pyrazole ring-forming reaction is carried out using the enaminone of formula 8 and a substituted alkylhydrazine carboxylate of general formula W—(CH$_2$)$_q$—N(NH$_2$)—CO$_2$alkyl, where W is —OH or —COOalkyl and q is 2, 3 or 4. By this method, the regioisomer of formula (Ia-1) is prepared. Reaction of (Ia-1) with a halogenating or sulfonylating agent (when W is —OH) analogous to that described in Reaction Scheme 2 or with saponification agents such as NaOH (when W=—COOalkyl), provides the regioisomer of Formula (Ia-2), and reaction of (Ia-2) with (R")$_2$NH gives the regioisomer of formula (Ic-1).

Reaction Scheme 3a

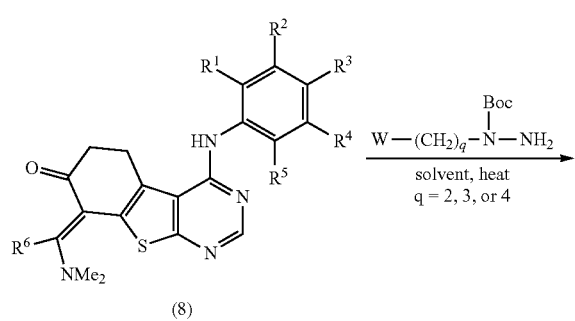

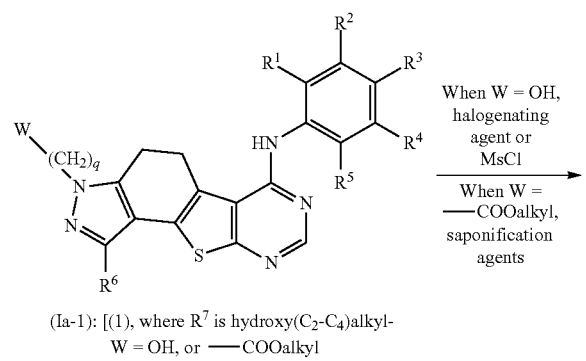

(Ia-1): [(1), where R$^7$ is hydroxy(C$_2$-C$_4$)alkyl-
W = OH, or —COOalkyl

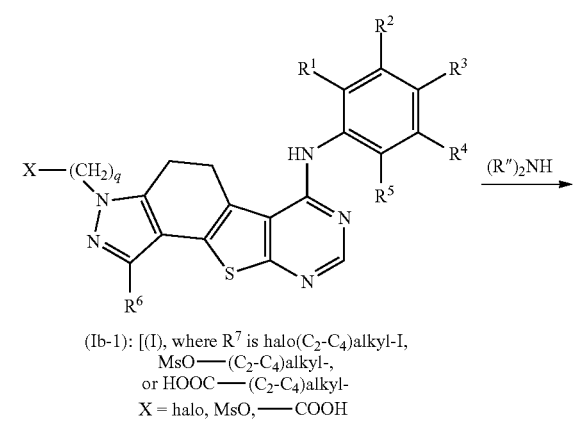

(Ib-1): [(I), where R$^7$ is halo(C$_2$-C$_4$)alkyl-I,
MsO—(C$_2$-C$_4$)alkyl-,
or HOOC—(C$_2$-C$_4$)alkyl-
X = halo, MsO, —COOH

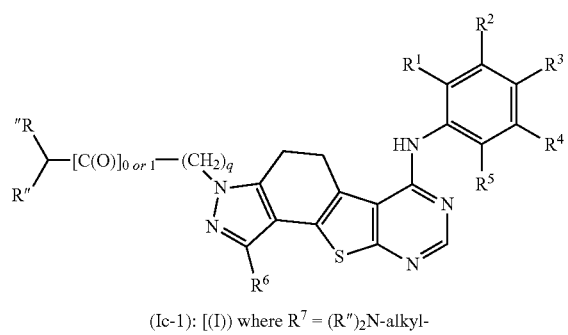

(Ic-1): [(I)) where R$^7$ = (R")$_2$N-alkyl-
R" = H, or alkyl or may be joined
to form a heterocyclic ring In Reaction Scheme 3b is illustrated the preparation of the compounds of formulae Ib-2, Ib-2 and Ib-2, examples of the other formula (I) regioisomer. In the first, or pyrazole ring-forming step of this scheme, W—(CH$_2$)$_q$—NH—NH—CO$_2$alkyl, where W is —OH or —COOalkyl and q is 2, 3 or 4, is allowed to react with the compound of formula (8) to provide the compound of formula (Ia-2). The preparation of compounds of formula (Ib-2) and (Ic-2) is then carried out in a manner identical to that described for formulae (Ib-1) and (Ic-1): The substituted alkylpyrazole (Ia-2) is converted to (Ib-2, and (Ib-2) is then converted to (Ic-2) by reaction with an amine of general formula (R")$_2$NH.

Reaction Scheme 3b

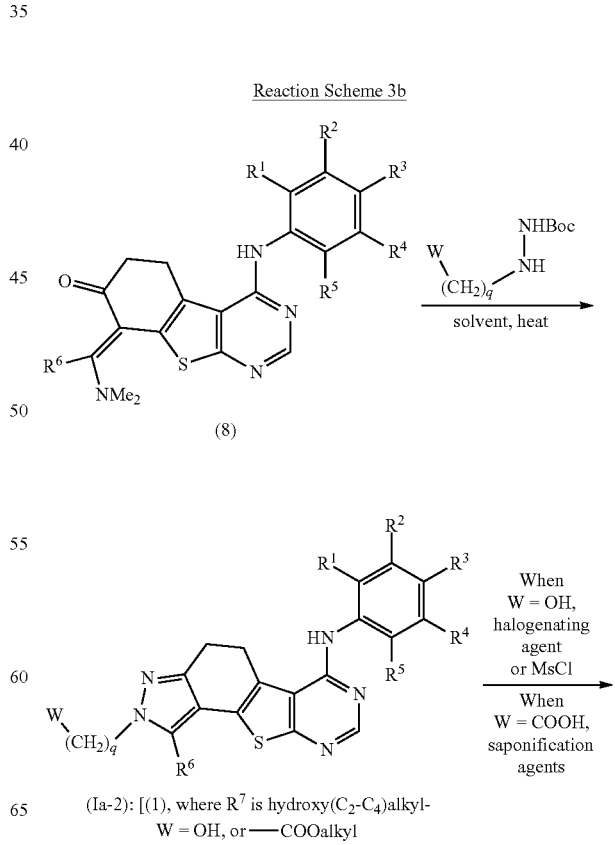

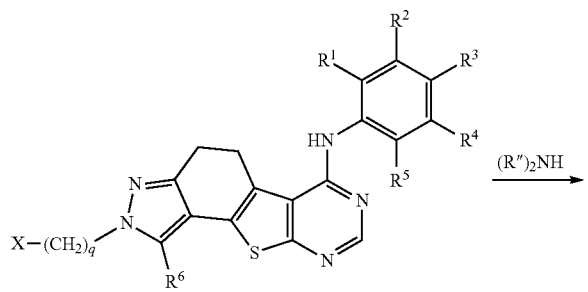

(Ib-2): [(I), where $R^7$ is halo($C_2$-$C_4$)alkyl-I
or MsO—($C_2$-$C_4$)alkyl-,
X = halo, MsO,—COOH

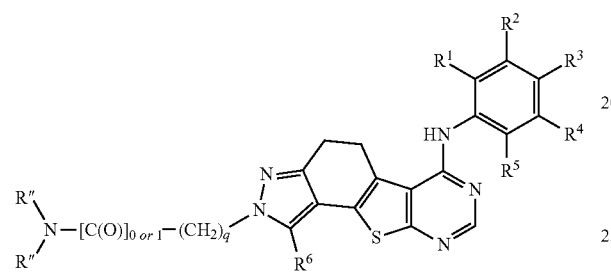

(Ic-2): [(I)) where $R^7$ = ($R''$)$_2$N-alkyl-
$R''$ = H, or alkyl or may be joined to
form a heterocyclic ring An alternative synthesis of formula (Ic-2) compounds is shown in Reaction Scheme 4. In contrast to Schemes 1 and 3b, the phenyl group bearing $R^1$-$R^5$ substituents, is introduced in the last step. In this approach, an O-protected tetracyclic compound of formula (9), prepared as shown below in Reaction Schemes 5 and 6, is converted to the compound of formula (10) by reaction with a secondary amine of general formula ($R'''$)$_2$NH. An example of a protecting group suitable for this sequence is the 4-nitrophenylethyl group, introduced as shown in Reaction Scheme 5. Deprotection of the compound of formula (10) is carried out under standard conditions, for example, a 4-nitrophenylethyl protecting group is removed by reaction of (10) with DBU and pyridine at room temperature. Conversion of the compound of hydroxy tetracycle formula (11) to the chloro compound of formula (12) is carried out by reaction with a chlorinating agent such as POCl$_3$. The formula (12) intermediate is allowed to react with the aniline of formula (20) to produce the formula (Ic-2) compound.

Reaction Scheme 4

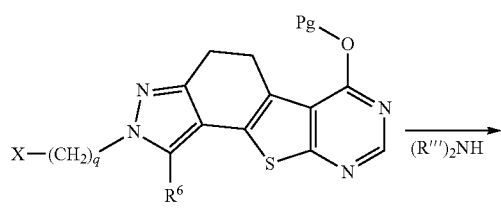

(9)
where Pg = a protecting group
X = MsO or halo

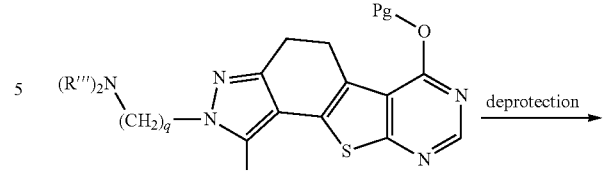

(10)
$R'''$ = alkyl or may be joined
to form a heterocyclic ring

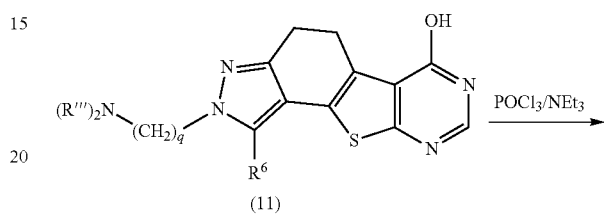

(11)

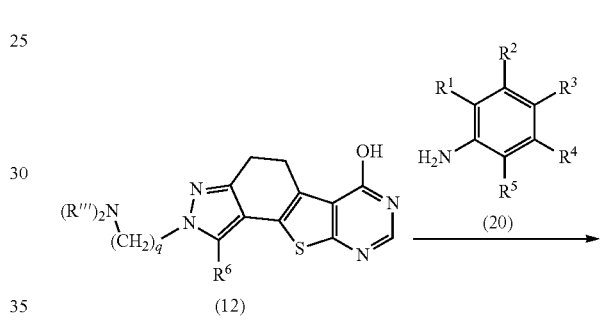

(12)

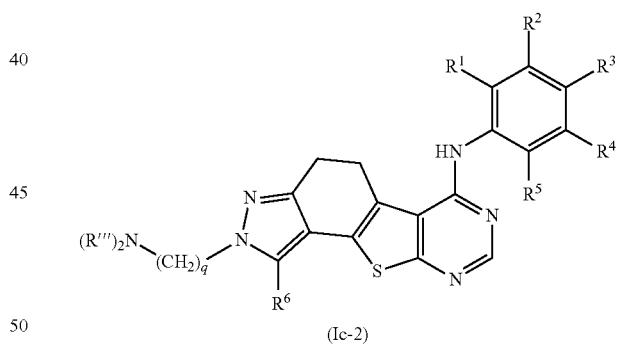

(Ic-2)

The preparation of the intermediate of formula (9), used in Reaction Scheme 4, is shown in Reaction Schemes 5 and 6 below. The intermediate of formula (4) is prepared by the method shown in Reaction Scheme 1. The compound of formula (4) is then protected by reaction with a reagent of general formula Pg-lg, where Pg represents a suitable protecting group and lg represents a leaving group. For example, the compounds of formulae (13) and (14), where Pg is a 4-nitrophenylethyl group, may be prepared by reaction of (4) with 4-nitrophenylethanol (where lg=OH) under Mitsunobu conditions (e.g., DIAD, Ph$_3$P). The O-protected compound of formula (13) is the major product and may be separated from the minor product of formula (14) by chromatographic means.

Reaction Scheme 5

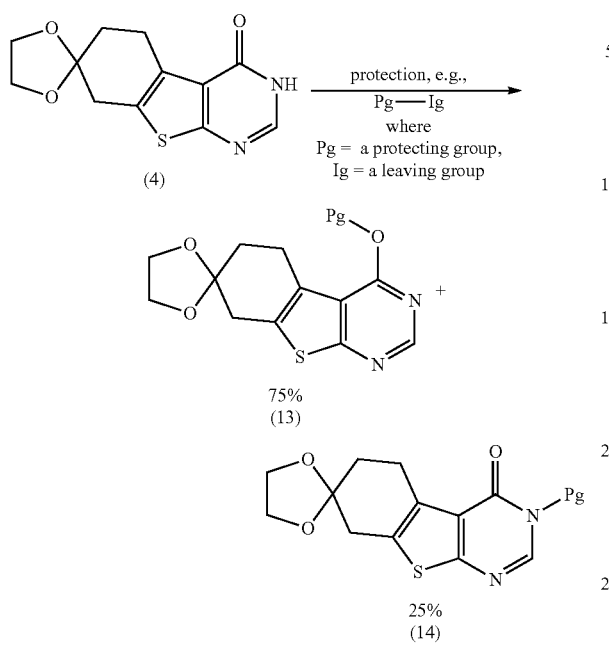

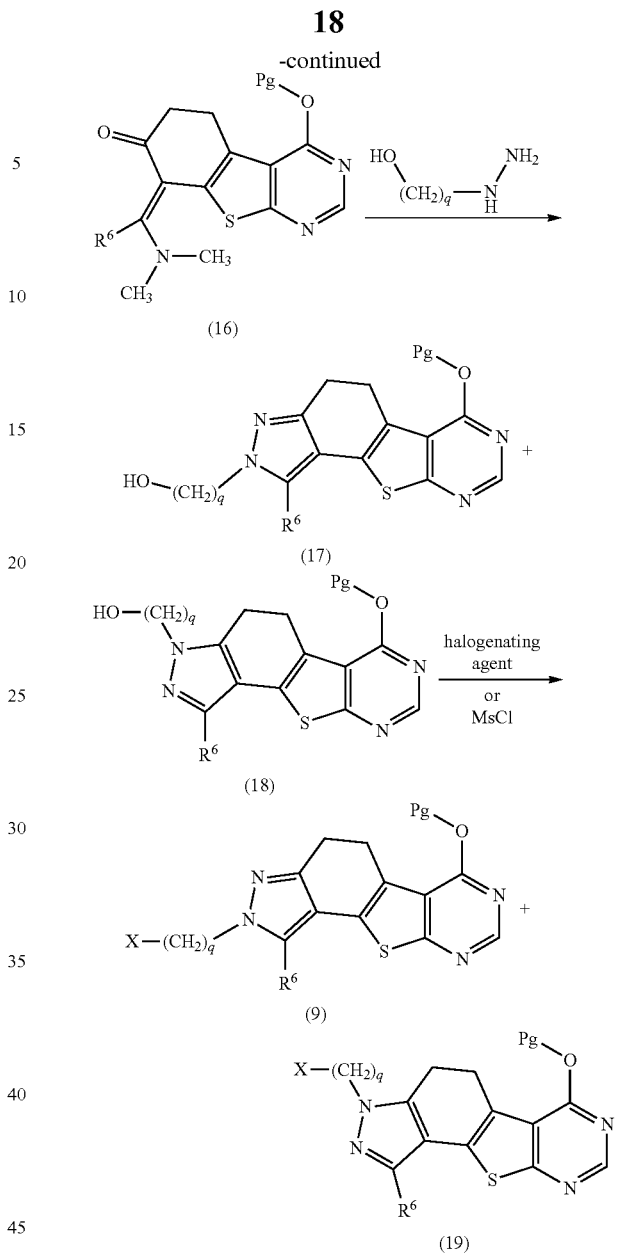

The compound of formula (13) is then allowed to react with aqueous acetic acid to provide the ketone intermediate of formula (15). This ketone is converted to the enaminone of formula (16) by reaction with a dimethylamide acetal reagent. Cyclization to the pyrazole is carried out in a manner analogous to that described above, namely reaction with an appropriately substituted hydrazine, to provide the intermediates of formula (17) and (18). Halogenation of alkanesulfonylation of the formula (18) compound provides a mixture of compounds of formulae (9) and (19), which are separated. The formula (9) compound is carried on to the compound of formula (Ic-2) as described in Reaction Scheme 4. If so desired, the formula (19) compound may also be used to prepare the compound of formula (Ic-1) in an analogous manner.

Reaction Scheme 6

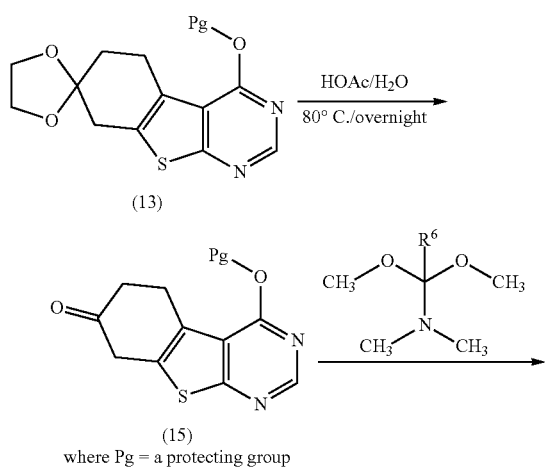

By using these general methods and adjusting the starting materials and conditions as needed, one skilled in the art can prepare the compounds of the invention.

Additional compounds of formula (I) can be prepared from other formula (I) compounds by elaboration of functional groups present. Such elaboration includes, but is not limited to, hydrolysis, reduction, oxidation, alkylation, acylation, esterification, amidation and dehydration reactives. Such transformations may in some instances require the use of protecting groups by the methods disclosed in T. W. Greene and P. G. M. Wuts, *Protective Groups in Organic Synthesis*; Wiley: New York, (1999), and incorporated herein by reference. Such methods would be initiated after synthesis of the desired compound or at another place in the synthetic route that would be readily apparent to one skilled in the art.

The compounds according to the invention exhibit an unforeseeable, useful pharmacological and pharmacokinetic activity spectrum. They are therefore suitable for use as medicaments for the treatment and/or prophylaxis of disorders in humans and animals.

The compounds according to the invention are because of their pharmacological properties useful alone or in combination with other active components for treating and/or preventing hyperproliferative disorders, especially cancer.

In another embodiment, the present invention provides a medicament containing at least one compound according to the invention. In another embodiment, the present invention provides a medicament containing at least one compound according to the invention together with one or more pharmacologically safe excipient or carrier substances, and also their use for the abovementioned purposes.

The active compound can act systemically and/or locally. For this purpose it can be administered in a suitable manner, such as for example by oral, parenteral, pulmonary, nasal, sublingual, lingual, buccal, rectal, dermal, transdermal, ophthalmic or otic administration or in the form of an implant or stent. The active compound can be administered in forms suitable for these modes of administration.

Suitable forms of oral administration are those according to the prior art which function by releasing the active compound rapidly and/or in a modified or controlled manner and which contain the active compound in a crystalline and/or amorphous and/or dissolved form, such as for example tablets (which are uncoated or coated, for example with enteric coatings or coatings which dissolve after a delay in time or insoluble coatings which control the release of the active compound), tablets or films/wafers which disintegrate rapidly in the oral cavity or films/lyophilisates, capsules (e.g. hard or soft gelatin capsules), dragées, pellets, powders, emulsions, suspensions and solutions.

Parenteral administration can be carried out by avoiding an absorption step (e.g. by intravenous, intraarterial, intracardial, intraspinal or intralumbar administration) or by including absorption (e.g. by intramuscular, subcutaneous, intracutaneous or intraperitoneal administration). Suitable parenteral administration forms are for example injection and infusion formulations in the form of solutions, suspensions, emulsions, lyophilisates and sterile powders.

Suitable forms of administration for the other modes of administration are for example inhalation devices (such as for example powder inhalers, nebulizers), nasal drops, solutions and sprays; tablets or films/wafers for lingual, sublingual or buccal administration or capsules, suppositories, ear and eye preparations, vaginal capsules, aqueous suspensions (lotions or shaking mixtures), lipophilic suspensions, ointments, creams, transdermal therapeutic systems, milky lotions, pastes, foams, dusting powders, implants or stents.

The active compounds can be converted into the abovementioned forms of administration in a manner known to the skilled man and in accordance with the prior art using inert, non-toxic, pharmaceutically suitable auxiliaries. The latter include for example excipients (e.g. microcrystalline cellulose, lactose, mannitol, etc.), solvents (e.g. liquid polyethylene glycols), emulsifiers and dispersants or wetting agents (e.g. sodium dodecyl sulphate, polyoxysorbitan oleate etc.), binders (e.g. polyvinyl pyrrolidone), synthetic and/or natural polymers (e.g. albumin), stabilizers (e.g. antioxidants, such as, for example, ascorbic acid), dyes (e.g. inorganic pigments such as iron oxides) or taste- and/or odour-corrective agents.

In general it has proven advantageous for parenteral administration to administer daily quantities of approximately from 0.001 to 300 mg/kg body weight, and preferably approximately from 0.10 to 150 mg/kg body weight in order to obtain effective results.

It may however be necessary to deviate from the abovementioned quantities, depending on the body weight, mode of administration, the individual patient response to the active compound, the type of preparation and the time or interval of administration.

The percentages in the tests and examples which follows are, unless otherwise stated, by weight; parts are by weight. Solvent ratios, dilution ratios and concentrations reported for liquid/liquid solutions are each based on the volume.

A. EXAMPLES

Abbreviations and Acronyms

When the following abbreviations are used throughout the disclosure, they have the following meaning:

| | |
|---|---|
| ACN | acetonitrile |
| aq | aqueous |
| CDCl$_3$-d | chloroform-d |
| CD$_2$Cl$_2$-d$_4$ | methylene chloride-d$_4$ |
| Celite ® | registered trademark of Celite Corp. brand of diatomaceous earth |
| DCM | methylene chloride |
| DIAD | diisopropylazodicarboxylate |
| DMF | N,N-dimethyl formamide |
| DMSO-d$_6$ | dimethylsulfoxide-d$_6$ |
| EtOAc | ethyl acetate |
| equiv | equivalent(s) |
| h | hour(s) |
| $^1$H NMR | proton nuclear magnetic resonance |
| Hex | hexanes |
| HPLC | high performance liquid chromatography |
| LCMS | liquid chromatography/mass spectroscopy |
| MeOH | methanol |
| min | minute(s) |
| MS | mass spectrometry |
| Pd/C | palladium on carbon |
| R$_f$ | TLC retention factor |
| rt | room temperature |
| RT | retention time (HPLC) |
| TFA | trifluoroacetic acid |
| THF | tetrahydrofuran |
| TLC | thin layer chromatography |

General Analytical Procedures

The structure of representative compounds of this invention were confirmed using the following procedures.

Electron impact mass spectra (EI-MS) were obtained with a Hewlett Packard® 5989A mass spectrometer equipped with a Hewlett Packard® 5890 Gas Chromatograph with a J & W DB-5 column (0.25 uM coating; 30 m×0.25 mm). The ion source is maintained at 250° C. and spectra were scanned from 50-800 amu at 2 sec per scan.

High pressure liquid chromatography-electrospray mass spectra (LC-MS) were obtained using either a:
(A) Hewlett-Packard® 1100 HPLC equipped with a quaternary pump, a variable wavelength detector set at 254 nm, a YMC pro C-18 column (2×23 mm, 120 A), and a Finnigan® LCQ ion trap mass spectrometer with electrospray ionization. Spectra were scanned from 120-1200 amu using a variable ion time according to the number of ions in the source. The eluents were A: 2% acetonitrile in water with 0.02% TFA and B: 2% water in acetonitrile with 0.018% TFA. Gradient elution from 10% B to 95% over 3.5 minutes at a flow rate of 1.0 mL/min is used with an initial hold of 0.5 minutes and a final hold at 95% B of 0.5 minutes. Total run time is 6.5 minutes.
or
(B) Gilson® HPLC system equipped with two Gilson 306 pumps, a Gilson 215 Autosampler, a Gilson® diode array detector, a YMC Pro C-18 column (2×23 mm, 120 A), and a Micromass LCZ single quadrupole mass spectrometer with z-spray electrospray ionization. Spectra were scanned from 120-800 amu over 1.5 seconds. ELSD (Evaporative Light Scattering Detector) data is also acquired as an analog channel. The eluents were A: 2% acetonitrile in water with 0.02% TFA and B: 2% water in acetonitrile with 0.018% TFA. Gradient elution from 10% B to 90% over 3.5 minutes at a flowrate of 1.5 mL/min is used with an initial hold of 0.5 minutes and a final hold at 90% B of 0.5 minutes. Total run time is 4.8 minutes. An extra switching valve is used for column switching and regeneration.

Routine one-dimensional NMR spectroscopy is performed on 300 MHz Varian® Mercury-plus spectrometers. The samples were dissolved in deuterated solvents obtained from Cambridge Isotope Labs®, and transferred to 5 mm ID Wilmad® NMR tubes. The spectra were acquired at 293 K. The chemical shifts were recorded on the ppm scale and were referenced to the appropriate solvent signals, such as 2.49 ppm for DMSO-$d_6$, 1.93 ppm for $CD_3CN$-$d_3$, 3.30 ppm for $CD_3OD$-$d_4$, 5.32 ppm for $CD_2Cl_2$-$d_4$ and 7.26 ppm for $CDCl_3$-d for $^1H$ spectra.

Example 1

Preparation of 2-{6-[(3-chloro-4-fluorophenyl)amino]-4,5-dihydro-2H-pyrimido[5',4':4,5]thieno[2,3-e]indazol-2-yl}ethanol

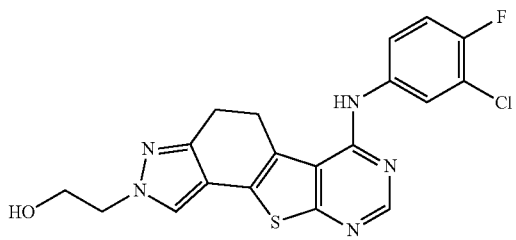

Step 1. Preparation of Ethyl 2-amino-4,7-dihydro-5H-spiro[1-benzothiophene-6,2'-[1,3]dioxolane]-3-carboxylate

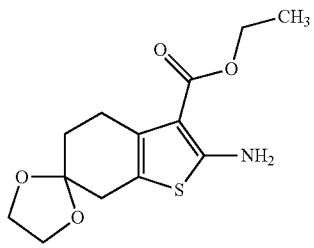

To 600 mL ethanol were sequentially 1,4-Dioxa-spiro[4.5]decan-8-one (25.0 g, 0.160 mol), ethyl cyanoacetate (18.1 g, 0.160 mol), morpholine (14.0 g, 0.160 mol), and sulfur (5.5 g, 0.160 mol). The heterogeneous contents were stirred at room temperature for 4 days, after which time all the sulfur had dissolved. The homogeneous contents were concentrated under reduced pressure, and the residue diluted with EtOAc (200 mL). The mixture was washed with water (200 mL), and the layers were separated. The organic layer was dried over $MgSO_4$, filtered, and concentrated under reduced pressure to afford the desired product as a dark colored oil (45.0 g, 99%). $^1H$-NMR (DMSO-$d_6$) δ 7.20 (s, 2H), 4.10 (q, 2H), 3.87 (s, 4H), 2.66 (t, 2H), 2.59 (s, 2H), 1.71 (t, 2H), 1.18 (t, 3H); LCMS RT=2.58 min; [M+H]$^+$=284.2.

Step 2. Preparation of 3,5,6,8-tetrahydro-4H-spiro[1-benzothieno[2,3-d]pyrimidine-7,2'-[1,3]dioxolan]-4-one

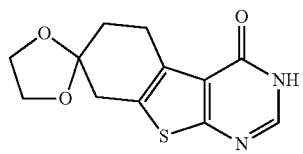

To a stirring solution of ethyl 2-amino-4,7-dihydro-5H-spiro[1-benzothiophene-6,2'-[1,3]dioxolane]-3-carboxylate (40.0 g, 0.142 mol) in formamide (225 mL) was added ammonium formate (17.8 g, 0.282 mol). The resulting mixture was stirred with at 140° C. for 16 h, after which time the heterogeneous contents were removed from heating, and allowed to cool to rt. The contents were filtered, the solid filter cake was washed with water (2×60 mL), and suction dried overnight to afford the desired product as an off-white solid (33.0 g, 88%). $^1H$-NMR (DMSO-$d_6$) δ 12.35 (broad s, 1H), 8.00 (s, 1H), 3.92 (s, 4H), 2.95 (t, 2H), 2.91 (s, 2H), 1.83 (t, 2H); LCMS RT=1.87 min; [M+H]$^+$=265.2.

Step 3. Preparation of 4-chloro-5,8-dihydro-6H-spiro[1-benzothieno[2,3-d]pyrimidine-7,2'-[1,3]dioxolane]

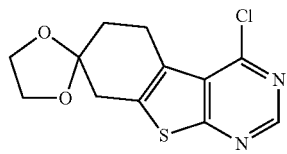

To a stirring solution of 3,5,6,8-tetrahydro-4H-spiro[1-benzothieno[2,3-d]pyrimidine-7,2'-[1,3]dioxolan]-4-one (20.0 g, 0.076 mol) in $POCl_3$ (200 mL) at 0° C. was added triethylamine (200 mL) over a 15 min. period. The resulting mixtures were allowed to warm to rt, and then heated to 80° C. After 3 h, the contents were removed from heating, and allowed to cool to rt. The heterogeneous mixture was concentrated under reduced pressure. The residue was diluted with EtOAc (100 mL), and concentrated again to further remove the volatile materials. The residue was then diluted with EtOAc (100 mL) and the heterogeneous mixture poured onto a stirring mixture of ice-water/aq $NaHCO_3$ (800 mL). After 5 min. stirring, the contents (pH≈7) were filtered and the solid filter cake washed with water. The product was dried in vacuum oven overnight to afford the desired product (20.7 g, 97%) as an off-white solid. $^1H$-NMR (DMSO-$d_6$) δ 8.82 (s, 1H), 3.97 (s, 4H), 3.10 (t, 2H), 3.07 (s, 2H), 1.95 (t, 2H); LCMS RT=2.45 min; [M+H]⁺=283.1.

Step 4. Preparation of N-(3-chloro-4-fluorophenyl)-5,8-dihydro-6H-spiro[1-benzothieno[2,3-d]pyrimidine-7,2'-[1,3]dioxolan]-4-amine

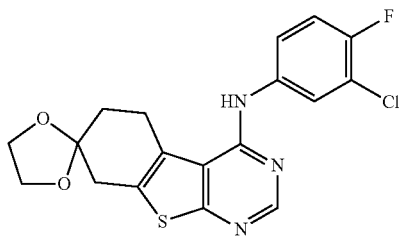

To a stirring solution of 4-chloro-5,8-dihydro-6H-spiro[1-benzothieno[2,3-d]pyrimidine-7,2'-[1,3]dioxolane] (7.0 g, 24.8 mmol) in ethanol (100 mL) was added 4-fluoro-3-chloroaniline (3.6 g, 24.8 mmol) and HCl (4N in dioxane, 0.05 mL). The contents were heated to reflux for 5 h, after which time the contents were removed from heating and allowed to cool to rt. The solvent was removed under reduced pressure, the crude residue suspended in aq NaHCO₃ (100 mL), and stirred for 15 min. The contents were again filtered, and the solid filter cake washed with water. The collected yellow solid was triturated with diethyl ether (50 mL) to afford the final product (5.5 g, 57%) as a light yellow solid. ¹H-NMR (DMSO-d₆) δ 8.41 (s, 1H), 8.28 (s, 1H), 7.78 (dd, 1H), 7.58 (m, 1H), 7.35 (t, 1H), 3.97 (s, 4H), 3.22 (t, 2H), 3.00 (s, 2H), 1.93 (t, 2H); LCMS RT=3.26 min; [M+H]⁺=392.3.

Step 5. Preparation of 4-(3-Chloro-4-fluoro-phenylamino)-5,8-dihydro-6H-benzo[4,5]thieno[2,3-d]pyrimidin-7-one

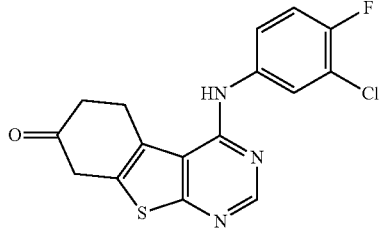

To a stirring acetic acid/water solution (4:1, 300 mL) was added N-(3-chloro-4-fluorophenyl)-5,8-dihydro-6H-spiro[1-benzothieno[2,3-d]pyrimidine-7,2'-[1,3]dioxolan]-4-amine (5.5 g, 14 mmol), and the contents heated at 80° C. for 12 h. The dark colored mixture was cooled to rt, and the solvent was removed under reduced pressure. The crude residue was suspended in aq NaHCO₃ (1N, 100 mL), stirred for 10 min., and filtered. The filtered solid was triturated with diethyl ether (100 mL) to afford the desired product (4.8 g, 98%) as a dark yellow solid. ¹H-NMR (DMSO-d₆) δ 8.53 (s, 1H), 8.46 (s, 1H), 7.87 (dd, 1H), 7.60 (m, 1H), 7.40 (t, 1H), 3.73 (s, 2H), 3.43 (t, 2H), 2.64 (s, 2H); LCMS RT=3.01 min; [M+H]⁺=348.2.

Step 6. Preparation of 4-(3-Chloro-4-fluoro-phenylamino)-8-dimethylaminomethylene-5,8-dihydro-6H-benzo[4,5]thieno[2,3-d]pyrimidin-7-one

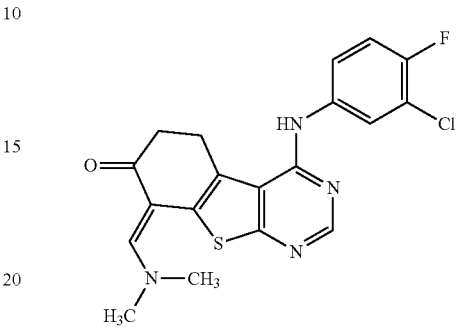

A slurry of 4-(3-Chloro-4-fluoro-phenylamino)-5,8-dihydro-6H-benzo[4,5]thieno[2,3-d]pyrimidin-7-one (8.0 g, 0.023 mol) in toluene (80 mL) was prepared and N,N-dimethylformamide dimethyl acetal (3.2 mL, 0.024 mol) was added. The orange slurry turned dark purple upon heating in an oil bath at 80° C. After 1 h the solvent was evaporated in vacuo to yield a medium brown solid that was carried on directly to the next step. LCMS RT=3.06 min; [M+H]⁺=403.2.

Step 7. Preparation of 2-{6-[(3-chloro-4-fluorophenyl)amino]-4,5-dihydro-2H-pyrimido[5',4':4,5]thieno[2,3-e]indazol-2-yl}ethanol

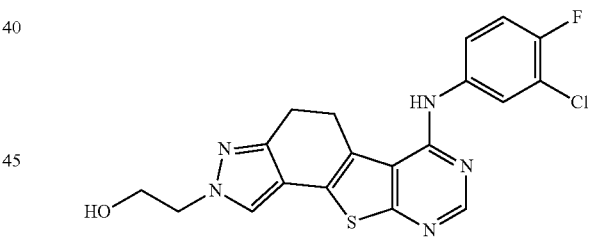

To a solution of 4-(3-Chloro-4-fluoro-phenylamino)-8-dimethylaminomethylene-5,8-dihydro-6H-benzo[4,5]thieno[2,3-d]pyrimidin-7-one (0.023 mol) in ethanol (93 mL) was added hydroxyethyl hydrazine (2.14 g, 0.024 mol). The slurry was heated in an oil bath at 50° C. for 3 h and then allowed to cool to room temperature overnight. The reaction mixture was filtered and the resulting solid was dried by vacuum filtration on a Buchner funnel for 2 h to yield an orange powdery solid (7.68 g, 80%). ¹H NMR indicates a mixture of regioisomers (3:2 ratio of example 1 vs example 88). The above batch (7.2 g) of alcohol was combined with another batch (3.0 g, 3:1 ratio of example 1 vs example 88) and heated to near homogeneity in methoxybenzene (250 mL) at reflux. The mixture was cooled to 80° C. and EtOH (100 mL) was added while maintaining the internal temperature at ~80° C. The mixture was allowed to cool to room temperature with stirring. An orange solid precipitated and was collected by vacuum filtration (8.5 g, 7:3 ratio of example 1 vs example 88). The collected solid was transferred into a flask, reheated to reflux with methoxybenzene (300 mL), cooled to ~80° C., and diluted with EtOH (150 mL). The mixture was allowed to cool to room temperature overnight. The orange solid was collected by vacuum filtration (3.8 g, 93% regioisomeric purity by LC). The filtrate (2:3 ratio of example 1 vs example 88 by $^1$H NMR) was set aside for the preparation of the example 88. $^1$H NMR (DMSO-$d_6$) δ 8.58 (s, 1H), 8.39 (s, 1H), 7.94 (s, 1H), 7.88 (m, 1H), 7.61 (m, 1H), 7.40 (t, 1H), 4.93 (t, 1H), 4.11 (t, 2H), 3.75 (dt, 2H), 3.39 (t, 2H), 2.94 (t, 2H); LCMS RT=2.78 min; [M+H]$^+$=416.4.

Example 8

Preparation of N-(3-chloro-4-fluorophenyl)-2-[2-(4-methylpiperazin-1-yl)ethyl]-4,5-dihydro-2H-pyrimido[5',4':4,5]thieno[2,3-e]indazol-6-amine

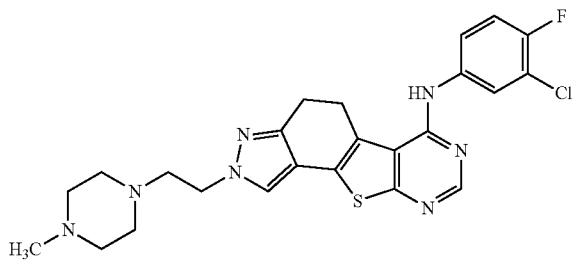

Step 1. Preparation of 2-(2-bromoethyl)-N-(3-chloro-4-fluorophenyl)-4,5-dihydro-2H-pyrimido[5',4':4,5]thieno[2,3-e]indazol-6-amine

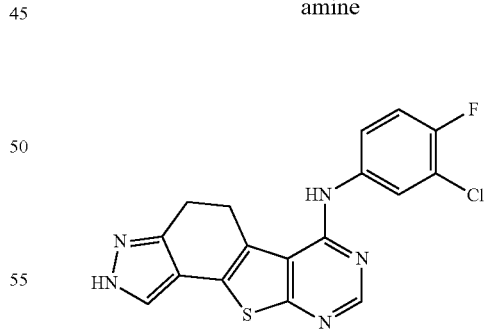

To a stirring solution of 2-{6-[(3-chloro-4-fluorophenyl)amino]-4,5-dihydro-2H-pyrimido[5',4':4,5]thieno[2,3-e]indazol-2-yl}ethanol (11.4 g, 27.4 mmol) in CH$_2$Cl$_2$ (240 mL) were added triphenylphosphine (13.5 g, 48.0 mmol) and carbon tetrabromide (17.0 g, 48 mmol). The mixture was stirred at room temperature for 1.5 h, and the solvent was then removed under reduced pressure. The crude residue was purified via flash chromatography (1:1 hexanes/EtOAc) to afford the desired product (4.0 g, 30%) as an off-white solid. $^1$H-NMR (CDCl$_3$) δ 3.05 (t, 2H), 3.27 (t, 2H), 3.66 (s, 2H), 4.40 (t, 2H), 6.93 (s, 1H), 7.05 (t, 1H), 7.34-7.40 (m, 1H), 7.44 (s, 1H), 7.78 (dd, 1H), 8.40 (s, 1H); LCMS RT=3.81 min; [M+H]$^+$=478.2, 480.2.

Step 2. Preparation of N-(3-chloro-4-fluorophenyl)-2-[2-(4-methylpiperazin-1-yl)ethyl]-4,5-dihydro-2H-pyrimido[5',4':4,5]thieno[2,3-e]indazol-6-amine

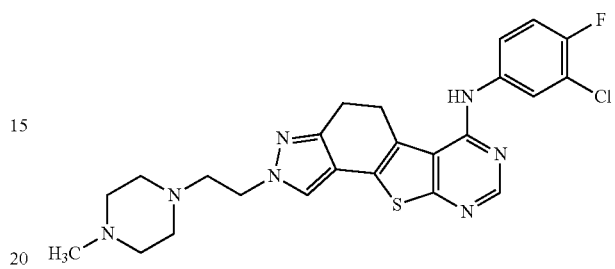

To a stirring solution of 2-(2-bromoethyl)-N-(3-chloro-4-fluorophenyl)-4,5-dihydro-2H-pyrimido[5',4':4,5]thieno[2,3-e]indazol-6-amine (100 mg, 0.2 mmol) in DMF solution (5 mL) were sequentially added 1-methyl-piperazine (0.03 mL, 0.31 mmol), sodium iodide (31.3 mg, 0.21 mmol), and sodium carbonate (44.3 mg, 0.42 mmol). The mixture was stirred at 60° C. for 4 h, after which time the contents were allowed to cool to rt and the solvent then removed under reduced pressure. The crude product was purified via reverse phase HPLC to afford the desired product (66 mg, 63%) as a white solid. $^1$H-NMR (CD$_3$OD) δ 2.25 (s, 3H), 2.40-2.60 (m, 8H), 2.76 (t, 2H), 2.95 (t, 2H), 3.28 (t, 2H), 4.17 (t, 2H), 7.10 (t, 1H), 7.45-7.50 (m, 1H), 7.69 (s, 1H), 7.84 (dd, 1H), 8.42 (s, 1H); LCMS RT=2.46 min; [M+H]$^+$=498.2.

Using the method described above and the appropriate starting materials, Examples 2-38, and 41-42 were similarly prepared.

Example 40

Preparation of N-(3-chloro-4-fluorophenyl)-4,5-dihydro-2H-pyrimido[5',4':4,5]thieno[2,3-e]indazol-6-amine To a solution of 4-(3-Chloro-4-fluoro-phenylamino)-8-dimethylaminomethylene-5,8-dihydro-6H-benzo[4,5]thieno[2,3-d]pyrimidin-7-one (100 mg, 0.25 mmol) in anhydrous ethanol (2 mL) was added hydrazine (12 mg, 0.37 mmol). The resulting mixture was stirred at rt for 5 h. The solid was filtered and washed with EtOAc and then with water. It yielded N-(3-chloro-4-fluorophenyl)-4,5-dihydro-2H-pyrimido[5',4':4,5]thieno[2,3-e]indazol-6-amine as a red solid (52 mg, 56%). $^1$H-NMR (DMSO-$d_6$) δ 12.73 (s, 1H), 8.58 (s, 1H), 8.39 (s, 1H), 7.99 (s, 1H), 7.88 (s, 1H), 7.61 (m, 1H), 7.40 (t, 1H), 3.40 (t, 2H), 2.96 (t, 2H); LCMS RT=2.98 min; [M+H]⁺=372.3.

Example 43

Preparation of (S)-3-[6-(3-Chloro-4-fluoro-phenylamino)-4,5-dihydro-10-thia-2,3,7,9-tetraaza-cyclopenta[a]fluoren-2-yl}-propane-1,2-diol

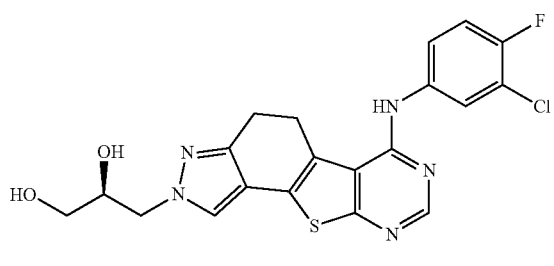

Step 1. Preparation of (2S)-3-(N'-tert-butyloxycarbonyl)hydrazino-1,2-propanediol

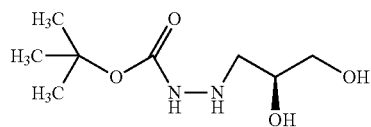

(R)-(+)-glycidol (105 mg, 1.42 mmol) was reacted with tert-butyl carbazate (562 mg, 4.25 mmol, 3.0 eq) to give a light yellow oil (168.6 mg, 57%) as desired product. The detailed procedure was described in step 1 in example 44. (2S)-3-(N'-tert-butyloxycarbonyl)hydrazino-1,2-propanediol has: ¹H-NMR (CDCl₃) δ 3.85 (m, 1H), 3.70 (d, J=11.7 Hz, 1H), 3.54 (m, 1H), 2.97 (d, J=12.8 Hz, 1H), 2.88 (m, 1H), 1.45 (s, 9H). TLC R$_f$=0.3 [Merck Co., Kiesel gel 60 F254, DCM:MeOH (9:1)].

Step 2. Preparation of (S)-3-[6-(3-Chloro-4-fluoro-phenylamino)-4,5-dihydro-10-thia-2,3,7,9-tetraaza-cyclopenta[a]fluoren-2-yl}-propane-1,2-diol

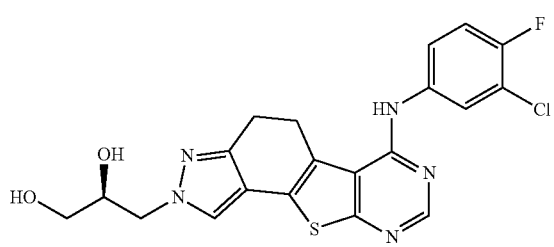

(2S)-3-(N'-tert-butyloxycarbonyl)hydrazino-1,2-propanediol (46.8 mg, 0.23 mmol) was reacted with 4-(3-chloro-4-fluoro-phenylamino)-8 dimethylaminomethylene-5,8-dihydro-6H-benzo[4,5]thieno[2,3-d]pyrimidin-7-one (83.0 mg, 0.21 mmol) to give off-white solid as desired product (22.2 mg, 24%). The detailed procedure was described in example 76. ¹H-NMR (DMSO-d₆) δ 8.58 (s, 1H), 8.38 (s, 1H), 7.89 (s, 1H), 7.88 (m, 1H) 7.61 (m, 1H), 7.40 (t, 1H), 5.0 (d, J=5.6 Hz, 1H), 4.76 (t, 1H), 4.18 (dd, J=3.7, 13.4 Hz, 1H), 3.94 (m, 1H), 3.81 (m, 1H), 3.38 (t, 2H), 2.92 (t, 2H); LCMS RT=2.74 min; [M+H]⁺=446.2/448.2.

Example 44

Preparation of (R)-3-[6-(3-Chloro-4-fluoro-phenylamino)-4,5-dihydro-10-thia-2,3,7,9-tetraaza-cyclopenta[a]fluoren-2-yl}-propane-1,2-diol

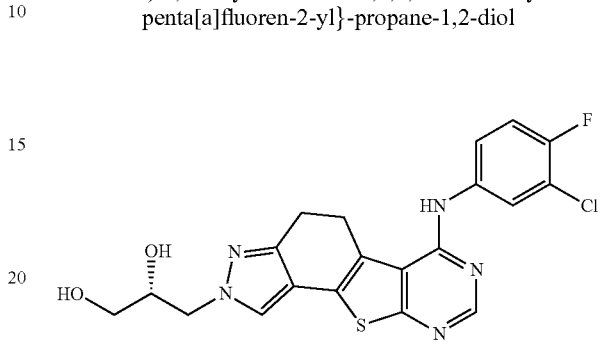

Step 1. Preparation of (2R)-3-(N'-tert-butyloxycarbonyl)hydrazino-1,2-propanediol

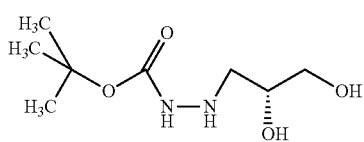

To a stirring solution of (S)-(−)-glycidol (85 mg, 1.15 mmol) in ethanol (2 mL) was added tert-butyl carbazate (455 mg, 3.44 mmol, 3.0 equiv). The resulting mixture was stirred at room temperature for 3 days. The reaction solution was concentrated under reduced pressure and the residue was purified by flash chromatography [silica gel, first DCM followed by MeOH/DCM (5:95)] to give a light yellow oil (166.7 mg, 70%) as desired product.
¹H-NMR (CDCl₃) δ 3.85 (m, 1H), 3.70 (d, J=11.7 Hz, 1H), 3.54 (m, 1H), 2.97 (d, J=12.8 Hz, 1H), 2.88 (m, 1H), 1.45 (s, 9H). TLC R$_f$=0.3 [Merck Co., Kiesel gel 60 F254, DCM:MeOH (9:1)].

Step 2. Preparation of (R)-3-[6-(3-Chloro-4-fluoro-phenylamino)-4,5-dihydro-10-thia-2,3,7,9-tetraaza-cyclopenta[a]fluoren-2-yl}-propane-1,2-diol

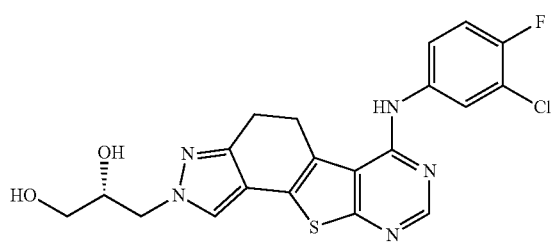

(2R)-3-(N'-tert-butyloxycarbonyl)hydrazino-1,2-propanediol (55 mg, 0.27 mmol) was reacted with 4-(3-chloro- 4-fluoro-phenylamino)-8-dimethylaminomethylene-5,8-dihydro-6H-benzo[4,5]thieno[2,3-d]pyrimidin-7-one (97.7 mg, 0.24 mmol) to give 20.3 mg (18.8%) of desired product as an off-white solid. The detailed procedure was described in example 76. ¹H-NMR (DMSO-d₆) δ 8.58 (s, 1H), 8.38 (s, 1H), 7.89 (s, 1H), 7.88 (m, 1H) 7.61 (m, 1H), 7.40 (t, 1H), 5.0 (d, J=5.6 Hz, 1H), 4.76 (t, 1H), 4.18 (dd, J=3.7, 13.4 Hz, 1H), 3.94 (m, 1H), 3.81 (m, 1H), 3.38 (t, 2H), 2.92 (t, 2H); LCMS RT=2.74 min; [M+H]⁺=446.2/448.2.

Example 48

Preparation of N-(3-chloro-4-morpholin-4-ylphenyl)-2-[2-(4-methylpiperazin-1-yl)ethyl]-4,5-dihydro-2H-pyrimido[5',4':4,5]thieno[2,3-e]indazol-6-amine

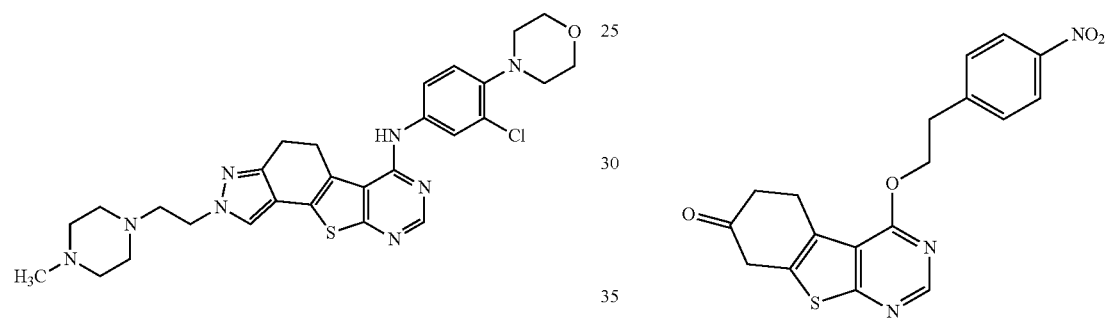

Step 1. Preparation of 4-[2-(4-nitrophenyl)ethoxy]-5,8-dihydro-6H-spiro[1-benzothieno[2,3-d]pyrimidine-7,2'-[1,3]dioxolane]

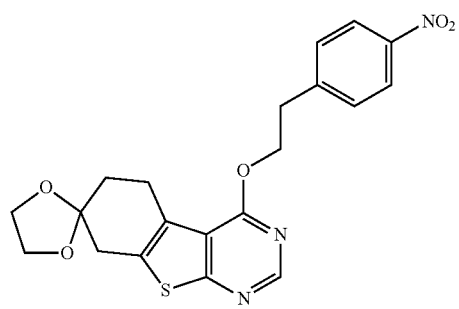

To a stirring solution of 3,5,6,8-tetrahydro-4H-spiro[1-benzothieno[2,3-d]pyrimidine-7,2'-[1,3]dioxolan]-4-one (10.96 g, 41.47 mmol), triphenylphosphine (14.12 g, 53.91 mmol), and 4-nitrophenylethyl alcohol (9.20 g, 53.91 mmol) in THF (500 mL) at 0° C. was added diisopropyl azocarboxylate (11.47 g, 53.91 mmol) dropwise. The resulting solution was allowed to warm to room temperature and stirred overnight, after which time analytical HPLC indicated no more starting material present. Solvents were evaporated and the residue was dissolved in DCM and the resulting solution was left in fume hood for a few hours after which time some precipitates were formed. The precipitates were filtered and air dried to afford a peach color solid (7.26 g). This solid contains the desired product (O-alkylated product) as well as the N-alkylated compound. The filtrates were concentrated and purified by flash chromatography [silica gel, hexanes/EtOAc (2:1 and 1/1)]. The desired product was obtained as a white solid (10.95 g, 64%). ¹H-NMR (DMSO-d₆) δ 8.55 (s, 1H), 8.18 (d, 2H), 7.63 (d, 2H), 4.76 (t, 2H), 3.93 (m, 4H), 3.27 (t, 2H), 2.97 (S, 2H), 2.74 (t, 2H), 1.83 (t, 2H); LCMS RT=3.40 min; [M+H]⁺=414.1.

Step 2. Preparation of 4-[2-(4-nitrophenyl)ethoxy]-5,8-dihydro[1]benzothieno[2,3-d]pyrimidin-7(6H)-one This compound was prepared in a similar fashion as described in Example 1, step 5. ¹H-NMR (DMSO-d₆) δ 8.58 (s, 1H), 8.17 (d, 2H), 7.62 (d, 2H), 4.77 (t, 2H), 3.70 (s, 2H), 3.27 (t, 2H), 3.06 (t, 2H), 2.59 (t, 2H); LCMS RT=3.55 min; [M+H]⁺=370.1.

Step 3. Preparation of (8E)-8-[(dimethylamino)methylene]-4-[2-(4-nitrophenyl)ethoxy]-5,8-dihydro[1]benzothieno[2,3-d]pyrimidin-7(6H)-one This compound was prepared in a similar fashion as described in Example 1, step 6. ¹H-NMR (DMSO-d₆) δ 8.42 (s, 1H), 8.18 (d, 2H), 7.62 (d, 2H), 7.09 (s, 1H), 4.76 (m, 2H), 3.26 (t, 2H), 3.12 (s, 6H), 3.03 (m, 2H), 2.90 (t, 2H); LCMS RT=3.07 min; [M+H]⁺=425.2.

Step 4. Preparation of 2-{6-[2-(4-nitrophenyl)ethoxy]-4,5-dihydro-2H-pyrimido[5',4':4,5]thieno[2,3-e]indazol-2-yl}ethanol

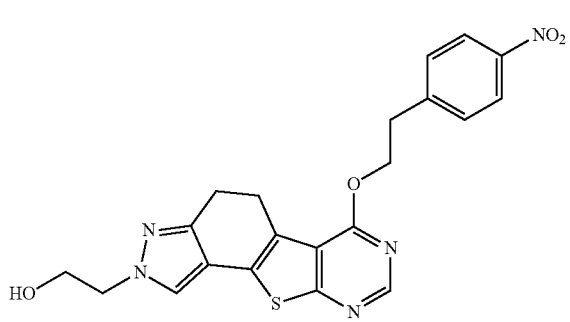

This compound was prepared in a similar fashion as described in Example 1, step 7. ¹H-NMR (DMSO-d₆) δ 8.52 (s, 1H), 8.19 (d, 2H), 7.93 (s, 1H), 7.63 (d, 2H), 4.89 (broad s, 1H), 4.79 (t, 2H), 4.09 (m, 2H), 3.71 (m, 2H), 3.04 (m, 4H), 2.79 (t, 2H); LCMS RT=2.93 min; [M+H]⁺=438.2.

Step 5. Preparation of 2-(2-bromoethyl)-6-[2-(4-nitrophenyl)ethoxy]-4,5-dihydro-2H-pyrimido[5',4':4,5]thieno[2,3-e]indazole

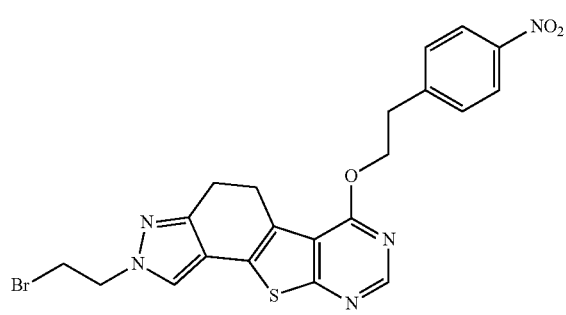

To a suspension of 2-{6-[2-(4-nitrophenyl)ethoxy]-4,5-dihydro-2H-pyrimido[5',4':4,5]thieno[2,3-e]indazol-2-yl}ethanol (5.34 g, 12.21 mmol) in THF (300 mL) were sequentially added carbon tetrabromide (8.10 g, 24.41 mmol), and triphenylphosphine (6.40 g, 24.41 mmol). The resulting reaction mixture was stirred at room temperature for 3 h, after which time analytical HPLC showed no more starting material present. Evaporation of solvents gave a yellow solid, which was suspended in hot MeOH. The solid was collected by filtration. The collected solid was re-suspended in hot MeOH, and the solid was collected by filtration and air-dried to afford a light yellow solid (4.01 g, 66%) as the pure desired product (the filtrates contain both the desired product and the 3-substituted pyrazole compound). ¹H-NMR (DMSO-d₆) δ 8.53 (s, 1H), 8.18 (d, 2H), 8.03 (s, 1H), 7.63 (d, 2H), 4.78 (t, 2H), 4.45 (t, 2H), 3.84 (t, 2H), 3.28 (t, 2H), 3.03 (t, 2H), 2.80 (t, 2H); LCMS RT=3.59 min; [M+H]⁺=500.0/502.0.

Step 6. Preparation of 2-[2-(4-methylpiperazin-1-yl)ethyl]-6-[2-(4-nitrophenyl)ethoxy]-4,5-dihydro-2H-pyrimido[5',4':4,5]thieno[2,3-e]indazole

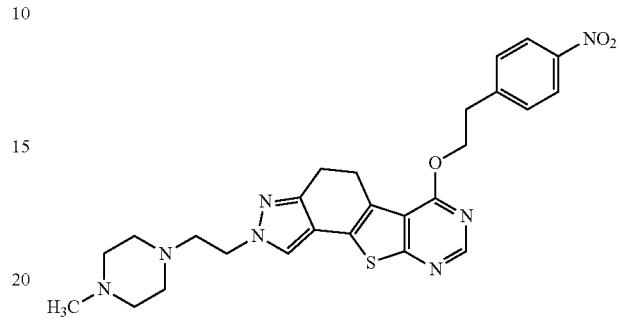

To a suspension of 2-(2-bromoethyl)-6-[2-(4-nitrophenyl)ethoxy]-4,5-dihydro-2H-pyrimido[5',4':4,5]thieno[2,3-e]indazole (4.0 g, 7.99 mmol), K₂CO₃ (2.21 g, 15.99 mmol), and NaI (1.20 g, 7.99 mmol) in acetonitrile (300 mL) was added N-methyl piperazine (3.20 g, 31.98 mmol). Resulting mixture was heated at 80° C. for 4.5 h after which time analytical HPLC showed no more starting material present and a new major peak appeared. Solvents were evaporated and the residue was dissolved in water and CH₂Cl₂. The organic layer was separated, dried (Na₂SO₄), and concentrated to afford a light yellow solid. The solid material was further washed with ether, air-dried to afford a pale solid (4.14 g, 95%) as the desired product. ¹H-NMR (DMSO-d₆) δ 8.52 (s, 1H), 8.19 (d, 2H), 7.95 (s, 1H), 7.63 (d, 2H), 4.78 (t, 2H), 4.14 (t, 2H), 3.28 (t, 2H), 3.01 (t, 2H), 2.78 (t, 2H), 2.67 (t, 2H), 2.40 (broad, 4H), 2.26 (broad, 4H), 2.11 (s, 3H); LCMS RT=2.42 min; [M+H]⁺=520.2.

Step 7. Preparation of 2-[2-(4-methylpiperazin-1-yl)ethyl]-4,5-dihydro-2H-pyrimido[5',4':4,5]thieno[2,3-e]indazol-6-ol

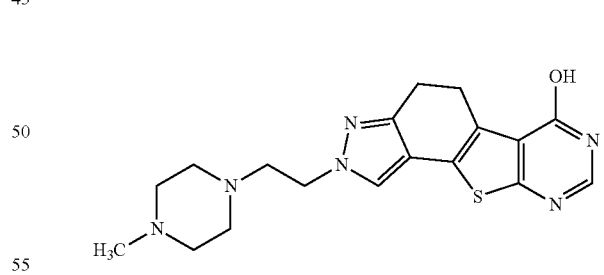

To a solution of 2-[2-(4-methylpiperazin-1-yl)ethyl]-6-[2-(4-nitrophenyl)ethoxy]-4,5-dihydro-2H-pyrimido[5',4':4,5]thieno[2,3-e]indazole (4.12 g, 7.93 mmol) in pyridine (100 mL) was added DBU (4.83 g, 31.72 mmol) and the resulting reaction mixture was stirred at room temperature overnight. Analytical HPLC showed no more starting material present and two new peaks appeared. Solvents were evaporated and the residue was dissolved in water and CH₂Cl₂. pH of the aqueous layer was adjusted to about 7. The organic phase contains the N-alkylated side product and no desired product. The desired product is in the aqueous phase. After separation of the layers, the pH of the aqueous was further adjusted to about 10 and it was concentrated to dryness. The resulting solid was washed with MeOH, then small amount of water, and air dried to afford a light yellow solid (0.79 g, 27%) as the desired product. The MeOH filtrates were concentrated to give a yellow solid, which was washed with EtOAc, air-dried to give another batch of desired product (1.5 g, 36%) as a light yellow solid. $^1$H-NMR (D$_2$O) δ 7.82 (s, 1H), 7.56 (s, 1H), 4.26 (t, 2H), 3.30 (broad, 4 h), 3.21 (t, 2H), 3.07 (broad, 4H), 2.99 (t, 2H), 2.78 (s, 3H), 2.67 (t, 2H); LCMS RT=0.30 min; [M+H]$^+$=371.3.

Step 8. Preparation of 6-chloro-2-[2-(4-methylpiperazin-1-yl)ethyl]-4,5-dihydro-2H-pyrimido[5',4':4,5]thieno[2,3-e]indazole

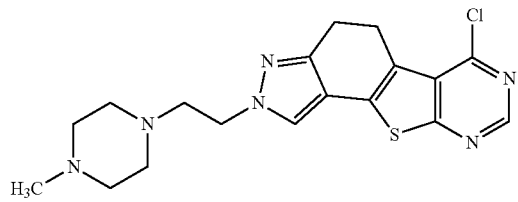

This compound was prepared in a similar fashion as Example 1, step 3. $^1$H-NMR (DMSO-d$_6$) δ 8.76 (s, 1H), 8.10 (s, 1H), 4.18 (t, 2H), 3.39 (t, 2H), 2.94 (t, 2H), 2.70 (t, 2H), 2.46 (broad, 4H), 2.36 (broad, 4H), 2.17 (s, 3H); LCMS RT=1.55 min; [M+H]$^+$=389.4/391.2.

Step 9. Preparation of N-(3-chloro-4-morpholin-4-ylphenyl)-2-[2-(4-methylpiperazin-1-yl)ethyl]-4,5-dihydro-2H-pyrimido[5',4':4,5]thieno[2,3-e]indazol-6-amine

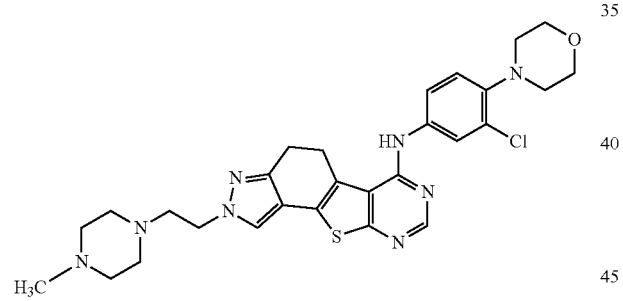

To a suspension of 6-chloro-2-[2-(4-methylpiperazin-1-yl)ethyl]-4,5-dihydro-2H-pyrimido[5',4':4,5]thieno[2,3-e]indazole (50 mg, 0.13 mmol) and 3-chloro-4-morpholinoaniline (82 mg, 0.39 mmol) in isopropanol (3 mL) was added HCl in dioxane (4M, 0.26 mL, 1.03 mmol). The reaction mixture was sealed in a microwave reaction vessel and it was placed in a microwave instrument at 160° C. for 10 min. After it was cooled to room temperature, solvents were evaporated and the residue was dissolved in water/DMF and purified by prep. HPLC. After drying, the TFA salt was neutralized with aq saturated NaHCO$_3$ and extracted with a mixture of CHCl$_3$:isopropanol (3:1). The organic phase was dried over Na$_2$SO$_4$ and concentrated to dryness. The desired product was obtained as a pale solid (40 mg, 55%). $^1$H-NMR (CD$_2$Cl$_2$) δ 8.43 (s, 1H), 7.84 (d, 1H), 7.53 (m, 2H), 7.08 (m, 2H), 4.20 (t, 2H), 3.86 (m, 4H), 3.37 (t, 2H), 3.11 (t, 2H), 3.04 (m, 4H), 2.80 (t, 2H), 2.53 (m, 4H), 2.43 (m, 4H), 2.26 (s, 3H); LCMS RT=2.29 min; [M+H]$^+$=565.4.

Using the method described above and the appropriate starting materials, Examples 39, 45-54, 324-338, 340-344, 347, and 348 were similarly prepared.

Example 55

Preparation of 2-(2-{[tert-butyl(dimethyl)silyl]oxy}ethyl)N-{3-chloro-4-[(3-fluorobenzyl)oxy]phenyl}-4,5-dihydro-2H-pyrimido[5',4':4,5]thieno[2,3-e]indazol-6-amine

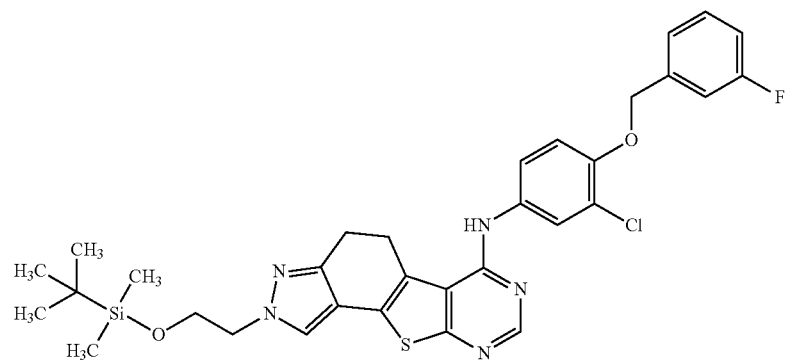

Step 1. Preparation of 2-tert-butyldimethylsilyloxy-1-tert-butyloxycarbonyl-ethylhydrazine

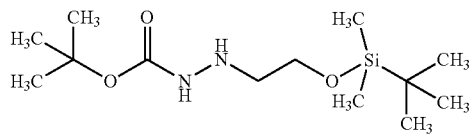

To 300 mL toluene were added (tert-butyldimethylsilyloxy)acetaldehyde (9.6 g, 49.6 mmol) and tert-butylcarbazate (6.75 g, 49.6 mmol). The mixture was stirred at 65° C. for 12 h, after which time the contents were removed from heating and allowed to cool to rt. The solvent was removed under reduced pressure to afford a colorless viscous oil (14.2 g, 97%). This oil was dissolved in ethanol (220 mL), the solution transferred to a 1 L Parr vessel, and 2.84 g Pd/C (10%) were added. The mixture was hydrogenated in a Parr shaker at 50 psi of $H_2$ atmosphere for 15 h. The contents were filtered through a thin pad of Celite® to remove the catalyst, and the filtrate concentrated in vacuo to afford the final product (14 g, 98%) as a white solid. $^1$H-NMR ($CD_2Cl_2$) δ 0.06 (s, 6H), 0.90 (s, 9H), 1.43 (s, 9H), 2.90 (t, 2H), 3.69 (t, 2H), 4.16 (br, 1H), 6.34 (br, 1H); LCMS RT=3.11 min; [M+H]$^+$=290.8.

Step 2. Preparation of 3-Chloro-4-(3-fluoro-benzyloxy)-phenylamine

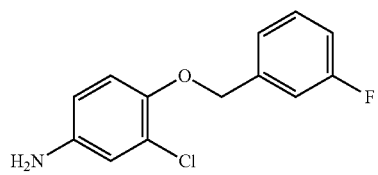

To 90 mL $CH_3CN$ was added 2-chloro-4-nitrophenol (15 g, 86.4 mmol) followed by potassium carbonate (17.9 g, 129.6 mmol). To the stirring suspension was added via dropping funnel a 10 mL $CH_3CN$ solution of 3-fluoro-benzylbromide (16.3 g, 86.4 mmol). The contents were stirred and heated at 70° C. for 18 h, after which time the bright yellow mixture was allowed to cool to it The yellow contents were poured onto $H_2O$ (200 mL) and stirred, upon which solid formation occurs. The solid was filtered and filter cake washed with additional $H_2O$ (50 mL). The collected solid was dried in vacuo, yielding 2-chloro-1-(3-fluoro-benzoyloxy)-4-nitrobenzene (23 g, 94%) as a white solid.

2-chloro-1-(3-fluoro-benzoyloxy)-4-nitro-benzene (10 g, 35.5 mmol) was suspended in 50 mL acetic acid and 150 mL EtOAc in a 500 mL flask. Iron (9.9 g (177.5 mmol) was added to this suspension, and the mixture stirred at rt overnight. The reaction mixture was filtered through a thin pad of Celite®. The filtrate was concentrated in vacuo and neutralized with saturated $Na_2CO_3$ aq solution, followed by EtOAc extraction. The organic layer was washed with brine, dried over $Na_2SO_4$, and concentrated in vacuo. The resulting crude material was purified by flash chromatography eluting with 15% EtOAc/hexanes yielding 3-Chloro-4-(3-fluoro-benzyloxy)-phenylamine as a brown solid [8.5 g, 95%, TLC $R_f$=0.4, 30% EtOAc/HEX. (3:7)]. $^1$H-NMR (DMSO-$d_6$) δ 4.94 (s, 2H), 5.00 (s, 2H), 6.40 (dd, 1H), 6.60 (s, 1H), 6.87 (d, 1H), 7.10-7.18 (m, 1H), 7.20-7.28 (m, 2H), 7.37-7.44 (m, 1H).

Step 3. Preparation of N-(3-Chloro-4-(3-fluoro-benzyloxy)phenylamine)-5,8-dihydro-6H-spiro[1-benzothieno[2,3-d]pyrimidine-7,2'-[1,3]dioxolan]-4-amine

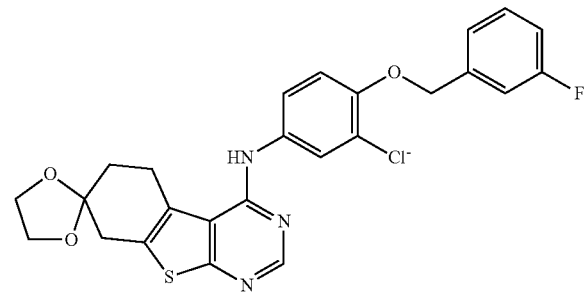

To 2-propanol (300 mL) were sequentially added 4-chloro-5,8-dihydro-6H-spiro[1-benzothieno[2,3-d]pyrimidine-7,2'-[1,3]dioxolane] (20.7 g, 73.2 mmol), 3-Chloro-4-(3-fluoro-benzyloxy)-phenylamine (18.4 g, 73.2 mmol), and HCl in dioxane (4N, 0.92 mL). The suspension was stirred with heating to 80° C., upon which the contents turn brown and homogeneous. After 15 h, the dark orange-yellow heterogeneous mixture was removed from heating, and allowed to cool to rt. The contents were filtered and the collected solid product dried under hi-vac. The filtrate was concentrated under reduced pressure and the residue suspended in $CH_3OH$ (50 mL), upon which formation of a second crop of product ensues. The second crop was collected, and from this filtrate a third crop could also be obtained. The solid product crops were combined to afford the final product (33.5 g, 92%) as an off-white solid. $^1$H-NMR (DMSO-$d_6$) δ 1.90 (t, 2H), 3.00 (s, 2H), 3.26 (t, 2H), 3.97 (s, 4H), 5.22 (s, 2H), 7.11-7.30 (m, 4H), 7.41-7.55 (m, 2H), 7.74 (s, 1H), 8.33 (s, 1H), 8.39 (s, 1H); LCMS RT=3.63 min; [M+H]$^+$=498.3.

Step 4. Preparation of N-(3-Chloro-4-(3-fluoro-benzyloxy)-phenylamine)-5,8-dihydro-6H-benzo[4,5]thieno[2,3-d]pyrimidin-7-one

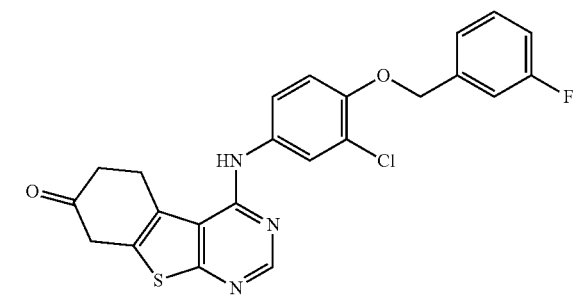

To a stirring acetic acid/$H_2O$ solution (4:1, 600 mL) was added N-(3-Chloro-4-(3-fluoro-benzyloxy)-phenylamine)-

5,8-dihydro-6H-spiro[1-benzothieno[2,3-d]pyrimidine-7,2'-[1,3]dioxolan]-4-amine (34.8 g, 69.8 mmol), and the contents heated at 80° C. for 16 h. The dark colored mixture was cooled to rt, and the solvent removed under reduced pressure. The crude residue was suspended in 1N NaHCO₃ aq Solution (500 mL), stirred for 10 min., and filtered. The collected solid was again vigorously washed with H₂O (500 mL) and filtered to afford the desired product, which was vacuum dried with heating at 40° C. for 24 h. The final product was collected (30.8 g, 97%) as an orange solid. ¹H-NMR (DMSO-d₆) δ 2.66 (t, 2H), 3.44 (t, 2H), 3.74 (s, 2H), 5.23 (s, 2H), 7.14-7.32 (m, 4H), 7.40-7.52 (m, 2H), 7.75 (d, 1H), 8.34 (s, 1H), 8.39 (s, 1H); LCMS RT=3.50 min; [M+H]⁺=454.1.

Step 5. Preparation of N-(3-Chloro-4-(3-fluoro-benzyloxy)-phenylamine)-8-dimethylaminomethylene-5,8-dihydro-6H-benzo[4,5]thieno[2,3-d]pyrimidin-7-one

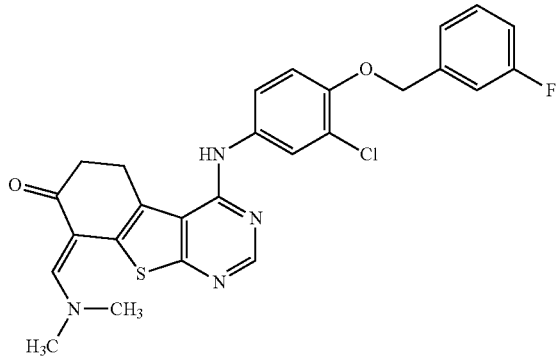

To 150 mL toluene were added N-(3-Chloro-4-(3-fluoro-benzyloxy)-phenylamine)-5,8-dihydro-6H-benzo[4,5]thieno[2,3-d]pyrimidin-7-one (9.6 g, 18 mmol) and dimethylformamide-dimethylacetal (4.78 mL, 36 mmol). The contents were stirred at 70° C. for 4 h, after which time they were allowed to cool to rt. The heterogeneous mixture was filtered, collected solid washed with acetone (5 mL), and dried under hi-vac. The final product was collected (7.0 g, 70%) as a yellow solid. ¹H-NMR (DMSO-d₆) (major rotamer) δ 2.53 (t, 2H), 3.16 (s, 6H), 3.24 (t, 2H), 5.21 (s, 2H), 7.10-7.21 (m, 3H), 7.26-7.33 (m, 2H), 7.40-7.50 (m, 2H), 7.75 (s, 1H), 8.15-8.40 (broad s, 1H), 8.30 (s, 1H); LCMS RT=3.75 min; [M+H]⁺=509.2.

Step 6. Preparation of 2-(2-{[tert-butyl(dimethyl)silyl]oxy}ethyl)N-{3-chloro-4-[(3-fluorobenzyl)oxy]phenyl}-4,5-dihydro-2H-pyrimido[5',4':4,5]thieno[2,3-e]indazol-6-amine

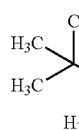

To 325 mL ethanol were added N-(3-Chloro-4-(3-fluoro-benzyloxy)-phenylamine)-8-dimethylaminomethylene-5,8-dihydro-6H-benzo[4,5]thieno[2,3-d]pyrimidin-7-one (8.60 g, 16.9 mmol), and then 2-tert-butyldimethylsilyloxy-1-tert-butyloxycarbonyl-ethylhydrazine (7.36 g, 25.3 mmol) as a 50 mL ethanol solution via dropping funnel over a 5 min. period. The contents were stirred at reflux for 40 h, after which time they were then allowed to cool to rt over a 24 h period. The heterogeneous mixture was filtered to afford a light yellow solid. The filtrate was concentrated and the residue suspended in ethanol (50 mL), from which a second crop of product precipitates. The solid product crops were combined and dried under hi-vac to furnish the final product (8.45 g, 79%) as a light yellow solid. ¹H-NMR (DMSO-d₆) δ -0.05 (s, 6H), 0.87 (s, 9H), 2.95 (t, 2H), 3.42 (t, 2H), 3.95 (t, 2H), 4.20 (t, 2H), 5.33 (s, 2H), 7.21-7.42 (m, 4H), 7.50-7.62 (m, 2H), 7.82 (s, 1H), 7.99 (s, 1H), 8.42 (s, 1H), 8.50 (s, 1H); LCMS RT=4.62 min; [M+H]⁺=636.2.

Example 56

Preparation of 2-[6-({3-chloro-4-[(3-fluorobenzyl)oxy]phenyl}amino)-4,5-dihydro-2H-pyrimido[5',4':4,5]thieno[2,3-e]indazol-2-yl]ethanol

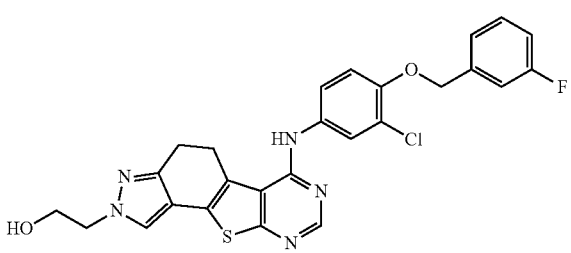

To 250 mL THF cooled to 0° C. was added 2-(2-{[tert-butyl(dimethyl)silyl]oxy}ethyl)-N-{3-chloro-4-[(3-fluorobenzyl)

oxy]phenyl}-4,5-dihydro-2H-pyrimido[5',4':4,5]thieno[2,3-e]indazol-6-amine (7.70 g, 10.9 mmol). To the homogeneous mixture was then added aq HCl 2M, 6.5 mL), upon which the contents darken. The contents were stirred with warming to rt over a 4 h period, after which time the solvent was removed under reduced pressure. The crude residue was diluted with aq Na$_2$CO$_3$ (2M, 100 mL) to attain a pH=11 solution which was vigorously stirred, and the contents then filtered to a light brown solid which was dried under hi-vac. The collected product was triturated two times from hot ethanol to afford the final product (5.05 g, 89%) as a light tan solid. $^1$H-NMR (DMSO-d$_6$) δ 2.90 (t, 2H), 3.36 (t, 2H), 3.72 (m, 2H), 4.06 (t, 2H), 4.90 (s, 1H), 5.24 (s, 2H), 7.14-7.34 (m, 4H), 7.41-7.54 (m, 2H), 7.78 (d, 1H), 7.95 (s, 1H), 8.35 (s, 1H), 8.40 (s, 1H); LCMS RT=3.39 min; [M+H]$^+$=522.2.

Example 57

Preparation of 2-[6-({3-chloro-4-[(3-fluorobenzyl)oxy]phenyl}amino)-4,5-dihydro-2H-pyrimido[5',4':4,5]thieno[2,3-e]indazol-2-yl]ethyl methanesulfonate

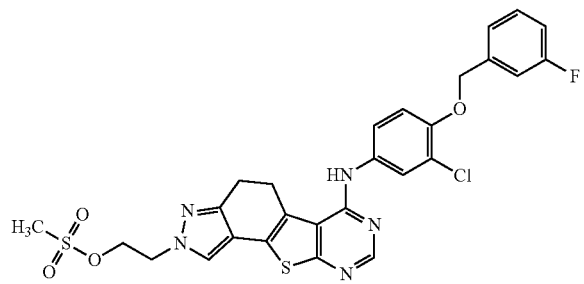

Method A

To 400 mL CH$_2$Cl$_2$ cooled to 0° C. were sequentially added 2-[6-({3-chloro-4-[(3-fluorobenzyl)oxy]phenyl}amino)-4,5-dihydro-2H-pyrimido[5',4':4,5]thieno[2,3-e]indazol-2-yl]ethanol (5.4 g, 10.3 mmol), pyridine (2.76 mL, 34.1 mmol), and methanesulfonyl anhydride (4.51 g, 25.9 mmol). The opaque brown suspension was stirred with warming to rt over a 6 h period, after which time stirring was halted. After 18 h, the heterogeneous mixture was filtered, and the filtrate twice washed with H$_2$O (100 mL). The organic layer was dried over MgSO$_4$, filtered, and the solvent removed under reduced pressure to afford the desired product (5.8 g, 93%) as an off-white solid. $^1$H-NMR (DMSO-d$_6$) δ 2.91 (t, 2H), 3.14, (s, 3H), 3.36 (t, 2H), 4.40 (m, 2H), 4.55 (t, 2H), 5.23 (s, 2H), 7.11-7.32 (m, 4H), 7.40-7.50 (m, 2H), 7.76 (d, 1H), 8.01 (s, 1H), 8.35 (s, 1H), 8.42 (s, 1H); LCMS RT=3.53 min; [M+H]$^+$= 600.1.

Using the method described above and the appropriate starting materials, Example 258 was similarly prepared.

Method B

Step 1. Preparation of 2-[6-({3-chloro-4-[(3-fluorobenzyl)oxy]phenyl}amino)-4,5-dihydro-2H-pyrimido[5',4':4,5]thieno[2,3-e]indazol-2-yl]ethanol ("Regioisomer A"), and 2-[6-({3-chloro-4-[(3-fluorobenzyl)oxy]phenyl}amino)-4,5-dihydro-3H-pyrimido[5',4':4,5]thieno[2,3-e]indazol-3-yl]ethanol ("Regioisomer B")

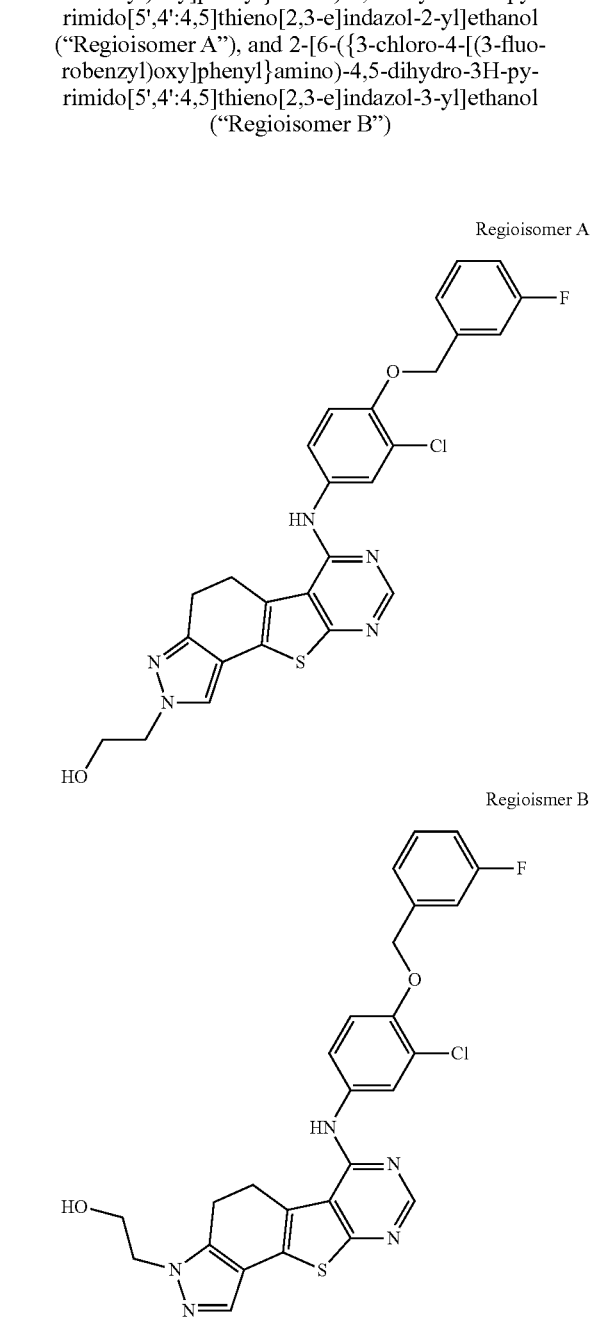

To 50 mL ethanol was added N-(3-Chloro-4-(3-fluorobenzyloxy)-phenylamine)-8-dimethylaminomethylene-5,8-dihydro-6H-benzo[4,5]thieno[2,3-d]pyrimidin-7-one (4.20 g, 16.9 mmol), and then 2-hydroxyethylhydrazine (1.19 g, 14.0 mmol) as a 5 mL ethanol solution. The contents were stirred at reflux for 30 min., after which time they were removed from heating and allowed to cool to rt. The heterogeneous mixture was cooled to 0° C., and filtered to afford a light beige solid. The filter cake was washed with CH$_3$OH and dried under hi-vac. The final product was collected (4.0 g, 93%, ca. 2:1 mixture of regioisomers by $^1$H NMR in favor of "Regioisomer A.") as an off-white solid.

Data for "Regioisomer A": ¹H-NMR (DMSO-d₆) δ 2.90 (t, 2H), 3.36 (t, 2H), 3.72 (m, 2H), 4.06 (t, 2H), 4.90 (s, 1H), 5.24 (s, 2H), 7.14-7.34 (m, 4H), 7.41-7.54 (m, 2H), 7.78 (d, 1H), 7.95 (s, 1H), 8.35 (s, 1H), 8.40 (s, 1H); LCMS RT=3.39 min; [M+H]⁺=522.2.

Data for "Regioisomer B": ¹H-NMR ("Regioisomer B") (DMSO-d₆) δ 3.02 (t, 2H), 3.33 (t, 2H), 3.66 (m, 2H), 4.12 (m, 2H), 4.87 (m, 1H), 5.24 (s, 2H), 7.10-7.30 (m, 4H), 7.40-7.53 (m, 2H), 7.61 (s, 1H), 7.73 (s, 1H), 8.31 (s, 1H), 8.38 (s, 1H); LCMS RT=3.30 min; [M+H]⁺=522.1.

Step 2. Preparation of 2-[6-({3-chloro-4-[(3-fluorobenzyl)oxy]phenyl}amino)-4,5-dihydro-2H-pyrimido[5',4':4,5]thieno[2,3-e]indazol-2-yl]ethyl-methanesulfonate ("Regioisomer A") and 2-[6-({3-chloro-4-[(3-fluorobenzyl)oxy]phenyl}amino)-4,5-dihydro-3H-pyrimido[5',4':4,5]thieno[2,3-e]indazol-3-yl]ethyl methanesulfonate ("Regioisomer B")

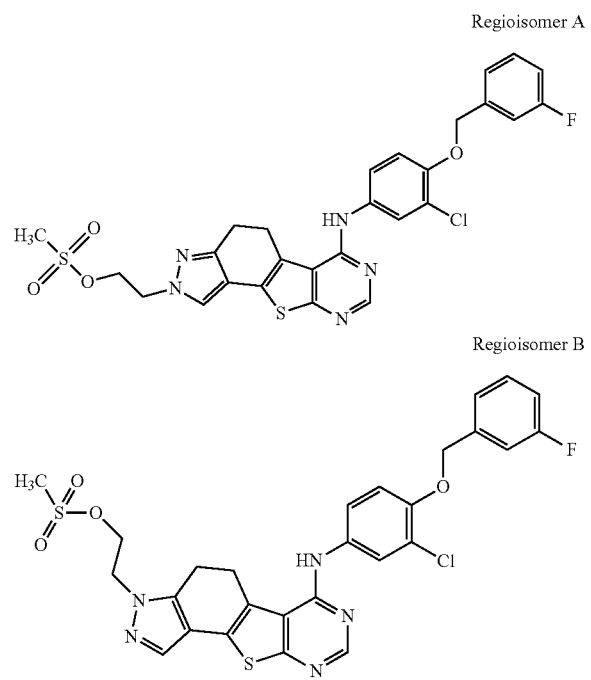

To 100 mL CH₂Cl₂ cooled to 0° C. containing a mixture of 2-[6-({3-chloro-4-[(3-fluorobenzyl)oxy]phenyl}amino)-4,5-dihydro-2H-pyrimido[5',4':4,5]thieno[2,3-e]indazol-2-yl]ethanol and 2-[6-({3-chloro-4-[(3fluorobenzyl)oxy]phenyl}amino)-4,5-dihydro-3H-pyrimido[5',4':4,5]thieno[2,3-e]indazol-3-yl]ethanol (2.5 g, 4.79 mmol), were sequentially added pyridine (1.28 mL, 15.8 mmol), and methanesulfonyl anhydride (1.5 g, 8.62 mmol). The opaque light brown suspension was stirred with warming to rt over a 3 h period, after which time stirring was halted. The heterogeneous mixture was filtered, and the filtrate concentrated in vacuo to afford the regioisomeric mixture of mesylates (2.5 g, 88%) as an off-white solid. Trituration of the product mixture with CH₂Cl₂ results in selective precipitation of "Regioisomer B" in very high purity. Repeated trituration of the product mixture with CH₂Cl₂ would afford additional amounts of "Regioisomer B."

Data for "Regioisomer A" example 57: ¹H-NMR (DMSO-d₆) δ 2.91 (t, 2H), 3.14, (s, 3H), 3.36 (t, 2H), 4.40 (m, 2H), 4.55 (t, 2H), 5.23 (s, 2H), 7.11-7.32 (m, 4H), 7.40-7.50 (m, 2H), 7.76 (d, 1H), 8.01 (s, 1H), 8.35 (s, 1H), 8.42 (s, 1H); LCMS RT=3.53 min; [M+H]⁺=600.1.

Data for "Regioisomer B" example 258: ¹H-NMR (DMSO-d₆) δ 3.05 (t, 2H), 3.09, (s, 3H), 3.19 (t, 2H), 4.46-4.58 (m, 4H), 5.24 (s, 2H), 7.14-7.23 (m, 2H), 7.25-7.34 (m, 2H), 7.41-7.53 (m, 2H), 7.74 (s, 1H), 7.77 (d, 1H), 8.35 (s, 1H), 8.42 (s, 1H); LCMS RT=3.48 min; [M+H]⁺=600.2.

Example 62

Preparation of N-{3-chloro-4-[(3-fluorobenzyl)oxy]phenyl}-2-[2-(4-methylpiperazin-1-yl)ethyl]-4,5-dihydro-2H-pyrimido[5',4':4,5]thieno[2,3-e]indazol-6-amine

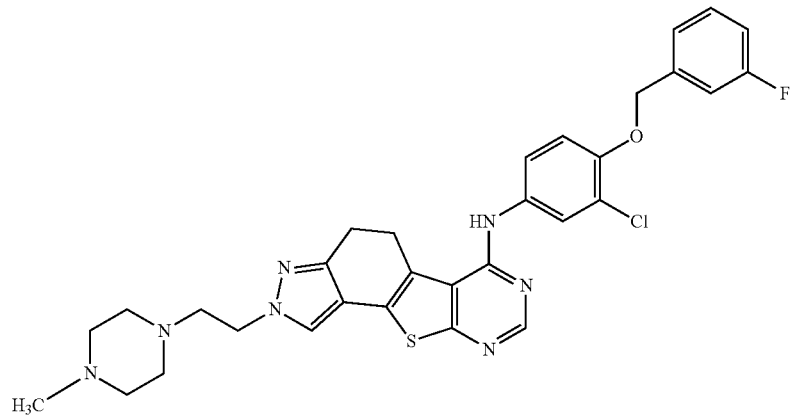

To 250 mL CH₃CN were sequentially added 2-[6-({3-chloro-4-[(3-fluorobenzyl)oxy]phenyl}amino)-4,5-dihydro-2H-pyrimido[5',4':4,5]thieno[2,3-e]indazol-2-yl]ethyl methanesulfonate (5.80 g, 9.67 mmol), 1-methylpiperazine (3.22 mL, 29.0 mmol), and diisopropylethylamine (3.37 mL, 19.3 mmol). The opaque white suspension was stirred with heating to reflux, upon which the contents turn brown and homogeneous. After 15 h the mixture was removed from heating, and allowed to cool to rt. The contents were concentrated under reduced pressure to 10% volume, diluted with CH₂Cl₂ (150 mL), and washed with aq NH₄Cl (50 mL). The aqueous layer was separated and extracted with CH₂Cl₂ (50 mL), and the combined organic layers then washed with sat. NaHCO₃ (2×100 mL). The organic layer was dried over MgSO₄, filtered, and concentrated in vacuo. The solid product was triturated from methanol and then recrystallized from ethanol to afford the final product (3.22 g, 55%) as an off-white solid. ¹H-NMR (CD₂Cl₂) δ 1.98 (s, 3H), 2.30-2.50 (broad m, 8H), 2.68 (t, 2H), 2.98 (t, 2H), 3.25 (t, 2H), 4.08 (t, 2H), 5.07 (s, 2H), 6.93-7.00 (m, 3H), 7.14-7.20 (m, 2H), 7.25-7.39 (m, 2H), 7.75 (s, 1H), 8.31 (s, 1H); LCMS RT=3.15 min; [M+H]⁺= 604.3.

Using the method described above and the appropriate starting materials, Examples 58-6.1, 63-73, 77-79, 121-122, and 176 were similarly prepared.

Example 74

Preparation of N-{3-chloro-4-[(3-fluorobenzyl)oxy]phenyl}-4,5-dihydro-2H-pyrimido[5',4':4,5]thieno[2,3-e]indazol-6-amine

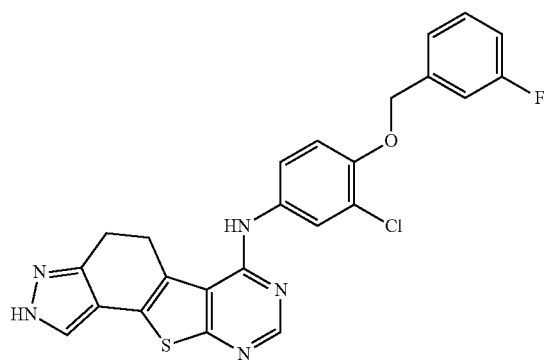

To a suspension of N-(3-Chloro-4-(3-fluoro-benzyloxy)-phenylamine)-8-dimethylaminomethylene-5,8-dihydro-6H-benzo[4,5]thieno[2,3-d]pyrimidin-7-one (110 mg, 0.19 mmol) in ethanol (1 mL) was added a solution of hydrazine hydrate (8 mg, 0.21 mmol) in ethanol (1 mL) at room temperature. The resulting reaction mixture was heated up to 50° C. for 1 h. The solvent was removed under reduced pressure and the resulting solid was washed with water and ether in sequence to afford the desired product as a brown-red solid (90 mg, 92%). ¹H-NMR (DMSO-d₆) δ 12.75 (br, 1H), 8.42 (s, 1H), 8.35 (s, 1H), 7.99 (s, 1H), 7.77 (s, 1H), 7.52 (dd, 1H), 7.49 (m, 1H), 7.33 (m, 2H), 7.22 (d, 1H), 7.18 (dd, 1H), 5.25 (s, 2H), 3.40 (t, 2H), 2.96 (t, 2H); LCMS RT=3.39 min; [M+H]⁺=478.2.

Using the method described above and the appropriate starting materials, Examples 109, 120, 127, 288, and 309 were similarly prepared.

Example 75

Preparation of (S)-3-{6-[3-Chloro-4-(3-fluoro-benzyloxy)-phenylamino]-4,5-dihydro-10-thia-2,3,7,9-tetraaza-cyclopenta[a]fluoren-2-yl}-propane-1,2-diol

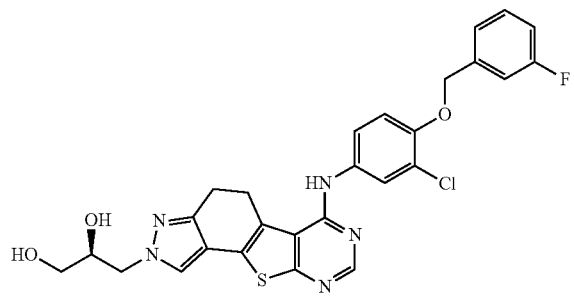

(2S)-3-(N'-tert-butyloxycarbonyl)hydrazino-1,2-propanediol (81 mg, 0.39 mmol) was reacted with 4-[3-chloro-4-(3-fluoro-benzyloxy)-phenylamino-]-8-dimethylaminomethylene-5,8-dihydro-6H-benzo[4,5]thieno[2,3-d]pyrimidin-7-one (100 mg, 0.20 mmol) to give off-white solid as desired product (33.9 mg, 30%). The detailed procedure was described in example 76. ¹H-NMR (DMSO-d₆) δ 8.41 (s, 1H), 8.33 (s, 1H), 7.87 (s, 1H), 7.25 (d, J=2.6 Hz, 1H) 7.50 (dd, J=2.6, 9.0 Hz, 1H), 7.45 (m, 1H), 7.30 (m, 2H), 7.21 (d, J=9.0 Hz, 1H), 7.16 (m, 1H), 5.24 (s, 2H), 5.0 (d, J=4.8 Hz, 1H), 4.76 (t, 1H), 4.18 (dd, J=3.7, 13.4 Hz, 1H), 3.94 (m, 1H), 3.81 (m, 1H), 3.38 (t, 2H), 2.92 (t, 2H); LCMS RT=3.12 min; [M+H]⁺=552.1/554.2.

Example 76

Preparation of (R)-3-{6-[3-Chloro-4-(3-fluoro-benzyloxy)-phenylamino]-4,5-dihydro-10-thia-2,3,7,9-tetraaza-cyclopenta[a]fluoren-2-yl}-propane-1,2-diol

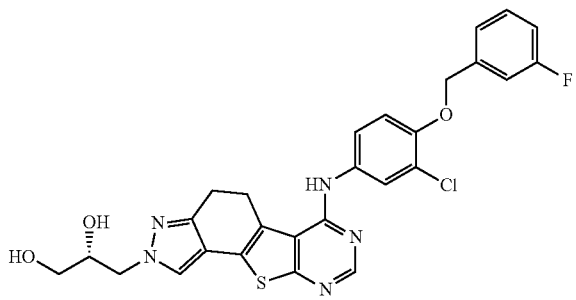

To a solution of 4-[3-chloro-4-(3-fluoro-benzyloxy)-phenylamino-]-8-dimethylaminomethylene-5,8-dihydro-6H-benzo[4,5]thieno[2,3-d]pyrimidin-7-one (83.9 mg, 0.16 mmol) in ethanol (2 mL) was added (2R)-3-(N'-tert-butyloxycarbonyl)hydrazino-1,2-propanediol (68 mg, 0.33 mmol) under nitrogen at room temperature. The resulting mixture was heated up to 87° C. for 66 h. The reaction mixture was cooled down to room temperature and the solvent was concentrated under reduced pressure. DCM (4 mL) and TFA (1.5 mL) was added to the residue and it was stirred at room temperature for 6 h. The mixture was poured into EtOAc (10 mL) and saturated aq solution of NaHCO$_3$ (10 mL) and extracted with EtOAc (3×10 mL). The combined organic layers were dried (Na$_2$SO$_4$), filtered, and evaporated in vacuo. The crude product was purified by preparative TLC [(MeOH:DCM (1:9)] to give 23.8 mg (25.4%) of desired product as an off-white solid. $^1$H-NMR (DMSO-d$_6$) δ 8.41 (s, 1H), 8.33 (s, 1H), 7.87 (s, 1H), 7.25 (d, J=2.6 Hz, 1H) 7.50 (dd, J=2.6, 9.0 Hz, 1H), 7.45 (m, 1H), 7.30 (m, 2H), 7.21 (d, J=9.0 Hz, 1H), 7.16 (m, 1H), 5.24 (s, 2H), 5.0 (d, J=4.8 Hz, 1H), 4.76 (t, 1H), 4.18 (dd, J=3.7, 13.4 Hz, 1H), 3.94 (m, 1H), 3.81 (m, 1H), 3.38 (t, 2H), 2.92 (t, 2H); LCMS RT=3.12 min; [M+H]$^+$=552.1/554.2.

The same reaction can also be carried out under microwave condition. To a solution of 4-[3-chloro-4-(3-fluoro-benzyloxy)-phenylamino-]-8-dimethylaminomethylene-5,8-dihydro-6H-benzo[4,5]thieno[2,3-d]pyrimidin-7-61.7 mg, 0.12 mmol) in ethanol (2 mL) was added (2R)-3-(N'-tert-butyloxycarbonyl)hydrazino-1,2-propanediol (50 mg, 0.24 mmol) under nitrogen at room temperature. The resulting mixture was heated in microwave synthesizer at 180° C. for 15 min. The reaction mixture was rapidly cooled down to 40° C. by the unit. The solvent was removed under reduced pressure and the crude product was purified by pre-HPLC to obtain an off-white solid as desired product (64 mg, 97%).

Using the methods described above in examples 75 and 76 and the appropriate starting materials, examples 350-359 were similarly prepared.

Example 80

Preparation of 2-[6-({3-chloro-4-[(3-fluorobenzyl)oxy]phenyl}amino)-4,5-dihydro-3H-pyrimido[5',4':4,5]thieno[2,3-e]indazol-3-yl]ethanol

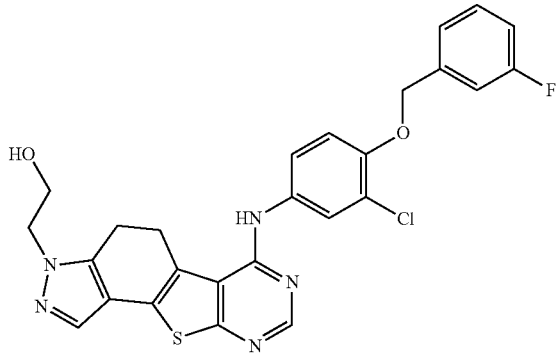

To 200 mL ethanol were added N-(3-Chloro-4-(3-fluoro-benzyloxy)-phenylamine)-8-dimethylaminomethylene-5,8-dihydro-6H-benzo[4,5]thieno[2,3-d]pyrimidin-7-one (12.0 g, 23.6 mmol), and then 2-tert-butyloxycarbonyl-2-hydroxy-ethylhydrazine (6.23 g, 35.4 mmol) as a 50 mL ethanol solution via dropping funnel over a 5 minute period. The contents were stirred at reflux for 24 h, after which time they were removed from heating and allowed to cool to rt. The heterogeneous mixture was cooled to 0° C. and filtered to a light tan solid which was dried under hi-vac and collected as 9.8 g (65%). This solid was then dissolved in CH$_2$Cl$_2$ (100 mL) and cooled to 0° C. To the stirring suspension was added TFA (60 mL, 99%) via dropping funnel over a 15 minute period, during which time the contents become dark brown and homogeneous. The mixture was stirred with warming to rt over a 12 h period. The contents were concentrated to ca. 10% volume, diluted with CH$_2$Cl$_2$/H$_2$O (100 mL, 2:1), and stirred with cooling to 0° C. To the stirring mixture was added 175 mL aq 1N NaOH, to afford a pH=10 mixture which becomes heterogeneous on complete addition of base. The heterogeneous mixture was filtered and the filter cake washed with water. The collected solid was recrystallized from ethanol to furnish the final product (4.0 g, 67%, 44% for the two steps) as a light tan solid. $^1$H-NMR (DMSO-d$_6$) δ 3.02 (t, 2H), 3.33 (t, 2H), 3.66 (m, 2H), 4.12 (m, 2H), 4.87 (m, 1H), 5.24 (s, 2H), 7.10-7.30 (m, 4H), 7.40-7.53 (m, 2H), 7.61 (s, 1H), 7.73 (s, 1H), 8.31 (s, 1H), 8.38 (s, 1H); LCMS RT=3.30 min; [M+H]$^+$=522.1.

Example 81

Preparation of 3-(2-bromoethyl)-N-{3-chloro-4-[(3-fluorobenzyl)oxy]phenyl}-4,5-dihydro-3H-pyrimido[5',4':4,5]thieno[2,3-e]indazol-6-amine

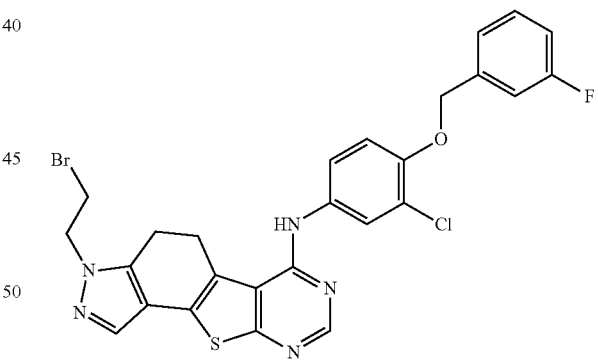

To 10 mL CH$_2$Cl$_2$ cooled to 0° C. was added 2-[6-({3-chloro-4-[(3-fluorobenzyl)oxy]phenyl}amino)-4,5-dihydro-3H-pyrimido[5',4':4,5]thieno[2,3-e]indazol-3-yl]ethanol (295 mg, 0.57 mmol) followed by thionyl bromide (0.11 mL, 1.41 mmol), and the contents allowed to stir with warming to rt. After 4 h stirring at rt, the contents were diluted with H$_2$O (10 mL). The layers were separated and the aqueous layer extracted with CH$_2$Cl$_2$ (3×10 mL). The combined organic layers were dried over MgSO$_4$, filtered, and concentrated in vacuo. The crude product was triturated from methanol to afford the final product (205 mg, 62%) as an off-white solid. $^1$H-NMR (DMSO-d$_6$) δ 3.09 (t, 2H), 3.39 (t, 2H), 3.85 (m, 2H), 4.52 (m, 2H), 5.24 (s, 2H), 7.14-7.34 (m, 4H), 7.40-7.53

(m, 2H), 7.75 (s, 1H), 7.79 (d, 1H), 8.35 (s, 1H), 8.40 (s, 1H); LCMS RT=3.82 min; [M+H]⁺=584.0, 586.0.

Example 86

Preparation of N-{3-chloro-4-[(3-fluorobenzyl)oxy]phenyl}-3-(2-morpholin-4-ylethyl)-4,5-dihydro-3H-pyrimido[5',4':4,5]thieno[2,3-e]indazol-6-amine

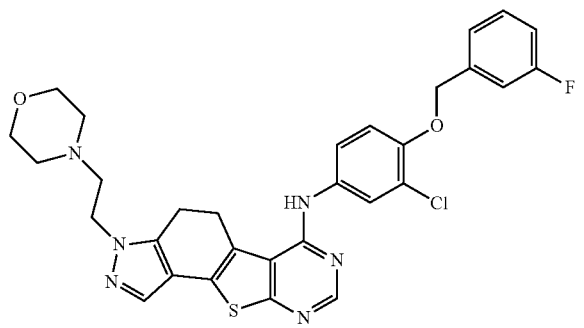

To 2 mL CH₃CN were sequentially added 2-[6-({3-chloro-4-[(3-fluorobenzyl)oxy]phenyl}amino)-4,5-dihydro-3H-pyrimido[5',4':4,5]thieno[2,3-e]indazol-3-yl]ethyl methanesulfonate (80 mg, 0.13 mmol), morpholine (18 mg, 0.20 mmol), and diisopropylethylamine (35 mg, 0.27 mmol). The reaction mixture was then heated up to 70° C. for 14 h. Upon cooling down, the crude was purified by HPLC to afford the desired product as an off-white solid (45 mg, 54%). ¹H-NMR (DMSO-d₆) δ 8.38 (s, 1H), 7.80 (d, 1H), 7.53 (s, 1H), 7.44 (dd, 1H), 7.38 (m, 1H), 7.24 (m, 2H), 7.04 (td, 1H), 6.98 (d, 1H), 6.95 (s, 1H), 5.13 (s, 2H), 4.18 (t, 2H), 3.63 (t, 4H), 3.35 (t, 2H), 3.14 (t, 2H), 2.78 (t, 2H), 2.45 (t, 4H); LCMS RT=2.72 min; [M+H]⁺=591.2.

Using the method described above and the appropriate starting materials (amines) and either corresponding mesylate or bromide precursor, examples 82-85, 87, and 259-267 were similarly prepared.

Example 88

Preparation of 2-{6-[(3-chloro-4-fluorophenyl)amino]-4,5-dihydro-3H-pyrimido[5',4':4,5]thieno[2,3-e]indazol-3-yl}ethanol

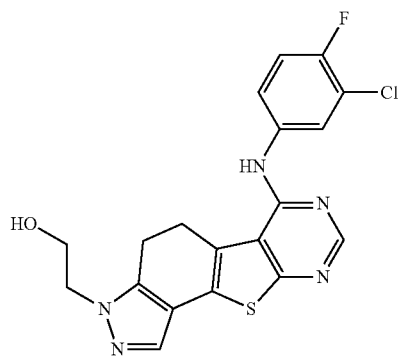

Method A.

The final filtrate (2:3 ratio of example 1 vs. example 88 by ¹H-NMR) mentioned in the preparation of 2-{6-[(3-chloro-4-fluorophenyl)amino]-4,5-dihydro-2H-pyrimido[5',4':4,5]thieno[2,3-e]indazol-2-yl}ethanol (example 1) was concentrated in vacuo to about half of its original volume. The resulting solid was collected by vacuum filtration (3.4 g, 2:3 ratio of example 1 vs. example 88 by ¹H NMR). The solid was heated to reflux in methoxybenzene (75 mL). The resulting cloudy mixture was allowed to cool to room temperature overnight. The solid that precipitated was filtered. The filtrate was enriched in the title compound (1:3). The filtrate was concentrated slightly in vacuo, resulting in the precipitation of solid. The solid was filtered to yield the title compound (350 mg, 98% regioisomeric purity by LC). ¹H NMR (DMSO-d₆) δ 8.56 (s, 1H), 8.38 (s, 1H), 7.88 (m, 1H), 7.66 (s, 1H), 7.61 (m, 1H), 7.40 (t, 1H), 4.93 (t, 1H), 4.16 (t, 2H), 3.73 (dt, 2H), 3.42 (t, 2H), 3.10 (t, 2H); LCMS RT=2.76 min; [M+H]⁺=416.4.

Method B.

Step 1. Preparation of tert-butyl 1-(2-hydroxyethyl)hydrazinecarboxylate

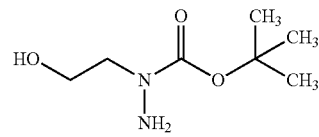

The title compound was prepared according to the literature (Krapcho, A. P. *J. Heterocyclic Chem.* 2000, 37, 47. ¹H-NMR (CDCl₃) δ 3.81 (t, 2H), 3.73 (br, 3H), 3.57 (t, 2H), 1.48 (s, 9H); LCMS RT=1.74 min @ 100% aqueous; [M+H]⁺= 176.9.

Step 2. Preparation of 2-{6-[(3-chloro-4-fluorophenyl)amino]-4,5-dihydro-3H-pyrimido[5',4':4,5]thieno[2,3-e]indazol-3-yl}ethanol

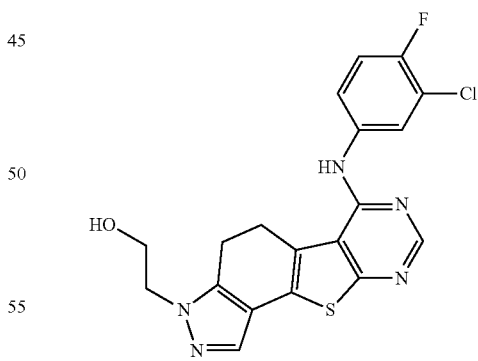

4-(3-Chloro-4-fluoro-phenylamino)-8-dimethylaminomethylene-5,8-dihydro-6H-benzo[4,5]thieno[2,3-d]pyrimidin-7-one (10.6 g, 0.026 mol) was heated to near homogeneity in dioxane (250 mL). The heat was turned off and nitrogen was bubbled through the murky solution for ~20 min while it cooled. The reaction flask was then evacuated and filled with nitrogen three times. In a separate flask, tert-butyl 1-(2-hydroxyethyl)hydrazinecarboxylate (13.9 g, 0.079 mol) was dissolved in toluene, concentrated in vacuo to a residue, redissolved in dioxane, and sparged with nitrogen for ~10 minutes. The solution of tert-butyl 1-(2-hydroxyethyl)hydrazinecarboxylate was evacuated and filled with nitrogen three times and then was cannulated into the flask containing the enamine. The resulting mixture became a clear red solution upon heating in an oil bath at ~80° C. After 6 h the reaction mixture was concentrated in vacuo to half its original volume. Xylenes (250 mL) was added and the mixture was again concentrated to half the original volume. Xylenes (250 mL) was added and the mixture was concentrated to half the original volume a final time. During the solvent swap, a yellow-orange solid precipitated. The resulting slurry was submerged in an ice-bath and TFA (200 mL) was added dropwise via an addition funnel. The slurry became a brown-red solution that was allowed to stir overnight at room temperature. Two liquid phases were present the next morning. Solvent (~200 mL) was removed in vacuo at ~40° C. The remaining mixture (~300 mL) was diluted with EtOAc (500 mL) and washed twice with 500 mL portions of 1.0 N NaOH. Significant emulsions formed during the final base wash, so more EtOAc (500 mL) was added with brine (100 mL) before collecting the aqueous layer. The organic layer was then washed with brine (2×300 mL). The organic layer was filtered through a small pad of silica gel (~1" diameter×2") and the pad was washed with EtOAc (750 mL). The filtrate was concentrated to a total volume of ~200 mL, resulting in the precipitation of solid. The slurry was filtered by vacuum filtration on a Buchner funnel and the resulting solid was allowed to dry overnight on the filter. An orange solid was obtained (7.25 g, 66%, >98% regioisomeric purity by $^1$H-NMR). $^1$H NMR (DMSO-$d_6$) δ 8.56 (s, 1H), 8.38 (s, 1H), 7.88 (m, 1H), 7.66 (s, 1H), 7.61 (m, 1H), 7.40 (t, 1H), 4.93 (t, 1H), 4.16 (t, 2H), 3.73 (dt, 2H), 3.42 (t, 2H), 3.10 (t, 2H); LCMS RT=2.76 min; [M+H]$^+$= 416.4.

Example 89

Preparation of 2-{6-[(3-chloro-4-fluorophenyl)amino]-4,5-dihydro-3H-pyrimido[5',4':4,5]thieno[2,3-e]indazol-3-yl}ethyl methanesulfonate

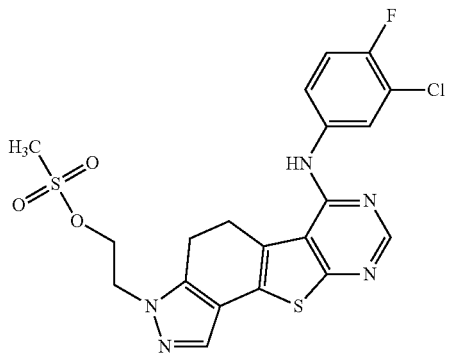

To a suspension of 2-{6-[(3-chloro-4-fluorophenyl)amino]-4,5-dihydro-3H-pyrimido[5',4':4,5]thieno[2,3-e]indazol-3-yl}ethanol (300 mg, 0.72 mmol in acetonitrile (10 mL) was added pyridine (171 mg, 2.16 mmol) and methanesulfonic anhydride (226 mg, 1.3 mmol). The resulting mixture was stirred at rt for 2 h. The reaction mixture was filtered and the yellow solid was washed with EtOAc to get the first crop of product. The filtrate was then concentrated and filtered to get the second crop of product. The combined product 2-{6-[(3-chloro-4-fluorophenyl)amino]-4,5-dihydro-3H-pyrimido[5',4':4,5]thieno[2,3-e]indazol-3-yl}ethyl methanesulfonate was 350 mg (quantitative yield). $^1$H-NMR (CDCl$_3$) δ 8.42 (s, 1H), 7.82 (m, 1H), 7.59 (s, 1H), 7.49 (m, 1H), 7.16 (t, 1H), 4.64 (t, 2H), 4.46 (t, 2H), 3.47 (t, 2H), 3.19 (t, 2H), 2.94 (s, 3H); LCMS RT=3.18 min, [M+H]$^+$=494.1.

Example 94

Preparation of N-(3-chloro-4-fluorophenyl)-3-(2-piperazin-1-ylethyl)-4,5-dihydro-3H-pyrimido[5',4':4,5]thieno[2,3-e]indazol-6-amine

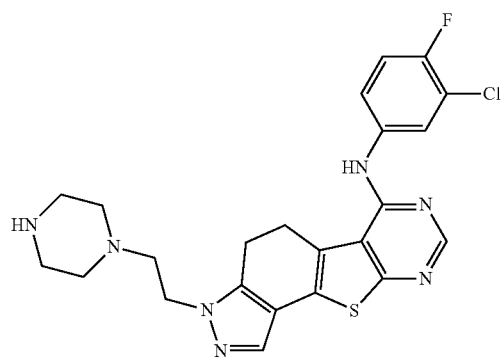

2-{6-[(3-chloro-4-fluorophenyl)amino]-4,5-dihydro-3H-pyrimido[5',4':4,5]thieno[2,3-e]indazol-3-yl}ethyl methanesulfonate (80 mg, 0.1 mmol), piperazine (25.1 mg, 0.29 mmol) and diisopropylethylamine (25 mg, 0.19 mmol) were mixed in 2 mL DMF. The reaction mixture was stirred at 80° C. for 16 h. The reaction mixture was diluted with water and extracted with EtOAc. The combined organic layer was concentrated under reduced pressure and purified by prep HPLC. The combined fractions were treated with saturated Na$_2$CO$_3$ and dried to afford free base product N-(3-chloro-4-fluorophenyl)-3-(2-piperazin-1-ylethyl)-4,5-dihydro-3H-pyrimido[5',4':4,5]thieno[2,3-e]indazol-6-amine (18.8 mg, 40%). $^1$H-NMR (DMSO-$d_6$) δ 8.65 (broad s, 1H), 8.30 (s, 1H), 7.86 (dd, 1H), 7.60 (s, 1H), 7.56 (m, 1H), 7.35 (t, 1H), 4.19 (t, 2H), 4.34 (t, 2H), 3.20 (broad, 1H), 3.08 (t, 2H), 2.62 (m, 6H), 2.31 (m, 4H). LCMS RT=2.35 min, [M+H]$^+$=484.1

Using the method described above and the appropriate starting material, examples 90-93, and 95-97 were similarly prepared.

Example 98

Preparation of 2-(2-{[tert-butyl(dimethyl)silyl]oxy}ethyl)-N-[3-chloro-4-(pyridin-2-ylmethoxy)phenyl]-4,5-dihydro-2H-pyrimido[5',4':4,5]thieno[2,3-e]indazol-6-amine

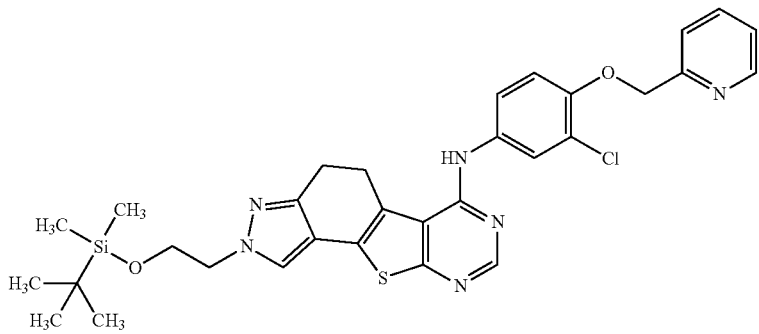

Step 1. Preparation of 3-Chloro-4-(pyridin-2-ylmethoxy)-phenylamine

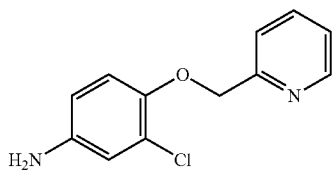

2-chloro-4-nitro phenol 10 g (57.6 mmol, 1 eq), 2-pycolyl chloride hydrogen chloride 9.45 g (57.6 mmol, 1 equiv) cesium carbonate 41.3 (126.8 mmol, 2.2 equiv) and sodium iodide 8.64 g (57.6 mmol, 1 equiv) were suspended in 200 mL acetonitrile. The reaction mixture was stirred at 60° C. for 5 h. The resulted suspension was filtered and washed with 400 mL water, yielding 2-(2-chloro-4-nitro-phenoxymethyl)-pyridine (8 g, 52%) as a red solid.

2-(2-chloro-4-nitro-phenoxymethyl)-pyridine (8 g, 30.2 mmol, 1 equiv) and 8.44 g iron (151.1 mmol, 5 equiv) were mixed in 100 mL acetic acid and 50 mL EtOAc and were stirred at rt overnight. The reaction mixture was filtered through a pad of Celite®. The filtrate was concentrated in vacuo and neutralized with saturated $Na_2CO_3$ solution. The solution was extracted with EtOAc and the organic layer was washed with brine and concentrated in vacuo. The resulting crude material was purified by flash chromatography eluting with EtOAc/hexane (3:7) to give 3-Chloro-4-(pyridin-2-ylmethoxy)-phenylamine (3.2 g, 52%) as a white solid. $^1$H-NMR (CDCl$_3$) δ 5.18 (s, 2H), 6.50 (dd, 1H), 6.76 (d, 1H), 6.80 (d, 1H), 7.22 (m, 1H), 7.64 (d, 1H), 7.73 (td, 1H), 8.55 (m, 1H); LCMS RT=0.89 min; [M+H]$^+$=235.1.

Step 2. Preparation of N-[3-chloro-4-(pyridin-2-ylmethoxy)phenyl]-5,8-dihydro-6H-spiro[1-benzothieno[2,3-d]pyrimidine-7,2'-[1,3]dioxolan]-4-amine hydrochloride

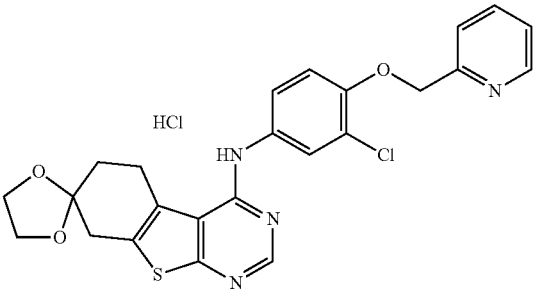

To ethanol (60 mL) were sequentially added 4-chloro-5,8-dihydro-6H-spiro[1-benzothieno[2,3-d]pyrimidine-7,2'-[1,3]dioxolane] (5.70 g, 20.2 mmol), 3-Chloro-4-(pyridin-2-ylmethoxyl)-phenylamine (4.78 g, 20.37 mmol), and HCl in ethanol (1N, 4 mL). The suspension was stirred with heating to 80° C., upon which time the contents turn brown and homogeneous. After 12 h, the dark orange-yellow heterogeneous mixture was removed from heating, and allowed to cool to rt. The contents were concentrated down to about 30 mL in volume and the precipitate was collected by filtration as a light-brown solid (10.1 g, 92%). $^1$H-NMR (DMSO-d$_6$) δ 8.71 (d, 1H), 8.40 (s, 1H), 8.33 (s, 1H), 8.10 (td, 1H), 7.80 (d, 1H), 7.75 (d, 1H), 7.56 (m, 2H), 7.25 (d, 1H), 5.48 (br, 1H), 5.38 (s, 2H), 3.99 (s, 4H), 3.28 (t, 2H), 3.03 (s, 2H), 1.97 (t, 2H); LCMS RT=2.73 min; [M+H]$^+$=481.1.

Step 3. Preparation of 4-{[3-chloro-4-(pyridin-2-ylmethoxy)phenyl]amino}-5,8-dihydro[1]benzothieno[2,3-d]pyrimidin-7(6H)-one hydrochloride

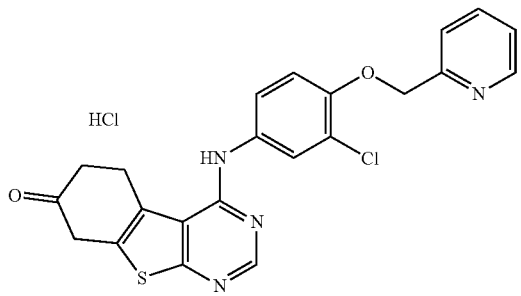

To a stirring acetic acid/H₂O solution (4:1, 250 mL) was added N-[3-chloro-4-(pyridin-2-ylmethoxy)phenyl]-5,8-dihydro-6H-spiro[1-benzothieno[2,3-d]pyrimidine-7,2'-[1,3]dioxolan]-4-amine hydrochloride (10.0 g, 19.3 mmol), and the contents heated at 80° C. for 40 h. The dark colored mixture was cooled to rt, and the solvent removed under reduced pressure. The crude residue was suspended in water (200 mL), stirred for 10 min., and filtered. The collected solid was further washed with H₂O (300 mL) and ether (100 mL) to afford the desired product as a brown solid (8.1 g, 89%). ¹H-NMR (DMSO-d₆) δ 8.71 (d, 1H), 8.54 (s, 1H), 8.42 (s, 1H), 8.10 (td, 1H), 7.78 (d, 1H), 7.75 (d, 1H), 7.56 (m, 2H), 7.25 (d, 1H), 5.38 (s, 2H), 5.08 (br, 1H), 3.76 (s, 2H), 3.50 (t, 2H), 2.69 (t, 2H); LCMS RT=2.44 min; [M+H]⁺=437.3.

Step 4. Preparation of 4-(3-Chloro-4-(pyridin-2-yl-methoxy)-phenylamine)-8-dimethylaminomethyl-ene-5,8-dihydro-6H-benzo[4,5]thieno[2,3-d]pyrimidin-7-one

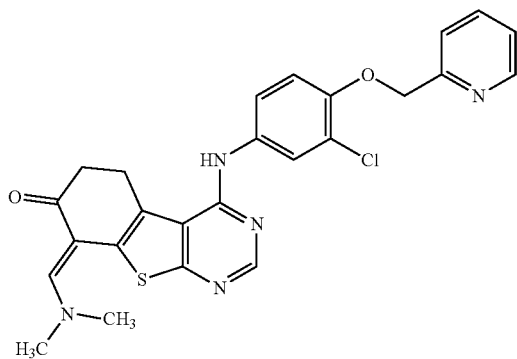

To 130 mL toluene were added N-(3-Chloro-4-(pyridin-2-yl-methoxy)-phenylamine)-5,8-dihydro-6H-benzo[4,5]thieno[2,3-d]pyrimidin-7-one (8.1 g, 17.1 mmol) and dimethylformamide-dimethylacetal (4.55 mL, 34.2 mmol). The contents were stirred at 70° C. for 6 h, after which time the crude mixture was concentrated down to about 60 mL. The heterogeneous mixture was filtered, the collected solid washed with ether (30 mL) and acetone (5 mL), and dried under hi-vac. The desired product was collected (4.9 g, 58%) as a yellow solid. ¹H-NMR (DMSO-d₆) (major rotomer) δ 8.60 (d, 1H), 8.27 (s, 1H), 8.19 (s, 1H), 7.88 (td, 1H), 7.78 (s, 1H), 7.56 (d, 1H), 7.52 (dd, 1H), 7.37 (td, 1H), 7.23 (d, 1H), 7.08 (s, 1H), 5.28 (s, 2H), 3.28 (t, 2H), 3.14 (s, 6H), 2.59 (t, 2H); LCMS RT=2.52 min; [M+H]⁺=492.0.

Step 5. Regiocontrolled Preparation of 2-(2-{[tert-butyl(dimethyl)silyl]oxy}ethyl)-N-[3-chloro-4-(pyridin-2-ylmethoxy)phenyl]-4,5-dihydro-2H-pyrimido[5',4':4,5]thieno[2,3-e]indazol-6-amine

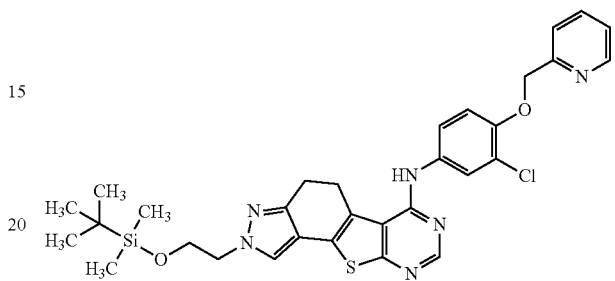

To 80 mL ethanol were added N-(3-Chloro-4-(pyridin-2-ylmethoxy)-phenylamine)-8-dimethylaminomethylene-5,8-dihydro-6H-benzo[4,5]thieno[2,3-d]pyrimidin-7-one (2.3 g, 4.7 mmol), and then 2-tert-butyldimethylsilyloxy-1-tert-butyloxycarbonyl-ethylhydrazine (2.1 g, 6.5 mmol) as a 8 mL ethanol solution dropwise. The contents were stirred at reflux for 58 h, after which time they were then allowed to cool to rt. The heterogeneous mixture was filtered to afford a light yellow solid. The filtrate was concentrated and the residue suspended in ethanol (20 mL), from which a second crop of product precipitated. The solid product crops were combined to furnish the final product (2.1 g, 72%) as a light yellow solid. ¹H-NMR (DMSO-d₆) δ 8.60 (d, 1H), 8.43 (s, 1H), 8.35 (s, 1H), 7.91 (s, 1H), 7.88 (dd, 1H), 7.78 (d, 1H), 7.59 (d, 1H), 7.54 (dd, 1H), 7.37 (t, 1H), 7.24 (d, 1H), 5.29 (s, 2H), 4.14 (t, 2H), 3.90 (t, 2H), 3.38 (t, 2H), 2.92 (t, 2H), 0.80 (s, 9H), −0.07 (s, 6H); LCMS RT=4.09 min; [M+H]⁺=619.2.

Example 99

Preparation of 2-(6-{[3-chloro-4-(pyridin-2-ylmethoxy)phenyl]amino}-4,5-dihydro-2H-pyrimido[5',4':4,5]thieno[2,3-e]indazol-2-yl)ethanol

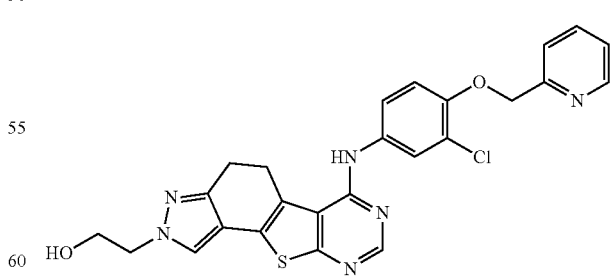

To 80 mL THF cooled to 0° C. was added 2-(2-{[tert-butyl(dimethyl)silyl]oxy}ethyl)-N-[3-chloro-4-(pyridin-2-ylmethoxy)phenyl]-4,5-dihydro-2H-pyrimido[5',4':4,5]thieno[2,3-e]indazol-6-amine (2.40 g, 3.9 mmol). To the homogeneous mixture was then added TBAF in THF (1M, 4.3 mL). The dark contents were then stirred with warming to rt over a 1 h period, after which time the solvent was removed under reduced pressure. The crude residue was diluted with water (100 mL) and vigorously stirred. The precipitate formed was collected by filtration and further triturated with ethanol to afford the desired product (1.90 g, 92%) as a light-brown solid. $^1$H-NMR (DMSO-$d_6$) δ 8.60 (d, 1H), 8.43 (s, 1H), 8.36 (s, 1H), 7.94 (s, 1H), 7.88 (td, 1H), 7.78 (d, 1H), 7.60 (d, 1H), 7.54 (dd, 1H), 7.38 (t, 1H), 7.24 (d, 1H), 5.29 (s, 2H), 4.94 (t, 1H), 4.12 (t, 2H), 3.74 (q, 2H), 3.39 (t, 2H), 2.93 (t, 2H); LCMS RT=2.32 min; [M+H]$^+$=505.3.

Example 100

Preparation of 2-(6-{[3-chloro-4-(pyridin-2-yl-methoxy)phenyl]amino}-4,5-dihydro-2H-pyrimido[5',4':4,5]thieno[2,3-e]indazol-3-yl)ethanol

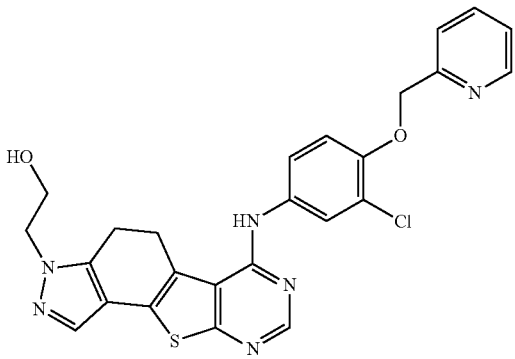

To 60 mL ethanol were added N-(3-Chloro-4-(pyridin-2-ylmethoxy)-phenylamine)-8-dimethylaminomethylene-5,8-dihydro-6H-benzo[4,5]thieno[2,3-d]pyrimidin-7-one (2.18 g, 4.4 mmol), and then 2-tert-butyloxycarbonyl-2-hydroxyethylhydrazine (1.22 g, 6.2 mmol) as a 6 mL ethanol solution. The contents were stirred at reflux for 24 h. Upon cooling down to rt, there was precipitate coming out. The heterogeneous mixture was cooled to 0° C. and filtered to collect a light tan solid. The filtrate was concentrated to dryness and triturated with methanol carefully to collect another solid crop. The two solid product crops were combined (1.93 g) and used directly in next step.

This solid collected above was added to CH$_2$Cl$_2$ (30 mL) and cooled to 0° C. To the stirring suspension was added TFA (15 mL, 99%) dropwise, during which time the contents become dark brown and homogeneous. The mixture was stirred with warming to rt over a 12 h period. The contents were concentrated to ca. 10% volume, diluted with CH$_2$Cl$_2$/H$_2$O (20 mL, 2:1), and stirred with cooling to 0° C. To the stirring mixture was added 30 mL aq 1N NaOH, to afford a pH=10 mixture which becomes heterogeneous on complete addition of the base. The heterogeneous mixture was filtered and the filter cake washed with water. The collected solid was triturated with ethanol to furnish the final product (0.95 g, 42% for the two steps) as a light tan solid. $^1$H-NMR (DMSO-$d_6$) δ 8.60 (d, 1H), 8.40 (s, 1H), 8.35 (s, 1H), 7.88 (td, 1H), 7.79 (d, 1H), 7.66 (s, 1H), 7.57 (d, 1H), 7.54 (dd, 1H), 7.37 (t, 1H), 7.25 (d, 1H), 5.29 (s, 2H), 4.93 (t, 1H), 4.16 (t, 2H), 3.74 (q, 2H), 3.42 (t, 2H), 3.09 (t, 2H); LCMS RT=2.41 min; [M+H]$^+$=505.1.

Example 101

Preparation of 2-(2-bromoethyl)-N-[3-chloro-4-(pyridin-2-ylmethoxy)phenyl]-4,5-dihydro-2H-pyrimido[5',4':4,5]thieno[2,3-e]indazol-6-amine

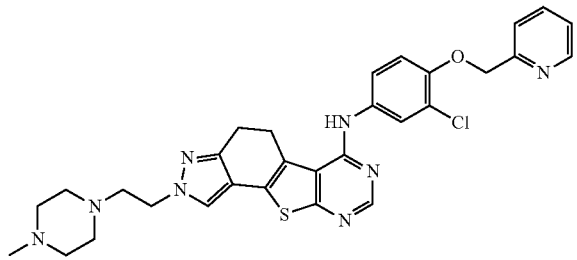

To 60 mL CH$_2$Cl$_2$ cooled to 0° C. was added 2-(6-{[3-chloro-4-(pyridin-2-ylmethoxy)phenyl]amino}-4,5-dihydro-2H-pyrimido[5',4':4,5]thieno[2,3-e]indazol-2-yl)ethanol (1.60 g, 3.2 mmol), followed by thionyl bromide (2.31 g, 11.1 mmol). The contents were then stirred with warming to it over a 24 h period, after which time water (5 mL) was added to quench the reaction mixture. The solvent was removed under reduced pressure. The crude residue was diluted with aq. 2M Na$_2$CO$_3$ and vigorously stirred for 1 h. The precipitate was collected by filtration and triturated with methanol (30 mL) to afford the desired product (1.70 g, 94%) as a light-brown solid. $^1$H-NMR (DMSO-$d_6$) δ 8.59 (d, 1H), 8.41 (s, 1H), 8.36 (s, 1H), 8.01 (s, 1H), 7.82 (dd, 1H), 7.78 (s, 1H), 7.47-7.60 (m, 2H), 7.30 (dd, 1H), 7.19 (d, 1H), 5.27 (s, 2H), 4.42 (t, 2H), 3.82 (t, 2H), 3.38 (t, 2H), 2.90 (t, 2H); LCMS RT=2.89 min; [M+H]$^+$=567.4.

Example 102

Preparation of N-[3-chloro-4-(pyridin-2-ylmethoxy)phenyl]-2-[2-(4-methylpiperazin-1-yl)ethyl]-4,5-dihydro-2H-pyrimido[5',4':4,5]thieno[2,3-e]indazol-6-amine To a stirring solution of 2-(2-bromoethyl)-N-[3-chloro-4-(pyridin-2-ylmethoxy)phenyl]-4,5-dihydro-2H-pyrimido[5',4':4,5]thieno[2,3-e]indazol-6-amine (100 mg, 0.16 mmol) in DMF (4 mL) were sequentially added 1-methyl-piperazine (0.023 mL, 0.24 mmol), sodium iodide (23.8 mg, 0.16 mmol), and sodium carbonate (33.6 mg, 0.32 mmol). The mixture was stirred at 60° C. for 4 h, after which time the contents were allowed to cool to rt and the solvent removed under reduced pressure. The crude product was purified via reverse phase HPLC to afford the desired product (32 mg, 34%) as a white solid. $^1$H-NMR (DMSO-d$_6$) δ 8.58 (d, 1H), 8.40 (s, 1H), 8.36 (s, 1H), 7.93 (s, 1H), 7.83 (dd, 1H), 7.78 (s, 1H), 7.47-7.59 (m, 2H), 7.31 (dd, 1H), 7.19 (d, 1H), 5.25 (s, 2H), 4.12 (t, 2H), 3.35 (t, 2H), 2.85 (t, 2H), 2.63 (t, 2H), 2.35-2.45 (br s, 4H), 2.22-2.32 (br s, 4H), 2.12 (s, 3H); LCMS RT=2.18 min; [M+H]$^+$=587.4.

Using the method described above and the appropriate starting material, examples 103-108 were similarly prepared.

Example 110

Preparation of 3-(2-bromoethyl)-N-[3-chloro-4-(pyridin-2-ylmethoxy)phenyl]-4,5-dihydro-3H-pyrimido[5',4':4,5]thieno[2,3-e]indazol-6-amine

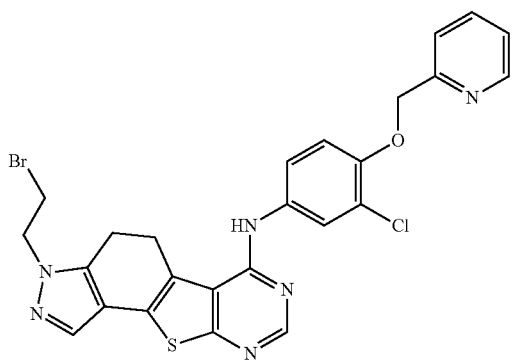

To 30 mL dichloromethane cooled to 0° C. was added 2-(6-{[3-chloro-4-(pyridin-2-ylmethoxy)phenyl]amino}-4,5-dihydro-3H-pyrimido[5',4':4,5]thieno[2,3-e]indazol-3-yl)ethanol (800 mg, 1.58 mmol), followed by thionyl bromide (1.15 g, 5.54 mmol). The contents were then stirred with warming to rt over a 24 h period, after which time water (5 mL) was added to quench the reaction mixture. The solvent was removed under reduced pressure. The crude residue was diluted with aq. 1M Na$_2$CO$_3$ and vigorously stirred for 1 h. The mixture was extracted with CH$_2$Cl$_2$, and the combined organic layers dried over MgSO$_4$, filtered, and concentrated in vacuo. The resulting solid was triturated with methanol (15 mL) to a light-brown solid (600 mg, 67%) containing 80% of the desired product, and 20% of the aromatized product. A sample of the crude product was purified via reverse phase HPLC to afford the desired product as a white solid. $^1$H-NMR (DMSO-d$_6$) δ 8.58 (d, 1H), 8.38 (br s, 1H), 8.36 (s, 1H), 7.81 (dd, 1H), 7.78 (s, 1H), 7.70 (s, 1H), 7.44-7.60 (m, 2H), 7.31 (td, 1H), 7.19 (d, 1H), 5.23 (s, 2H), 4.30 (t, 2H), 3.82 (t, 2H), 3.38 (t, 2H), 3.07 (t, 2H); LCMS RT=2.77 min; [M+H]$^+$=567.0.

Example 111

Preparation of N-[3-chloro-4-(pyridin-2-ylmethoxy)phenyl]-3-(2-morpholin-4-ylethyl)-4,5-dihydro-3H-pyrimido[5',4':4,5]thieno[2,3-e]indazol-6-amine

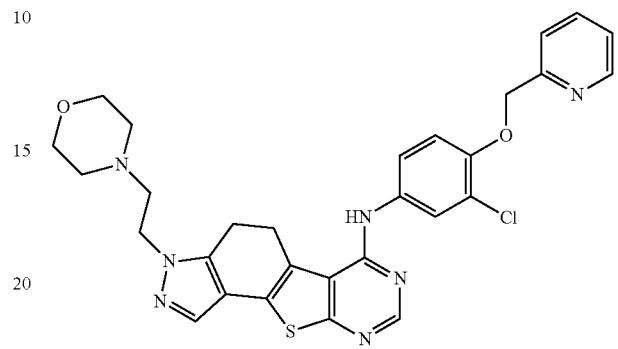

Using the method described for the preparation of example 102 along with the appropriate starting materials, example 111 was similarly prepared from example 110. $^1$H-NMR (CD$_2$Cl$_2$-d$_2$/CD$_3$OD-d$_4$, 4:1) δ 8.50 (s, 1H), 8.30 (s, 1H), 7.78 (d, 1H), 7.75 (s, 1H), 7.64 (d, 1H), 7.55 (s, 1H), 7.35-7.41 (m, 1H), 7.23-7.35 (m, 1H), 7.00 (d, 1H), 5.20 (s, 2H), 4.16 (t, 2H), 3.50-3.65 (br s, 4H), 3.36 (t, 2H), 3.07 (t, 2H), 2.75 (t, 2H), 2.30-2.50 (bs, 4H); LCMS RT=2.21 min; [M+H]$^+$=574.1.

Using the method described above and the appropriate starting material, examples 112-114 were similarly prepared.

Example 115

Preparation of 2-[6-({3-chloro-4-[6-methylpyridin-2-yl)methoxy]phenyl}amino)-4,5-dihydro-2H-pyrimido[5',4':4,5]thieno[2,3-e]indazol-2-yl]ethanol

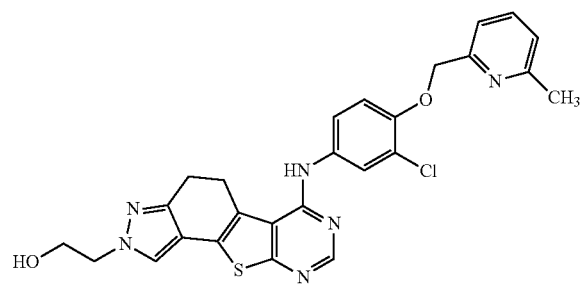

Step 1. Preparation of to 3-chloro-4-[(6-methylpyridin-2-yl)methoxy]aniline

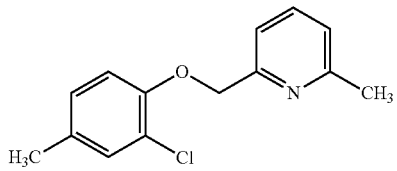

To 35 mL CH₃CN was added (6-Methyl-pyridin-2-yl)-methanol (3.5 g, 28.4 mmol), followed by potassium carbonate (17.9 g, 129.6 mmol), and 2-Chloro-1-fluoro-4-nitrobenzene (6.48 g, 36.9 mmol). The suspension was stirred and heated at 70° C. for 30 h, after which time the bright yellow mixture was allowed to cool to rt. The contents were cooled to rt, filtered, and washed with CH₂Cl₂. The filtrate was concentrated in vacuo to a a light yellow solid which was triturated with Hex/EtOAc (5:1), yielding 2-[(2-chloro-4-nitrophenoxy)methyl]-6-methylpyridine (4.87 g, 61%) as a white solid.

2-[(2-chloro-4-nitrophenoxy)methyl]-6-methylpyridine (4.87 g, 17.5 mmol) and iron powder (4.87 g, 87.4 mmol) were mixed in 150 mL acetic acid, and were stirred at rt overnight. The reaction mixture was filtered through a pad of Celite®, and washed with EtOAc. The filtrate was concentrated in vacuo and neutralized with saturated Na₂CO₃ solution. The contents were extracted with EtOAc (5×300 mL). The combined organic layers were washed with brine, dried over MgSO₄, filtered, and concentrated in vacuo. The resulting crude material was triturated with Hex/EtOAc (2:1) to afford 3-chloro-4-[(6-methylpyridin-2-yl)methoxy]aniline (3.84 g, 88%) as a white solid. $^1$H-NMR (DMSO) δ 7.70 (dd, 1H), 7.31 (d, 1H), 7.17 (d, 1H), 6.88 (d, 1H), 6.65 (d, 1H), 6.44 (dd, 1H), 5.01 (s, 2H), 4.93 (s, 2H), 2.46 (s, 3H); LCMS RT=0.25 min; [M+H]⁺=249.2.

Step 2. Preparation of N-{3-chloro-4-[(6-methylpyridin-2-yl)methoxy]phenyl}-5,8-dihydro-6H-spiro[1-benzothieno[2,3-d]pyrimidine-7,2'-[1,3]dioxolan]-4-amine

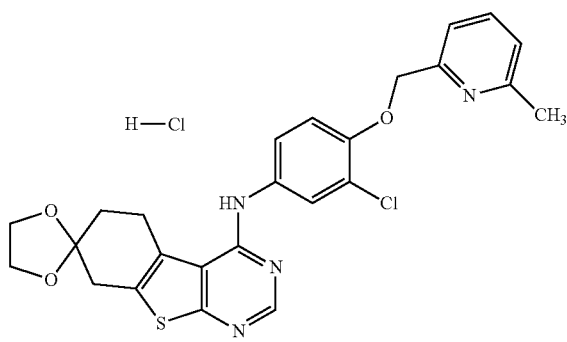

To isopropanol (80 mL) was sequentially added 4-chloro-5,8-dihydro-6H-spiro[1-benzothieno[2,3-d]pyrimidine-7,2'-[1,3]dioxolane] (5.5 g, 19.4 mmol), 3-chloro-4-[(6-methylpyridin-2-yl)methoxy]aniline (4.61 g, 18.5 mmol), and 4N HCl in dioxane (0.8 mL). The suspension was stirred with heating to 80° C., upon which time the contents turn brown and homogeneous. After 8 h, the heterogeneous mixture was removed from heating, and allowed to cool to rt. The resultant precipitate was collected by filtration as a light-brown solid (5.67 g, 81%), which was used without further purification. $^1$H-NMR (DMSO-d₆) δ 8.35 (s, 1H), 8.16 (s, 1H), 7.78 (d, 1H), 7.73 (d, 1H), 7.51 (dd, 1H), 7.34 (d, 1H), 7.21 (m, 1H), 7.19 (d, 1H), 5.21 (s, 2H), 3.97 (s, 4H), 3.26 (t, 2H), 3.01 (s, 2H), 2.48 (s, 3H), 1.95 (t, 2H); LCMS RT=2.78 min; [M+H]⁺=495.2.

Step 3. Preparation of 4-({3-chloro-4-[(6-methylpyridin-2-yl)methoxy]phenyl}amino)-5,8-dihydro[1]benzothieno[2,3-d]pyrimidin-7(6H)-one

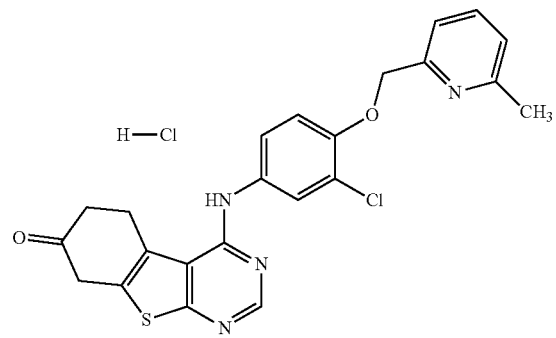

The title compound was prepared following the method described for example 98 step 3, utilizing N-{3-chloro-4-[(6-methylpyridin-2-yl)methoxy]phenyl}-5,8-dihydro-6H-spiro[1-benzothieno[2,3-d]pyrimidine-7,2'-[1,3]dioxolan]-4-amine (3.9 g, 7.9 mmol). The desired product was collected as a light brown solid (2.7 g, 76%). $^1$H-NMR (DMSO-4) δ 8.44 (s, 1H), 8.41 (s, 1H), 8.10 (t, 1H), 7.78 (d, 1H), 7.62 (d, 1H), 7.56 (d, 1H), 7.52 (dd, 1H), 7.25 (d, 1H), 5.37 (s, 2H), 3.76 (s, 2H), 3.49 (t, 2H), 2.70 (t, 2H), 2.62 (s, 3H); LCMS RT=2.36 min, [M+H]⁺=451.1.

Step 4. Preparation of (8E)-4-({3-chloro-4-[(6-methylpyridin-2-yl)methoxy]phenyl}amino)-8-[(dimethylamino)methylene]-5,8-dihydro[1]benzothieno[2,3-d]pyrimidin-7(6H)-one

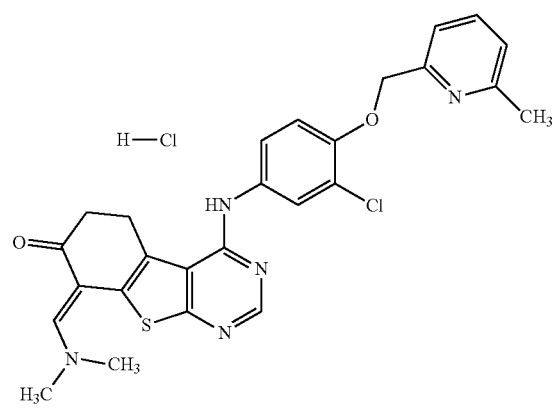

The title compound was prepared following the method described for example 98 step 4, utilizing 4-({3-chloro-4-[(6- methylpyridin-2-yl)methoxy]phenyl}amino)-5,8-dihydro[1]benzothieno[2,3-d]pyrimidin-7(6H)-one (435 mg, 1.0 mmol) and dimethylformamide-dimethylacetal (230 mg, 1.9 mmol). The desired product was collected as a yellow solid (302 mg, 62%). $^1$H-NMR (DMSO-$d_6$) (major rotomer) δ 8.26 (s, 1H), 8.18 (s, 1H), 7.75 (d, 1H), 7.72 (d, 1H), 7.51 (dd, 1H), 7.34 (d, 1H), 7.21 (d, 1H), 7.18 (d, 1H), 7.07 (s, 1H), 5.21 (s, 2H), 3.27 (t, 2H), 3.12 (s, 3H), 3.09 (s, 3H), 2.57 (t. 2H); LCMS RT=2.38 min; [M+H]$^+$=506.1.

Step 5. Regiocontrolled Preparation of 2-[6-({3-chloro-4-[(6-methylpyridin-2-yl)methoxy]phenyl}amino)-4,5-dihydro-2H-pyrimido[5',4':4,5]thieno[2,3-e]indazol-2-yl]ethanol

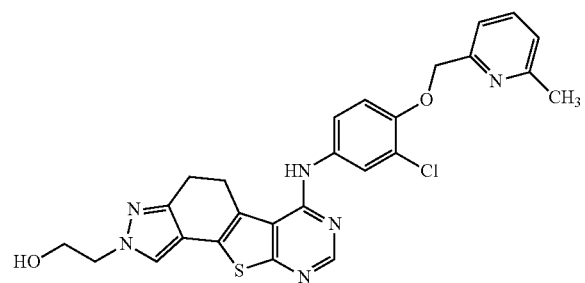

To 15 mL ethanol was added (8E)-4-({3-chloro-4-[(6-methylpyridin-2-yl)methoxy]phenyl}amino)-8-[(dimethylamino)methylene]-5,8-dihydro[1]benzothieno[2,3-d]pyrimidin-7(6H)-one (547 mg, 1.1 mmol), and then 2-tert-butyldimethylsilyloxy-1-tert-butyloxycarbonyl-ethylhydrazine (471 mg, 1.6 mmol) as a 6 mL ethanol solution, dropwise. The contents were stirred at reflux for 72 h, after which time they were then allowed to cool to rt. The heterogeneous mixture was filtered to afford a light yellow solid. The filtrate was concentrated to dryness.

The residue and light yellow solid were diluted with 30 mL THF, and cooled to 0° C. To the homogeneous mixture was then added aq. 2M HCl (0.85 mL), upon which the contents slowly become heterogeneous with a yellow precipitate. The contents were stirred with warming to rt over a 4 h period, after which time the solvent was removed under reduced pressure. The crude residue was diluted with EtOAc (1 mL) and aq. 2M Na$_2$CO$_3$ (20 mL) to attain a pH=11 solution, which was vigorously stirred for 1 h. The contents were filtered to a light brown solid, which was washed with water, and then hexanes. The collected product was dried under hi-vac, to afford the final product (570 mg, 81%) as a light brown solid. $^1$H-NMR (DMSO-$d_6$) δ (Note: the OH proton does not appear) 8.43 (br s, 1H), 8.34 (s, 1H), 7.92 (s, 1H), 7.77 (d, 1H), 7.73 (d, 1H), 7.51 (dd, 1H), 7.35 (d, 1H), 7.22 (s, 1H), 7.19 (d, 1H), 5.22 (s, 2H), 4.10 (t, 2H), 3.74 (t, 2H), 3.38 (t, 2H), 2.92 (t, 2H), 2.48 (s, 3H); LCMS RT=2.36 min; [M+H]$^+$=519.2.

Example 116

Preparation of 2-[6-({3-chloro-4-[(6-methylpyridin-2-yl)methoxy]phenyl}amino)-4,5-dihydro-2H-pyrimido[5',4':4,5]thieno[2,3-e]indazol-2-yl]ethyl methanesulfonate

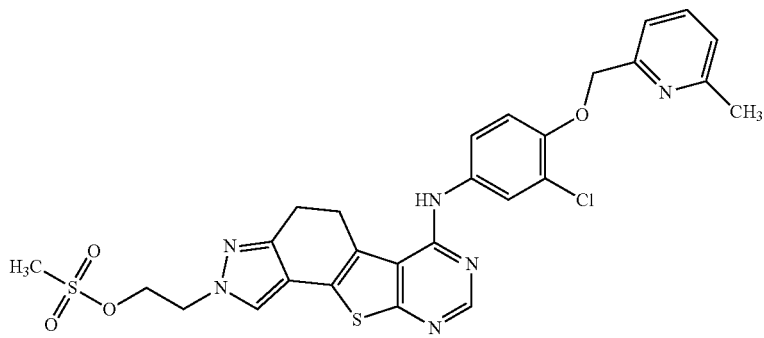

The title compound was prepared following the procedure described for example 57 method A, utilizing 2-[6-({3-chloro-4-[(6-methylpyridin-2-yl)methoxy]phenyl}amino)-4,5-dihydro-2H-pyrimido[5',4':4,5]thieno[2,3-e]indazol-2-yl]ethanol (275 mg, 1.6 mmol), and pyridine (0.17 mL, 2.1 mmol). The desired product was collected as a light brown solid (350 mg, 93%). $^1$H-NMR (DMSO-$d_6$) δ 8.43 (s, 1H), 8.35 (s, 1H), 8.02 (s, 1H), 7.76 (d, 1H), 7.73 (d, 1H), 7.51 (dd, 1H), 7.34 (d, 1H), 7.22 (s, 1H), 7.19 (s, 1H), 5.22 (s, 2H), 4.57 (t, 2H), 4.42 (t, 2H), 3.39 (t, 2H), 3.13 (s, 3H), 2.94 (t, 2H), 2.48 (s, 3H); LCMS RT=2.69 min; [M+H]$^+$=597.3.

Example 117

Preparation of N-{3-chloro-4-[(6-methylpyridin-2-yl)methoxy]phenyl}-2-[2-(4-methylpiperazin-1-yl)ethyl]-4,5-dihydro-2H-pyrimido[5',4':4,5]thieno[2,3-e]indazol 6-amine

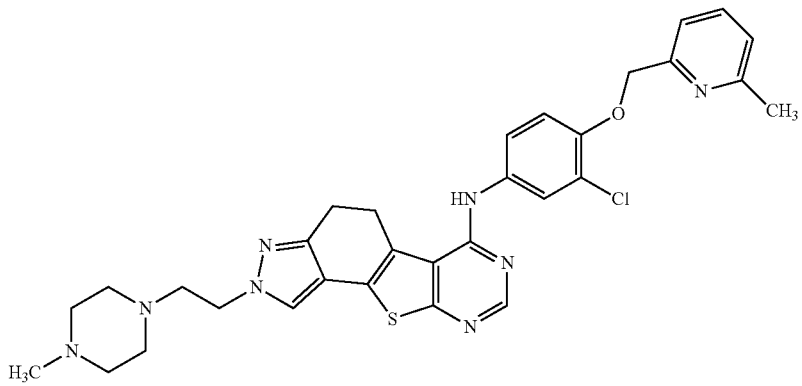

To 4 mL $CH_3CN$ were sequentially added 2-[6-({3-chloro-4-[(6-methylpyridin-2-yl)methoxy]phenyl}amino)-4,5-dihydro-2H-pyrimido[5',4':4,5]thieno[2,3-e]indazol-2-yl] ethyl methanesulfonate (100 mg, 0.17 mmol), 1-methylpiperazine (0.06 mL, 0.5 mmol), and diisopropylethylamine (0.06 mL, 0.33 mmol). The mixture was stirred at 70° C. for 16 h after which time the mixture was removed from heating, and allowed to cool to rt. The reaction mixture was diluted with water and extracted with EtOAc. The combined organic layers were concentrated under reduced pressure and purified by prep HPLC. The combined fractions were treated with saturated $Na_2CO_3$ and dried to afford free base product (43 mg, 43%) as a white solid. $^1$H-NMR (DMSO-$d_6$) δ 8.43 (s, 1H), 8.34 (s, 1H), 7.95 (s, 1H), 7.77 (d, 1H), 7.73 (d, 1H), 7.51 (dd, 1H), 7.35 (d, 1H), 7.22 (s, 1H), 7.19 (s, 1H), 5.22 (s, 2H), 4.17 (t, 2H), 3.38 (t, 2H), 2.91 (t, 2H), 2.70 (t, 2H), 2.48 (s, 3H), 2.40-2.48 (br s, 4H), 2.25-2.35 (br s, 4H), 2.13 (s, 3H); LCMS RT=2.07-2.24 min, $[M+H]^+$= 601.4.

Using the method described above and the appropriate starting material, examples 118-119 were similarly prepared.

Example 123

Preparation of N-[4-(benzyloxy)-3-chlorophenyl]-2-(2-{[tert-butyl(dimethyl)silyl]oxy}ethyl)-4,5-dihydro-2H-pyrimido[5',4':4,5]thieno[2,3-e]indazol-6-amine

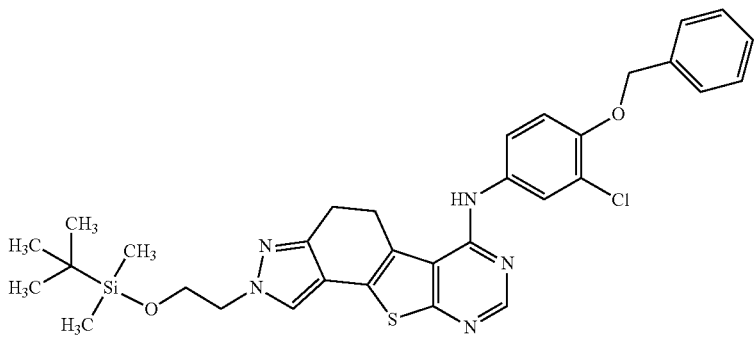

Step 1. Preparation of 4-Benzyloxy-3-chloro-phenylamine

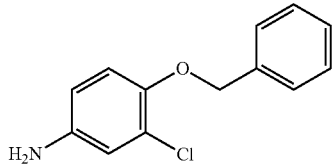

To 90 mL CH₃CN was added 2-Cl-4-nitrobenzene (15 g, 86.4 mmol), followed by potassium carbonate (17.9 g, 129.64 mmol), and benzyl bromide (14.78 g, 86.4 mmol) as a 10 mL CH₃CN solution. The suspension was stirred and heated at 70° C. for 2 h, after which time the bright yellow mixture was allowed to cool to rt. The contents were poured onto 200 mL water with stirring, upon which a solid crashes out of solution. The contents were filtered, and washed with water, and dried in vac. ven at ca. 40° C. yielding 1-Benzyloxy-2-chloro-4-nitro-benzene (4.87 g, 61%) as white solid.

1-Benzyloxy-2-chloro-4-nitrobenzene (10.0 g, 37.9 mmol) and iron powder (10.6 g, 189.6 mmol) were mixed in 250 mL acetic acid and were stirred at rt overnight. The reaction mixture was filtered through a pad of Celite®, and washed with EtOAc. The filtrate was concentrated in vacuo and neutralized with saturated Na₂CO₃ solution. The contents were extracted with EtOAc (6×300 mL). The combined organic layers were washed with brine, dried over MgSO₄, filtered, and concentrated in vacuo. The resulting crude material was triturated with Hex/EtOAc (2:1) to furnish 4-Benzyloxy-3-chloro-phenylamine (7.8 g, 88%) as a white solid. ¹H-NMR (DMSO-d₆) δ 7.43-7.30 (m, 5H), 6.90 (d, 1H), 6.63 (d, 1H), 6.46 (dd, 1H), 4.99 (s, 2H), 4.92 (s, 2H); LCMS RT=2.09 min; [M+H]⁺=234.5.

Step 2. Preparation of N-(4-Benzyloxy-3-chloro-phenylamine)-5,8-dihydro-6H-spiro[1-benzothieno[2,3-d]pyrimidine-7,2'-[1,3]dioxolan]-4-amine

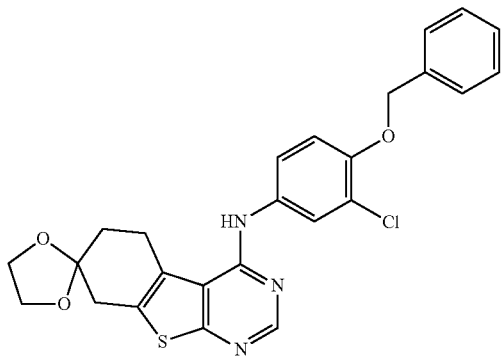

To isopropanol (30 mL) was sequentially added 4-chloro-5,8-dihydro-6H-spiro[1-benzothieno[2,3-d]pyrimidine-7,2'-[1,3]dioxolane] (3.30 g, 11.6 mmol), 4-Benzyloxy-3-chloro-phenylamine (2.58 g, 11.05 mmol), and 4N HCl in dioxane (0.03 mL). The suspension was stirred with heating to 80° C., upon which time the contents turn brown and homogeneous. After 15 h, the heterogeneous mixture was removed from heating, and allowed to cool to rt. The resultant precipitate was collected by filtration as a light-brown solid (4.6 g, 83%). ¹H-NMR (DMSO-d₆) δ 8.41 (s, 1H), 8.38 (s, 1H), 7.74 (d, 1H), 7.52-7.33 (m, 6H), 7.23 (d, 1H), 5.22 (s, 2H), 3.98 (s, 4H), 3.27 (t, 2H), 3.02 (s, 2H), 1.96 (t, 2H); LCMS RT=3.85 min; [M+H]⁺=480.3.

Step 3. Preparation of N-(4-Benzyloxy-3-chloro-phenylamine)-5,8-dihydro-6H-benzo[4,5]thieno[2,3-d]pyrimidin-7-one

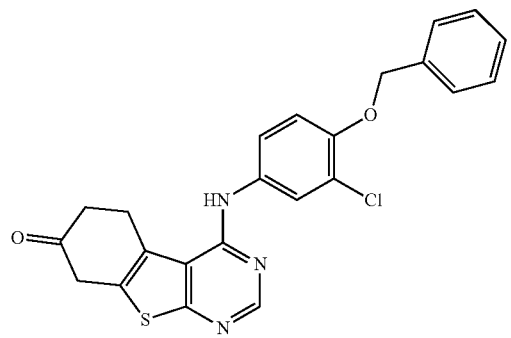

The title compound was prepared following the method described for example 55 step 4, utilizing N-(4-Benzyloxy-3-chloro-phenylamine)-5,8-dihydro-6H-spiro[1-benzothieno[2,3-d]pyrimidine-7,2'-[1,3]dioxolan]-4-amine (4.35 g, 9.06 mmol). The desired product was collected as a light brown solid (3.9 g, 99%). ¹H-NMR (DMSO-d₆) δ 8.52 (s, 1H), 8.42 (s, 1H), 7.74 (d, 1H), 7.33-7.52 (m, 6H), 7.24 (d, 1H), 5.22 (s, 2H), 3.76 (s, 2H), 3.49 (t, 2H), 2.69 (t, 2H); LCMS RT=3.47 min; [M+H]⁺=436.2.

Step 4. Preparation of N-(4-Benzyloxy-3-chloro-phenylamine)-8-dimethylaminomethylene-5,8-dihydro-6H-benzo[4,5]thieno[2,3-d]pyrimidin-7-one

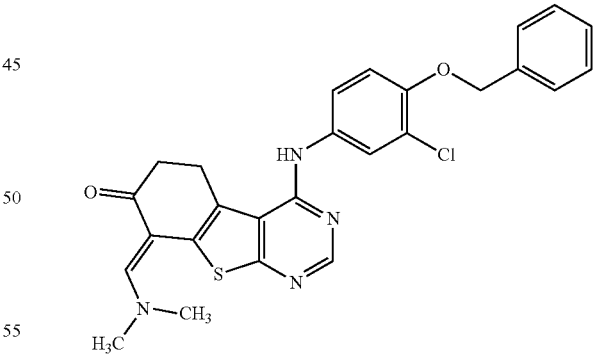

The title compound was prepared following the method described for example 55 step 5, utilizing N-(4-Benzyloxy-3-chloro-phenylamine)-5,8-dihydro-6H-benzo[4,5]thieno[2,3-d]pyrimidin-7-one (1000 mg, 2.29 mmol) and dimethylformamide-dimethylacetal (547 mg, 4.59 mmol). The desired product was collected as a yellow solid (770 mg, 68%). ¹H-NMR (DMSO-d₆) (major rotomer) δ 8.26 (s, 1H), 8.18 (s, 1H), 7.74 (s, 1H), 7.33-7.51 (m, 6H), 7.21 (d, 1H), 7.07 (s, 1H), 5.20 (s, 2H), 3.27 (t, 2H), 3.13 (s, 3H), 3.09 (s, 3H), 2.58 (t. 2H); LCMS RT=3.04 min; [M+H]⁺=491.1.

Step 5. Regiocontrolled Preparation of N-[4-(benzyloxy)-3-chlorophenyl]-2-(2-{[tert-butyl(dimethyl)silyl]oxy}ethyl)-4,5-dihydro-2H-pyrimido[5',4':4,5]thieno[2,3-e]indazol-6-amine

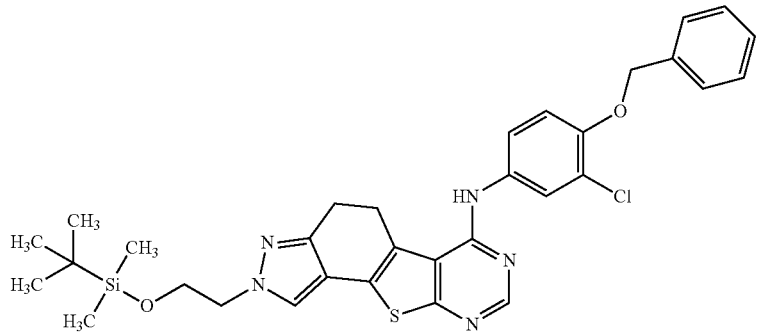

The title compound was prepared following the method described for example 55 step 6, utilizing N-(4-Benzyloxy-3-chloro-phenylamine)-8-dimethylaminomethylene-5,8-dihydro-6H-benzo[4,5]thieno[2,3-d]pyrimidin-7-one (1054 mg, 2.2 mmol) and 2-tert-butyldimethylsilyloxy-1-tert-butyloxycarbonyl-ethylhydrazine (935 mg, 3.2 mmol). The desired product was collected as a light brown solid (1045 mg, 79%). $^1$H-NMR (DMSO-d$_6$) δ 8.40 (s, 1H), 8.34 (s, 1H), 7.90 (s, 1H), 7.74 (d, 1H), 7.38-7.53 (m, 6H), 7.23 (d, 1H), 5.21 (s, 2H), 4.14 (t, 2H), 3.90 (t, 2H), 3.37 (t, 2H), 2.92 (t, 2H). 0.79 (s, 9H), −0.08 (s, 6H); LCMS RT=4.74 min; [M+H]$^+$=618.2.

Example 124

Preparation of 2-(6-{[4-(benzyloxy)-3-chlorophenyl]amino}-4,5-dihydro-2H-pyrimido[5',4':4,5]thieno[2,3-e]indazol-2-yl)ethanol

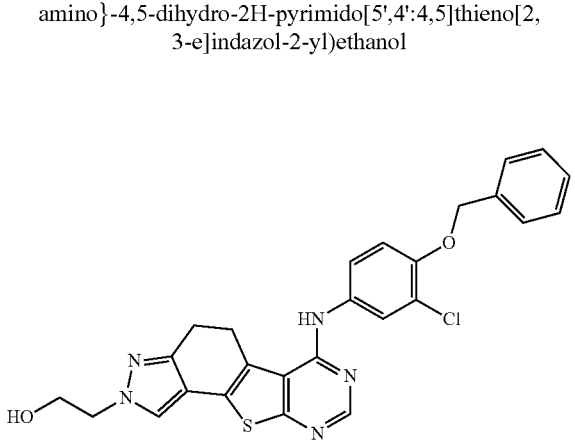

To a stirred and cooled (0° C.) solution of N-[4-(benzyloxy)-3-chlorophenyl]-2-(2-{[tert-butyl(dimethyl)silyl]oxy}ethyl)-4,5-dihydro-2H-pyrimido[5',4':4,5]thieno[2,3-e]indazol-6-amine (1673 mg, 2.7 mmol) in THF (55 mL) was added aq. HCl (2M, 1.6 mL). The resulting clear solution slowly became heterogeneous with a yellow precipitate. The mixture was warmed to rt over a 5 h period, after which time the solvent was removed in vacuo. The crude residue was diluted with EtOAc (5 mL) and aq. Na$_2$CO$_3$ (2M, 100 mL) to attain a pH=11 solution which was vigorously stirred for 1 h. The contents were filtered to a light yellow solid, which was washed with water (400 mL), and then hexanes (500 mL). The collected product was dried under vacuum, to afford the final product (817 mg, 60%) as a light yellow solid. $^1$H-NMR (DMSO-d$_6$) δ 8.41 (s, 1H), 8.34 (s, 1H), 7.93 (s, 1H), 7.75 (d, 1H), 7.33-7.53 (m, 6H), 7.23 (s, 1H), 5.21 (s, 2H), 4.92 (t, 1H), 4.10 (t, 2H), 3.73 (td, 2H), 3.38 (t, 2H), 2.92 (t, 2H); LCMS RT=3.56 min; [M+H]$^+$=504.2.

Example 125

Preparation of 2-(6-{[4-(benzyloxy)-3-chlorophenyl]amino}-4,5-dihydro-2H-pyrimido[5',4':4,5]thieno[2,3-e]indazol-2-yl)ethyl methanesulfonate The title compound was prepared following the procedure described for example 57 method A, utilizing 2-(6-{[4-(benzyloxy)-3-chlorophenyl]amino}-4,5-dihydro-2H-pyrimido[5',4':4,5]thieno[2,3-e]indazol-2-yl)ethanol (817 mg, 1.6 mmol), methanesulfonic anhydride (706 mg, 4.0 mmol), and pyridine (0.4 mL, 5.4 mmol). The desired product was collected as a light brown solid (920 g, 98%). $^1$H-NMR (DMSO-d$_6$) δ 8.42 (s, 1H), 8.35 (s, 1H), 8.03 (s, 1H), 7.75 (d, 1H), 7.33-7.533 (m, 6H), 7.23 (d, 1H), 5.21 (s, 2H), 4.58 (t, 2H), 4.42 (t, 2H), 3.39 (t, 2H), 3.14 (s, 3H), 2.94 (t, 2H); LCMS RT=3.79 min; [M+H]$^+$=582.1.

Example 126

Preparation of N-[4-(benzyloxy)-3-chlorophenyl]-2-(2-morpholin-4-ylethyl)-4,5-dihydro-2H-pyrimido[5',4':4,5]thieno[2,3-e]indazol-6-amine

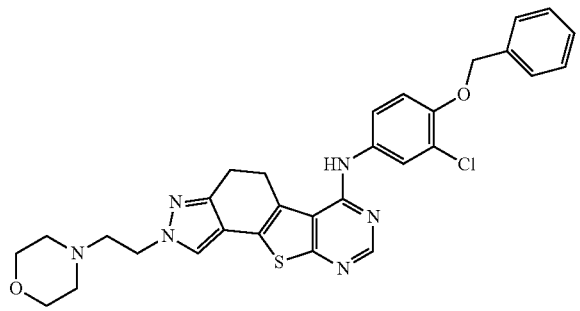

To CH$_3$CN (4 mL) were sequentially added 2-(6-{[4-(benzyloxy)-3-chlorophenyl]amino}-4,5-dihydro-2H-pyrimido[5',4':4,5]thieno[2,3-e]indazol-2-yl)ethyl methanesulfonate (85 mg, 0.15 mmol), morpholine (0.04 mL, 0.44 mmol), and diisopropylethylamine (0.05 mL, 0.29 mmol). The mixture was stirred at 70° C. for 16 h after which time the mixture was removed from heating, and allowed to cool to rt. The reaction mixture was diluted with water and extracted with EtOAc. The combined organic layers were concentrated under reduced pressure and purified by prep HPLC. The combined fractions were treated with saturated Na$_2$CO$_3$ and dried to afford free base product (35 mg, 42%) as a white solid. $^1$H-NMR (DMSO-d$_6$) δ 8.42 (s, 1H), 8.25 (s, 1H), 7.93 (s, 1H), 7.72 (d, 1H), 7.33-7.49 (m, 6H), 7.18 (d, 1H), 5.19 (s, 2H), 4.18 (t, 2H), 3.55 (m, 4H), 3.39 (t, 2H), 2.89 (t, 2H), 2.71 (t, 2H), 2.42 (m, 4H); LCMS RT=1.98 min, [M+H]$^+$=573.4.

Example 128

Preparation of 2-allyl-N-{3-chloro-4-[(3-fluorobenzyl)oxy]phenyl}-4,5-dihydro-2H-pyrimido[5',4':4,5]thieno[2,3-e]indazol-6-amine trifluoroacetate (Salt)

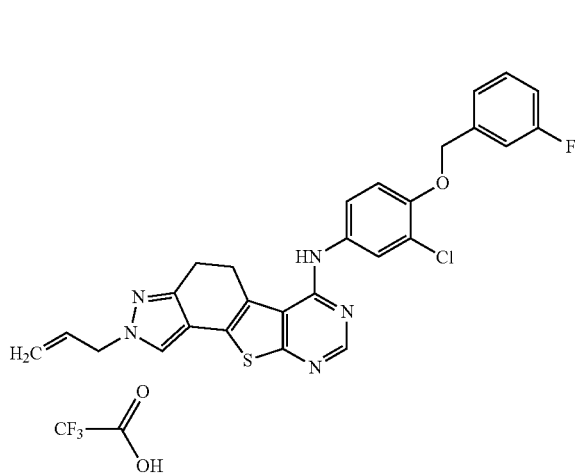

Step 1. Preparation of N-Allyl-hydrazinecarboxylic acid tert-butyl ester and N'-Allyl hydrazinecarboxylic acid tert-butyl ester

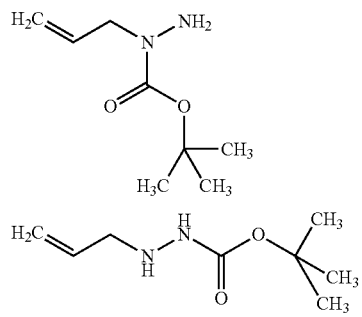

A solution of di-tert-butyl bicarbonate (3.02 g, 13.87 mmol) in dry ethanol (15 mL) was added under nitrogen atmosphere to a cooled (0° C.) aqueous solution of allyl hydrazine (1.00 g, 70%) over 30 mins. The resulting solution was warmed to room temperature and stirred for additional 12 hours. The ethanol was removed in vacuo. The residue was dissolved in EtOAc (60 mL) and the resulting solution was washed with water (2×20 mL), dried over sodium sulfate and concentrated in vacuo to yield the mixture of N-Allyl-hydrazinecarboxylic acid tert-butyl ester and N'-Allyl-hydrazinecarboxylic acid tert-butyl ester ((2.0 g, 80%, ratio: 9:1 by NMR spectrum) as a colorless oil. LCMS [M+H]$^+$=172.8. For N-Allyl-hydrazinecarboxylic acid tert-butyl ester: $^1$H NMR (CD$_3$CN) δ 5.85 (m, 1H), 5.13 (m, 2H), 3.93 (d, 2H), 1.47 (s, 9H). For N'-Allyl-hydrazinecarboxylic acid tert-butyl ester: $^1$H NMR (CD$_3$CN) δ 5.85 (m, 1H), 5.20 (md, 2H), 4.03 (d, 2H), 1.45 (s, 9H).

Step 2: Preparation of 2-allyl-N-{3-chloro-4-[(3-fluorobenzyl)oxy]phenyl}-4,5-dihydro-2H-pyrimido[5',4':4,5]thieno[2,3-e]indazol-6-amine trifluoroacetate (Salt)

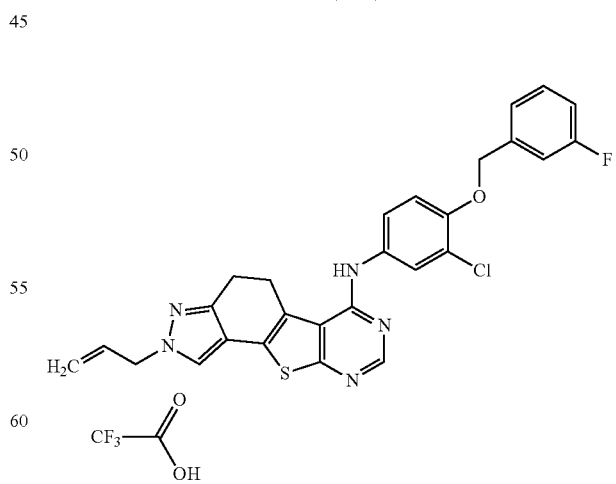

To a mixture of N-(3-Chloro-4-(3-fluoro-benzyloxy)-phenylamine)-8-dimethylaminomethylene-5,8-dihydro-6H- benzo[4,5]thieno[2,3-d]pyrimidin-7-one (600 mg, 1.18 mmol) and the mixture of Step 1 (2.0 eq, 406 mg, 2.36 mmol) was added 5 mL of dry ethanol in microwave tube. The resulting solution was stirred at 170° C. in microwave reactor for 25 mins. The reaction was then allowed to cool to rt and the solvent was removed in vacuo. The residue was triturated by ether to yield a yellow solid (470 mg, 69%). An aliquot of the crude material (10 mg) was separated by preparative HPLC and gave 2-allyl-N-{3-chloro-4-[(3-fluorobenzyl)oxy]phenyl}-4,5-dihydro-2H-pyrimido[5',4':4,5]thieno[2,3-e]indazol-6-amine (2.3 mg, 21%) as a trifluoroacetic salt. $^1$H NMR (CD$_3$CN) δ 8.33 (s, 1H), 7.82 (d, J=2.6 Hz, 1H), 7.65 (s, 1H), 7.50-7.43 (m, 2H), 7.33 (t, 1H), 7.28 (d, J=10 Hz, 1H), 7.14 (d, J=9 Hz, 1H), 7.12 (dt, 1H), 6.08 (m, 1H), 5.24 (m, 2H), 5.23 (s, 2H), 4.74 (d, 2H), 3.42 (t, 2H), 3.05 (t, 2H); %). LCMS RT=3.83 min, [M+H]$^+$=518.1.

Example 129

Preparation of 3-allyl-N-{3-chloro-4-[(3-fluorobenzyl)oxy]phenyl}-4,5-dihydro-3H-pyrimido[5',4':4,5]thieno[2,3-e]indazol-6-amine

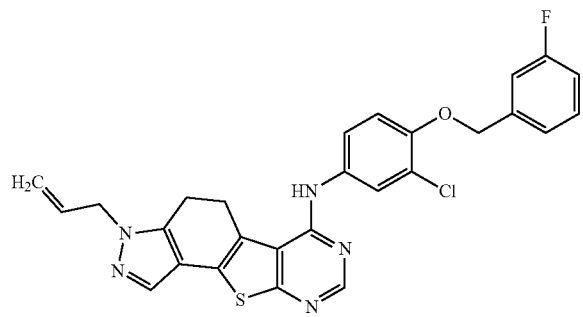

To a mixture of N-(3-Chloro-4-(3-fluoro-benzyloxy)-phenylamine)-8-dimethylaminomethylene-5,8-dihydro-6H-benzo[4,5]thieno[2,3-d]pyrimidin-7-one (50 mg, 0.10 mmol) and the mixture of Step 1 (33.8 mg, 0.20 mmol, 2.0 eq) was added 5 mL of dry ethanol in a microwave tube. The resulting solution was stirred at 170° C. in microwave reactor for 25 mins. The reaction was then allowed to cool to rt and the solvent was removed in vacuo. The residue was then separated by preparative HPLC and gave (3-Allyl-3a,4,5,10b-tetrahydro-3H-10-thia-2,3,7,9-tetraaza-cyclopenta[ro-benzyloxy)-phenyl]-amine (7.8 mg, 15%). $^1$H NMR (CD$_3$CN) δ 8.33 (s, 1H), 7.82 (d, J=2.6 Hz, 1H), 7.59 (s, 1H), 7.49 (dd, J=2.3, 8.9 Hz, 1H), 7.45 (m, 1H), 7.33 (t, 1H), 7.28 (d, J=10 Hz, 1H), 7.14 (d, J=9 Hz, 1H), 7.12 (dt, 1H), 6.08 (m, 1H), 5.24 (qd, J=10.3 Hz, 1H), 5.23 (s, 2H), 5.09 (qd, J=16.8 Hz, 1H), 4.79 (td, J=5.2 Hz, 2H), 3.45 (t, 2H), 3.09 (t, 2H); LCMS RT=3.74 min, [M+H]$^+$=518.1.

Example 130

Preparation of N-{3-chloro-4-[(3-fluorobenzyl)oxy]phenyl}-2-propyl-4,5-dihydro-2H-pyrimido[5',4':4,5]thieno[2,3-e]indazol-6-amine trifluoroacetate

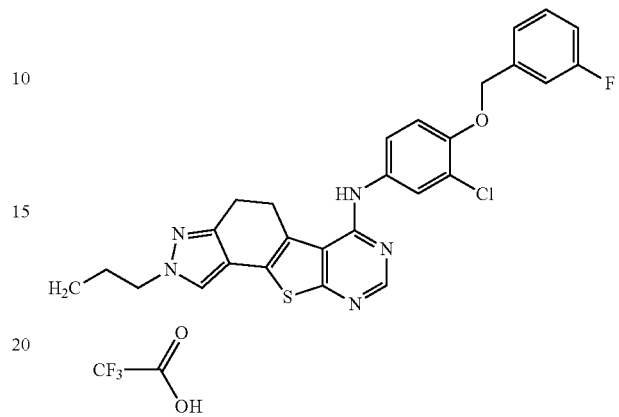

To a solution of 2-allyl-N-{3-chloro-4-[(3-fluorobenzyl)oxy]phenyl}-4,5-dihydro-2H-pyrimido[5',4':4,5]thieno[2,3-e]indazol-6-amine trifluoroacetate (25.0 mg, 0.05 mmol) in ethyl acetate (1.50 mL) was added Pd/C (2.0 mg, 10%) under nitrogen. The reaction was stirred at rt under hydrogen atmosphere (balloon, 1 atm) for 4 h. The Pd/C residue was removed by filtering through a pad of celite and pad was washed with EtOAc (2×3 mL). The combined EtOAc layers were dried over sodium sulfate and the solvent was removed in vacuo. The residue was then separated by preparative HPLC to give (N-{3-chloro-4-[(3-fluorobenzyl)oxy]phenyl}-2-propyl-4,5-dihydro-2H-pyrimido[5',4':4,5]thieno[2,3-e]indazol-6-amine trifluoroacetate (salt) (3.4 mg, 15%) as a yellow solid. $^1$H NMR (CD$_3$CN) δ 8.33 (s, 1H), 7.82 (d, J=2.6 Hz, 1H), 7.65 (s, 1H), 7.49 (dd, J=2.3, 8.9 Hz, 1H), 7.45 (m, 1H), 7.33 (t, 1H), 7.28 (d, J=10 Hz, 1H), 7.14 (d, J=9 Hz, 1H), 7.12 (dt, 1H), 5.23 (s, 2H), 4.08 (t, 2H), 3.40 (t, 2H), 3.04 (t, 2H), 1.88 (m, 2H), 0.94 (t, 3H); LCMS RT=3.91 min, [M+H]$^+$=520.1.

Example 132

Preparation of 3-[6-({3-chloro-4-[(3-fluorobenzyl)oxy]phenyl}amino)-4,5-dihydro-3Hpyrimido[5',4':4,5]thieno[2,3-e]indazol-3-yl]propane-1,2-diol

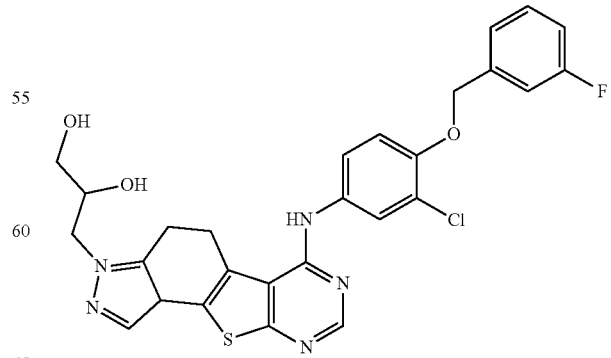

To a solution of 3-allyl-N-{3-chloro-4-[(3-fluorobenzyl)oxy]phenyl}-4,5-dihydro-3H-pyrimido[5',4':4,5]thieno[2,3- e]indazol-6-amine (300 mg, 0.52 mmol) and 4-methylmorpholine N-oxide monohydrate (133 mg, 1.14 mmol, 2.2 eq) in acetone (5 mL) and water (0.5 mL) was added a catalytic amount of osmium (VIII) tetraoxide (10 mg, 2.5 w % in t-BuOH). The reaction mixture was stirred at rt for 16 h. Sodium sulfite (1 g) was added to the stirred solution and the mixture was stirred for an additional 1 h. The mixture was passed through a pad of silicon gel and Celite mixture. The pad was washed with EtOAc (2×10 mL). The combined EtOAc layers were dried over sodium sulfate and then concentrated in vacuo. The residue was then purified by preparative-HPLC to give 3-[6-({3-chloro-4-[(3-fluorobenzyl)oxy]phenyl}amino)-4,5-dihydro-3H pyrimido[5',4':4,5]thieno[2,3-e]indazol-3-yl]propane-1,2-diol (25.5 mg, 8.9%) as a white solid. $^1$H NMR (CD$_3$CN) δ 8.31 (s, 1H), 7.82 (d, J=2.6 Hz, 1H), 7.59 (s, 1H), 7.45 (dd, J=2.3, 8.9 Hz, 1H), 7.45 (m, 1H), 7.33 (t, 1H), 7.28 (d, J=10 Hz, 1H), 7.14 (d, J=9 Hz, 1H), 7.12 (m, 1H), 5.23 (s, 2H), 4.25 (m, 1H), 3.67 (m, 4H), 3.43 (t, 2H), 3.15 (t, 2H); LCMS RT=3.17 min, [M+H]$^+$=552.0

Example 133 & 134

Preparation of (2R)-1-[6-({3-chloro-4-[(3-fluorobenzyl)oxy]phenyl}amino)-4,5-dihydro-2H-pyrimido[5',4':4,5]thieno[2,3-e]indazol-2-yl]-3-[4-(2-methoxyethyl)piperazin-1-yl]propan-2-ol (Example 133) and (2R)-1-[6-({3-chloro-4-[(3-fluorobenzyl)oxy]phenyl}amino)-4,5-dihydro-3H-pyrimido[5',4':4,5]thieno[2,3-e]indazol-3-yl]-3-[4-(2-methoxyethyl)piperazin-1-yl]propan-2-ol (Example 134)

Step 1. Preparation of [3-Chloro-4-(3-fluoro-benzyloxy)-phenyl]-(4,5-dihydro-2H-10-thia-2,3,7,9-tetraaza-cyclopenta[a]fluoren-6-yl)-amine

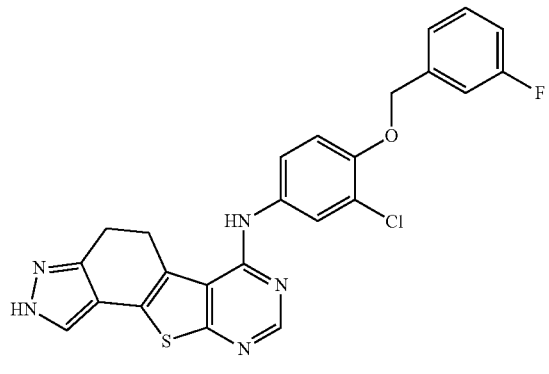

See also example 74 for the preparation of the same material. To a mixture of N-(3-Chloro-4-(3-fluoro-benzyloxy)-phenylamine)-8-dimethylaminomethylene-5,8-dihydro-6H-benzo[4,5]thieno[2,3-d]pyrimidin-7-one (1000 mg, 1.96 mmol) and hydrazine (1.5 eq, 94.4 mg, 2.95 mmol) was added 20 mL of dry ethanol in a microwave tube. The reaction was stirred at 170° C. in microwave reactor for 20 mins. The reaction was then allowed to cool to rt and the solvent was removed under reduced pressure. Use crude material to carry out the Step 2 reaction. LCMS [M+H]$^+$=477.9.

Example 133

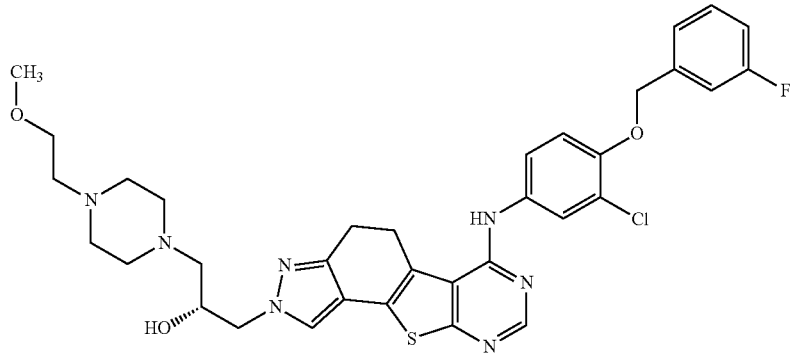

Example 134

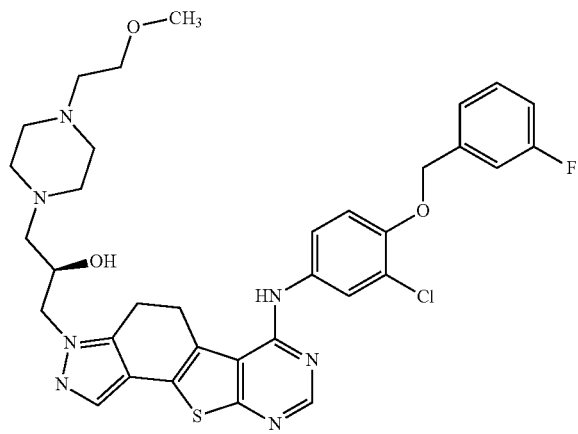

Step 2. Preparation the mixture of [3-Chloro-4-(3-fluoro-benzyloxy)-phenyl]-(2-oxiranylmethyl-4,5-dihydro-2H-10-thia-2,3,7,9-tetraaza-cyclopenta[a]fluoren-6-yl)-amine (Regiomer A) and [3-Chloro-4-(3-fluoro-benzyloxy)-phenyl]-(3-oxiranylmethyl-4,5-dihydro-3H-10-thia-2,3,79-tetraaza-cyclopenta[a]fluoren-6-yl)-amine (Regiomer B)

To a solution of crude material [3-Chloro-4-(3-fluoro-benzyloxy)-phenyl]-(4,5-dihydro-2H-10-thia-2,3,7,9-tetraaza-cyclopenta[a]fluoren-6-yl)-amine (939.2 mg, 1.97 mmol) from Step 1 in N-methyl-pyrrolidinone (10 mL) was added NaOH (94.3 mg, 2.36 mmol, 1.2 eq) under nitrogen. The reaction mixture was heated at 50° C. for 3 min before cooled to rt. (R)-(+)-glycidyl 3-nitrobenzene sulfonate (611.3 mg, 2.36 mmol, 1.2 eq) was added to the reaction mixture. The reaction mixture was stirred at rt for 3 days after which time a mixture of water (30 mL) and EtOAc (30 mL). The layers were separated and the organic layer was washed with water (4×30 mL), dried over sodium sulfate and concentrated under reduced pressure to give the crude mixture of regiomer A & B as a yellow solid (1 g, 95%). LCMS [M+H]$^+$=533.9.

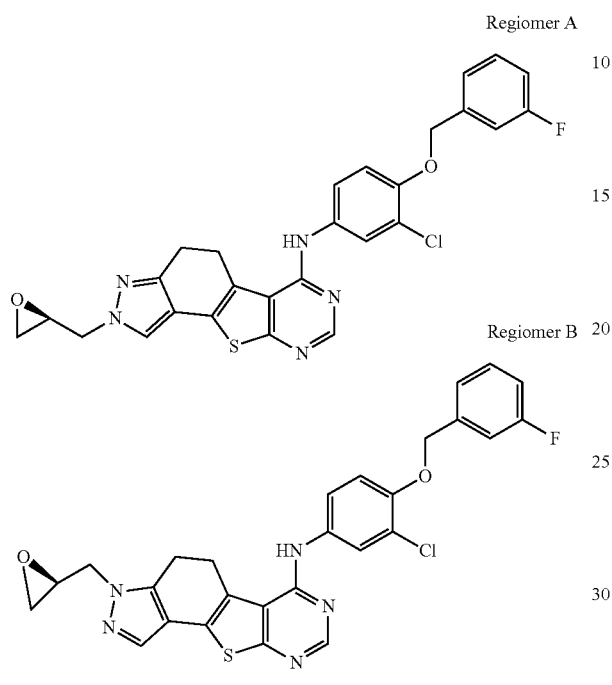

Regiomer A

Regiomer B

Step 3: Preparation of (2R)-1-[6-({3-chloro-4-[(3-fluorobenzyl)oxy]phenyl}amino)-4,5-dihydro-2H-pyrimido[5',4':4,5]thieno[2,3-e]indazol-2-yl]-3-[4-(2-methoxyethyl)piperazin-1-yl]propan-2-ol (Example 133) and (2R)-1-[6-({3-chloro-4-[(3-fluorobenzyl)oxy]phenyl}amino)-4,5-dihydro-3H-pyrimido[5',4':4,5]thieno[2,3-e]indazol-3-yl]-3-[4-(2-methoxyethyl)piperazin-1-yl]propan-2-ol (Example 134)

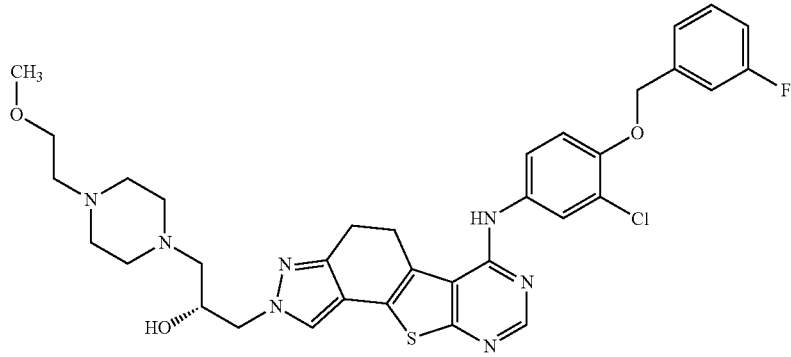

Example 133

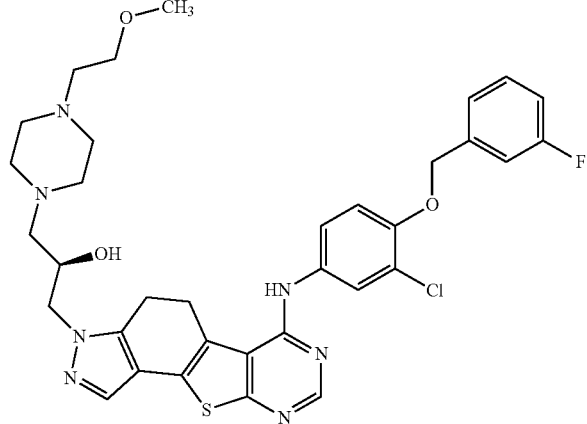

Example 134

To a mixture of crude material from Step 2 (80 mg, 0.15 mmol) and 1-(2-methoxy-ethyl)-piperazine (64.8 mg, 0.45 mmol, 3 eq) in a microwave tube was added a mixture of dioxane/water (10:1, 3 mL). The resulting mixture was stirred at 150° C. in a microwave reactor for 10 min. The mixture was then allowed to cool to rt and the solvents were removed under reduced pressure. The residue was purified by chiral HPLC to give (2R)-1-[6-({3-chloro-4-[(3-fluorobenzyl)oxy]phenyl}amino)-4,5-dihydro-2H-pyrimido[5',4':4,5]thieno[2,3-e]indazol-2-yl]-3-[4-(2-methoxyethyl)piperazin-1-yl]propan-2-ol (example 133) as a white solid (11 mg, 10.6%): $^1$H NMR (CD$_3$OD) δ 8.29 (s, 1H), 7.72 (d, J=2.6 Hz, 1H), 7.67 (s, 1H), 7.43 (dd, J=2.3, 8.9 Hz, 1H), 7.39 (m, 1H); 7.30 (d, J=7.7 Hz, 1H), 7.24 (d, J=10 Hz, 1H), 7.15 (d, J=9 Hz, 1H), 7.05 (t, 1H), 5.23 (s, 2H), 4.30 (m, 2H), 4.19 (m, 1H), 3.71 (m, 4H), 3.52 (m, 4H), 3.40 (s, 3H), 3.34 (m, 4H), 3.22 (t, 2H), 3.12 (t, 2H), 2.84 (m, 2H), LCMS [M+H]$^+$=678.1; and (2R)-1-[6-({3-chloro-4-[(3-fluorobenzyl)oxy]phenyl}amino)-4,5-dihydro-2H-pyrimido[5',4':4,5]thieno[2,3-e]indazol-2-yl]-3-[4-(2-methoxyethyl)piperazin-1-yl]propan-2-ol (example 134) (3.0 mg, 2.9%) as a white solid: $^1$H NMR (CD$_3$OD) δ 8.29 (s, 1H), 7.72 (d, J=2.6 Hz, 1H), 7.67 (s, 1H), 7.43 (dd, J=2.3, 8.9 Hz, 1H), 7.39 (m, 1H), 7.30 (d, J=7.7 Hz, 1H), 7.24 (d, J=10 Hz, 1H), 7.15 (d, J=9 Hz, 1H), 7.05 (t, 1H), 5.23 (s, 2H), 4.30 (m, 2H), 4.19 (m, 1H), 3.71 (m, 4H), 3.52 (m, 4H), 3.40 (s, 3H), 3.34 (m, 4H), 3.22 (t, 2H), 3.12 (t, 2H), 2.84 (m, 2H).

Using the method described above and the appropriate starting materials, Examples 135-173 were similarly prepared.

Example 174

Preparation of ethyl [6-({3-chloro-4-[3-fluorobenzyl)oxy]phenyl}amino)-4,5-dihydro-2H-pyrimido[5',4':4,5]thieno[2,3-e]indazol-2-yl]acetate

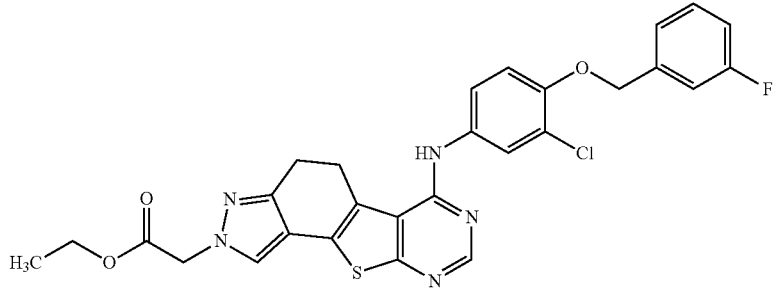

Step 1: Preparation of (N$_β$'-tert-Butoxycarbonyl-hydrazino)-acetic acid ethyl ester

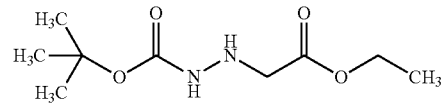

To a solution of tert-butylcarbazate (59.4 g, 449.1 mmol) in DMF (120 mL) was added ethyl bromoacetate (16.6 mL, 149.7 mmol) in DMF (30 mL) via a dropping funnel over 15 min. The homogenous contents were stirred at rt. for 8 h. and the glyoxylic acid solution was added [It was prepared as follows: glyoxylic acid (66 ml, 50% w/w in water) was added to a 0.4 M solution of aq. K$_2$HPO$_4$ (10.5 g in 150 ml water), and the solution adjusted to pH=5.2 by addition of aq. 6N NaOH (req. 100 ml)]. via a dropping funnel over 15 min. The resulting mixture was allowed to stir at rt overnight. The crude mixture was slowly poured onto aq. NaHCO$_3$ (900 ml), and the contents extracted with ethyl ether (5×300 mL). The combined organic layers were washed with brine (2×150 ml), dried over MgSO$_4$, filtered, and concentrated in vacuo yielding (N$_β$'-tert-Butoxycarbonyl-hydrazino)-acetic acid ethyl ester (20.7 g, 63%) as a yellow oil. $^1$H-NMR (CDCl$_3$) δ 4.18 (q, 2H), 3.65 (s, 2H), 1.43 (s, 9H), 1.25 (t, 3H); LCMS RT=2.13 min; [M+Na]$^+$=241.0.

Step 2. Regiocontrolled Preparation of ethyl [6-({3-chloro-4-[(3-fluorobenzyl)oxy]phenyl}amino)-4,5-dihydro-2H-pyrimido[5',4':4,5]thieno[2,3-e]indazol-2-yl]acetate

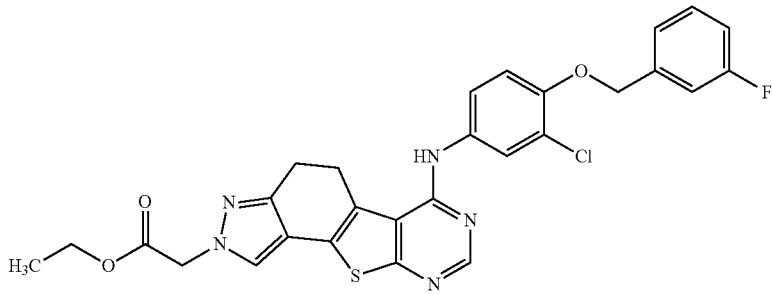

The title compound was prepared following the method described for example 98 step 5, utilizing N-(3-Chloro-4-(3-fluoro-benzyloxy)-phenylamine)-8-dimethylaminomethylene-5,8-dihydro-6H-benzo[4,5]thieno[2,3-d]pyrimidin-7-one (4.3 g, 8.5 mmol) and (N$_\beta$'-tert-Butoxycarbonyl-hydrazino)-acetic acid ethyl ester (2.8 g, 12.7 mmol). The desired product was collected as a light brown solid (2.54 g, 53%). $^1$H-NMR (DMSO-d$_6$) δ 8.44 (s, 1H), 8.36 (s, 1H), 7.96 (s, 1H), 7.76 (d, 1H), 7.54-7.43 (m, 2H), 7.17-7.33 (m, 4H), 5.24 (s, 2H), 5.03 (s, 2H), 4.15 (q, 2H), 3.40 (t, 2H), 2.93 (t, 2H), 1.22 (t, 3H); LCMS RT=3.78 min; [M+H]$^+$=564.1.

Example 175

Preparation of [6-({3-chloro-4-[(3-fluorobenzyl)oxy]phenyl}amino)-4,5-dihydro-2H-pyrimido[5',4':4,5]thieno[2,3-e]indazol-2-yl]acetic acid To THF/MeOH/H$_2$O (150 mL, 10/1/1) cooled to 0° C. was added ethyl [6-({3-chloro-4-[(3-fluorobenzyl)oxy]phenyl}amino)-4,5-dihydro-2H-pyrimido[5',4':4,5]thieno[2,3-e]indazol-2-yl]acetate (1673 mg, 2.7 mmol), followed by a solution of potassium hydroxide (1.2 g, 21.6 mmol) in THF/MeOH/H$_2$O (20 mL, 10/1/1). The contents were stirred with warming to rt over 1 h, after which time the solvent was removed under reduced pressure. The crude residue was diluted with water (200 mL) which was vigorously stirred for 0.5 h, neutralized with aq. 1N HCl (12.0 mL) to pH=2-3. The contents were filtered to a light yellow solid, which was washed with water, and then hexanes. The collected product was dried in vacuo, to afford the final product (2.3 g, 99%) as a light yellow solid. $^1$H-NMR (DMSO-d$_6$) δ 13.1 (br s, 1H), 8.44 (s, 1H), 8.36 (s, 1H), 7.95 (s, 1H), 7.77 (d, 1H), 7.52 (dd, 1H), 7.45 (dd, 1H), 7.14-7.33 (m, 4H), 5.24 (s, 2H), 4.92 (s, 2H), 3.39 (t, 2H), 2.95 (t, 2H); LCMS RT=3.32 min; [M+H]$^+$=536.1.

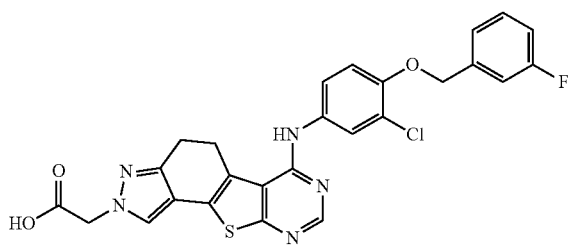

Example 177

Preparation of N-{3-chloro-4-[(3-fluorobenzyl)oxy]phenyl}-2-{2-[(3S)-3-(dimethylamino)pyrrolidin-1-yl]-2-oxoethyl}-4,5-dihydro-2H-pyrimido[5',4':4,5]thieno[2,3-e]indazol-6-amine

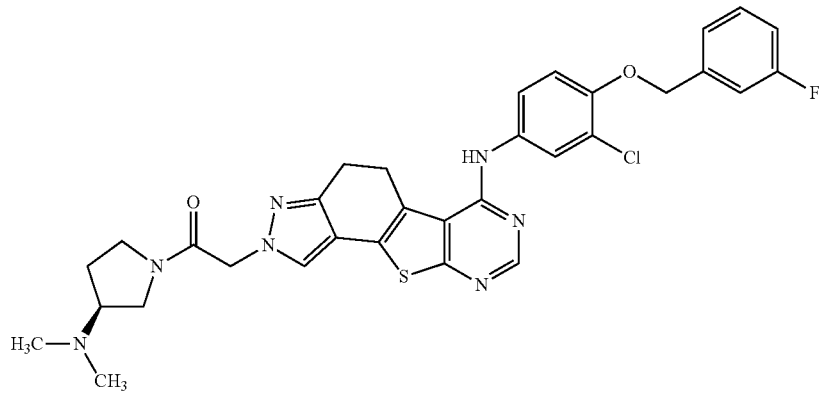

To DMF (3 mL) were sequentially added [6-({3-chloro-4-[(3-fluorobenzyl)oxy]phenyl}amino)-4,5-dihydro-2H-pyrimido[5',4':4,5]thieno[2,3-e]indazol-2-yl]acetic acid (80 mg, 0.15 mmol), 3(R)-(−)-3(Dimethylamino)pyrrolidine (23 mg, 0.20 mmol), (3-Dimethylamino-propyl)-ethyl-carbodiimide (50 mg, 0.26 mmol), 4-methylmorpholine (0.03 ml, 0.29 mmol), and 1-Hydroxybenzotriazole (39 mg, 0.29 mmol). The mixture was stirred at rt for 14 h after which time the reaction mixture was concentrated in vacuo. The residue was diluted with water and extracted with EtOAc. The combined organic layers were concentrated in vacuo and purified by prep HPLC. The combined fractions were treated with saturated $Na_2CO_3$ and dried to afford free base product (35 mg, 42%) as a white solid. $^1$H-NMR ($CD_2Cl_2$) δ 8.38 (s, 1H), 7.81 (d, 1H), 7.53 (s, 1H), 7.45 (dd, 1H), 7.38 (dd, 1H), 7.28-7.22 (m, 2H), 6.97-7.08 (m, 3H), 5.15 (s, 2H), 4.84 (s, 2H), 3.64-3.80 (m, 2H), 3.15-3.53 (m, 3H), 3.07 (t, 2H), 2.61-2.81 (m, 1), 2.25 (s, 3H), 2.23 (s, 3H), 1.69-2.20 (m, 3H); LCMS RT=3.80 min, [M+H]$^+$=632.2

Using the method described above and the appropriate starting materials, Examples 2-38, and 178-189 were similarly prepared.

Example 190

Preparation of ethyl [6-({3-chloro-4-[(3-fluorobenzyl)oxy]phenyl}amino)-4,5-dihydro-3H-pyrimido[5',4':4,5]thieno[2,3-e]indazol-3-yl]acetate

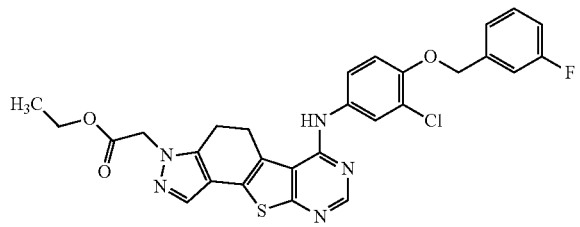

To ethanol (45 mL) was added N-(3-Chloro-4-(3-fluorobenzyloxy)-phenylamine)-8-dimethylaminomethylene-5,8-dihydro-6H-benzo[4,5]thieno[2,3-d]pyrimidin-7-one (1.5 g g, 2.95 mmol), and ethyl hydrazinylacetate hydrochloride (0.55 g, 3.54 mmol). The contents were stirred at reflux for 1 h, after which time they were then allowed to cool to rt. The slightly heterogeneous mixture was concentrated in vacuo and the crude residue chromatographed on silica (eluting with 1% to 6% $CH_3OH$ in $CH_2Cl_2$ gradient) to afford the title compound (0.78 g, 47%) as a white solid, as the major regioisomer (the minor regioisomer is example 174, as confirmed by 2D H NMR studies). Data for example 190: ($CD_2Cl_2$-$d_4$) 8.30 (s, 1H), 7.70 (d, 1H), 7.47 (s, 1H), 7.40 (dd, 1H), 7.27-7.37 (dd, 1H), 7.10-7.20 (m, 3H), 6.92-7.01 (m, 2H), 5.08 (s, 2H), 4.81 (s, 2H), 4.12 (q, 2H), 3.30 (t, 2H), 2.96 (t, 2H), 1.19 (t, 3H). The regiochemical assignment was verified by 2D H-NMR, wherein a strong NOE coupling is observed between the methylene protons at 2.96 ppm and 4.81 ppm. LCMS RT=3.74 min; [M+H]$^+$=564.3.

Example 191

Preparation of [6-({3-chloro-4-[(3-fluorobenzyl)oxy]phenyl}amino)-4,5-dihydro-3H-pyrimido[5',4':4,5]thieno[2,3-e]indazol-3-yl]acetic acid

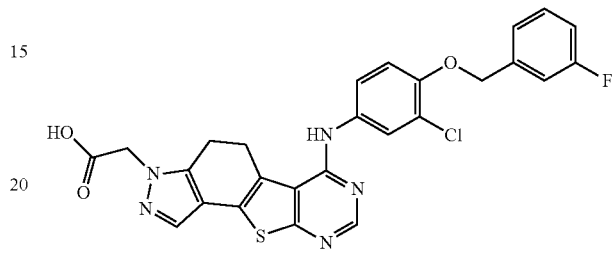

Method A

To MeOH/$H_2O$ (30 mL, 3/1) cooled to 0° C. was added ethyl [6-({3-chloro-4-[(3-fluorobenzyl)oxy]phenyl}amino)-4,5-dihydro-3H-pyrimido[5',4':4,5]thieno[2,3-e]indazol-3-yl]acetate (600 mg, 1.06 mmol), followed by potassium hydroxide (298 mg, 5.32 mmol). The contents were heated to 40° C. for 1 h, after which time the mixture was allowed to cool to rt, and the solvent removed under reduced pressure. The crude residue was diluted with water (5 mL) and neutralized with 1N HCl (0.5 ml). The contents were filtered to a light yellow solid which was washed with water. The collected product was dried under hi-vac, to afford the final product (520 mg, 91%) as a light yellow solid. $^1$H-NMR (DMSO-$d_6$) δ 13.2 (br s, 1H), 8.37 (s, 1H), 8.34 (s, 1H), 7.76 (d, 1H), 7.66 (s, 1H), 7.52 (dd, 1H), 7.45 (m, 1H), 7.29-7.31 (m, 2H), 7.22 (d, 1H), 7.16 (m, 1H), 5.24 (s, 2H), 5.02 (s, 2H), 3.41 (t, 2H), 3.00 (t, 2H). The regiochemical assignment is confirmed by 2D H-NMR, wherein a strong NOE coupling is observed between the methylene protons at 3.00 ppm and 5.02 ppm. LCMS RT=3.32 min; [M+H]$^+$=536.2.

Method B

Step 1. Preparation of ($N_α$'-tert-Butoxycarbonylhydrazino)-acetic acid ethyl ester

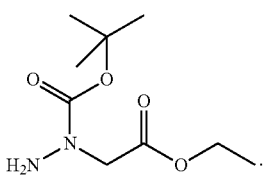

Ethyl hydrazinylacetate hydrochloride (10.5, 67.9 mmol) was dissolved in EtOH/$H_2O$ (65 mL, 1:1), and the stirring solution cooled to 0° C. Slowly added to the stirring mixture was di-tert-butyl carbonate (14.8 g, 67.9 mmol), and 4-methylmorpholine (7.56 g, 74.7 mmol). After stirring to rt over 2 h, the contents were returned to 0° C. Added slowly to the stirring contents was 6N NaOH (25 mL), and the mixture stirred with warming to rt over 1 h. The contents diluted with brine (100 mL), and vigorously stirred for 10 min. The mixture was extracted with ether (100 mL). The aq. layer was cooled to 0° C., and with stirring was added 50 mL aq. 2.5M citric acid solution to afford a pH 3 solution. This mixture was extracted with ether (3×100 mL). All the combined organic layers were washed with water (100 mL), dried over MgSO$_4$, filtered, and concentrated in vacuo to a thick clear oil, which solidifies on standing at rt. The saved aq. layers were further extracted with ethyl acetate (2×100 mL), and then ether (50 mL). These combined organic layers were similarly washed, dried, and concentrated to furnish additional crude product. The combined crude product crops were triturated with hexanes/EtOAc (95:5) to afford (N$_\alpha$'-tert-Butoxycarbonyl-hydrazino)-acetic acid ethyl ester (6 g, 46%) as white solid. $^1$H-NMR (DMSO-d$_6$) δ 7.00-8.00 (br s, 2H), 3.93 (s, 2H), 3.40 (s, 1H), 1.41 (s, 9H). The regiochemical assignment was verified by an HMBC experiment. Strong couplings are observed between the methylene protons at 3.93 ppm and both of the carbonyl carbon atoms 157 ppm and 172 ppm.

Step 2. Regiocontrolled Preparation of [6-({3-chloro-4-[(3-fluorobenzyl)oxy]phenyl}amino)-4,5-dihydro-3H-pyrimido[5',4':4,5]thieno[2,3-e]indazol-3-yl]acetic acid

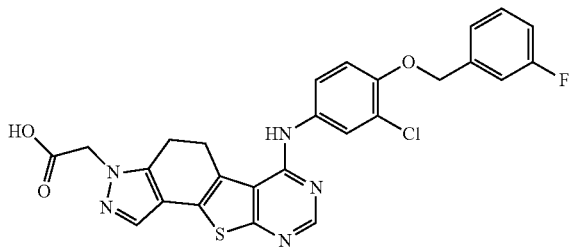

N-(3-Chloro-4-(3-fluoro-benzyloxy)-phenylamine)-8-dimethylaminomethylene-5,8-dihydro-6H-benzo[4,5]thieno [2,3-d]pyrimidin-7-one (4.3 g, 8.5 mmol) was dissolved in ethanol (240 mL) and (N$_\alpha$'-tert-Butoxycarbonyl-hydrazino)-acetic acid ethyl ester (2.8 g, 14.7 mmol) was added as a 30 mL ethanol solution via dropping funnel. The reaction mixture was stirred at 80° C. for 6 h, and then cooled down to rt. The mixture was concentrated under reduced pressure and dried to give brown foam, which was diluted with CH$_2$Cl$_2$ (145 mL) and cooled to 0° C. Next added to the solution was TFA (45 mL) in a dropwise manner, and the mixture was allowed to stir with warming to rt over a 12 h period. The contents were concentrated in vacuo to near dryness, and the residue diluted with water (250 mL). The contents were cooled to 0° C. and 105 mL 1M NaOH was added via dropping funnel to afford a pH 2 solution, which is heterogenous. The contents were filtered to afford a dark orange colored solid. The crude product was twice triturated with hot ethanol (75 mL), to afford the final pure product (3.6 g, 64%) as a light tan solid. The characterization data for the material prepared by this method is observed to be identical as that from method A.

Example 192

Preparation of 2-[6-({3-chloro-4-[(3-fluorobenzyl) oxy]phenyl}amino)-4,5-dihydro-3H-pyrimido[5',4': 4,5]thieno[2,3-e]indazol-3-yl]-N-[4-(dimethylamino) phenyl]acetamide

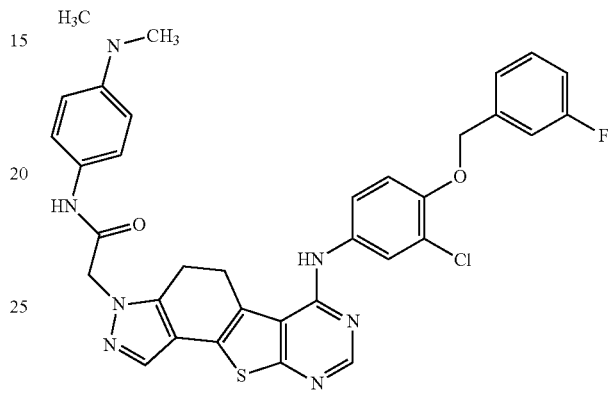

Using the method described for the preparation of example 177 along with the appropriate starting materials, the title compound was prepared from [6-({3-chloro-4-[(3-fluorobenzyl)oxy]phenyl}amino)-4,5-dihydro-3H-pyrimido[5', 4':4,5]thieno[2,3-e]indazol-3-yl]acetic acid (80 mg, 0.15 mmol). The product was collected (31 mg, 32%) as a white solid. $^1$H-NMR (DMSO-d$_5$) δ 10.1 (br s, 1H), 8.40 (s, 1H), 8.35 (s, 1H), 7.77 (d, 1H), 7.67 (s, 1H), 7.14-7.55 (m, 8H), 6.75 (m, 2H), 5.24 (s, 2H), 5.02 (s, 2H), 2.43 (t, 2H), 3.07 (t, 2H), 2.86 (s, 6H); LCMS RT=2.96 min, [M+H]$^+$=654.3

Using the method described above and the appropriate starting materials, examples 193-215 were similarly prepared.

Example 216

Preparation of tert-butyl 4-[6-({3-chloro-4-[(3-fluorobenzyl)oxy]phenyl}amino)-4,5-dihydro-2H-pyrimido[5',4':4,5]thieno[2,3-e]indazol-2-yl]piperidine-1-carboxylate Step 1. Preparation of tert-butyl 4-[(tert-butoxycarbonyl)hydrazono]piperidine-1-carboxylate

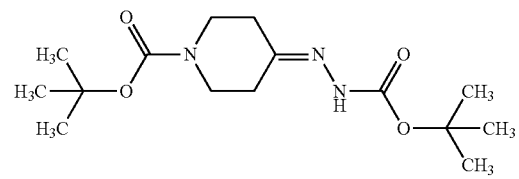

To a solution of tert-butyl 4-oxopiperidine-1-carboxylate (2 g, 10 mmol, 1 eq) in toluene (50 mL) was added tert-butyl carbazate (1.3 g, 10 mmol, 1 eq). The contents were stirred at 70° C. for 17 h. Precipitate was formed upon cooling down to rt. Filtration of the heterogeneous mixture gave a white solid (2.3 g). The filtrate was concentrated to dryness and triturated with ether carefully to collect another crop of solid (400 mg). The two solid product crops were combined (2.7 g, 85%) and used directly in the next step. $^1$H-NMR (CH$_3$CN-d$_3$) δ 8.11 (s, 1H), 3.49 (m, 4H), 2.34 (m, 4H), 1.47 (s, 9H), 1.45 (s, 9H); LCMS RT=3.04 min; [M+Na]$^+$=336.1.

Step 2. Preparation of tert-butyl 4-[2-(tert-butoxycarbonyl)hydrazino]piperidine-1-carboxylate

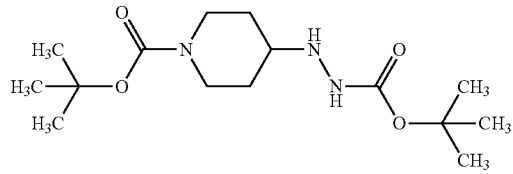

To a suspension of Pd/C (10% wt on activated carbon, 270 mg) in THF was added tert-butyl 4-[6-({3-chloro-4-[(3-fluorobenzyl)oxy]phenyl}amino)-4,5-dihydro-2H-pyrimido[5',4':4,5]thieno[2,3-e]indazol-2-yl]piperidine-1-carboxylate (2.7 g, 8.6 mmol) in THF (60 ml). The flask was vacuumed and hydrogen gas was introduced. The reaction mixture was stirred under hydrogen atmosphere at rt for 16 h. The Pd/C was carefully filtered and the filtrate was concentrated to yield a white solid (2.5 g, 92%). $^1$H-NMR (CH$_3$CN-d$_3$) δ 6.74 (s, 1H), 3.99 (s, 1H), 3.86 (m, 2H), 2.91 (m, 3H), 1.70 (m, 2H), 1.43 (s, 18H), 1.20 (m, 2H), LCMS RT=2.63 min; [M+H]$^+$=315.9.

Step 3. Preparation of tert-butyl 4-[6-({3-chloro-4-[(3-fluorobenzyl)oxy]phenyl}amino)-4,5-dihydro-2H-pyrimido[5',4':4,5]thieno[2,3-e]indazol-2-yl]piperidine-1-carboxylate

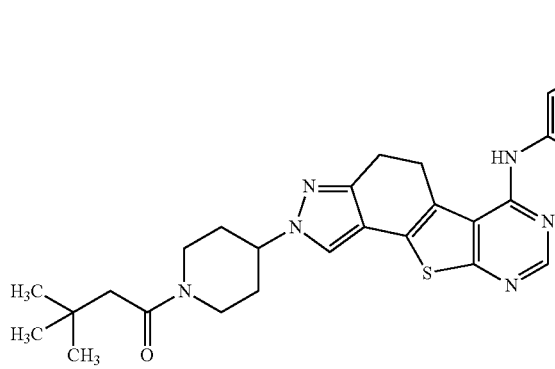

To a solution of tert-butyl 4-[2-(tert-butoxycarbonyl)hydrazino]piperidine-1-carboxylate (1 g, 3.17 mmol, 1.4 eq) in ethanol (70 mL) was added N-(3-Chloro-4-(3-fluoro-benzyloxy)-phenylamine)-8-dimethylaminomethylene-5,8-dihydro-6H-benzo[4,5]thieno[2,3-d]pyrimidin-7-one (see Example 55, step 5) (1.15 g, 2.26 mmol, 1 eq). The contents were heated at 90° C. for 105 h and some precipitation was formed. The heterogeneous mixture was filtered to give a pure product (0.25 g). The filtrate was concentrated to dryness and triturated with ether carefully to collect another crop of yellow solid (1.3 g) which contained some hydrazino starting material. The combined solids (1.55 g, quantitative) was used directly for the next step reaction. $^1$H-NMR (DMSO-d$_6$) δ 8.43 (s, 1H), 8.34 (s, 1H), 8.05 (s, 1H), 7.76 (d, 1H), 7.52 (dd, 1H), 7.45 (m, 1H), 7.3 (m, 2H), 7.22 (d, 1H), 7.17 (m, 1H), 5.24 (s, 2H), 4.3 (m, 1H), 4.04 (m, 2H), 3.39 (t, 2H), 2.94 (t, 2H), 2.0 (m, 2H), 1.8 (m, 2H), 1.43 (s, 9H), 1.2 (m, 2H); LCMS RT=4.22 min; [M+H]$^+$=661.1.

Example 217

Preparation of N-{3-chloro-4-[(3-fluorobenzyl)oxy]phenyl}-2-piperidin-4-yl-4,5-dihydro-2H-pyrimido[5',4':4,5]thieno[2,3-e]indazol-6-amine

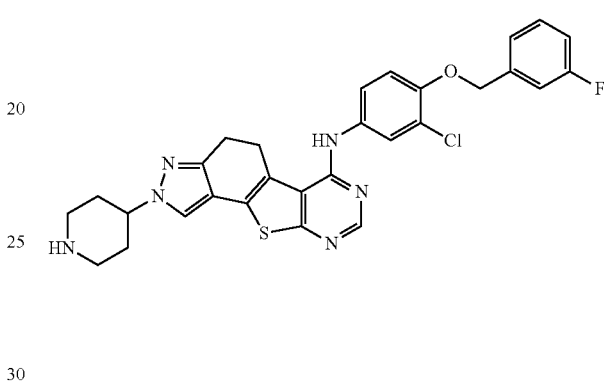

To a suspension of tert-butyl 4-[6-({3-chloro-4-[(3-fluorobenzyl)oxy]phenyl}amino)-4,5-dihydro-2H-pyrimido[5',4':4,5]thieno[2,3-e]indazol-2-yl]piperidine-1-carboxylate 1.2 g (1.8 mmol, 1 eq) in DCM (40 mL) was added trifluoroacetic acid (4.2 mL, 30 eq). The reaction mixture was stirred at rt for 3 h. The Volatile material was evaporated and the residue was diluted with EtOAc. Sat. Na$_2$CO$_3$ was added until pH about 7. The layers were separated and the aqueous layer was extracted with EtOAc (3 times) and the combined organic layers were concentrated to give a brown solid (1 g, quantitative). $^1$H-NMR (DMSO-d$_6$) δ 8.41 (s, 1H), 8.33 (s, 1H), 8.01 (s, 1H), 7.74 (d, 1H), 7.47 (m, 2H), 7.30 (m, 2H), 7.20 (m, 2H), 5.24 (s, 2H), 4.25 (m, 1H), 3.40 (t, 2H), 3.18 (m, 2H), 2.93 (t, 2H), 2.76 (t, 2H), 2.05 (m, 2H), 1.91 (m, 2H). LCMS RT=2.83 min; [M+H]$^+$=561.2.

Using the method described above and the appropriate starting materials, examples 232, and 247 were similarly prepared.

Example 218

Preparation of 2-[1-(chloroacetyl)piperidin-4-yl]-N-{3-chloro-4-[(3-fluorobenzyl)oxy]phenyl}-4,5-dihydro-2H-pyrimido[5',4':4,5]thieno[2,3-e]indazol-6-amine

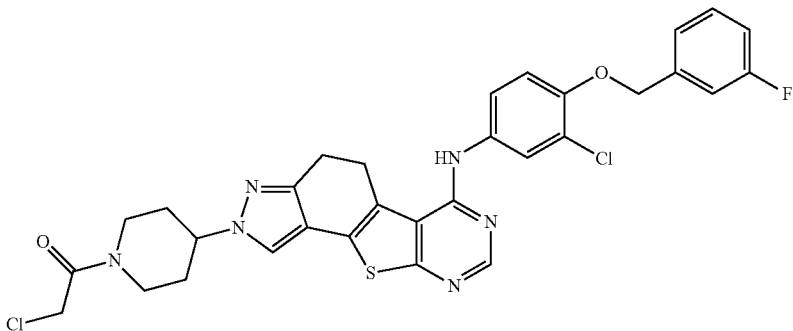

To a suspension of N-{3-chloro-4-[(3-fluorobenzyl)oxy]phenyl}-2-piperidin-4-yl-4,5-dihydro-2H-pyrimido[5',4':4,5]thieno[2,3-e]indazol-6-amine 500 mg (0.89 mmol, 1 eq) in DCM (10 mL) was added chloroacetyl chloride (100 mg, 0.89 mmol, 1 eq) and triethylamine (90 mg, 0.89 mmol, 1 eq). It was stirred at rt for 3 h after which time it was diluted with water. It was then was extracted 3 times with EtOAc. The combined organic layers were dried over $MgSO_4$ and concentrated to yield the desired product (400 mg, 70%). $^1$H-NMR (DMSO-$d_6$) δ 8.45 (broad, 1H), 8.33 (s, 1H), 8.04 (s, 1H), 7.74 (d, 1H), 7.5 (dd, 1H), 7.44 (m, 1H), 7.29 (m, 2H), 7.20 (m, 2H), 5.23 (s, 2H), 4.45 (m, 4H), 3.93 (m, 1H), 3.38 (t, 2H), 3.24 (m, 1H), 2.92 (t, 2H), 2.83 (m, 1H), 2.08 (m, 2H), 1.97 (m, 1H), 1.80 (m, 1H). LCMS RT=3.68 min; [M+H]$^+$=637.4.

Using the method described above and the appropriate starting materials, example 233 was similarly prepared.

Example 219

Preparation of N-{3-chloro-4-[(3-fluorobenzyl)oxy]phenyl}-2-(1-{[(3R)-3-(dimethylamino)pyrrolidin-1-yl]acetyl}piperidin-4-yl)-4,5-dihydro-2H-pyrimido[5',4':4,5]thieno[2,3-e]indazol-6-amine

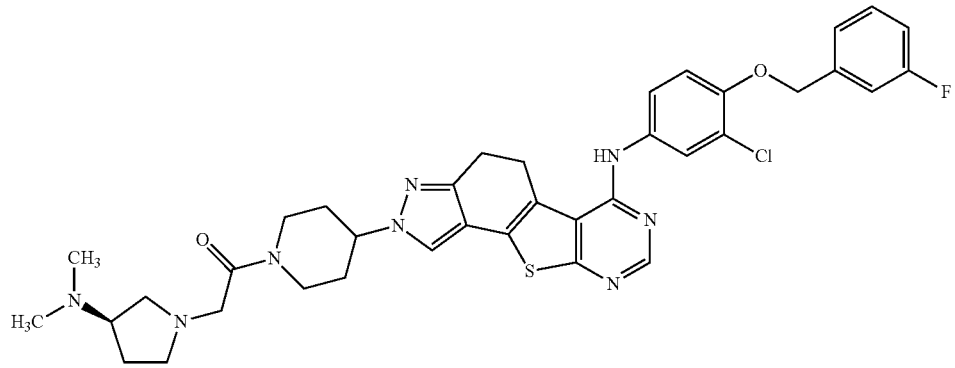

To a suspension of 2-[1-(chloroacetyl)piperidin-4-yl]-N-{3-chloro-4-[(3-fluorobenzyl)oxy]phenyl}-4,5-dihydro-2H-pyrimido[5',4':4,5]thieno[2,3-e]indazol-6-amine (60 mg, 0.09 mmol, 1 eq) in NMP (1 mL) was added 3(R)-3-dimethylamino pyrrolidine 21.5 mg (0.18 mmol, 2 eq), sodium iodide (28 mg, 0.18 mmol, 2 eq) and sodium carbonate (20 mg, 0.18 mmol, 2 eq). It was stirred at 60° C. for 16 h. The mixture was purified by preparative HPLC to yield the desired product (18 mg, 27% yield). $^1$H-NMR (DMSO-$d_6$) δ 8.41 (s, 1H), 8.33 (s, 1H), 8.02 (s, 1H), 7.74 (d, 1H), 7.5 (dd, 1H), 7.44 (m, 1H), 7.29 (m, 2H), 7.20 (m, 2H), 5.24 (s, 2H), 4.41 (m, 3H), 4.11 (m, 1H), 3.35 (m, 2H), 3.29 (t, 2H), 3.14 (m, 2H), 2.93 (t, 2H), 2.69 (m, 4H), 2.34 (m, 1H), 2.16 (m, 1H), 2.08 (s, 6H), 2.03 (m, 1H), 1.88 (m, 2H), 1.60 (m, 1H); LCMS RT=2.62 min; [M+H]$^+$=715.2.

Using the method described above and the appropriate starting materials, examples 220-224, and 234-242 were similarly prepared.

Example 225

Preparation of 4-[6-({3-chloro-4-[(3-fluorobenzyl)oxy]phenyl}amino)-4,5-dihydro-2H-pyrimido[5',4':4,5]thieno[2,3-e]indazol-2-yl]-1,1-dimethylpiperidinium trifluoroacetate

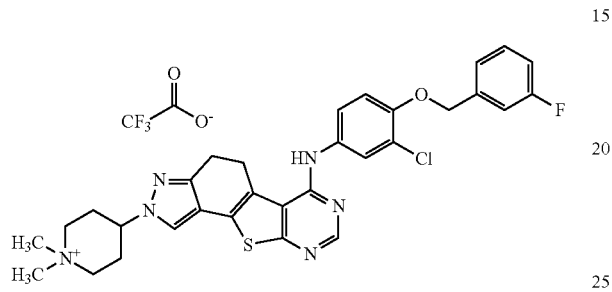

To a solution of N-{3-chloro-4-[(3-fluorobenzyl)oxy]phenyl}-2-piperidin-4-yl-4,5-dihydro-2H-pyrimido[5',4':4,5]thieno[2,3-e]indazol-6-amine (40 mg, 0.07 mmol, 1 eq) in THF (1 mL) was added acetone (8 mg, 0.14 mmol, 2 eq), sodium triacetoxyborohydride (23 mg, 0.11 mmol, 1.5 eq) and trace amount of acetic acid. It was stirred at rt for 16 h. The mixture was purified by preparative HPLC to yield the desired product (15.4 mg, 36%). $^1$H-NMR (DMSO-$d_6$) δ 8.41 (broad, 1H), 8.32 (d, 1H), 8.01 (d, 1H), 7.74 (d, 1H), 7.5 (dd, 1H), 7.44 (m, 1H), 7.29 (m, 2H), 7.20 (d, 1H), 7.15 (m, 1H), 5.24 (s, 2H), 4.04 (m, 1H), 3.36 (m, 4H), 2.92 (m, 3H), 2.74 (m, 1H), 2.25 (m, 1H), 2.02 (m, 2H), 1.89 (m, 2H), 0.99 (d, 6H). LCMS RT=2.87 min; [M+H]$^+$=603.2.

To a solution of N-{3-chloro-4-[(3-fluorobenzyl)oxy]phenyl}-2-piperidin-4-yl-4,5-dihydro-2H-pyrimido[5',4':4,5]thieno[2,3-e]indazol-6-amine (50 mg, 0.09 mmol, 1 eq) in DMF (1 mL) was added cesium carbonate (58 mg, 0.18 mmol, 2 eq) and iodomethane (13 mg, 0.09 mmol, 1 eq). It was stirred at 40° C. for 2 h. The mixture was purified by preparative HPLC to yield the desired product (29 mg, 46% yield). $^1$H-NMR (DMSO-$d_6$) δ 8.47 (broad, 1H), 8.34 (s, 1H), 8.17 (s, 1H), 7.45 (d, 1H), 7.5 (dd, 1H), 7.44 (m, 1H), 7.29 (m, 2H), 7.21 (d, 1H), 7.15 (m, 1H), 5.24 (s, 2H), 4.43 (m, 1H), 3.56 (m, 4H), 3.40 (t, 2H), 3.18 (d, 6H), 2.95 (t, 2H), 2.40 (m, 2H), 2.28 (m, 2H). LCMS RT=2.87 min; [M]$^+$=589.3.

Using the method described above and the appropriate starting materials, example 226 was similarly prepared.

Example 227

Preparation of N-{3-chloro-4-[(3-fluorobenzyl)oxy]phenyl}-2-(1-isopropylpiperidin-4-yl)-4,5-dihydro-2H-pyrimido[5',4':4,5]thieno[2,3-e]indazol-6-amine

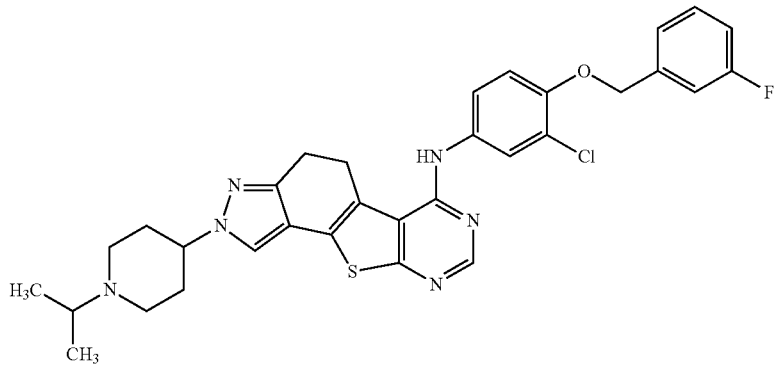

Using the method described above and the appropriate starting materials, examples 228-257 were similarly prepared.

Example 268

Preparation of 3-[6-({3-chloro-4-[(3-fluorobenzyl)oxy]phenyl}amino)-4,5-dihydro-3H-pyrimido[5',4':4,5]thieno[2,3-e]indazol-3-yl]propan-1-ol

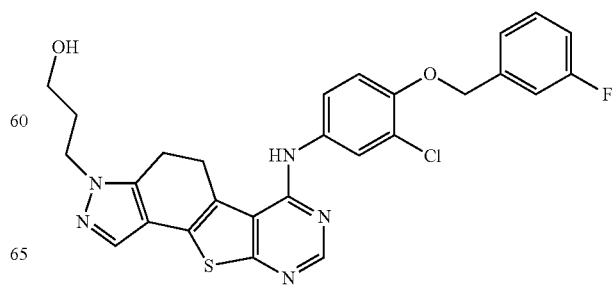

Step 1. Preparation of N-[3-(tert-Butyl-dimethyl-silanyloxy)-propyl]-hydrazinecarboxylic acid tert-butyl ester

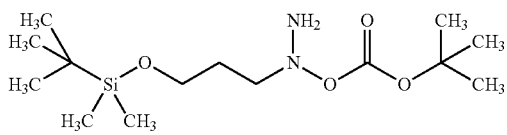

To 200 mL THF cooled to 0° C. was sequentially added N-aminophthalimide (5 g, 30.8 mmol), di-tert-butyl dicarbonate (39 g, 178.8 mmol), 4-Dimethylaminopyridine (0.38 g, 3.1 mmol), and triethylamine (24.9 ml, 178.8 mmol). The contents were stirred with warming to it over a 24 h period, after which time the solvent was removed under reduced pressure. The crude residue was triturated with EtOAc/Hex to afford N,N-bis(tert-butoxycarbonyl)aminophthalimide (7.0 g, 63%) as a white solid.

To 35 mL CH$_2$Cl$_2$ cooled to 0° C. was added N,N-Bis(tert-butoxycarbonyl)aminophthalimide (7 g, 19 mmol), followed by trifluroacetic acid (2.23 mL, 29 mmol). The contents were then stirred with warming to rt over a 30 h period, after which time the solvent was removed under reduced pressure. The crude residue was triturated with EtOAc/Hex yielding N-(tert-butoxycarbonylamino)phthalimide (3.3 g, 65%) as a white solid.

To 40 mL THF cooled to 0° C. were sequentially added N-(tert-butoxycarbonylamino)phthalimide (3.3 g, 12.6 mmol), triphenylphosphine (5 g, 18.9 mmol), and 3-[(tert-Butyldimethylsilyloxy)]propanol (3.6 g, 18.9 mmol). After the mixture had become homogenous, diisopropyl azodicarboxylate (3.72 mL, 18.9 mmol) was added as one portion. The contents were then stirred with warming to rt over a 24 h period, after which the solvent was removed under reduced pressure. To the residue was added EtOAc/Hex, and the precipitated salts filtered. The solid was washed with hexanes, and the combined filtrate concentrated to dryness in vacuo. The crude product was purified by chromatography to afford N,N-(tert-butoxycarbonyl-3-trimethylsilanyloxy-propyl)phthalimide (4.68 g, 86%) as a white solid.

To a solution of N,N-(tert-butoxycarbonyl-3-trimethylsilanyloxy-propyl)phthalimide (4.2 g, 9.7 mmol) in 180 mL THF cooled to 0° C. was added methyhydrazine (0.77 mL, 14.5 mmol). The mixture was stirred with warming to rt over a 20 h period, after which time the solid was filtered. The filtrate was concentrated to dryness, and purified by chromatography with Hex/EtOAc (6:1) to afford the final product (2.7 g, 92%) as a white solid. $^1$H-NMR (CDCl$_3$) δ 3.61 (t, 2H), 3.42 (t, 2H), 1.76 (dt, 2H), 1.43 (s, 9H), 0.86 (s, 9H), 0.02 (s, 6H); LCMS RT=3.48 min, [M+H]$^+$=305.0

Step 2. Regiocontrolled Preparation of 3-[6-({3-chloro-4-[(3-fluorobenzyl)oxy]phenyl}amino)-4,5-dihydro-3H-pyrimido[5',4':4,5]thieno[2,3-e]indazol-3-yl]propan-1-ol

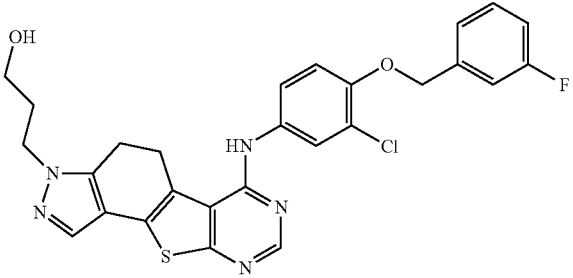

To 20 mL ethanol were added N-(3-Chloro-4-(3-fluorobenzyloxy)-phenylamine)-8-dimethylaminomethylene-5,8-dihydro-6H-benzo[4,5]thieno[2,3-d]pyrimidin-7-one (850 mg, 1.67 mmol), and then added N-[3-(tert-Butyl-dimethyl-silanyloxy)-propyl]-hydrazinecarboxylic acid tert-butyl ester (760 mg, 2.50 mmol) as a 10 mL ethanol solution via dropping funnel over a 5 min. period. The contents were stirred at reflux for 15 h, after which time they were then allowed to cool to rt. The heterogeneous mixture was concentrated under hi-vac and directly used for next step.

To the crude residue was added 15 mL CH$_2$Cl$_2$, and the mixture cooled to 0° C. To the homogeneous mixture was then added trifluoroacetic acid (7.5 mL) upon which the contents darken. The contents were stirred with warming to rt over 1 h, after which time the solvent was removed under a stream of N$_2$. The crude residue was diluted with methanol (10 mL), stirred for 5 min, then concentrated to dryness in vacuo. The residue diluted with water (20 mL), cooled to 0° C., and adjusted to pH=11 using aq. 1M NaOH. The mixture was vigorously stirred for 1 h, and then extracted with CH$_2$Cl$_2$ (3×100 mL). The combined organic layers were dried over MgSO$_4$, filtered, and concentrated in vacuo. The resulting solid was triturated with methanol to afford the desired product as a light brown solid (600 mg, 52%). $^1$H-NMR (DMSO-d$_6$) δ Note: The OH proton does not appear, 8.40 (s, 1H), 8.34 (s, 1H), 7.76 (d, 1H), 7.64 (s, 1H), 7.45-7.54 (m, 2H), 7.13-7.35 (m, 4H), 5.24 (s, 2H), 4.60 (t, 2H), 4.16 (t, 2H), 3.40 (t, 2H), 3.06 (t, 2H), 1.90 (dt, 2H); LCMS RT=3.65 min; [M+H]$^+$=536.3.

Example 269

Preparation of N-{3-chloro-4-[(3-fluorobenzyl)oxy]phenyl}-3-[3-(4-methylpiperazin-1-yl)propyl]-4,5-dihydro-3H-pyrimido[5',4':4,5]thieno[2,3-e]indazol-6-amine

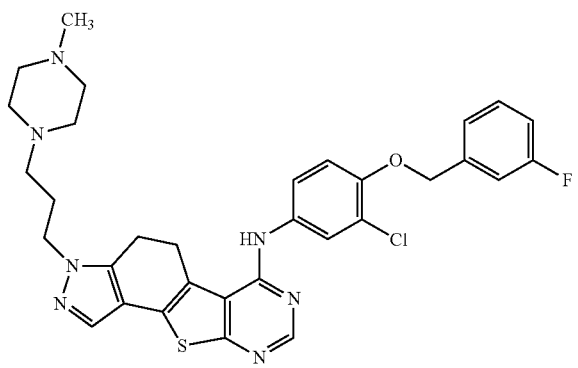

Using the methods described for the preparation of examples 116 and 126, along with the appropriate starting materials, N-{3-chloro-4-[(3-fluorobenzyl)oxy]phenyl}-3-[3-(4-methylpiperazin-1-yl)propyl]-4,5-dihydro-3H-pyrimido[5',4':4,5]thieno[2,3-e]indazol-6-amine was similarly prepared from 3-[6-({3-chloro-4-[(3-fluorobenzyl)oxy]phenyl}amino)-4,5-dihydro-3H-pyrimido[5',4':4,5]thieno[2,3-e]indazol-3-yl]propan-1-ol. The product was collected (17 mg, 12%) as white solid. $^{1}$H-NMR (CD$_{3}$OD) δ 8.23 (s, 1H), 7.73 (d, 1H), 7.57 (s, 1H), 7.34-7.38 (m, 2H), 7.24-7.28 (m, 2H), 7.01-7.15 (m, 2H), 4.17 (t, 2H), 3.39 (t, 2H), 3.12 (t, 2H), 2.48 (br s, 8H), 2.33 (t, 2H), 2.26 (s, 3H), 2.03 (dt, 2H); LCMS RT=2.73 min; [M+H]$^{+}$=618.2.

Using the method described above and the appropriate starting materials, examples 270-273 were similarly prepared.

Example 275

Preparation of 2-(6-{[1-(3-fluorobenzyl)-1H-indazol-5-yl]amino}-4,5-dihydro-2H-pyrimido[5',4':4,5]thieno[2,3-e]indazol-2-yl)ethanol

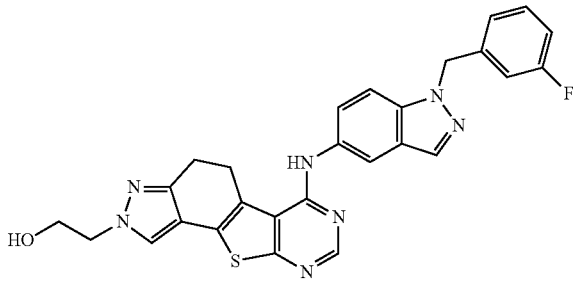

Step 1. Preparation of 5-amino-1-N-(3-fluorobenzyl)indazole

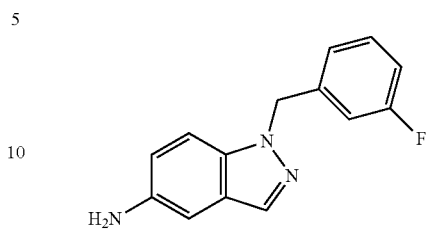

5-nitroindazole (15 g, 92 mmol, 1 eq), 3-fluorobenzylbromide (14.7 mL, 119.5 mmol, 1.3 eq) and potassium carbonate 25.4 g (184 mmol, 2 equiv) were suspended in 150 mL acetonitrile. The reaction mixture was stirred at 70° C. for 12 h, and then allowed to cool to rt. The resultant solid was filtered and washed with CH$_{2}$Cl$_{2}$, and the filtrate concentrated in vacuo. The crude mixture of regioisomeric products was purified by column chromatography (5:1 to 4:1 Hex/EtOAc), yielding 5-nitro-1-N-(3-fluorobenzyl)indazole (7.9 g, 32%) and 5-nitro-2-N-(3-fluorobenzyl)indazole (9.2 g, 37%) as yellow solids.

5-nitro-1-N-(3-fluorobenzyl)indazole (7.9 g, 29.1 mmol, 1 equiv) and iron (8.13 g, 145.6 mmol, 5 equiv) were mixed in 200 mL acetic acid and 50 mL EtOAc, and were stirred at rt for 36 h. The reaction mixture was filtered through a pad of Celite®. The filtrate was concentrated in vacuo to 10 mL volume. The contents were diluted with water (10 mL) and neutralized with saturated Na$_{2}$CO$_{3}$ solution. The solution was extracted with EtOAc (3×500 mL), the combined organic layers dried over MgSO$_{4}$, filtered, and concentrated in vacuo. The resulting crude material was purified by column chromatography eluting with hexanes/EtOAC (4:1 to 3:1) to give 5-amino-1-N-(3-fluorobenzyl)indazole (5.32 g, 76%) as a light brown solid. $^{1}$H-NMR (DMSO-d$_{6}$) δ 7.72 (s, 1H), 7.22-7.36 (m, 2H), 6.87-7.05 (m, 3H), 6.70-6.77 (m, 2H), 5.48 (s, 2H), 4.78 (br s, 2H); LCMS RT=1.66 min; [M+H]$^{+}$=242.2.

1-Pyridin-2-ylmethyl-1H-indazol-5-ylamine was prepared using the same method described above and the appropriate reagents; LC/MS RT=1.03 min; [M+H]$^{+}$=225.2.

Step 2. Preparation of N-[1-(3-fluorobenzyl)-1H-indazol-5-yl]amino]-5,8-dihydro-6H-spiro[1-benzothieno[2,3-d]pyrimidine-7,2'-[1,3]dioxolan]-4-amine hydrochloride

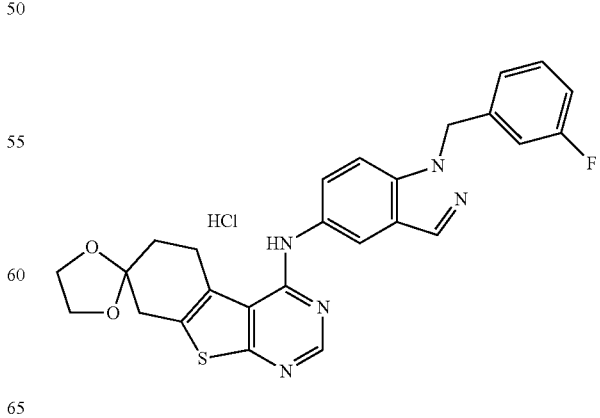

To isopropanol (80 mL) was sequentially added 4-chloro-5,8-dihydro-6H-spiro[1-benzothieno[2,3-d]pyrimidine-7,2'-

[1,3]dioxolane] (6.24 g, 22.1 mmol), 5-amino-1-N-(3-fluorobenzyl)indazole (5.38 g, 22.3 mmol), and 4N HCl in dioxane (0.05 mL). The suspension was stirred with heating to 80° C., upon which time the contents turn brown and homogeneous. After 8 h, the heterogeneous mixture was removed from heating, and allowed to cool to rt. The resultant precipitate was collected by filtration as a light-brown solid (8.3 g, 77%). $^1$H-NMR (DMSO-d$_6$) δ 8.80 (s, 1H), 8.40 (s, 1H), 8.35 (s, 1H), 7.98 (s, 1H), 7.71 (d, 1H), 7.50 (d, 1H), 7.30-7.38 (m, 1H), 7.00-7.14 (m, 3H), 5.70 (s, 2H), 3.99 (s, 4H), 3.27 (t, 2H), 3.02 (s, 2H), 1.95 (t, 2H); LCMS RT=3.16 min; [M+H]$^+$=488.4.

Step 3. Preparation of N-[1-(3-fluorobenzyl)-1H-indazol-5-yl]amino]-5,8-dihydro[1]benzothieno[2,3-d]pyrimidin-7(6H)-one hydrochloride

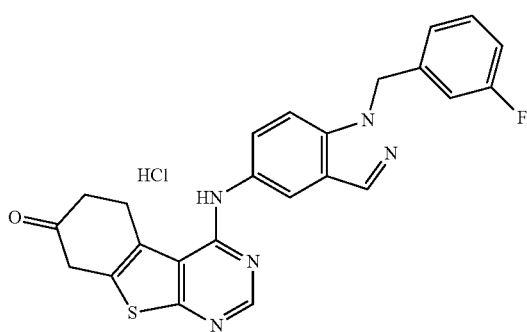

The title compound was prepared following the method described for example 98 step 3, utilizing N-[1-(3-fluorobenzyl)-1H-indazol-5-yl]amino]-5,8-dihydro-6H-spiro[1-benzothieno[2,3-d]pyrimidine-7,2'-[1,3]dioxolan]-4-amine hydrochloride (8.3 g, 17.0 mmol). The desired product was collected as a light brown solid (6.4 g, 85%). $^1$H-NMR (DMSO-d$_6$) δ 8.40 (s, 1H), 8.34 (s, 1H), 8.10 (s, 1H), 7.98 (s, 1H), 7.69 (d, 1H), 7.50 (d, 1H), 7.28-7.38 (m, 1H), 7.00-7.15 (m, 3H), 5.66 (s, 2H), 3.77 (s, 2H), 3.50 (t, 2H), 2.65 (t, 2H); LCMS RT=3.34 min; [M+H]$^+$=444.4.

Step 4. Preparation of N-[1-(3-fluorobenzyl)-1H-indazol-5-yl]amino]-8-dimethylaminomethylene-5,8-dihydro-6H-benzo[4,5]thieno[2,3-d]pyrimidin-7-one

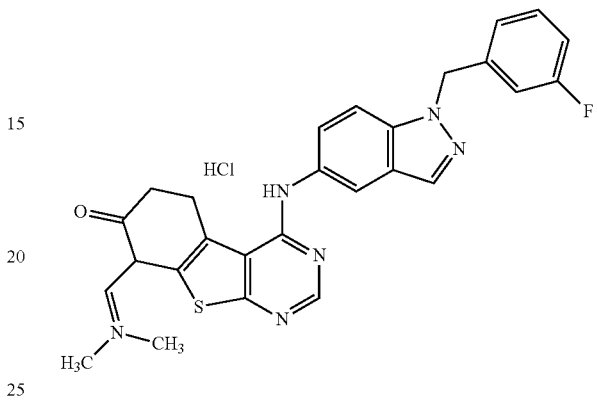

The title compound was prepared following the method described for example 98 step 4, utilizing N-[1-(3-fluorobenzyl)-1H-indazol-5-yl]amino]-5,8-dihydro[1]benzothieno[2,3-d]pyrimidin-7(6H)-one hydrochloride (6.33 g, 14.3 mmol) and dimethylformamide-dimethylacetal (3.79 mL, 28.6 mmol). The desired product was collected as a dark yellow solid (6.3 g, 89%). $^1$H-NMR (DMSO-d$_6$) δ 8.25 (s, 1H), 8.21 (s, 1H), 8.09 (s, 1H), 7.97 (s, 1H), 7.65-7.72 (m, 2H), 7.49 (d, 1H), 7.30-7.38 (m, 1H), 6.98-7.10 (m, 3H), 5.66 (s, 2H), 3.27 (t, 2H), 3.12 (s, 6H), 2.55 (t, 2H); LCMS RT=2.90 min; [M+H]$^+$=499.4

Step 5. Regiocontrolled Preparation of 2-(2-{[tert-butyl(dimethyl)silyl]oxy}ethyl)-N-[1-(3-fluorobenzyl)-1H-indazol-5-yl]amino]-4,5-dihydro-2H-pyrimido[5',4':4,5]thieno[2,3-e]indazol-6-amine

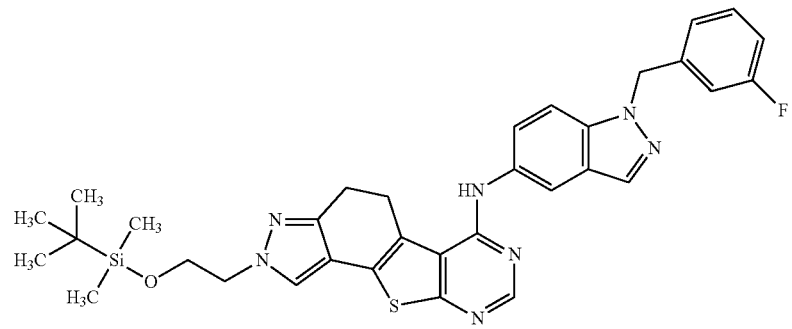

The title compound was prepared following the method described for example 98 step 5, utilizing N-[1-(3-fluorobenzyl)-1H-indazol-5-yl]amino]-8-dimethylaminomethylene-5,8-dihydro-6H-benzo[4,5]thieno[2,3-d]pyrimidin-7-one (3.0 g, 6.0 mmol) and 2-tert-butyldimethylsilyloxy-1-tert-butyloxycarbonyl-ethylhydrazine (2.72 g, 8.4 mmol). The desired product was collected as a light brown solid (2.5 g, 66%). $^1$H-NMR (DMSO-d$_6$) δ 8.59 (s, 1H), 8.39 (s, 1H), 8.20 (s, 1H), 8.06 (s, 1H), 7.98 (s, 1H), 7.76 (d, 1H), 7.60 (d, 1H), 7.40-7.48 (m, 1H), 7.08-7.21 (m, 3H), 5.78 (s, 2H), 4.00 (t, 2H), 3.94 (t, 2H), 3.46 (t, 2H), 2.95 (t, 2H). 0.90 (s, 9H), 0.01 (s, 6H); LCMS RT=4.42 min; [M+H]+=626.4

Using the method described above (steps 1-5) and the appropriate starting materials, N-(1-benzyl-1H-indazol-5-yl)-2-(2-{[tert-butyl(dimethyl)silyl]oxy}ethyl)-4,5-dihydro-2H-pyrimido[5',4':4,5]thieno[2,3-e]indazol-6-amine was similarly prepared.

Step 6. Preparation of 2-(6-{[1-(3-fluorobenzyl)-1H-indazol-5-yl]amino}-4,5-dihydro-2H-pyrimido[5',4': 4,5]thieno[2,3-e]indazol-2-yl)ethanol

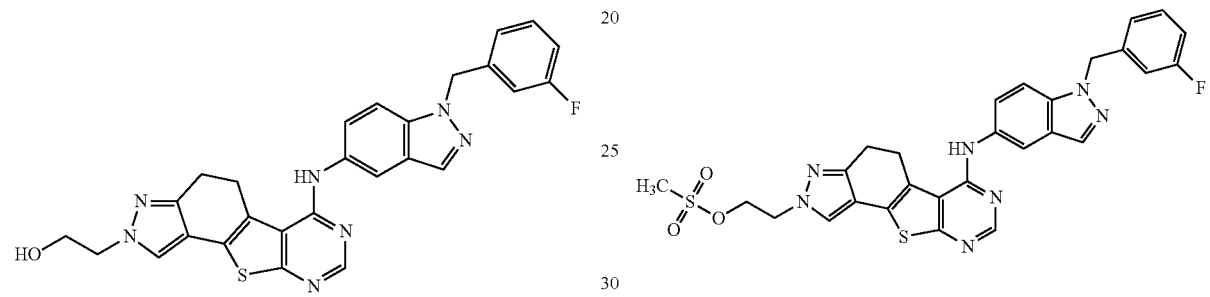

To 75 mL THF cooled to 0° C. was added 2-(2-{[tert-butyl (dimethyl)silyl]oxy}ethyl)-N-[1-(3-fluorobenzyl)-1H-indazol-5-yl]amino]-4,5-dihydro-2H-pyrimido[5',4':4,5]thieno [2,3-e]indazol-6-amine (2.4 g, 3.8 mmol). To the homogeneous mixture was then added aq. 2M HCl (2.8 mL), upon which the contents slowly become heterogenous with a yellow precipitate. The contents were stirred with warming to rt over a 2 h period, after which time the solvent was removed under reduced pressure. The crude residue was diluted with EtOAc (10 mL) and aq. 2M Na₂CO₃ (150 mL) to attain a pH=11 solution which was vigorously stirred for 1 h. The contents were filtered to a light yellow solid which was washed with water (400 mL), and then hexanes (500 mL). The collected product was dried under hi-vac, to afford the final product (1.84 g, 91%) as a light yellow solid. ¹H-NMR (DMSO-d₆) δ 8.49 (s, 1H), 8.23 (s, 1H), 8.08 (s, 1H), 7.95 (s, 1H), 7.90 (s, 1H), 7.64 (d, 1H), 7.50 (d, 2H), 7.30 (td, 1H), 6.97-7.10 (m, 2H), 5.63 (s, 2H), 4.80-5.00 (br s, 1H), 4.05 (t, 2H), 3.70 (t, 2H), 3.15 (t, 2H), 2.85 (t, 2H); LCMS RT=2.83 min; [M+H]+=512.3.

Using the method described above and the appropriate starting materials [N-(1-benzyl-1H-indazol-5-yl)-2-(2-{ [tert-butyl(dimethyl)silyl]oxy}ethyl)-4,5-dihydro-2H-pyrimido[5',4':4,5]thieno[2,3-e]indazol-6-amine], example 302 was similarly prepared.

Example 276

Preparation of 2-(6-{[1-(3-fluorobenzyl)-1H-indazol-5-yl]amino}-4,5-dihydro-2H-pyrimido[5',4':4,5] thieno[2,3-e]indazol-2-yl)ethyl methanesulfonate The title compound was prepared following the procedure described for example 57 method A, utilizing 2-(6-{[1-(3-fluorobenzyl)-1H-indazol-5-yl]amino}-4,5-dihydro-2H-pyrimido[5',4':4,5]thieno[2,3-e]indazol-2-yl)ethanol (1.53 g, 3.0 mmol), methanesulfonic anhydride (938 mg, 5.4 mmol), and pyridine (1.0 mL, 9.9 mmol). The desired product was collected as a light brown solid (1.72 g, 98%). ¹H-NMR (DMSO-d₆) δ 8.49 (s, 1H), 8.25 (s, 1H), 8.10 (s, 1H), 8.00 (s, 1H), 7.97 (s, 1H), 7.65 (d, 1H), 7.50 (d, 1H), 7.30 (d, 1H), 6.95-7.15 (m, 3H), 5.70 (s, 2H), 4.53 (t, 2H), 4.40 (t, 2H), 3.40 (t, 2H), 3.10 (s, 3H), 2.92 (t, 2H); LCMS RT=2.93 min; [M+H]+=590.4

Using the method described above and the appropriate starting materials, example 303 was similarly prepared.

Example 277

Preparation of N-{3-chloro-4-[(3-fluorobenzyl)oxy] phenyl}-2-[2-(4-methylpiperazin-1-yl)ethyl]-4,5-dihydro-2H-pyrimido[5',4':4,5]thieno[2,3-e]indazol-6-amine

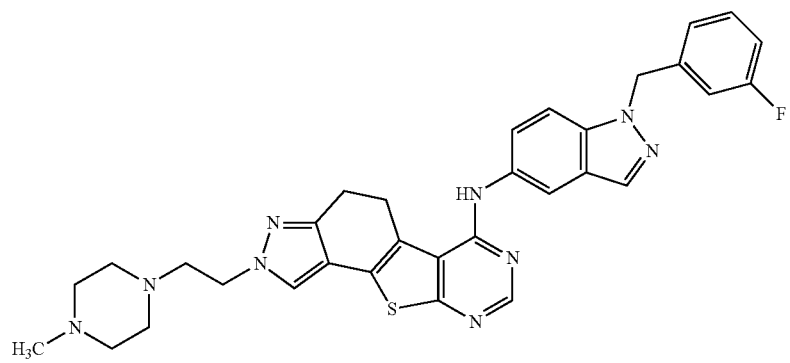

To 3 mL CH₃CN were sequentially added 2-(6-{[1-(3-fluorobenzyl)-1H-indazol-5-yl]amino}-4,5-dihydro-2H-pyrimido[5',4':4,5]thieno[2,3-e]indazol-2-yl)ethyl methanesulfonate (100 mg, 9.67 mmol), 1-methylpiperazine (0.025 mL, 0.25 mmol), and diisopropylethylamine (0.06 mL, 0.34 mmol). The mixture was stirred at 70° C. for 14 h after which time the mixture was removed from heating, and allowed to cool to rt. The reaction mixture was diluted with water and extracted with EtOAc. The combined organic layers were concentrated under reduced pressure and purified by prep HPLC. The combined fractions were treated with saturated Na₂CO₃ and dried to afford free base product (90 mg, 89%) as a white solid. ¹H-NMR (DMSO-d₆) δ 8.53 (s, 1H), 8.29 (s, 1H), 8.12 (s, 1H), 7.97 (d, 1H), 7.95 (s, 1H), 7.70 (d, 1H), 7.49 (dd, 1H), 7.31-7.40 (m, 7.00-7.16 (m, 3H), 5.70 (s, 2H), 4.15 (t, 2H), 3.40 (t, 2H), 2.90 (t, 2H), 2.67 (t, 2H), 2.40-2.48 (br s, 4H), 2.25-2.35 (br s, 4H), 2.14 (s, 3H). LCMS RT=2.82 min, [M+H]⁺=594.3

Using the method described above and the appropriate starting materials, examples 279-287, and 304-308 were similarly prepared.

Example 289

Preparation of 2-(6-{[1-(3-fluorobenzyl)-1H-indazol-5-yl]amino}-4,5-dihydro-3H-pyrimido[5',4':4,5]thieno[2,3-e]indazol-3-yl)ethanol

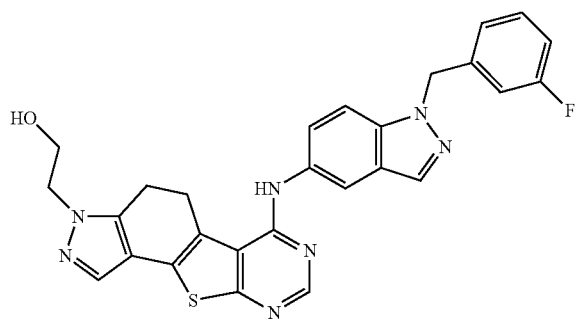

To 70 mL ethanol were added N-[1-(3-fluorobenzyl)-1H-indazol-5-yl]amino]-8-dimethylaminomethylene-5,8-dihydro-6H-benzo[4,5]thieno[2,3-d]pyrimidin-7-one (2.7 g, 5.42 mmol), and then 2-tert-butyloxycarbonyl-2-hydroxyethylhydrazine (1.48 g, 7.58 mmol) as an 8 mL ethanol solution. The contents were stirred at reflux for 24 h. Upon cooling down to rt, precipitation was observed. The heterogeneous mixture was concentrated to dryness and used directly in next step.

The crude residue collected was added to CH₂Cl₂ (48 mL) and cooled to 0° C. To the stirring suspension was added TFA (24 mL, 99%) dropwise, during which time the contents become dark brown and homogeneous. The mixture was stirred with warming to rt over a 12 h period. The contents were concentrated to near dryness, diluted with EtOAc (300 mL), and stirred with cooling to 0° C. To the stirring mixture was added aq 1N NaOH, to afford a pH=10 mixture which becomes heterogeneous on complete addition of the base. The heterogeneous mixture was filtered and the filter cake washed with water. The collected solid was triturated with EtOAc (40 mL) to furnish the final product (1.91 g, 69% for the two steps) as a light tan solid. ¹H-NMR (DMSO-d₆) δ 8.48 (s, 1H), 8.25 (s, 1H), 8.10 (s, 1H), 7.98 (s, 1H), 7.65 (d, 1H), 7.60 (s, 1H), 7.50 (dd, 1H), 7.30-7.38 (m, 1H), 6.97-7.10 (m, 3H), 5.68 (s, 2H), 4.90 (t, 1H), 4.15 (t, 2H), 3.70 (t, 2H), 3.40 (t, 2H), 3.03 (t, 2H); LCMS RT=3.16 min; [M+H]⁺=512.4.

Using the method described above and the appropriate starting materials, example 310 was similarly prepared.

Example 290

Preparation of 2-(6-{[1-(3-fluorobenzyl)-1H-indazol-5-yl]amino}-4,5-dihydro-3H-pyrimido[5',4':4,5]thieno[2,3-e]indazol-3-yl)ethyl methanesulfonate

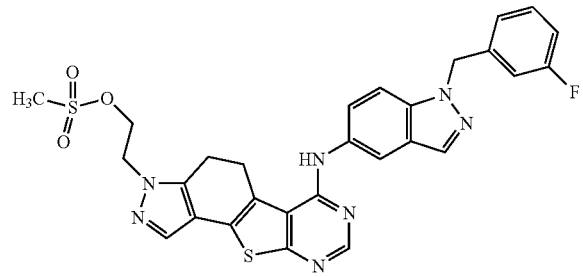

To 50 mL CH₂Cl₂ cooled to 0° C. were sequentially added 2-(6-{[1-(3-fluorobenzyl)-1H-indazol-5-yl]amino}-4,5-dihydro-3H-pyrimido[5',4':4,5]thieno[2,3-e]indazol-3-yl)ethanol (1.5 g, 2.93 mmol), pyridine (0.98 mL, 9.68 mmol), and methanesulfonyl anhydride (919 mg, 5.28 mmol). The opaque brown suspension was stirred with warming to rt over a 2 h period, after which time stirring was halted. The entire mixture was poured onto CH₂Cl₂/aq. Na₂CO₃ (1200 mL, 1:5). The organic layer was separated and dried over MgSO₄, filtered, and the solvent removed under reduced pressure to afford the desired product (1.7 g, 98%) as a light brown solid. ¹H-NMR (DMSO-d₆) δ 8.56 (s, 1H), 8.29, (s, 1H), 8.15 (s, 1H), 7.98 (s, 1H), 7.75 (d, 1H), 7.70 (s, 1H), 7.50 (dd, 1H), 7.30-7.38 (m, 1H), 6.97-7.13 (m, 3H), 5.70 (s, 2H), 4.62 (d, 2H), 4.50 (d, 2H), 3.41 (t, 2H), 3.08 (s, 3H), 3.04 (t, 2H); LCMS RT=2.76 min; [M+H]⁺=590.4.

Example 291

Preparation of N-[1-(3-fluorobenzyl)-1H-indazol-5-yl]-3-[2-(1H-imidazol-1-yl)ethyl]-4,5-dihydro-3H-pyrimido[5',4':4,5]thieno[2,3-e]indazol-6-amine

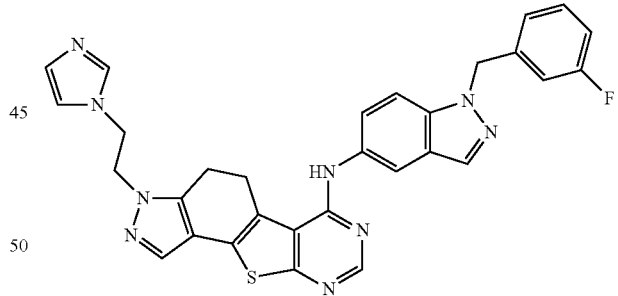

The title compound was prepared following the procedure described for example 277, utilizing 2-(6-{[1-(3-fluorobenzyl)-1H-indazol-5-yl]amino}-4,5-dihydro-3H-pyrimido[5',4':4,5]thieno[2,3-e]indazol-3-yl)ethyl methanesulfonate (1.53 g, 3.0 mmol), imidazole (17 mg, 0.25 mmol), and diisopropylethylamine (0.06 mL, 0.34 mmol). The desired product was collected as a white solid (37 mg, 39%). ¹H-NMR (CD₂Cl₂-d₂) δ 8.26 (s, 1H), 8.04 (s, 1H), 7.98 (s, 1H), 7.65 (s, 1H), 7.50 (d, 1H), 7.40 (d, 1H), 7.21-7.38 (m, 2H), 6.90-7.00 (m, 3H), 6.82 (dd, 1H), 6.72 (s, 1H), 5.60 (s, 2H), 4.42 (t, 2H), 4.35 (t, 2H), 3.17 (t, 2H), 2.40 (t, 2H); LCMS RT=2.58 min; [M+H]⁺=562.4

Using the method described above and the appropriate starting materials, examples 292-300 was similarly prepared.

Example 311

Preparation of 2-[6-({3-chloro-4-[(3-fluorobenzyl)oxy]phenyl}amino)-4,5-dihydro-2H-pyrimido[5',4':4,5]thieno[2,3-e]indazol-2-yl]ethyl sulfamate

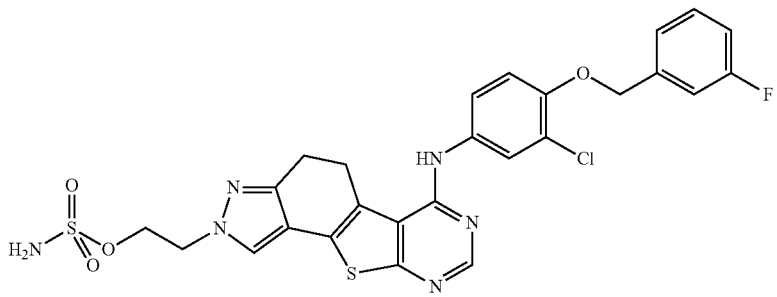

To 5 mL DMA cooled to 5° C. was added 2-[6-({3-chloro-4-[(3-fluorobenzyl)oxy]phenyl}amino)-4,5-dihydro-2H-pyrimido[5',4':4,5]thieno[2,3-e]indazol-2-yl]ethanol (100 mg, 0.19 mmol) followed by chlorosulfonyl amine (221 mg, 1.9 mmol). The mixture was stirred with warming to rt over a 2 h period, after which time stirring was halted. The entire mixture was poured onto cold brine (10 mL), upon which precipitation of a solid occurs. The mixture was filtered, and the filtrate extracted with $CH_2Cl_2$ (3×10 mL). The combined organic layers were dried over $MgSO_4$, filtered, and the solvent removed under reduced pressure. The crude residue was purified by reverse phase HPLC. The product fractions were combined and diluted with $CH_2Cl_2$ (50 mL), and neutralized with $NaHCO_3$ (50 mL). The organic layer was dried over $MgSO_4$, filtered, and the solvent removed under reduced pressure to afford the final pure product (30 mg, 26%) as a white solid. $^1$H-NMR (DMSO-$d_6$) δ 8.40 (s, 1H), 8.33 (s, 1H), 7.98 (s, 1H), 7.75 (s, 1H), 7.59 (s, 2H), 7.51 (dd, 1H), 7.40 (dd, 1H), 6.91-7.11 (m, 4H), 5.21 (s, 2H), 4.38 (br s, 4H), 3.32 (t, 2H), 2.90 (t, 2H); LCMS RT=3.45 min; $[M+H]^+$=601.2.

Example 312

Preparation of N-{3-chloro-4-[(3-fluorobenzyl)oxy]phenyl}-2-(2-methoxyethyl)-4,5-dihydro-2H-pyrimido[5',4':4,5]thieno[2,3-e]indazol-6-amine

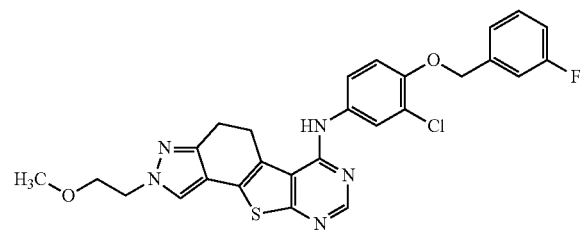

To 4 mL DMF cooled to 0° C. was added sodium hydride (16 mg (60%), 0.40 mmol). To the slightly yellow and heterogeneous mixture was added 2-[6-({3-chloro-4-[(3-fluorobenzyl)oxy]phenyl}amino)-4,5-dihydro-2H-pyrimido[5',4':4,5]thieno[2,3-e]indazol-2-yl]ethanol (100 mg, 0.19 mmol) as a 1 mL DMF solution, upon which the contents become brown and homogenous. The contents were allowed to stir with warming to it over 10 min., and added was iodomethane (0.01 mL, 0.23 mmol). The mixture was stirred for 90 min., after which time water (0.5 mL) was added. The contents were concentrated under reduced pressure to dryness, and the residue diluted with $CH_2Cl_2$ (10 mL). The organic layer was washed with water (3×10 mL). The organic layer was dried over $MgSO_4$, filtered, and the solvent removed under reduced pressure. The crude residue was purified by reverse phase HPLC. The fractions for each respective product were combined and diluted with $CH_2Cl_2$ (50 mL), and neutralized with $NaHCO_3$ (50 mL). The respective organic layers were dried over $MgSO_4$, filtered, and the solvent removed under reduced pressure to afford the final pure products. Example 312 (15 mg, 15%) and N-{3-chloro-4-[(3-fluorobenzyl)oxy]phenyl}-2-(2-methoxyethyl)-N-methyl-4,5-dihydro-2H-pyrimido[5',4':4,5]thieno[2,3-e]indazol-6-amine (8 mg, 8%) were each collected as white solids. Data for example 312: $^1$H-NMR ($CD_2Cl_2$-$d_2$) δ 8.50 (s, 1H), 7.39 (s, 1H), 7.20-7.28 (m, 1H), 7.07-7.17 (m, 2H), 6.90-6.99 (m, 2H), 6.72 (d, 1H), 6.62 (d, 1H), 4.99 (s, 2H), 4.08 (t, 2H), 3.80 (t, 2H), 3.42 (s, 3H), 2.48 (t, 2H), 2.20 (t, 2H); LCMS RT=3.32 min; $[M+H]^+$=536.3. Data for N-{3-chloro-4-[(3-fluorobenzyl)oxy]phenyl}-2-(2-methoxyethyl)-N-methyl-4,5-dihydro-2H-pyrimido[5',4':4,5]thieno[2,3-e]indazol-6-amine: $^1$H-NMR ($CD_2Cl_2$-$d_2$) δ 8.52 (s, 1H), 7.40 (s, 1H), 7.20-7.29 (m, 1H), 7.07-7.17 (m, 2H), 7.00 (s, 1H), 6.90-6.99 (m, 1H), 6.70 (d, 1H), 6.60 (d, 1H), 4.99 (s, 2H), 4.10 (t, 2H), 3.60 (t, 2H), 3.42 (s, 3H), 3.02 (s, 3H), 2.48 (t, 2H), 2.21 (t, 2H); LCMS RT=3.67 min; $[M+H]^+$=550.4.

Example 314

Preparation of 2-[6-({3-chloro-4-[(3-fluorobenzyl)oxy]phenyl}amino)-4,5-dihydro-2H-pyrimido[5',4':4,5]thieno[2,3-e]indazol-2-yl]ethyl N-(tert-butoxycarbonyl)glycinate

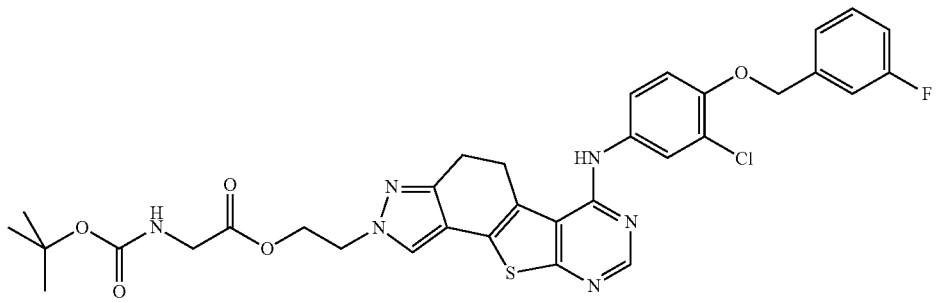

To a 5 mL $CH_2Cl_2$ solution of 2-[6-({3-chloro-4-[(3-fluorobenzyl)oxy]phenyl}amino)-4,5-dihydro-2H-pyrimido[5',4':4,5]thieno[2,3-e]indazol-2-yl]ethanol were sequentially added 1-[3-(Dimethylamino)propyl]-3-ethylcarbodiimide hydrochloride (EDCl) (74 mg, 0.38 mmol), 4-(Dimethylamino)pyridine (DMAP) (38 mg, 0.31 mmol) and a 2 mL $CH_2Cl_2$ solution N-Boc-glycine (67 mg, 0.38 mmol) via syringe. The initially opaque mixture was allowed to stir at rt for 30 min., after which the mixture is brown and homogenous. The reaction mixture was diluted with EtOAc (20 mL) and poured onto aq. $NH_4Cl$ (5 mL). The layers were separated, and the aqueous layer washed with EtOAC (5 mL). The combined organic layers were dried over $MgSO_4$, filtered, and the solvent removed under reduced pressure. The crude residue was triturated with MeOH (5 mL) to afford the desired product (100 mg, 77%) as an off-white solid. $^1$H-NMR ($CD_2Cl_2$-$d_2$) δ 8.35 (s, 1H), 7.72 (s, 1H), 7.44 (s, 1H), 7.38 (d, 1H), 7.30 (dd, 2H), 7.18 (d, 2H), 6.93-7.00 (m, 2H), 5.11 (s, 2H), 4.90-5.00 (br s, 1H), 4.40 (t, 2H), 4.28 (t, 2H), 3.78 (d, 2H), 3.27 (t, 2H), 3.00 (t, 2H), 1.37 (s, 9H); LCMS RT=3.84 min; [M+H]$^+$=679.3.

Example 315

Preparation of 2-[6-({3-chloro-4-[(3-fluorobenzyl)oxy]phenyl}amino)-4,5-dihydro-2H-pyrimido[5',4':4,5]thieno[2,3-e]indazol-2-yl]ethyl glycinate

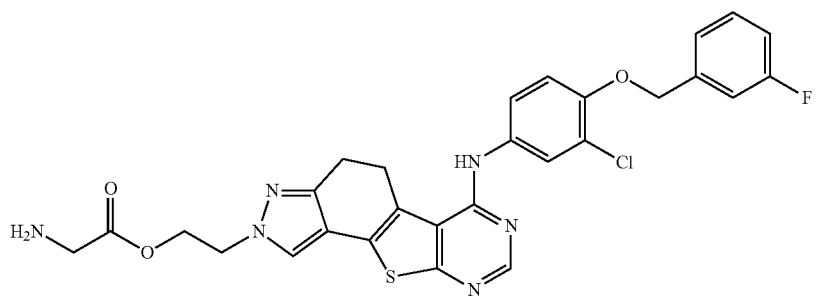

To 5 mL $CH_2Cl_2$ cooled to 0° C. was added 2-[6-({3-chloro-4-[(3-fluorobenzyl)oxy]phenyl}amino)-4,5-dihydro-2H-pyrimido[5',4':4,5]thieno[2,3-e]indazol-2-yl]ethyl N-(tert-butoxycarbonyl)glycinate. To the stirring suspension was added TFA (1 mL, 99%) dropwise, during which time the contents become dark brown and homogeneous. The mixture was stirred with warming to rt over a 12 h period. The contents were cooled to 0° C., and diluted with EtOAc (6 mL). The stirring mixture was neutralized with aq. $NaHCO_3$, and then aq 1N NaOH, to afford a pH=7 mixture. The mixture was then extracted with $CH_2Cl_2$/MeOH (3:1, 3×20 mL). The combined organic layers were washed with brine (30 mL), dried over $MgSO_4$, filtered, and concentrated in vacuo. The crude product was purified by reverse phase HPLC. The product fractions were combined and diluted with $CH_2Cl_2$ (50 mL), and neutralized with $NaHCO_3$ (50 mL). The organic layer was dried over MgSO$_4$, filtered, and the solvent removed under reduced pressure to afford the final pure product (20 mg, 31%) as a white solid. $^1$H-NMR (DMSO-d$_6$) δ 8.50 (s, 1H), 8.40 (s, 1H), 8.12 (s, 1H), 7.81 (s, 1H), 7.57 (dd, 1H), 7.50 (dd, 1H), 7.32-7.40 (m, 2H), 7.20-7.30 (m, 2H), 5.30 (s, 2H), 4.45 (t, 2H), 4.38 (t, 2H), 4.16 (t, 2H), 3.78 (d, 2H), 3.40 (t, 2H), 2.98 (t, 2H); LCMS RT=2.85 min; [M+H]$^+$=579.1.

Example 316

Preparation of 2-methyl-4-({3-[2-(4-methylpiperazin-1-yl)ethyl]-4,5-dihydro-3H-pyrimido[5',4':4,5]thieno[2,3-e]indazol-6-yl}amino)phenol

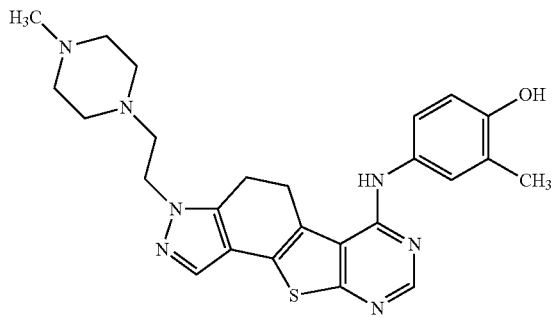

Step 1. Preparation of 2-{6[2-(4-nitro-phenyl)-ethoxy]-4,5-dihydro-10-thia-2,3,7,9-tetraaza-cyclopenta[a]fluoren-3-yl}-ethanol

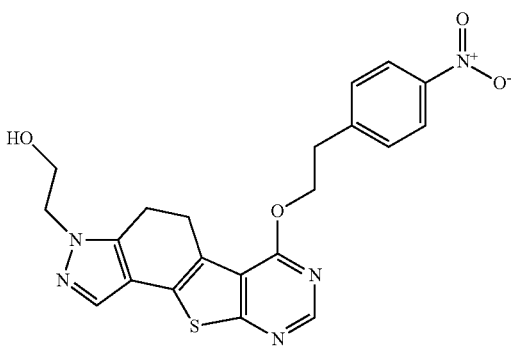

This compound was prepared in a similar fashion as described in Example 80 starting from (8E)-8-[(dimethylamino)methylene]-4-[2-(4-nitrophenyl)ethoxy]-5,8-dihydro[1]benzothieno[2,3-d]pyrimidin-7(6H)-one (7.05 g, 16.61 mmol) and 2-tert-butyloxycarbonyl-2-hydroxyethylhydrazine (4.39 g, 24.91 mmol). The desired product was obtained as a yellow solid (3.82 g, 53%). $^1$H-NMR (DMSO-d$_6$) δ 8.50 (s, 1H), 8.18 (m, 2H), 7.64 (m, 3H), 4.88 (m, 1H), 4.77 (t, 2H, J=6.1 Hz), 4.10 (t, 2H, J=5.5 Hz), 3.68 (m, 2H), 3.28 (m, 2H), 3.05 (m, 2H), 2.96 (m, 2H); LCMS RT=2.92 min; [M+H]$^+$=438.1

Step 2. Preparation of 3-(2-bromo-ethyl)-6-[2-(4-nitro-phenyl)-ethoxy]-4,5-dihydro-3H-10-thia-2,3,7,9-tetraaza-cyclopenta[a]fluorene

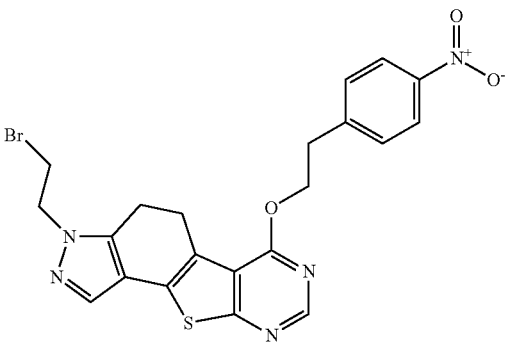

This compound was prepared in a similar fashion as described in Example 48 step 5 starting from 2-{6[2-(4-nitrophenyl)-ethoxy]-4,5-dihydro-10-thia-2,3,7,9-tetraaza-cyclopenta[a]fluoren-3-yl}-ethanol (4.2 g, 9.6 mmol), carbontetrabromide (6.37 g, 19.20 mmol), and triphenyl phosphine (5.03 g, 19.20 mmol). The desire product was obtained as a light yellow solid (2.6 g) in 54% yield. LCMS RT=3.55 min; [M+H]$^+$=500.1/502.0.

Step 3. Preparation of 3-[2-(4-methyl-piperazin-1-yl)-ethyl]-6-[2-(4-nitro-phenyl)-ethoxy]-4,5-dihydro-3H-10-thia-2,3,7,9-tetraaza-cyclopenta[a]fluorene

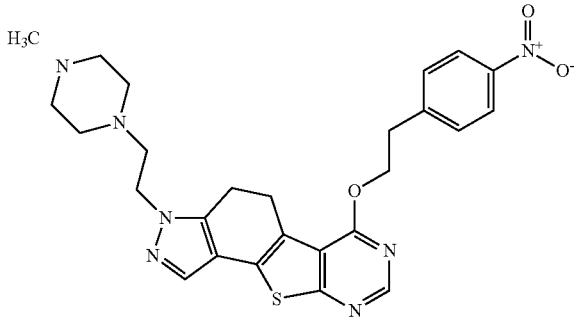

This compound was prepared in a similar fashion as described in Example 48 step 6 starting from 3-(2-bromo-ethyl)-6-[2-(4-nitro-phenyl)-ethoxy]-4,5-dihydro-3H-10-thia-2,3,7,9-tetraaza-cyclopenta[a]fluorene (2.6 g, 5.2 mmol) and N-methyl piperazine (1.56 g, 15.59 mmol). The crude desired product was obtained as a light yellow solid (2.7 g) in 100% yield.

Step 4. Preparation of 3-[2-(4-methyl-piperazin-1-yl)-ethyl]-4,5-dihydro-3H-10-thia-2,3,7,9-tetraaza-cyclopenta[a]fluorene-6-ol

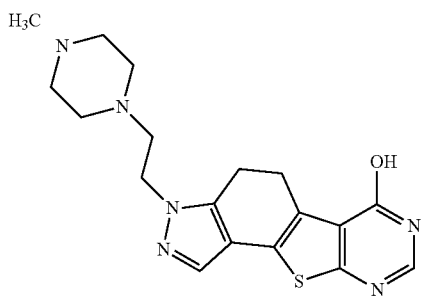

To a yellow suspension of 3-[2-(4-methyl-piperazin-1-yl)-ethyl]-6-[2-(4-nitro-phenyl)-ethoxy]-4,5-dihydro-3H-10-thia-2,3,7,9-tetraaza-cyclopenta[a]fluorene (2.7 g, 5.2 mmol) in THF (125 ml) was added potassium tert-butoxide (0.92 g, 7.79 mmol) in one portion. The reaction mixture became a solution and then turned into a dark black solution. After stirring for 30 min, analytical HPLC showed no more starting material and two new major peaks. Solvents were evaporated and the dark residue was suspended in EtOAc. To above suspension was added 5 ml of 4M HCl and it turned into a light yellow suspension. The crude HCl salt of the desired product was collected by filtration, washed with EtOAc, and air-dried to afford the crude product (2.2 g, 104%). RT=0.41 min; [M+H]$^+$=371.2.

Step 5. Preparation of 6-chloro-3-[2-(4-methyl-piperazin-1-yl)-ethyl]-4,5-dihydro-3H-10-thia-2,3,7,9-tetraaza-cyclopenta[a]fluorene

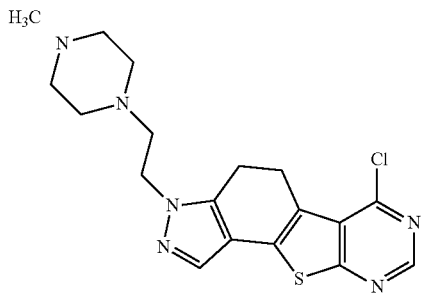

A suspension of 3-[2-(4-methyl-piperazin-1-yl)-ethyl]-4,5-dihydro-3H-10-thia-2,3,7,9-tetraaza-cyclopenta[a]fluorene-6-ol (2 g, 5.4 mmol) in POCl$_3$ (18 ml, 194 mmol) was heated at 105° C. (bath temperature) for 3 h. Analytical HPLC showed no more starting material and a new peak. Excess POCl$_3$ was removed under vacuum and the residue was neutralized with 1N NaOH, extracted with CHCl$_3$:isopropanol (v/v, 3/1). The organic phase was washed with brine, dried over Na$_2$SO$_4$, concentrated to afford a brown syrup, which was purified by silica gel column (CH$_2$Cl$_2$/2N NH$_3$ in MeOH=100/8). The desire product was obtained as a light yellow solid (1.5 g, 71%). $^1$H-NMR (CD$_2$Cl$_2$-d$_2$) δ 8.66 (s, 1H), 7.60 (s, 1H), 4.19 (t, 2H, J=6.2 Hz), 3.55 (t, 2H, J=8.5 Hz), 3.10 (t, 2H, J=8.3 Hz), 2.80 (t, 2H, J=6.0 Hz), 2.52-2.39 (b, 8H), 2.25 (s, 3H); LCMS RT=1.97 min; [M+H]$^+$=389.4.

Step 6. Preparation of 2-methyl-4-({3-[2-(4-methylpiperazin-1-yl)ethyl]-4,5-dihydro-3H-pyrimido[5',4':4,5]thieno[2,3-e]indazol-6-yl}amino)phenol

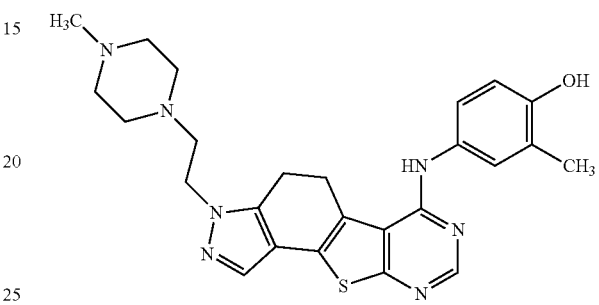

To a suspension of 6-chloro-3-[2-(4-methyl-piperazin-1-yl)-ethyl]-4,5-dihydro-3H-10-thia-2,3,7,9-tetraaza-cyclopenta[a]fluorene (150 mg, 0.39 mmol) and 4-amino-O-cresol (71 mg, 0.58 mmol) in isopropanol (5 mL) was added 4M HCl in dioxane (0.67 mL, 2.7 mmol). The reaction mixture was sealed in a microwave reaction vessel and it was placed in a microwave instrument at 160° C. for 10 min. After it was cooled to room temperature, solvents were evaporated and the residue was dissolved in MeOH/water/DMF and purified by prep. HPLC. After drying, the TFA salt was neutralized with saturated NaHCO$_3$ and extracted with a mixture of CHCl$_3$:isopropanol (v/v, 3:1). The organic phase was dried over Na$_2$SO$_4$ and concentrated to dryness. The desired product was obtained as a pale solid (174 mg, 95%). $^1$H-NMR (CD$_2$Cl$_2$-d$_2$) δ 8.34 (s, 1H), 7.55 (s, 1H), 7.28 (m, 2H), 6.88 (b, 1H), 6.80 (m, 1H), 4.20 (t, 2H, J=6.2 Hz), 3.38 (t, 2H, J=8.3 Hz), 3.13 (t, 2H, J=8.4 Hz), 2.85 (t, 2H, J=6.2 Hz), 2.62-2.45 (b, 8H), 2.30 (s, 3H), 2.26 (s, 3H); LCMS RT=1.89 min; [M+H]$^+$=476.2.

Using the method described above and the appropriate starting materials, examples 316-320, 322, and 323 were similarly prepared.

Example 347

N-[3-chloro-4-(1,3-thiazol-4-ylmethoxy)phenyl]-2-[2-(4-methylpiperazin-1-yl)ethyl]-4,5-dihydro-2H-pyrimido[5',4':4,5]thieno[2,3-e]indazol-6-amine bis(trifluoroacetate)

This example was prepared according to methods described in example 48 using the appropriate starting material. 3-Chloro-4-(thiazol-4-ylmethoxy)-phenylamine hydrochloride used in the preparation was synthesized as the following:

Step 1: Preparation of 3-Chloro-4-(thiazol-4-ylmethoxy)-phenylamine hydrochloride

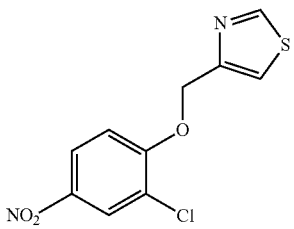

To a solution of 2-chloro-4-nitrophenol (1.00 g, 5.76 mmol) in acetonitrile (125 mL) were added 4-chloromethylthiazole hydrochloride (1.08 g, 6.34 mmol), Potassium carbonate (2.39 g, 17.29 mmol) and sodium iodide (1.73 g, 11.52 mmol). The reaction mixture was stirred at 60 C overnight. Water (60 mL) and DCM (10 mL) were added. After all solid material dissolved, layers formed were separated. The organic layer was washed with water and brine, dried over Na2SO4 and concentrated down to give the required material as a light yellow solid (1.29 mg, 83%). $^1$H-NMR (CD$_2$Cl$_2$) δ 8.87 (d, 1H), 8.32 (d, 1H), 8.16 (dd, 1H), 7.54-7.56 (m, 1H), 7.22 (d, 1H), 5.33-5.34 (m, 2H); LCMS RT=3.01 min; [M+H]$^+$=271.0.

Step 2: 3-Chloro-4-(thiazol-4-ylmethoxy)-phenylamine; hydrochloride

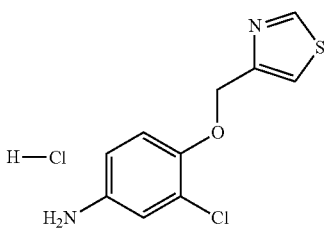

A mixture of A (1.00 g, 3.69 mmol), iron powder (2.06 g, 36.94 mmol), 2 M HCl (1.85 mL) and 85% ethanol (30 mL) was refluxed for 2.5 hours. The mixture was cooled down to room temperature, filtered through a pad of celite and concentrated under vacuum to give the required material as a dark brown solid (0.89 g, 87%). $^1$H-NMR (CD$_3$OD) δ 8.99 (d, 1H), 7.59-7.60 (m, 1H), 6.89 (d, 1H), 6.77 (d, 1H), 6.58 (dd, 1H), 5.15 (s, 2H); LCMS RT=1.28 min; [M+H]$^+$=241.0.

Example 360

Preparation of 2-[6-({3-chloro-4-[(3-fluorobenzyl)oxy]phenyl}amino)-4,5-dihydro-2H-pyrimido[5',4':4,5]thieno[2,3-e]indazol-2-yl)propane-1,3-diol

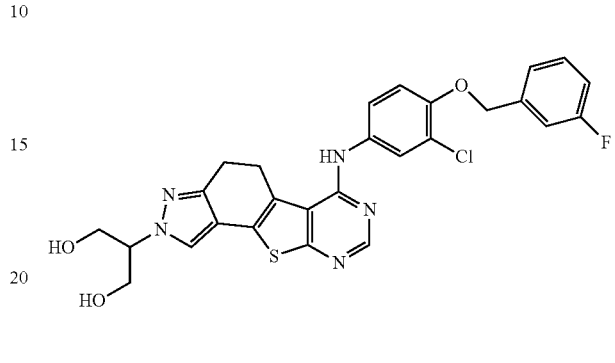

Step 1. Preparation of tert-butyl 2-[2-hydroxy-1-(hydroxymethyl)ethylidene]hydrazine carboxylate

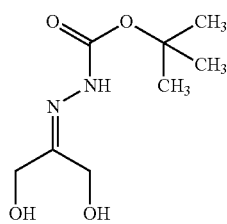

1,3-Dihydroxyacetone (3.0 g, 33.3 mmol) and ten-butyl hydrazinecarboxylate (4.4 g, 33.3 mmol) were dissolved in ethanol (150 ml) and the reaction mixture was stirred at rt for 15 hr. The solvent was removed under reduced pressure, and the residue recrystallized with EtOAc to furnish the desired product (6.5 g, 95.6%) as a white solid. $^1$H-NMR (DMSO-d$_6$) δ 9.98 (s, 1H), 5.60 (t, 1H), 4.92 (t, 1H), 4.23 (d, 2H), 3.94 (d, 2H), 1.40 (s, 9H); LCMS RT=1.38 min; [M+H]$^+$=204.9.

Step 2. Preparation of tert-butyl 2-[2-hydroxy-1-(hydroxymethyl)ethyl]hydrazine carboxylate

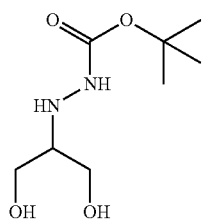

To a 0 THF solution of tert-butyl 2-[2-hydroxy-1-(hydroxymethyl)ethylidene]hydrazine carboxylate (1.0 g, 4.897 mmol) was added a solution of 1M BH$_3$-THF (10 mL) dropwise. The reaction mixture was stirred at rt for 30 min, after which time the mixture was quenched by slowly adding 5 mL of methanol. The mixture was concentrated under reduced pressure and dried to give the desired product (1.12 g, 100%). $^1$H-NMR (DMSO-$d_6$) δ 8.38 (s, 1H), 7.15 (s, 1H), 4.62 (s, 1H), 4.39 (t, 1H), 3.38 (q, 4H), 3.10 (s, 1H), 1.38 (s, 9H); LCMS RT=1.16 min; [M+H]$^+$=206.9.

Step 3. Regiocontrolled Preparation of 2-[6-({3-chloro-4-[(3-fluorobenzyl)oxy]phenyl}amino)-4,5-dihydro-2H-pyrimido[5',4':4,5]thieno[2,3-e]indazol-2-yl)propane-1,3-diol

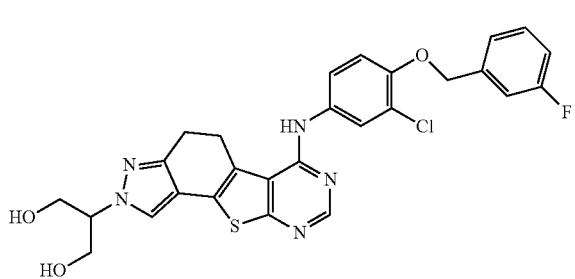

tert-Butyl 2-[2-hydroxy-1-(hydroxymethyl)ethyl]hydrazinecarboxylate (40.5 mg, 0.196 mmol) was added to an ethanol solution (3 mL) of N-(3-Chloro-4-(3-fluoro-benzyloxy)-phenylamine)-8-dimethylaminomethylene-5,8-dihydro-6H-benzo[4,5]thieno[2,3-d]pyrimidin-7-one (100 mg, 0.196 mmol). The reaction mixture was stirred at 80° C. for 12 h, and then cooled down to rt. The mixture was concentrated under reduced pressure and dried to give 160.5 mg of the crude product, which was diluted with CH$_2$Cl$_2$ (4 mL) and cooled to 0° C. Next added to the solution was TFA (2 mL) in a dropwise manner, and the mixture was stirred at rt for 1 hr. The contents were concentrated in vacuo to dryness, and the residue purified by reverse phase HPLC. The isolated product was treated with aq. NaHCO$_3$, dried over MgSO$_4$, filtered, and concentrated to give the desired product (22 mg, 16.2%) as a yellowish solid. $^1$H-NMR (DMSO-$d_6$) δ 8.41 (s, 1H), 8.35 (s, 1H), 7.94 (s, 1H), 7.76 (s, 1H), 7.50 (m, 2H), 7.30 (m, 2H), 7.08 (m, 2H), 5.14 (s, 2H), 4.93 (t, 2H), 4.10 (t, 1H), 4.75 (m, 4H), 3.38 (m, 2H), 2.95 (t, 2H); LCMS RT=3.17 min; [M+H]$^+$=552.2.

Using the method described above and the appropriate starting materials, example 363 was similarly prepared.

Example 361

Preparation of 2-[6-({3-chloro-4-[(3-fluorobenzyl)oxy]phenyl}amino)-4,5-dihydro-3H-pyrimido[5',4':4,5]thieno[2,3-e]indazol-3-yl)propane-1,3-diol

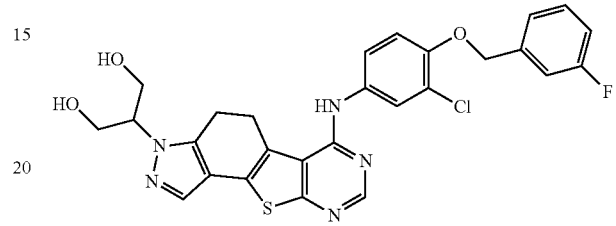

tert-Butyl 2-[2-hydroxy-1-(hydroxymethyl)ethyl]hydrazinecarboxylate (12.2 mg, 0.06 mmol) was added to an ethanol solution (1 mL) of N-(3-Chloro-4-(3-fluoro-benzyloxy)-phenylamine)-8-dimethylaminomethylene-5,8-dihydro-6H-benzo[4,5]thieno[2,3-d]pyrimidin-7-one (30 mg, 0.06 mmol). The reaction mixture was stirred at 80° C. for 12 h, and then cooled down to rt. The contents were concentrated in vacuo to dryness, and the residue purified by reverse phase HPLC. The isolated product was treated with aq. NaHCO$_3$, dried over MgSO$_4$, filtered, and concentrated to give the desired product (3.7 mg, 11.4%) as a yellowish solid. $^1$H-NMR (DMSO-$d_6$) δ 8.40 (s, 1H), 8.35 (s, 1H), 7.76 (d, 1H), 7.65 (s, 1H), 7.50 (m, 2H), 7.30 (m, 2H), 7.20 (m, 2H), 5.12 (s, 2H), 4.88 (m, 2H), 4.30 (m, 1H), 3.78 (m, 2H), 3.70 (m, 2H), 3.40 (t, 2H), 3.08 (t, 2H); LCMS RT=3.10 min; [M+H]$^+$=552.3.

Using the method described above and the appropriate starting materials, example 362 was similarly prepared.

Further compounds that were prepared according to the above mentioned methods are listed in the following table:

| Example No | Structure | IUPAC name | LCMS RT (min) | LCMS Ion [M + H]+ |
|---|---|---|---|---|
| 1 | 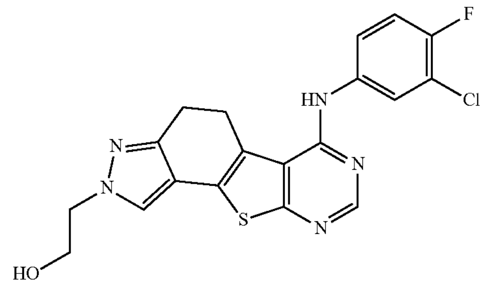 | 2-{6-[(3-chloro-4-fluorophenyl)amino]-4,5-dihydro-2H-pyrimido[5',4':4,5]thieno[2,3-e]indazol-2-yl}ethanol | 2.78 | 416.4 |
| 2 | 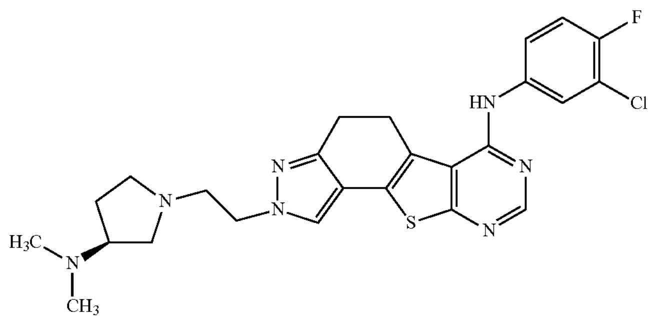 | N-(3-chloro-4-fluorophenyl)-2-{2-[(3S)-3-(dimethylamino)pyrrolidin-1-yl]ethyl}-4,5-dihydro-2H-pyrimido[5',4':4,5]thieno[2,3-e]indazol-6-amine | 2.56 | 512.2 |
| 3 | 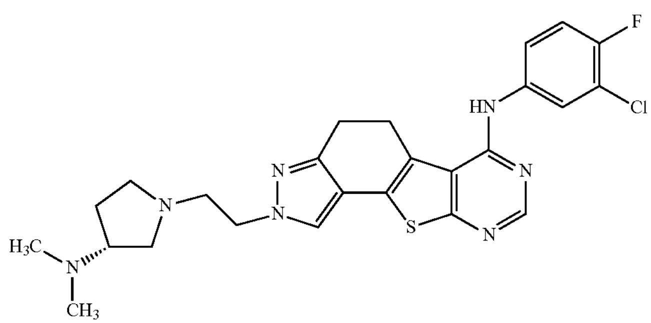 | N-(3-chloro-4-fluorophenyl)-2-{2-[(3R)-3-(dimethylamino)pyrrolidin-1-yl]ethyl}-4,5-dihydro-2H-pyrimido[5',4':4,5]thieno[2,3-e]indazol-6-amine | 2.07 | 512.2 |

-continued

| Example No | Structure | IUPAC name | LCMS RT (min) | LCMS Ion [M + H]+ |
|---|---|---|---|---|
| 4 | 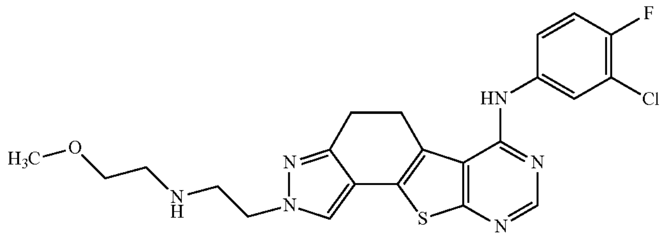 | N-(3-chloro-4-fluorophenyl)-2-{2-[(2-methoxyethyl)amino]ethyl}-4,5-dihydro-2H-pyrimido[5',4':4,5]thieno[2,3-e]indazol-6-amine | 2.86 | 473.3 |
| 5 | 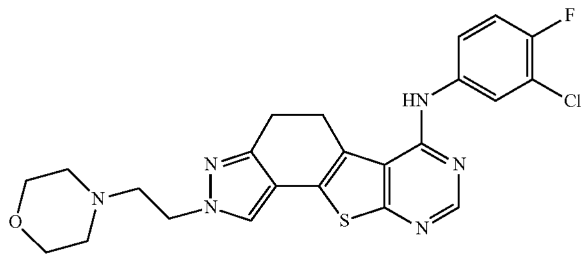 | N-(3-chloro-4-fluorophenyl)-2-(2-morpholin-4-ylethyl)-4,5-dihydro-2H-pyrimido[5',4':4,5]thieno[2,3-e]indazol-6-amine | 2.85 | 485.3 |
| 6 | 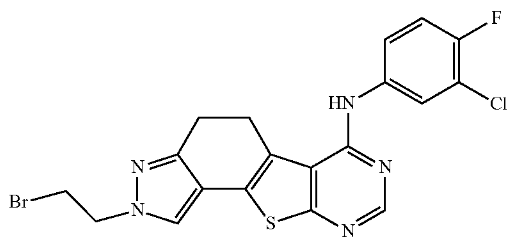 | 2-(2-bromoethyl)-N-(3-chloro-4-fluorophenyl)-4,5-dihydro-2H-pyrimido[5',4':4,5]thieno[2,3-e]indazol-6-amine | 3.81 | 478.2, 480.2 |
| 7 | 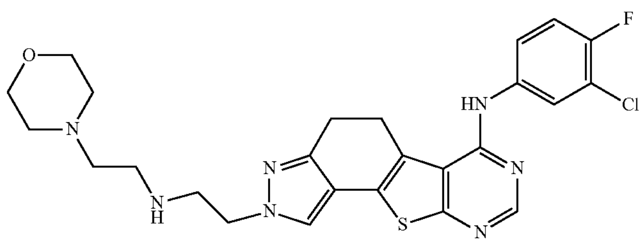 | N-(3-chloro-4-fluorophenyl)-2-{2-[(2-morpholin-4-ylethyl)amino]ethyl}-4,5-dihydro-2H-pyrimido[5',4':4,5]thieno[2,3-e]indazol-6-amine | 2.28 | 528.1 |

-continued

| Example No | Structure | IUPAC name | LCMS RT (min) | LCMS Ion [M + H]+ |
|---|---|---|---|---|
| 8 | 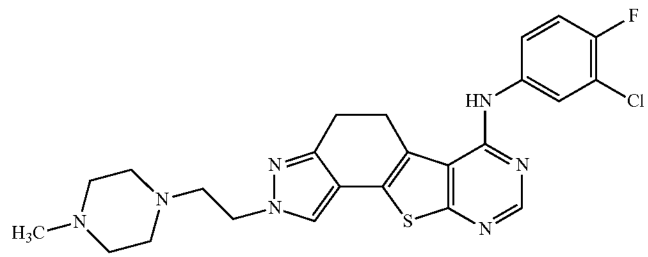 | N-(3-chloro-4-fluorophenyl)-2-[2-(4-methylpiperazin-1-yl)ethyl]-4,5-dihydro-2H-pyrimido[5',4':4,5]thieno[2,3-e]indazol-6-amine | 2.46 | 498.2 |
| 9 | 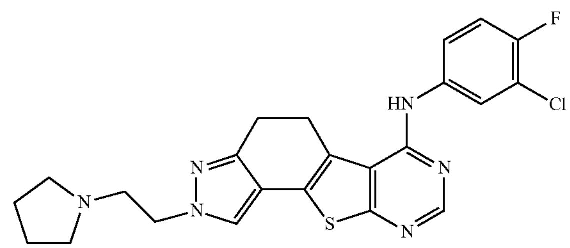 | N-(3-chloro-4-fluorophenyl)-2-(2-pyrrolidin-1-ylethyl)-4,5-dihydro-2H-pyrimido[5',4':4,5]thieno[2,3-e]indazol-6-amine | 2.82 | 469.2 |
| 10 | 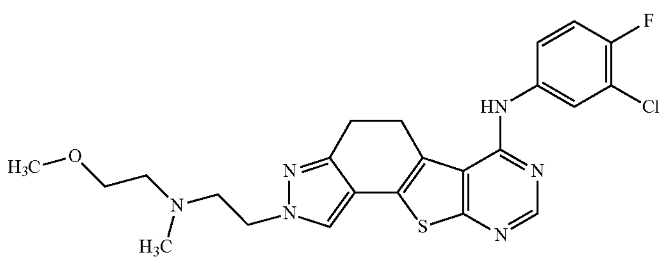 | N-(3-chloro-4-fluorophenyl)-2-{2-[(2-methoxyethyl)(methyl)amino]ethyl}-4,5-dihydro-2H-pyrimido[5',4':4,5]thieno[2,3-e]indazol-6-amine | 2.84 | 487.3 |
| 11 | 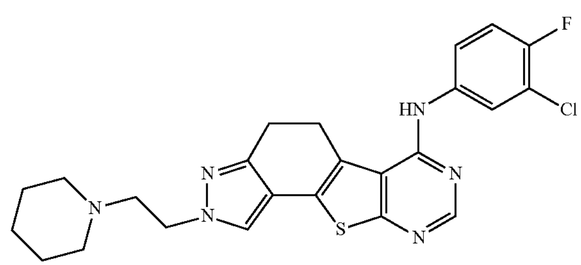 | N-(3-chloro-4-fluorophenyl)-2-(2-piperidin-1-ylethyl)-4,5-dihydro-2H-pyrimido[5',4':4,5]thieno[2,3-e]indazol-6-amine | 2.31 | 483.3 |

-continued

| Example No | Structure | IUPAC name | LCMS RT (min) | LCMS Ion [M + H]+ |
|---|---|---|---|---|
| 12 | 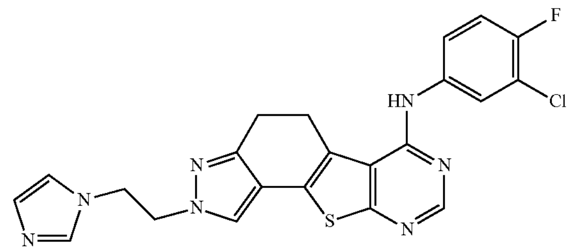 | N-(3-chloro-4-fluorophenyl)-2-[2-(1H-imidazol-1-yl)ethyl]-4,5-dihydro-2H-pyrimido[5',4':4,5]thieno[2,3-e]indazol-6-amine | 2.8 | 466.2 |
| 13 | 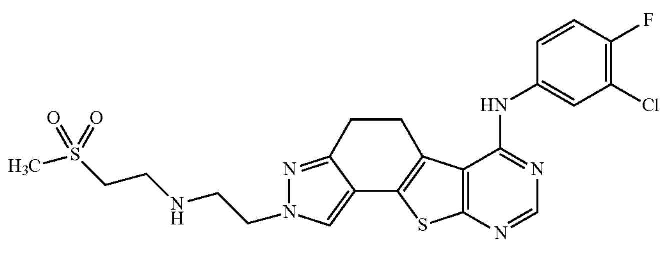 | N-(3-chloro-4-fluorophenyl)-2-(2-{[2-(methylsulfonyl)ethyl]amino}ethyl)-4,5-dihydro-2H-pyrimido[5',4':4,5]thieno[2,3-e]indazol-6-amine | 2.82 | 521.2 |
| 14 | 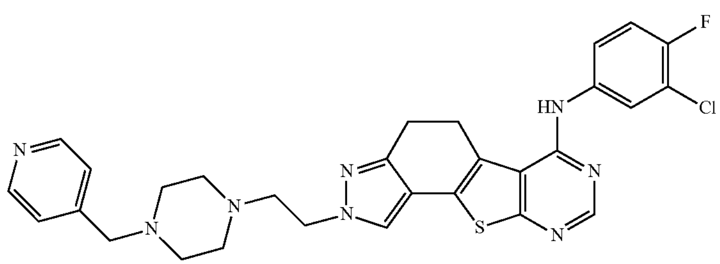 | N-(3-chloro-4-fluorophenyl)-2-{2-[4-(pyridin-4-ylmethyl)piperazin-1-yl]ethyl}-4,5-dihydro-2H-pyrimido[5',4':4,5]thieno[2,3-e]indazol-6-amine | 2.59 | 575.1 |

| Example No | Structure | IUPAC name | LCMS RT (min) | LCMS Ion [M + H]+ |
|---|---|---|---|---|
| 15 | 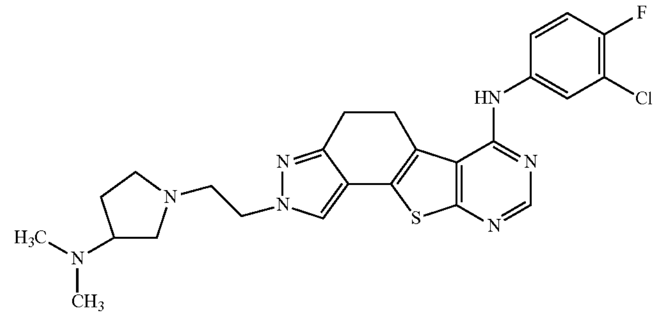 | N-(3-chloro-4-fluorophenyl)-2-{2-[3-(dimethylamino)pyrrolidin-1-yl]ethyl}-4,5-dihydro-2H-pyrimido[5',4':4,5]thieno[2,3-e]indazol-6-amine | 2.56 | 512.2 |
| 16 | 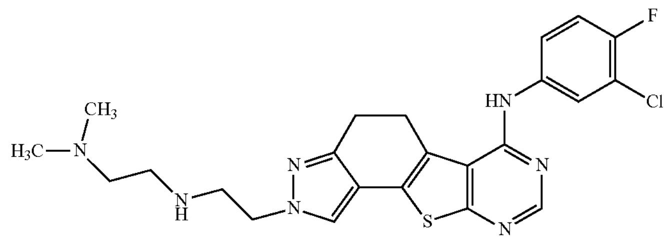 | N'-(2-{6-[(3-chloro-4-fluorophenyl)amino]-4,5-dihydro-2H-pyrimido[5',4':4,5]thieno[2,3-e]indazol-2-yl}ethyl)-N,N-dimethylethane-1,2-diamine | 2.56 | 486.2 |
| 17 | 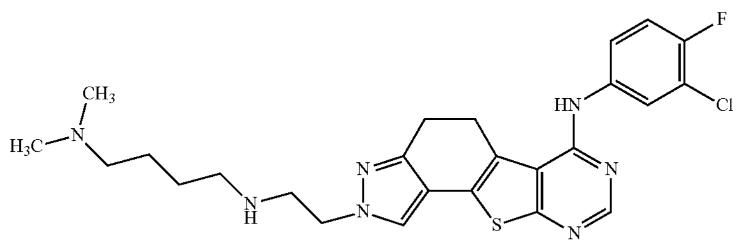 | N'-(2-{6-[(3-chloro-4-fluorophenyl)amino]-4,5-dihydro-2H-pyrimido[5',4':4,5]thieno[2,3-e]indazol-2-yl}ethyl)-N,N-dimethylbutane-1,4-diamine | 2.55 | 514.2 |
| 18 | 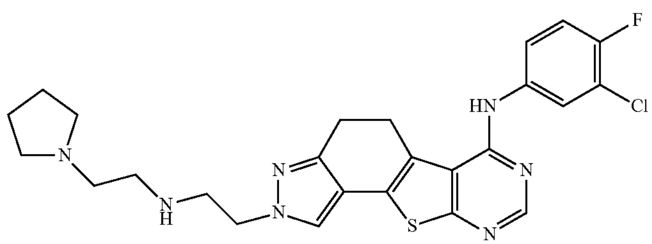 | N-(3-chloro-4-fluorophenyl)-2-{2-[(2-pyrrolidin-1-ylethyl)amino]ethyl}-4,5-dihydro-2H-pyrimido[5',4':4,5]thieno[2,3-e]indazol-6-amine | 2.55 | 512.2 |

-continued

| Example No | Structure | IUPAC name | LCMS RT (min) | LCMS Ion [M + H]+ |
|---|---|---|---|---|
| 19 | 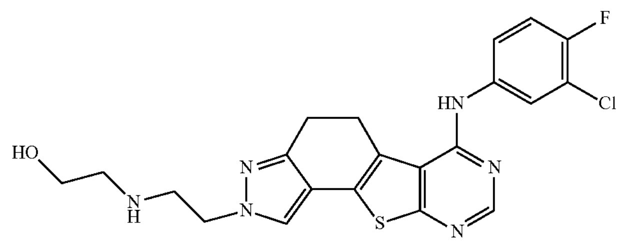 | 2-[(2-{6-[(3-chloro-4-fluorophenyl)amino]-4,5-dihydro-2H-pyrimido[5',4':4,5]thieno[2,3-e]indazol-2-yl}ethyl)amino]ethanol | 2.39 | 459.2 |
| 20 | 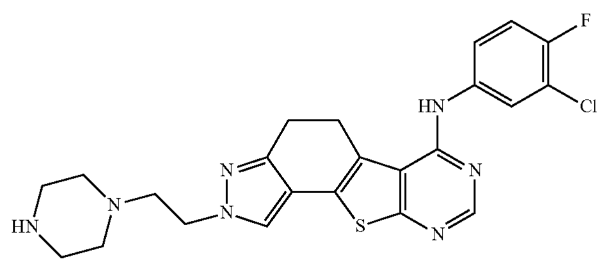 | N-(3-chloro-4-fluorophenyl)-2-(2-piperazin-1-ylethyl)-4,5-dihydro-2H-pyrimido[5',4':4,5]thieno[2,3-e]indazol-6-amine | 2.22 | 484.1 |
| 21 | 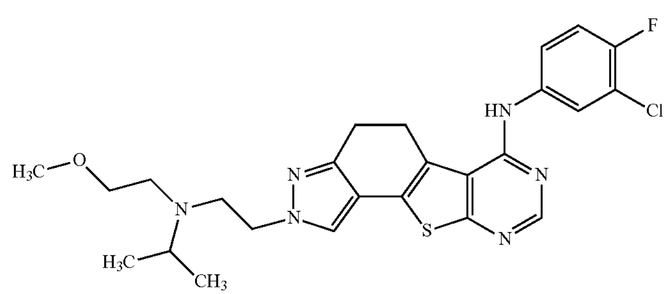 | N-(3-chloro-4-fluorophenyl)-2-{2-[isopropyl(2-methoxyethyl)amino]ethyl}-4,5-dihydro-2H-pyrimido[5',4':4,5]thieno[2,3-e]indazol-6-amine | 3 | 515.2 |

| Example No | Structure | IUPAC name | LCMS RT (min) | LCMS Ion [M + H]+ |
|---|---|---|---|---|
| 22 | 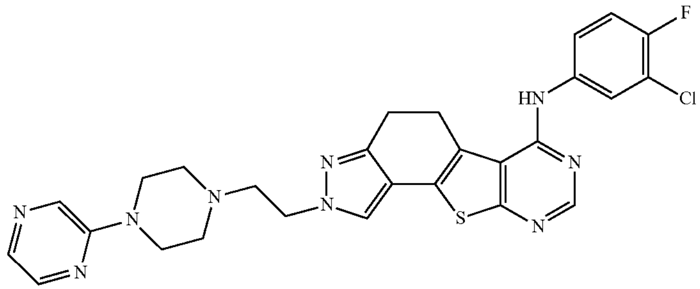 | N-(3-chloro-4-fluorophenyl)-2-[2-(4-pyrazin-2-ylpiperazin-1-yl)ethyl]-4,5-dihydro-2H-pyrimido[5',4':4,5]thieno[2,3-e]indazol-6-amine | 2.51 | 562.1 |
| 23 | 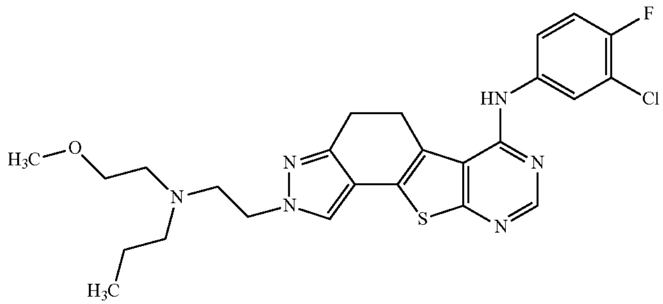 | N-(3-chloro-4-fluorophenyl)-2-{2-[(2-methoxyethyl)(propyl)amino]ethyl}-4,5-dihydro-2H-pyrimido[5',4':4,5]thieno[2,3-e]indazol-6-amine | 3.01 | 515.2 |
| 24 | 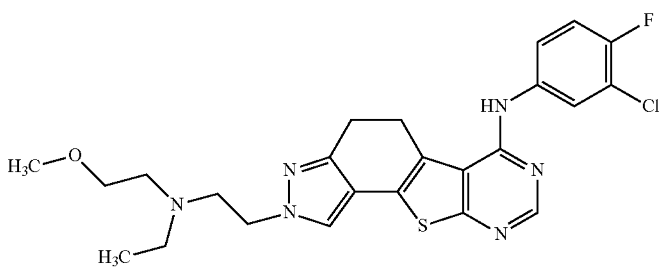 | N-(3-chloro-4-fluorophenyl)-2-{2-[ethyl(2-methoxyethyl)amino]ethyl}-4,5-dihydro-2H-pyrimido[5',4':4,5]thieno[2,3-e]indazol-6-amine | 2.52 | 501.1 |

-continued

| Example No | Structure | IUPAC name | LCMS RT (min) | LCMS Ion [M + H]+ |
|---|---|---|---|---|
| 25 | 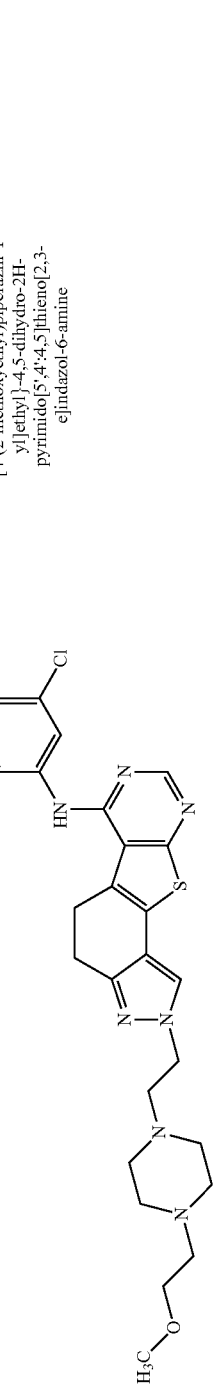 | N-(3-chloro-4-fluorophenyl)-2-{2-[4-(2-methoxyethyl)piperazin-1-yl]ethyl}-4,5-dihydro-2H-pyrimido[5',4':4,5]thieno[2,3-e]indazol-6-amine | 2.42 | 542.2 |
| 26 | 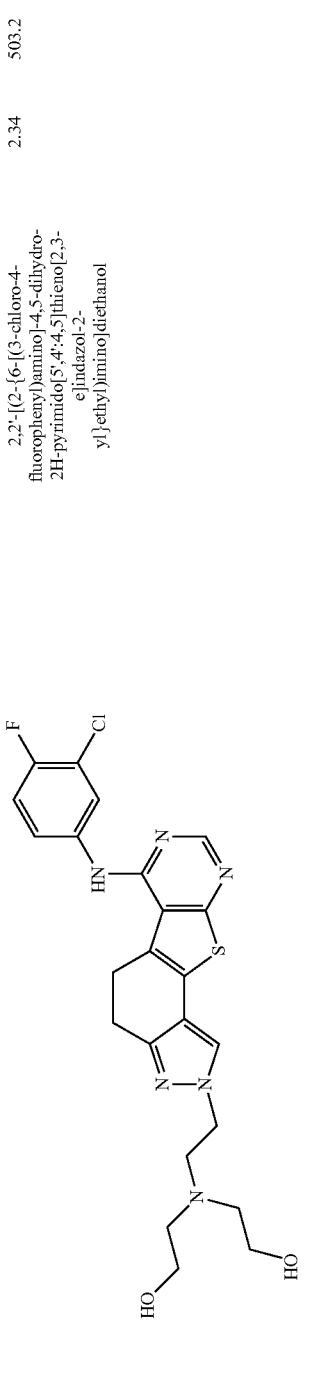 | 2,2'-[(2-{6-[(3-chloro-4-fluorophenyl)amino]-4,5-dihydro-2H-pyrimido[5',4':4,5]thieno[2,3-e]indazol-2-yl}ethyl)imino]diethanol | 2.34 | 503.2 |
| 27 | 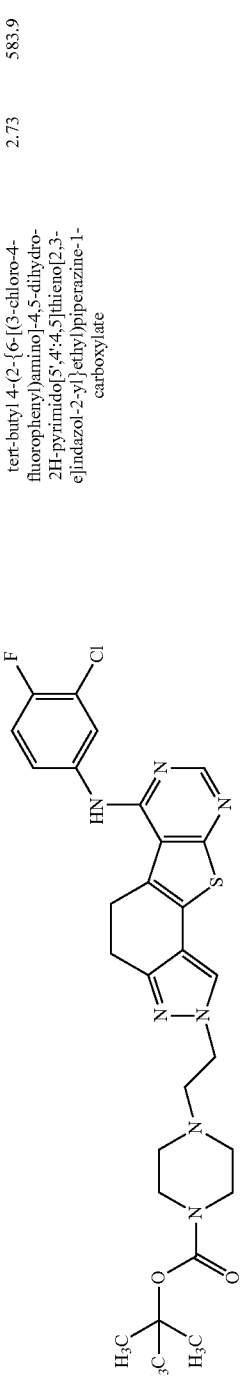 | tert-butyl 4-(2-{6-[(3-chloro-4-fluorophenyl)amino]-4,5-dihydro-2H-pyrimido[5',4':4,5]thieno[2,3-e]indazol-2-yl}ethyl)piperazine-1-carboxylate | 2.73 | 583.9 |

| Example No | Structure | IUPAC name | LCMS RT (min) | LCMS Ion [M + H]+ |
|---|---|---|---|---|
| 28 | 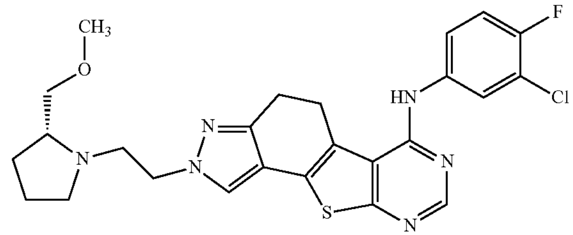 | N-(3-chloro-4-fluorophenyl)-2-{2-[(2R)-2-(methoxymethyl)pyrrolidin-1-yl]ethyl}-4,5-dihydro-2H-pyrimido[5',4':4,5]thieno[2,3-e]indazol-6-amine | 2.94 | 513.2 |
| 29 | 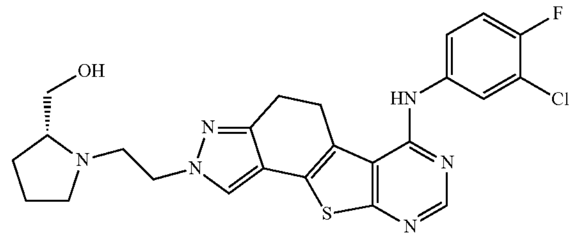 | [(2R)-1-(2-{6-[(3-chloro-4-fluorophenyl)amino]-4,5-dihydro-2H-pyrimido[5',4':4,5]thieno[2,3-e]indazol-2-yl}ethyl)pyrrolidin-2-yl]methanol | 2.85 | 499.2 |
| 30 | 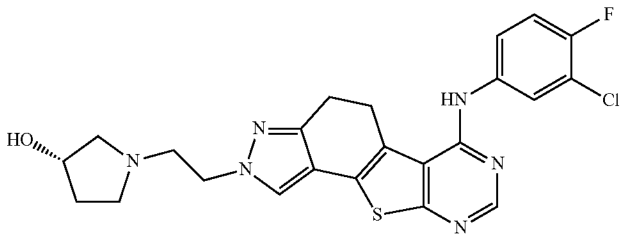 | (3S)-1-(2-{6-[(3-chloro-4-fluorophenyl)amino]-4,5-dihydro-2H-pyrimido[5',4':4,5]thieno[2,3-e]indazol-2-yl}ethyl)pyrrolidin-3-ol | 2.81 | 485.2 |
| 31 | 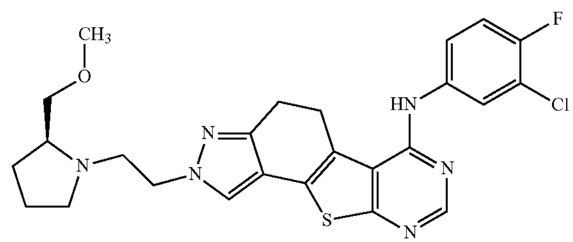 | N-(3-chloro-4-fluorophenyl)-2-{2-[(2S)-2-(methoxymethyl)pyrrolidin-1-yl]ethyl}-4,5-dihydro-2H-pyrimido[5',4':4,5]thieno[2,3-e]indazol-6-amine | 2.95 | 513.2 |

-continued

| Example No | Structure | IUPAC name | LCMS RT (min) | LCMS Ion [M+H]+ |
|---|---|---|---|---|
| 32 | 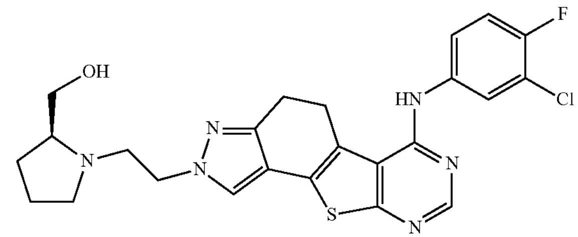 | [(2S)-1-(2-{6-[(3-chloro-4-fluorophenyl)amino]-4,5-dihydro-2H-pyrimido[5',4':4,5]thieno[2,3-e]indazol-2-yl}ethyl)pyrrolidin-2-yl]methanol | 2.84 | 499.2 |
| 33 | 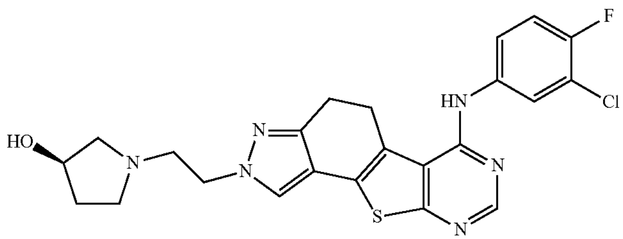 | (3R)-1-(2-{6-[(3-chloro-4-fluorophenyl)amino]-4,5-dihydro-2H-pyrimido[5',4':4,5]thieno[2,3-e]indazol-2-yl}ethyl)-pyrrolidin-3-ol | 2.8 | 485.2 |
| 34 | 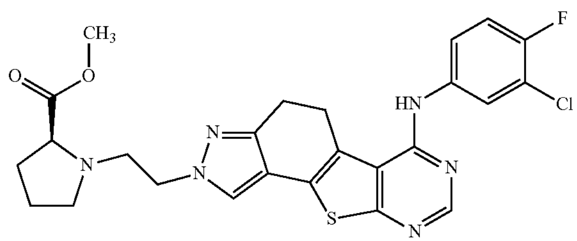 | methyl 1-(2-{6-[(3-chloro-4-fluorophenyl)amino]-4,5-dihydro-2H-pyrimido[5',4':4,5]thieno[2,3-e]indazol-2-yl}ethyl)-L-prolinate | 2.94 | 527.2 |
| 35 | 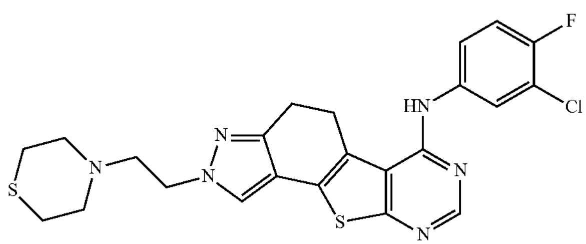 | N-(3-chloro-4-fluorophenyl)-2-(2-thiomorpholin-4-ylethyl)-4,5-dihydro-2H-pyrimido[5',4':4,5]thieno[2,3-e]indazol-6-amine | 2.91 | 501.2 |

-continued

| Example No | Structure | IUPAC name | LCMS RT (min) | LCMS Ion [M+H]+ |
|---|---|---|---|---|
| 36 | 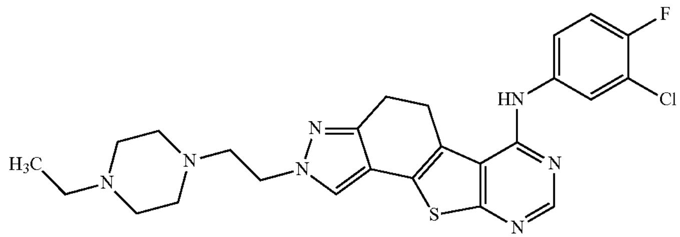 | N-(3-chloro-4-fluorophenyl)-2-[2-(4-ethylpiperazin-1-yl)ethyl]-4,5-dihydro-2H-pyrimido[5',4':4,5]thieno[2,3-e]indazol-6-amine | 2.82 | 512.2 |
| 37 | 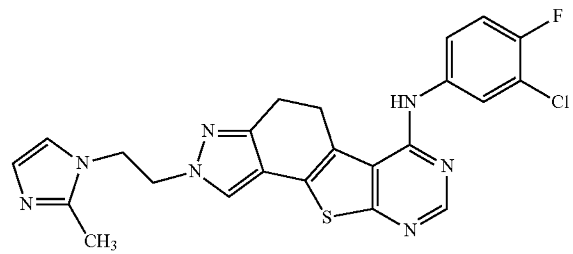 | N-(3-chloro-4-fluorophenyl)-2-[2-(2-methyl-1H-imidazol-1-yl)ethyl]-4,5-dihydro-2H-pyrimido[5',4':4,5]thieno[2,3-e]indazol-6-amine | 2.46 | 480.1 |
| 38 | 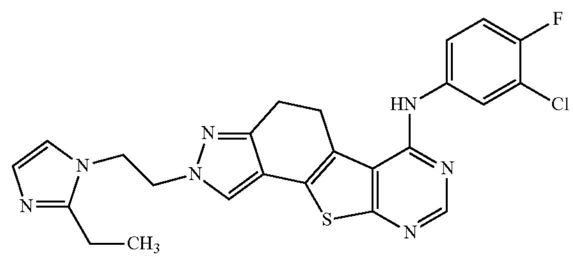 | N-(3-chloro-4-fluorophenyl)-2-[2-(2-ethyl-1H-imidazol-1-yl)ethyl]-4,5-dihydro-2H-pyrimido[5',4':4,5]thieno[2,3-e]indazol-6-amine | 2.88 | 494.2 |

| Example No | Structure | IUPAC name | LCMS RT (min) | LCMS Ion [M + H]+ |
|---|---|---|---|---|
| 39 | 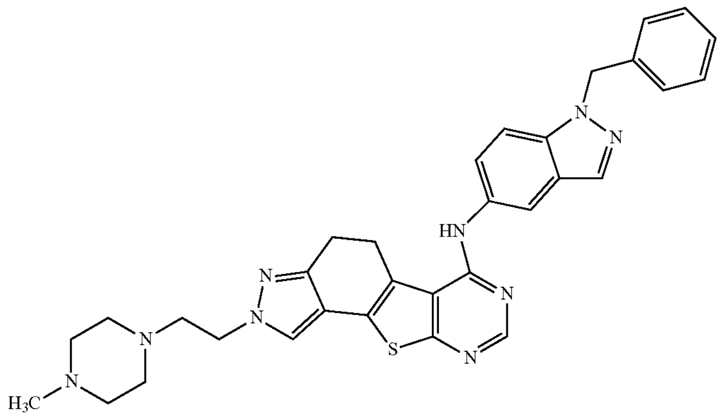 | N-(1-benzyl-1H-indazol-5-yl)-2-[2-(4-methylpiperazin-1-yl)ethyl]-4,5-dihydro-2H-pyrimido[5',4':4,5]thieno[2,3-e]indazol-6-amine | 2.39 | 576.2 |
| 40 | 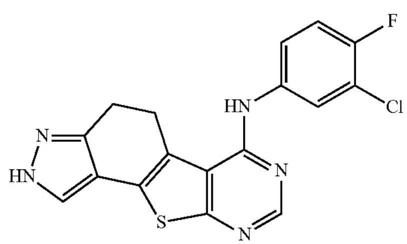 | N-(3-chloro-4-fluorophenyl)-4,5-dihydro-2H-pyrimido[5',4':4,5]thieno[2,3-e]indazol-6-amine | 2.98 | 372.3 |
| 41 | 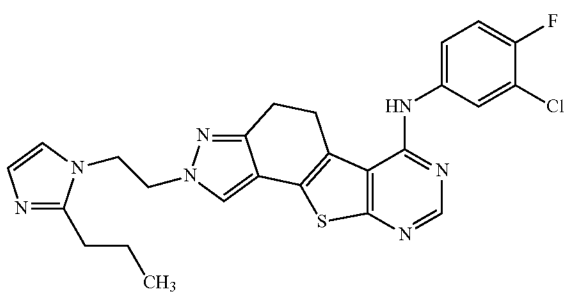 | N-(3-chloro-4-fluorophenyl)-2-[2-(2-propyl-1H-imidazol-1-yl)ethyl]-4,5-dihydro-2H-pyrimido[5',4':4,5]thieno[2,3-e]indazol-6-amine | 2.94 | 508.2 |

-continued

| Example No | Structure | IUPAC name | LCMS RT (min) | LCMS Ion [M + H]+ |
|---|---|---|---|---|
| 42 | 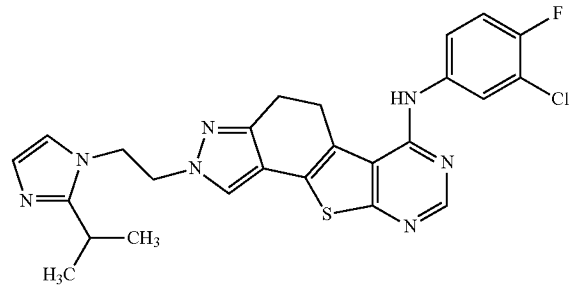 | N-(3-chloro-4-fluorophenyl)-2-[2-(2-isopropyl-1H-imidazol-1-yl)ethyl]-4,5-dihydro-2H-pyrimido[5',4':4,5]thieno[2,3-e]indazol-6-amine | 2.52 | 508.3 |
| 43 | 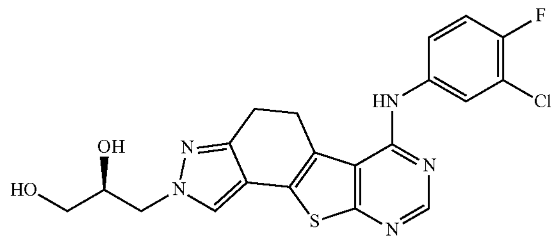 | (2S)-3-{6-[(3-chloro-4-fluorophenyl)amino]-4,5-dihydro-2H-pyrimido[5',4':4,5]thieno[2,3-e]indazol-2-yl}propane-1,2-diol | 2.74 | 446.2 |
| 44 | 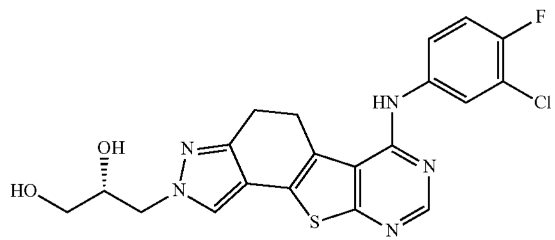 | (2R)-3-{6-[(3-chloro-4-fluorophenyl)amino]-4,5-dihydro-2H-pyrimido[5',4':4,5]thieno[2,3-e]indazol-2-yl}propane-1,2-diol | 2.74 | 446.2 |
| 45 | 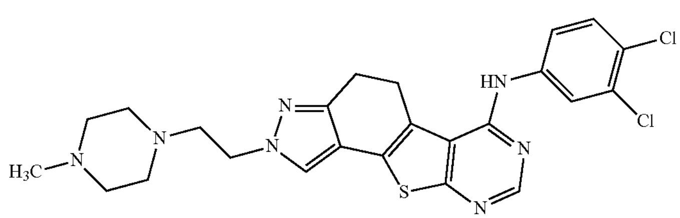 | N-(3,4-dichlorophenyl)-2-[2-(4-methylpiperazin-1-yl)ethyl]-4,5-dihydro-2H-pyrimido[5',4':4,5]thieno[2,3-e]indazol-6-amine | 2.57 | 514.3 |

| Example No | Structure | IUPAC name | LCMS RT (min) | LCMS Ion [M + H]+ |
|---|---|---|---|---|
| 46 | 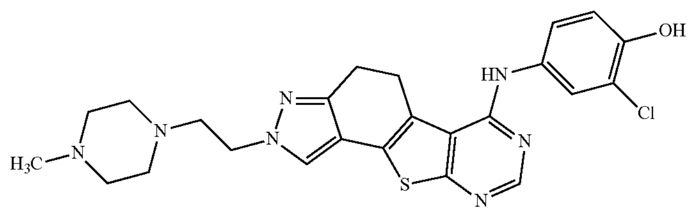 | 2-chloro-4-({2-[2-(4-methylpiperazin-1-yl)ethyl]-4,5-dihydro-2H-pyrimido[5',4':4,5]thieno[2,3-e]indazol-6-yl}amino)phenol | 1.96 | 496.4 |
| 47 | 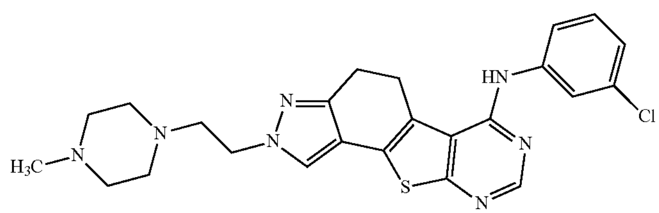 | N-(3-chlorophenyl)-2-[2-(4-methylpiperazin-1-yl)ethyl]-4,5-dihydro-2H-pyrimido[5',4':4,5]thieno[2,3-e]indazol-6-amine | 2.38 | 480.3 |
| 48 | 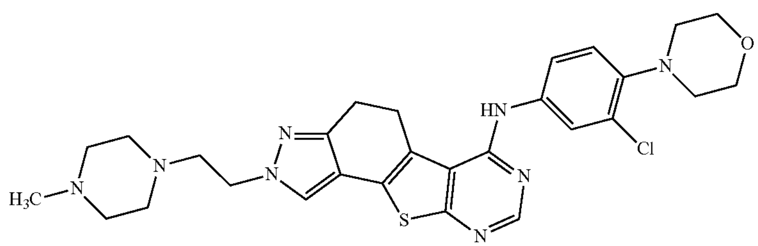 | N-(3-chloro-4-morpholin-4-ylphenyl)-2-[2-(4-methylpiperazin-1-yl)ethyl]-4,5-dihydro-2H-pyrimido[5',4':4,5]thieno[2,3-e]indazol-6-amine | 2.29 | 565.4 |
| 49 | 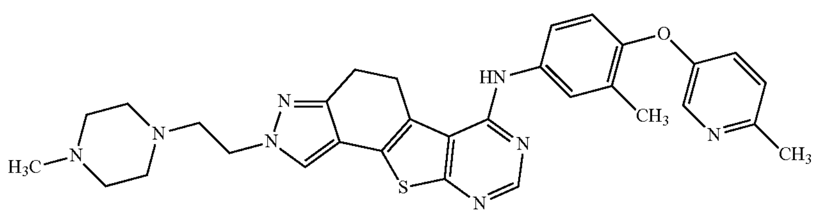 | N-{3-methyl-4-[(6-methylpyridin-3-yl)oxy]phenyl}-2-[2-(4-methylpiperazin-1-yl)ethyl]-4,5-dihydro-2H-pyrimido[5',4':4,5]thieno[2,3-e]indazol-6-amine | 1.97 | 567.2 |

| Example No | Structure | IUPAC name | LCMS RT (min) | LCMS Ion [M + H]+ |
|---|---|---|---|---|
| 50 | 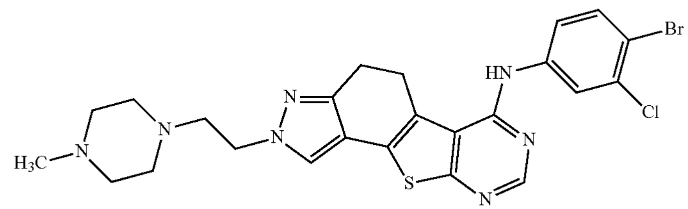 | N-(4-bromo-3-chlorophenyl)-2-[2-(4-methylpiperazin-1-yl)ethyl]-4,5-dihydro-2H-pyrimido[5',4':4,5]thieno[2,3-e]indazol-6-amine | 2.98 | 558.2 |
| 51 | 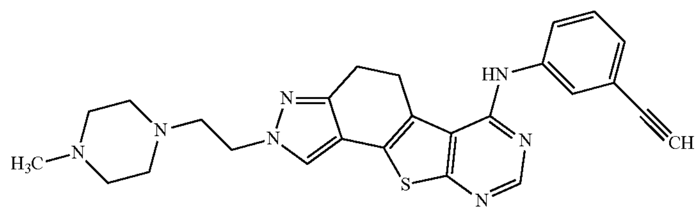 | N-(3-ethynylphenyl)-2-[2-(4-methylpiperazin-1-yl)ethyl]-4,5-dihydro-2H-pyrimido[5',4':4,5]thieno[2,3-e]indazol-6-amine | 2.71 | 470.3 |
| 52 | 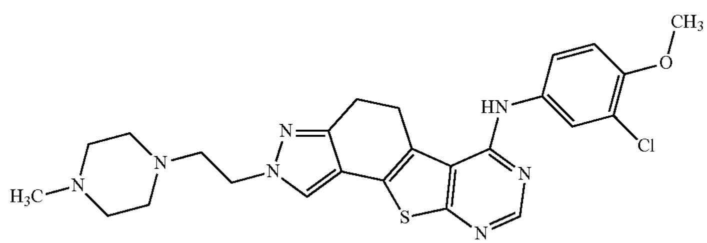 | N-(3-chloro-4-methoxyphenyl)-2-[2-(4-methylpiperazin-1-yl)ethyl]-4,5-dihydro-2H-pyrimido[5',4':4,5]thieno[2,3-e]indazol-6-amine | 2.67 | 510.3 |
| 53 | 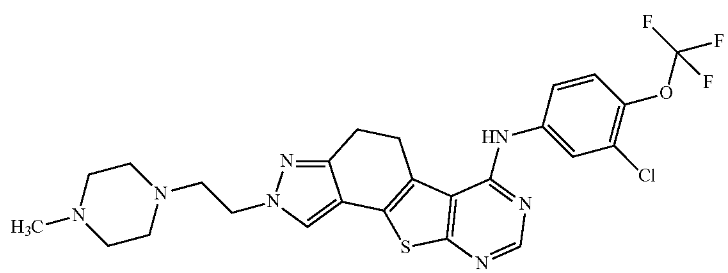 | N-[3-chloro-4-(trifluoromethoxy)phenyl]-2-[2-(4-methylpiperazin-1-yl)ethyl]-4,5-dihydro-2H-pyrimido[5',4':4,5]thieno[2,3-e]indazol-6-amine | 3.07 | 56403 |

| Example No | Structure | IUPAC name | LCMS RT (min) | LCMS Ion [M + H]+ |
|---|---|---|---|---|
| 54 | 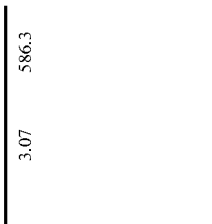 | N-[4-(benzyloxy)-3-chlorophenyl]-2-[2-(4-methylpiperazin-1-yl)ethyl]-4,5-dihydro-2H-pyrimido[5',4':4,5]thieno[2,3-e]indazol-6-amine | 3.07 | 586.3 |
| 55 | 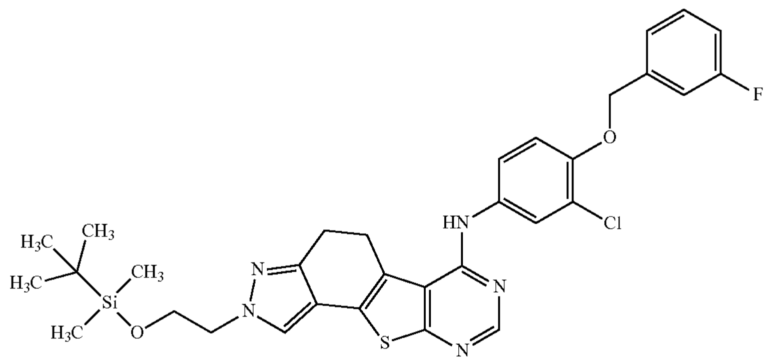 | 2-(2-{[tert-butyl(dimethyl)silyl]oxy}ethyl)-N-{3-chloro-4-[(3-fluorobenzyl)oxy]phenyl}-4,5-dihydro-2H-pyrimido[5',4':4,5]thieno[2,3-e]indazol-6-amine | 4.62 | 636.2 |
| 56 | 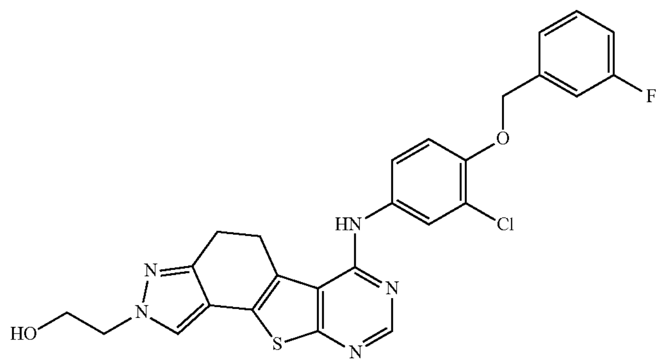 | 2-[6-({3-chloro-4-[(3-fluorobenzyl)oxy]phenyl}amino)-4,5-dihydro-2H-pyrimido[5',4':4,5]thieno[2,3-e]indazol-2-yl]ethanol | 3.39 | 522.2 |

-continued

| Example No | Structure | IUPAC name | LCMS RT (min) | LCMS Ion [M + H]+ |
|---|---|---|---|---|
| 57 | 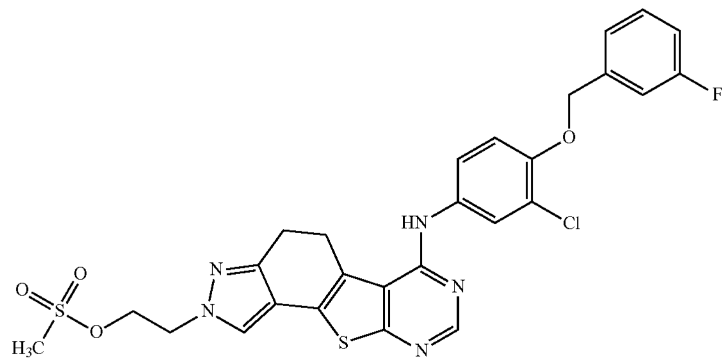 | 2-[6-({3-chloro-4-[(3-fluorobenzyl)oxy]phenyl}amino)-4,5-dihydro-2H-pyrimido[5',4':4,5]thieno[2,3-e]indazol-2-yl]ethyl methanesulfonate | 3.53 | 600.1 |
| 58 | 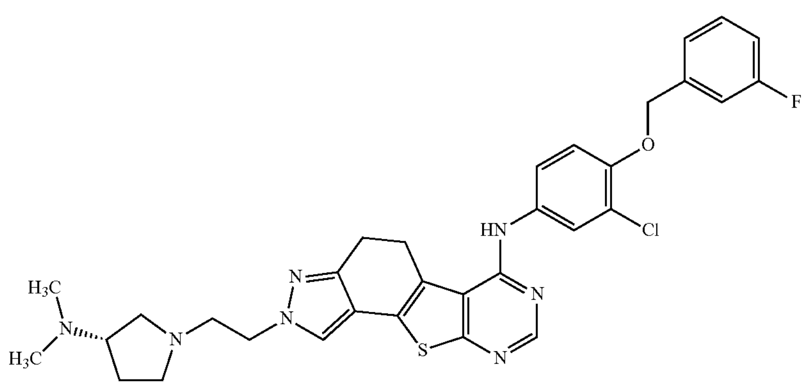 | N-{3-chloro-4-[(3-fluorobenzyl)oxy]phenyl}-2-{2-[(3S)-3-(dimethylamino)pyrrolidin-1-yl]ethyl}-4,5-dihydro-2H-pyrimido[5',4':4,5]thieno[2,3-e]indazol-6-amine | 2.48 | 618.2 |

| Example No | Structure | IUPAC name | LCMS RT (min) | LCMS Ion [M + H]+ |
|---|---|---|---|---|
| 59 | 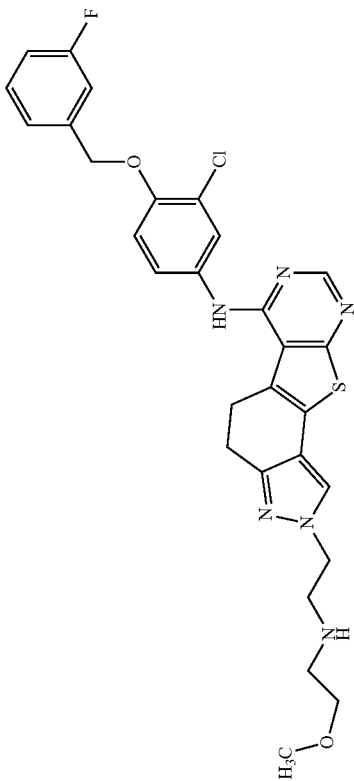 | N-{3-chloro-4-[(3-fluorobenzyl)oxy]phenyl}-2-{2-[(2-methoxyethyl)amino]ethyl}-4,5-dihydro-2H-pyrimido[5',4':4,5]thieno[2,3-e]indazol-6-amine | 2.69 | 579.2 |
| 60 | 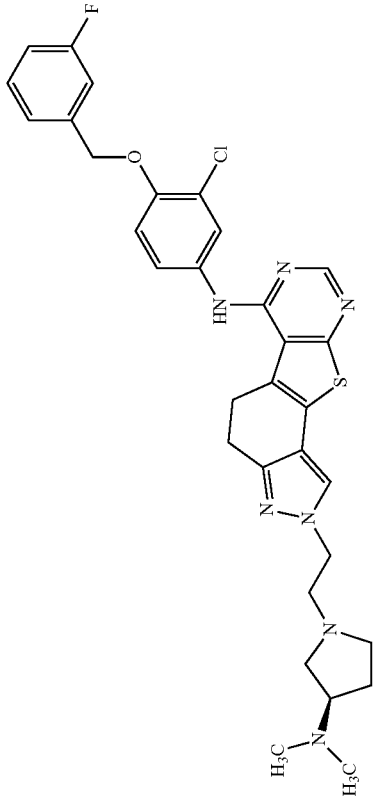 | N-{3-chloro-4-[(3-fluorobenzyl)oxy]phenyl}-2-{2-[(3R)-3-(dimethylamino)pyrrolidin-1-yl]ethyl}-4,5-dihydro-2H-pyrimido[5',4':4,5]thieno[2,3-e]indazol-6-amine | 2.91 | 618.3 |

-continued
| Example No | Structure | IUPAC name | LCMS RT (min) | LCMS Ion [M + H]+ |
|---|---|---|---|---|
| 61 | 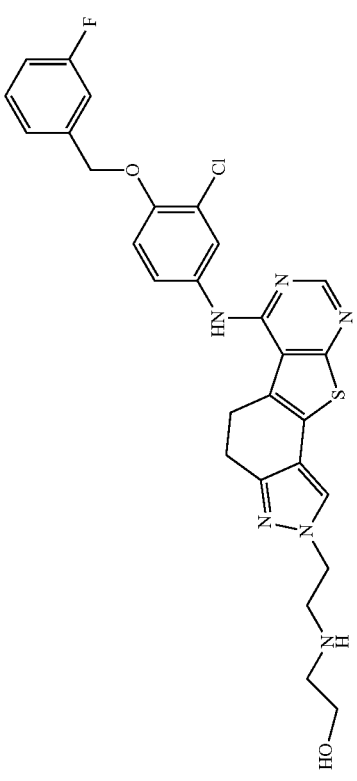 | 2-({2-[6-({3-chloro-4-[(3-fluorobenzyl)oxy]phenyl}amino)-4,5-dihydro-2H-pyrimido[5',4':4,5]thieno[2,3-e]indazol-2-yl]ethyl}amino)ethanol | 3.15 | 565.2 |
| 62 | 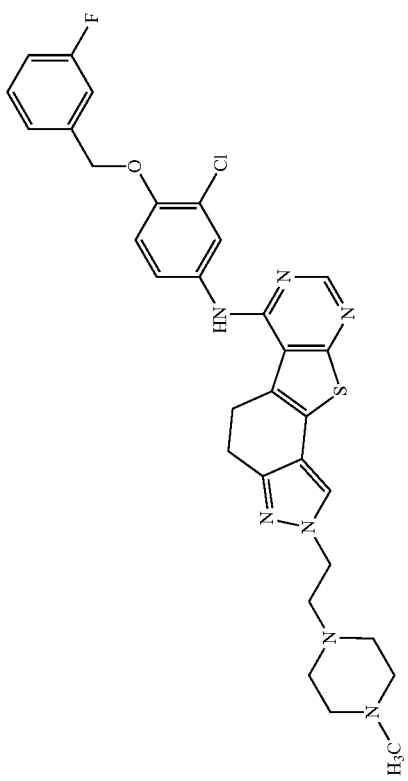 | N-{3-chloro-4-[(3-fluorobenzyl)oxy]phenyl}-2-[2-(4-methylpiperazin-1-yl)ethyl]-4,5-dihydro-2H-pyrimido[5',4':4,5]thieno[2,3-e]indazol-6-amine | 3.15 | 604.3 |

-continued
| Example No | Structure | IUPAC name | LCMS RT (min) | LCMS Ion [M+H]+ |
|---|---|---|---|---|
| 63 | 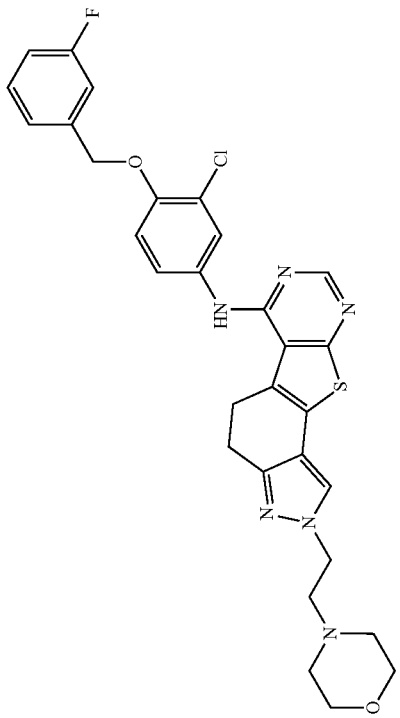 | N-{3-chloro-4-[(3-fluorobenzyl)oxy]phenyl}-2-(2-morpholin-4-ylethyl)-4,5-dihydro-2H-pyrimido[5',4':4,5]thieno[2,3-e]indazol-6-amine | 2.69 | 591.1 |
| 64 | 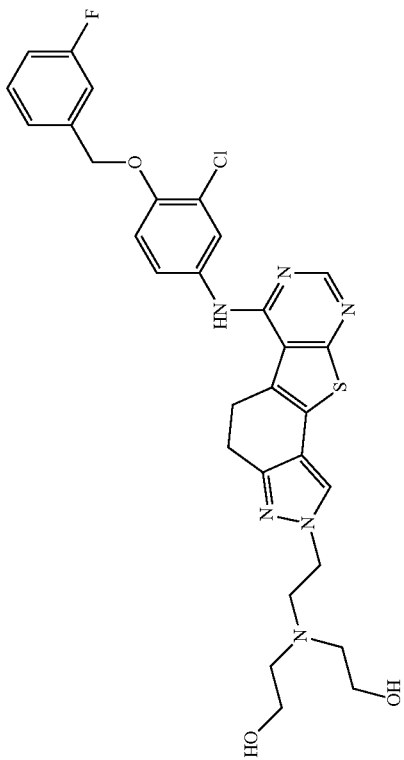 | 2,2'-({2-[6-({3-chloro-4-[(3-fluorobenzyl)oxy]phenyl}amino)-4,5-dihydro-2H-pyrimido[5',4':4,5]thieno[2,3-e]indazol-2-yl]ethyl}iminodiethanol | 2.61 | 609.2 |

| Example No | Structure | IUPAC name | LCMS RT (min) | LCMS Ion [M + H]+ |
|---|---|---|---|---|
| 65 | 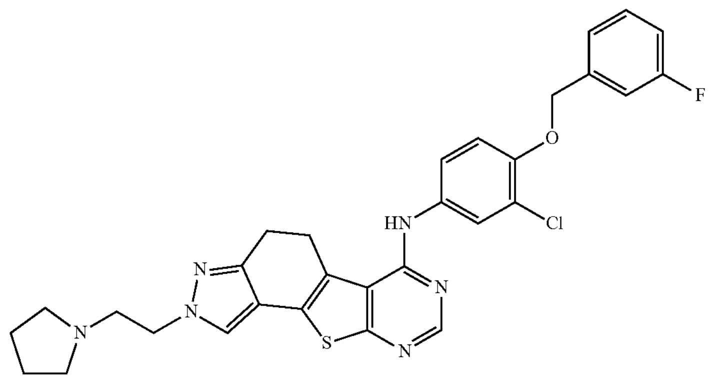 | N-{3-chloro-4-[(3-fluorobenzyl)oxy]phenyl}-2-(2-pyrrolidin-1-ylethyl)-4,5-dihydro-2H-pyrimido[5',4':4,5]thieno[2,3-e]indazol-6-amine | 3.2 | 575.3 |
| 66 | 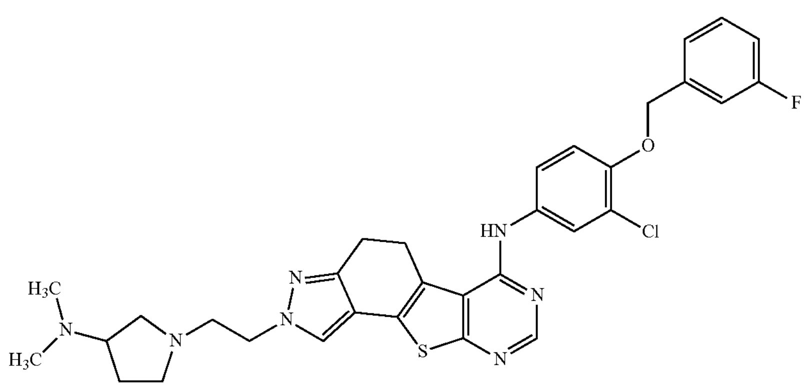 | N-{3-chloro-4-[(3-fluorobenzyl)oxy]phenyl}-2-{2-[3-(dimethylamino)pyrrolidin-1-yl]ethyl}-4,5-dihydro-2H-pyrimido[5',4':4,5]thieno[2,3-e]indazol-6-amine | 2.73 | 618.2 |

| Example No | Structure | IUPAC name | LCMS RT (min) | LCMS Ion [M + H]+ |
|---|---|---|---|---|
| 67 | 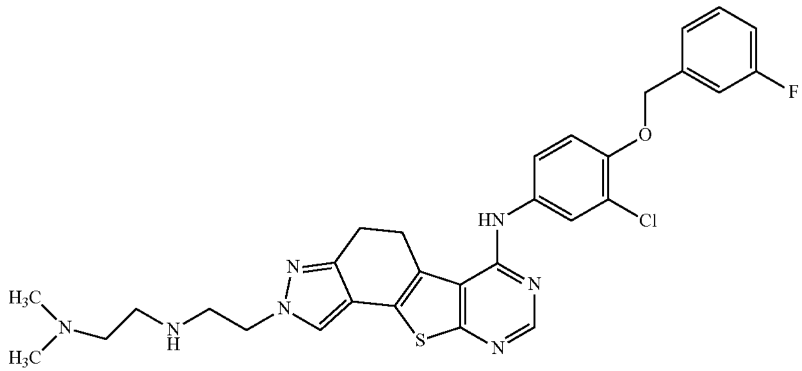 | N'-{2-[6-({3-chloro-4-[(3-fluorobenzyl)oxy]phenyl}amino)-4,5-dihydro-2H-pyrimido[5',4':4,5]thieno[2,3-e]indazol-2-yl]ethyl}-N,N-dimethylethane-1,2-diamine | 0.46 | 592.2 |
| 68 | 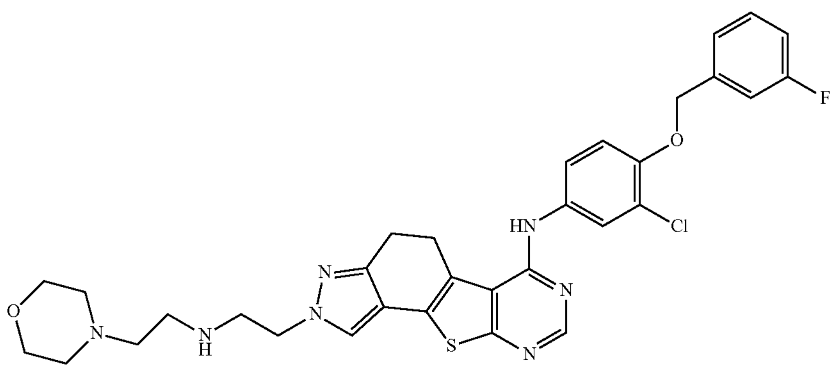 | N-{3-chloro-4-[(3-fluorobenzyl)oxy]phenyl}-2-{2-[(2-morpholin-4-ylethyl)amino]ethyl}-4,5-dihydro-2H-pyrimido[5',4':4,5]thieno[2,3-e]indazol-6-amine | 0.45 | 634.2 |

-continued

| Example No | Structure | IUPAC name | LCMS RT (min) | LCMS Ion [M + H]+ |
|---|---|---|---|---|
| 69 | 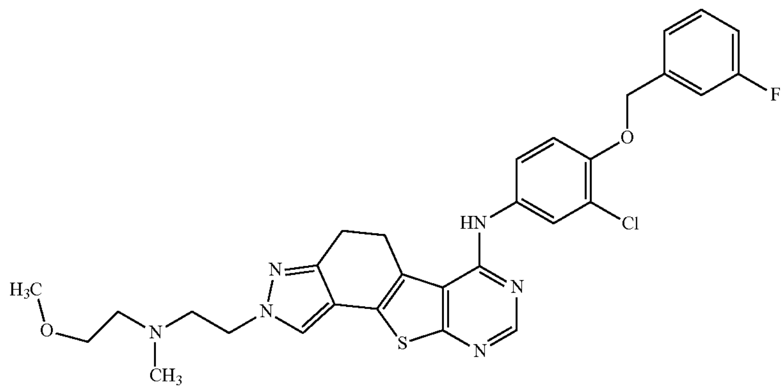 | N-{3-chloro-4-[(3-fluorobenzyl)oxy]phenyl}-2-{2-[(2-methoxyethyl)(methyl)amino]ethyl}-4,5-dihydro-2H-pyrimido[5',4':4,5]thieno[2,3-e]indazol-6-amine | 2.58 | 593.1 |
| 70 | 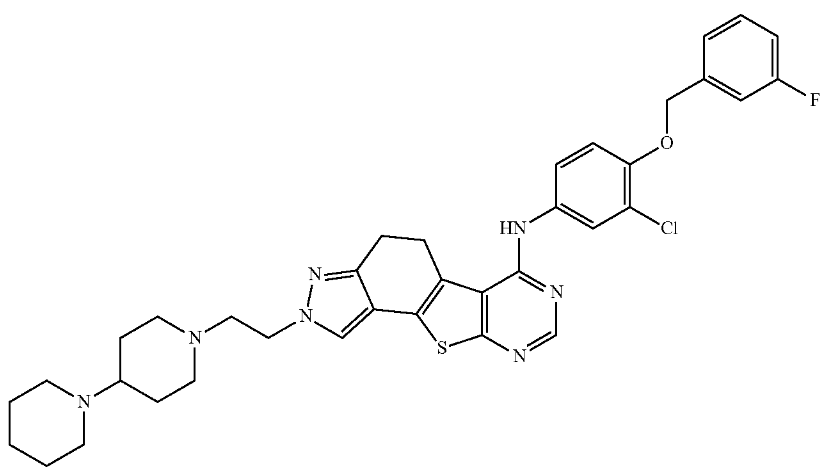 | 2-[2-(1,4'-bipiperidin-1'-yl)ethyl]-N-{3-chloro-4-[(3-fluorobenzyl)oxy]phenyl}-4,5-dihydro-2H-pyrimido[5',4':4,5]thieno[2,3-e]indazol-6-amine | 2.35 | 672.2 |

| Example No | Structure | IUPAC name | LCMS RT (min) | LCMS Ion [M + H]+ |
|---|---|---|---|---|
| 71 | 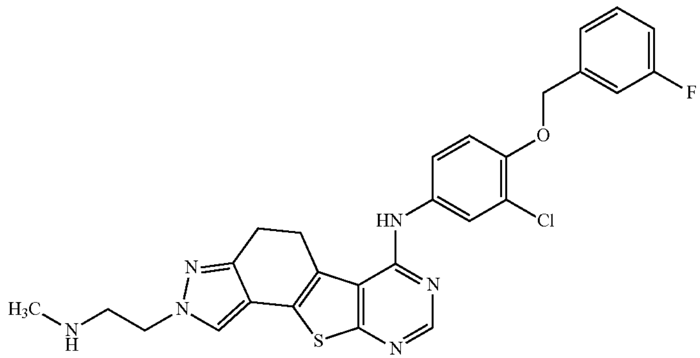 | N-[3-chloro-4-[(3-fluorobenzyl)oxy]phenyl]-2-[2-(methylamino)ethyl]-4,5-dihydro-2H-pyrimido[5′,4′:4,5]thieno[2,3-e]indazol-6-amine | 2.52 | 535.1 |
| 72 | 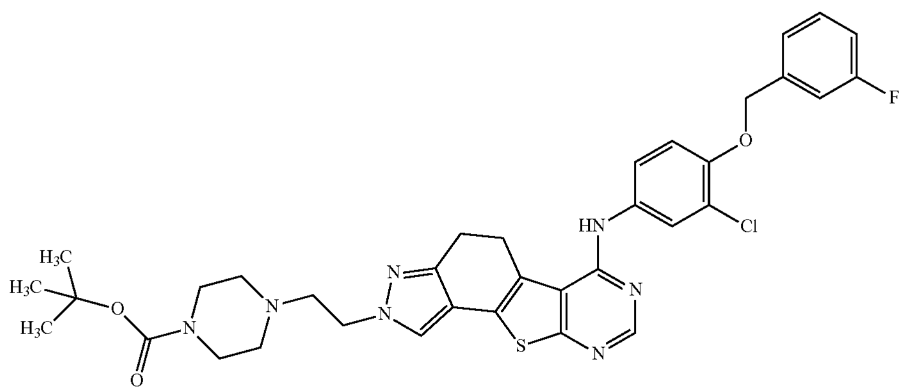 | tert-butyl 4-{2-[6-({3-chloro-4-[(3-fluorobenzyl)oxy]phenyl}amino)-4,5-dihydro-2H-pyrimido[5′,4′:4,5]thieno[2,3-e]indazol-2-yl]ethyl}piperazine-1-carboxylate | 2.85 | 690.1 |

| Example No | Structure | IUPAC name | LCMS RT (min) | LCMS Ion [M + H]+ |
|---|---|---|---|---|
| 73 | 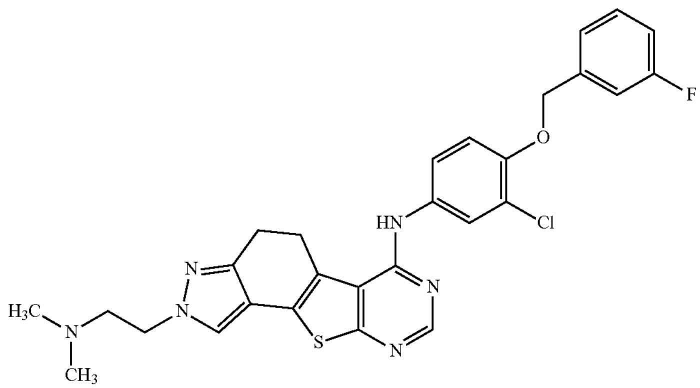 | N-{3-chloro-4-[(3-fluorobenzyl)oxy]phenyl}-2-[2-(dimethylamino)ethyl]-4,5-dihydro-2H-pyrimido[5',4':4,5]thieno[2,3-e]indazol-6-amine | 2.48 | 549.1 |
| 74 | 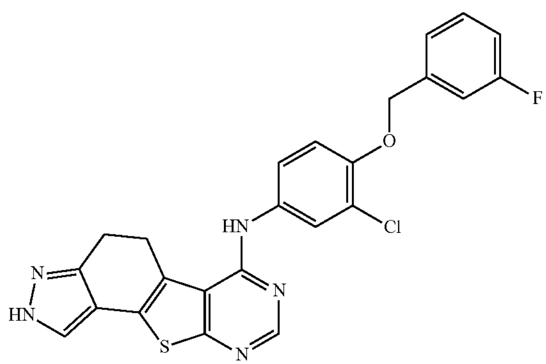 | N-{3-chloro-4-[(3-fluorobenzyl)oxy]phenyl}-4,5-dihydro-2H-pyrimido[5',4':4,5]thieno[2,3-e]indazol-6-amine | 3.39 | 478.2 |

| Example No | Structure | IUPAC name | LCMS RT (min) | LCMS Ion [M + H]+ |
|---|---|---|---|---|
| 75 | 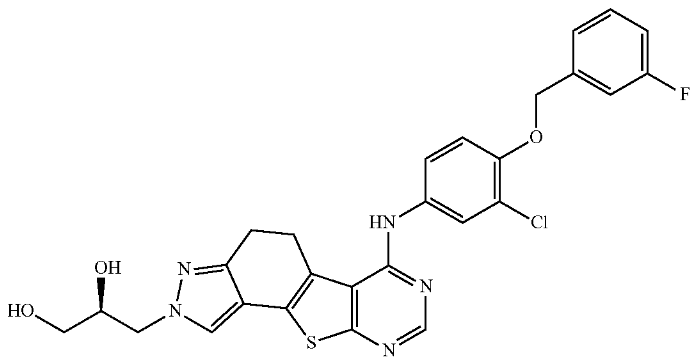 | (2S)-3-[6-({3-chloro-4-[(3-fluorobenzyl)oxy]phenyl}amino)-4,5-dihydro-2H-pyrimido[5',4':4,5]thieno[2,3-e]indazol-2-yl]propane-1,2-diol | 3.13 | 552.1 |
| 76 | 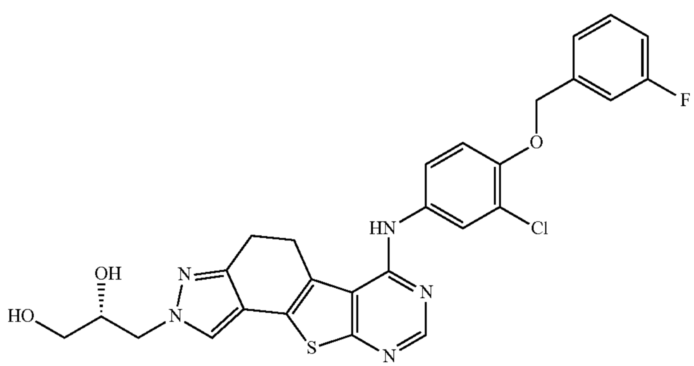 | (2R)-3-[6-({3-chloro-4-[(3-fluorobenzyl)oxy]phenyl}amino)-4,5-dihydro-2H-pyrimido[5',4':4,5]thieno[2,3-e]indazol-2-yl]propane-1,2-diol | 3.12 | 552.1 |

| Example No | Structure | IUPAC name | LCMS RT (min) | LCMS Ion [M + H]+ |
|---|---|---|---|---|
| 77 | 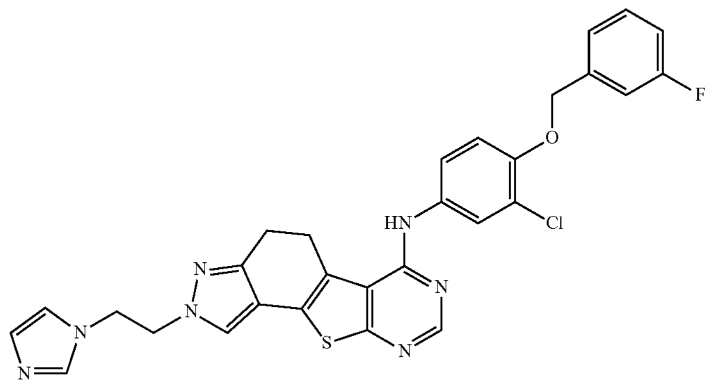 | N-{3-chloro-4-[(3-fluorobenzyl)oxy]phenyl}-2-[2-(1H-imidazol-1-yl)ethyl]-4,5-dihydro-2H-pyrimido[5',4':4,5]thieno[2,3-e]indazol-6-amine | 2.77 | 572.1 |
| 78 | 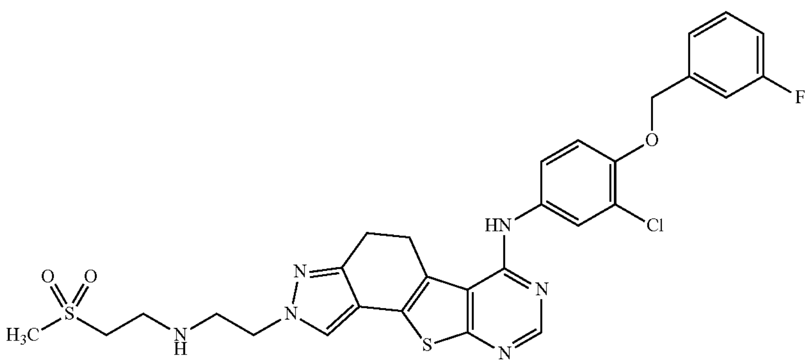 | N-{3-chloro-4-[(3-fluorobenzyl)oxy]phenyl}-2-(2-{[2-(methylsulfonyl)ethyl]amino}ethyl)-4,5-dihydro-2H-pyrimido[5',4':4,5]thieno[2,3-e]indazol-6-amine | 2.79 | 627.1 |

-continued
| Example No | Structure | IUPAC name | LCMS RT (min) | LCMS Ion [M + H]+ |
|---|---|---|---|---|
| 79 | 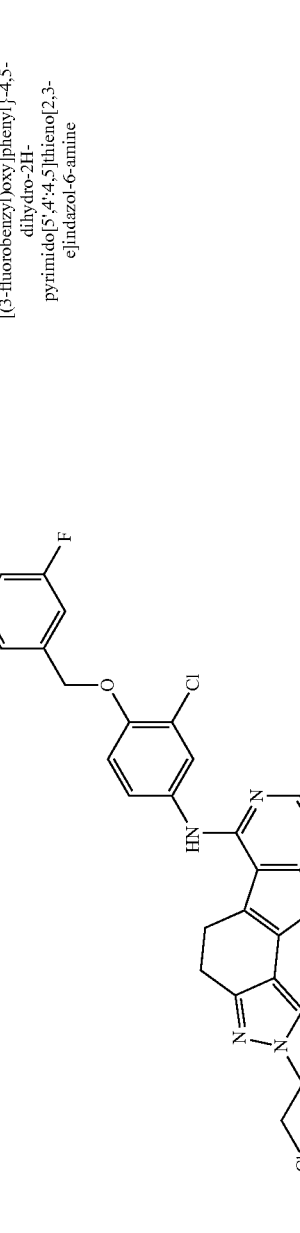 | 2-(2-chloroethyl)-N-{3-chloro-4-[(3-fluorobenzyl)oxy]phenyl}-4,5-dihydro-2H-pyrimido[5',4':4,5]thieno[2,3-e]indazol-6-amine | 3.78 | 540.1 |
| 80 | 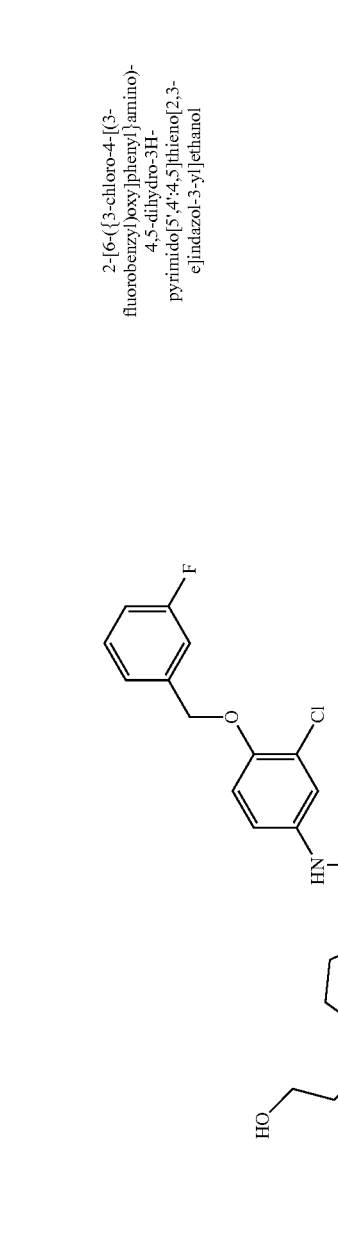 | 2-[6-({3-chloro-4-[(3-fluorobenzyl)oxy]phenyl}amino)-4,5-dihydro-3H-pyrimido[5',4':4,5]thieno[2,3-e]indazol-3-yl]ethanol | 3.3 | 522.1 |

| Example No | Structure | IUPAC name | LCMS RT (min) | LCMS Ion [M + H]+ |
|---|---|---|---|---|
| 81 | 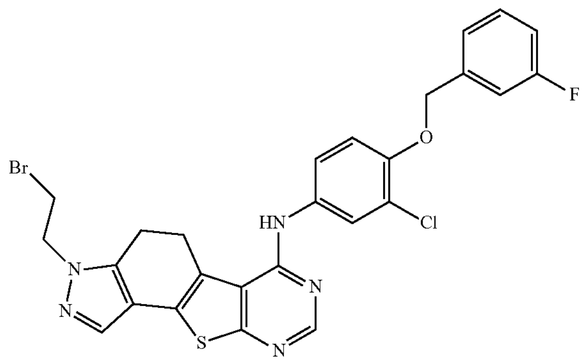 | 3-(2-bromoethyl)-N-{3-chloro-4-[(3-fluorobenzyl)oxy]phenyl}-4,5-dihydro-3H-pyrimido[5',4':4,5]thieno[2,3-e]indazol-6-amine | 3.82 | 586 |
| 82 | 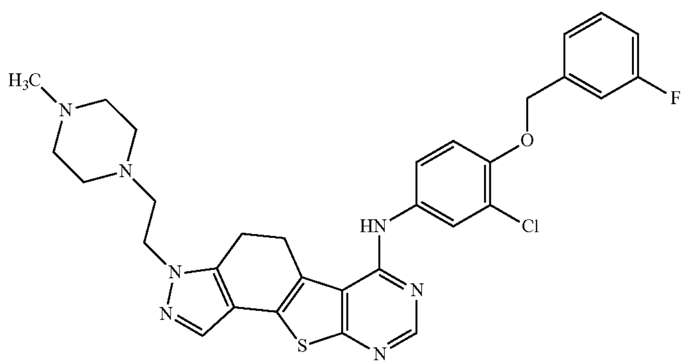 | N-{3-chloro-4-[(3-fluorobenzyl)oxy]phenyl}-3-[2-(4-methylpiperazin-1-yl)ethyl]-4,5-dihydro-3H-pyrimido[5',4':4,5]thieno[2,3-e]indazol-6-amine | 2.4 | 604.3 |

| Example No | Structure | IUPAC name | LCMS RT (min) | LCMS Ion [M + H]+ |
|---|---|---|---|---|
| 83 | 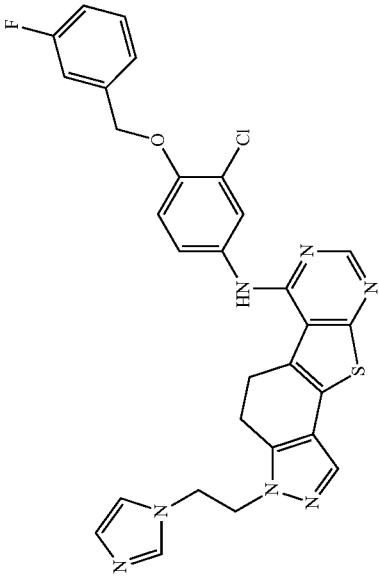 | N-{3-chloro-4-[(3-fluorobenzyl)oxy]phenyl}-3-[2-(1H-imidazol-1-yl)ethyl]-4,5-dihydro-3H-pyrimido[5',4':4,5]thieno[2,3-e]indazol-6-amine | 2.75 | 572.1 |
| 84 | 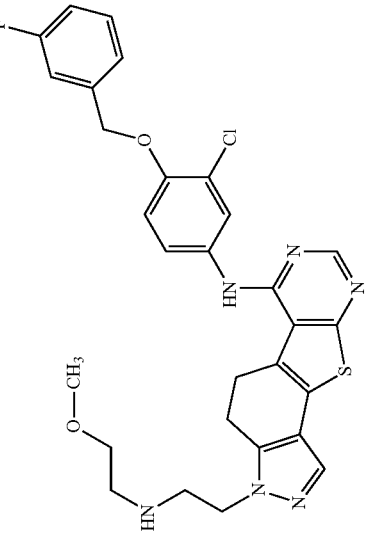 | N-{3-chloro-4-[(3-fluorobenzyl)oxy]phenyl}-3-{2-[(2-methoxyethyl)amino]ethyl}-4,5-dihydro-3H-pyrimido[5',4':4,5]thieno[2,3-e]indazol-6-amine | 2.67 | 579.1 |

-continued

| Example No | Structure | IUPAC name | LCMS RT (min) | LCMS Ion [M + H]+ |
|---|---|---|---|---|
| 85 | 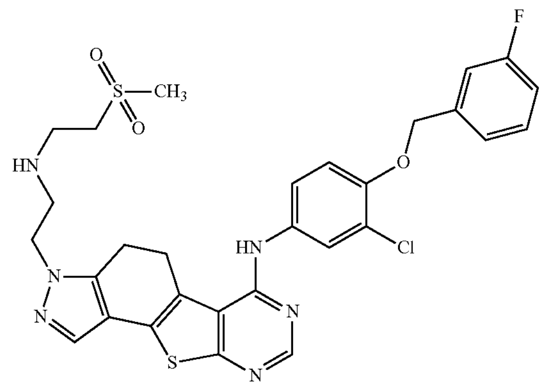 | N-{3-chloro-4-[(3-fluorobenzyl)oxy]phenyl}-3-(2-{[2-(methylsulfonyl)ethyl]amino}ethyl)-4,5-dihydro-3H-pyrimido[5',4':4,5]thieno[2,3-e]indazol-6-amine | 2.77 | 627.1 |
| 86 | 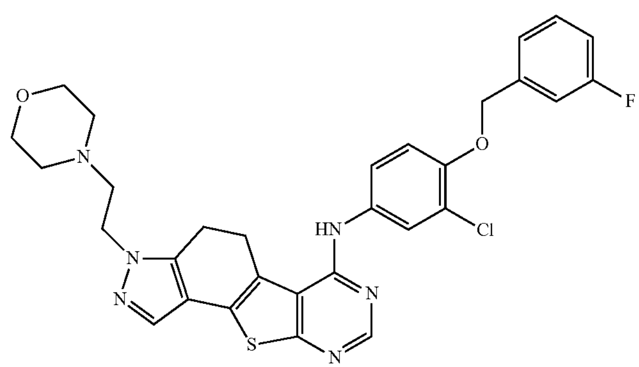 | N-{3-chloro-4-[(3-fluorobenzyl)oxy]phenyl}-3-(2-morpholin-4-ylethyl)-4,5-dihydro-3H-pyrimido[5',4':4,5]thieno[2,3-e]indazol-6-amine | 2.72 | 591.2 |

| Example No | Structure | IUPAC name | LCMS RT (min) | LCMS Ion [M + H]+ |
|---|---|---|---|---|
| 87 | 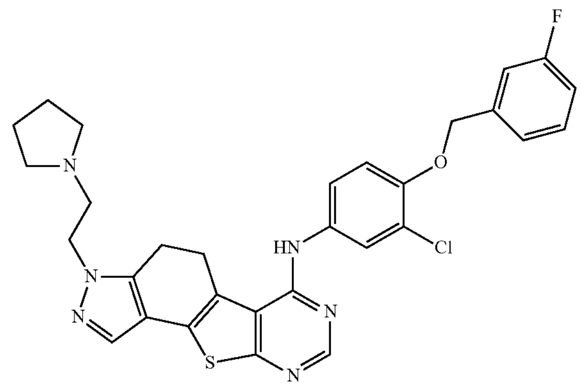 | N-{3-chloro-4-[(3-fluorobenzyl)oxy]phenyl}-3-(2-pyrrolidin-1-yl)ethyl)-4,5-dihydro-3H-pyrimido[5',4':4,5]thieno[2,3-e]indazol-6-amine | 2.78 | 575.1 |
| 88 | 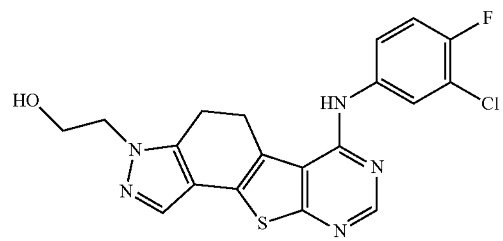 | 2-{6-[(3-chloro-4-fluorophenyl)amino]-4,5-dihydro-3H-pyrimido[5',4':4,5]thieno[2,3-e]indazol-3-yl}ethanol | 2.76 | 416.4 |
| 89 | 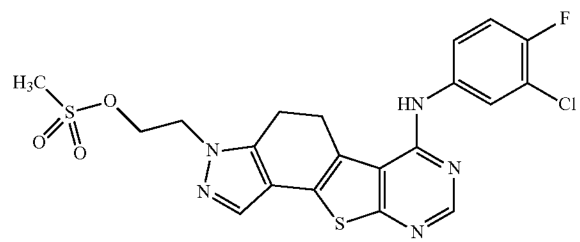 | 2-{6-[(3-chloro-4-fluorophenyl)amino]-4,5-dihydro-3H-pyrimido[5',4':4,5]thieno[2,3-e]indazol-3-yl}ethyl methanesulfonate | 3.18 | 494.1 |

-continued

| Example No | Structure | IUPAC name | LCMS RT (min) | LCMS Ion [M+H]+ |
|---|---|---|---|---|
| 90 | 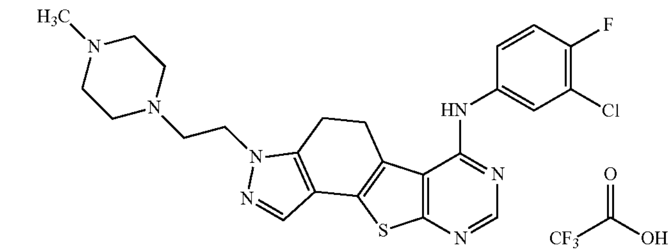 | N-(3-chloro-4-fluorophenyl)-3-[2-(4-methylpiperazin-1-yl)ethyl]-4,5-dihydro-3H-pyrimido[5',4':4,5]thieno[2,3-e]indazol-6-amine trifluoroacetate | 2.38 | 498.2 |
| 91 | 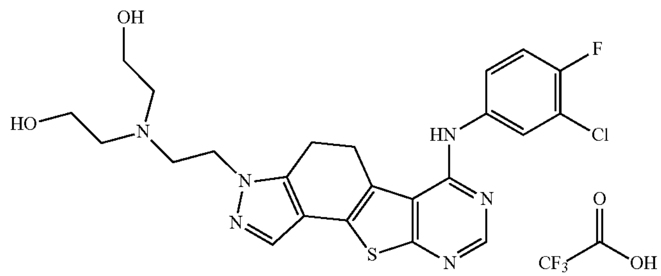 | 2,2'-[(2-{6-[(3-chloro-4-fluorophenyl)amino]-4,5-dihydro-3H-pyrimido[5',4':4,5]thieno[2,3-e]indazol-3-yl}ethyl)imino]diethanol trifluoroacetate (salt) | 2.36 | 503.2 |
| 92 | 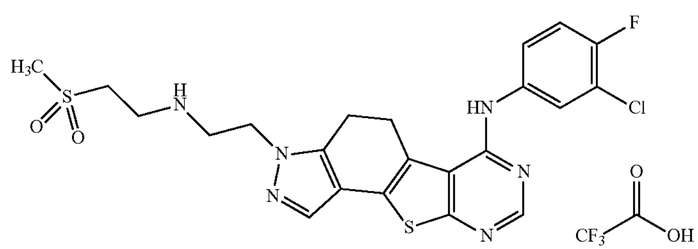 | N-(3-chloro-4-fluorophenyl)-3-(2-{[2-(methylsulfonyl)ethyl]amino}ethyl)-4,5-dihydro-3H-pyrimido[5',4':4,5]thieno[2,3-e]indazol-6-amine | 2.81 | 521.2 |
| 93 | 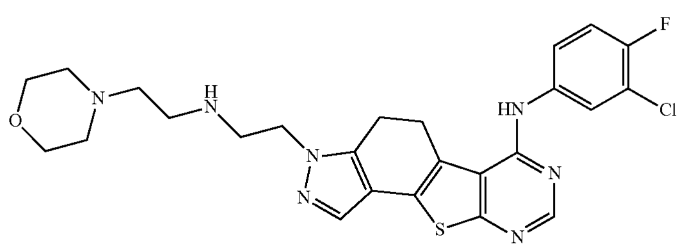 | N-(3-chloro-4-fluorophenyl)-3-{2-[(2-morpholin-4-ylethyl)amino]ethyl}-4,5-dihydro-3H-pyrimido[5',4':4,5]thieno[2,3-e]indazol-6-amine | 2.24 | 528.1 |

| Example No | Structure | IUPAC name | LCMS RT (min) | LCMS Ion [M + H]+ |
|---|---|---|---|---|
| 94 | 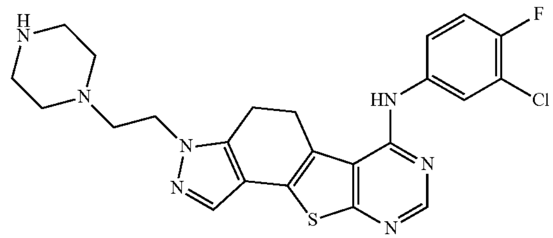 | N-(3-chloro-4-fluorophenyl)-3-(2-piperazin-1-ylethyl)-4,5-dihydro-3H-pyrimido[5',4':4,5]thieno[2,3-e]indazol-6-amine | 2.35 | 484.1 |
| 95 | 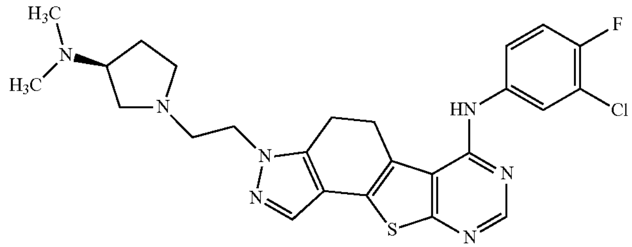 | N-(3-chloro-4-fluorophenyl)-3-{2-[3-(dimethylamino)pyrrolidin-1-yl]ethyl}-4,5-dihydro-3H-pyrimido[5',4':4,5]thieno[2,3-e]indazol-6-amine | 2.22 | 512.1 |
| 96 | 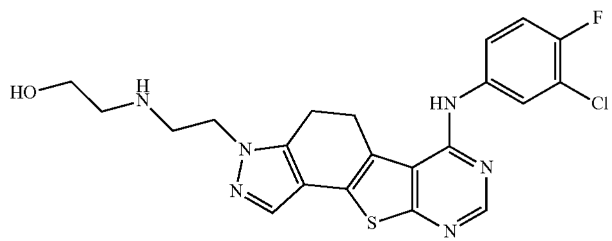 | 2-[(2-{6-[(3-chloro-4-fluorophenyl)amino]-4,5-dihydro-3H-pyrimido[5',4':4,5]thieno[2,3-e]indazol-3-yl}ethyl)amino]ethanol | 2.39 | 459.1 |
| 97 | 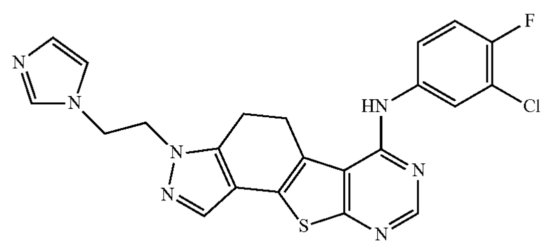 | N-(3-chloro-4-fluorophenyl)-3-[2-(1H-imidazol-1-yl)ethyl]-4,5-dihydro-3H-pyrimido[5',4':4,5]thieno[2,3-e]indazol-6-amine | 2.44 | 466.1 |

| Example No | Structure | IUPAC name | LCMS RT (min) | LCMS Ion [M + H]+ |
|---|---|---|---|---|
| 98 | 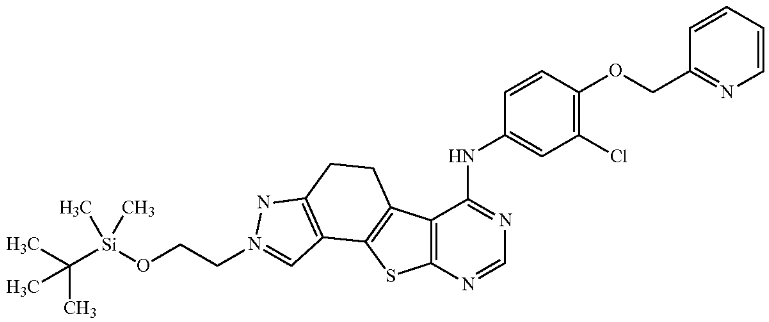 | 2-(2-{[tert-butyl(dimethyl)silyl]oxy}ethyl)-N-[3-chloro-4-(pyridin-2-ylmethoxy)phenyl]-4,5-dihydro-2H-pyrimido[5',4':4,5]thieno[2,3-e]indazol-6-amine | 4.09 | 619.2 |
| 99 | 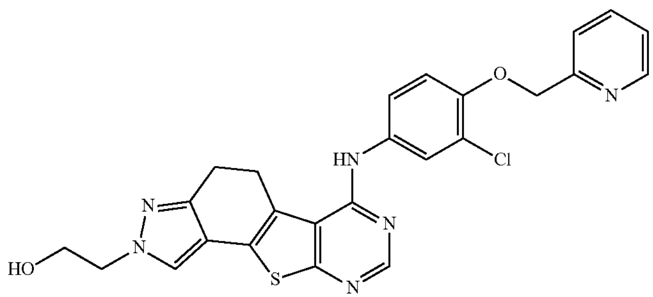 | 2-(6-{[3-chloro-4-(pyridin-2-ylmethoxy)phenyl]amino}-4,5-dihydro-2H-pyrimido[5',4':4,5]thieno[2,3-e]indazol-2-yl)ethanol | 2.32 | 505.3 |
| 100 | 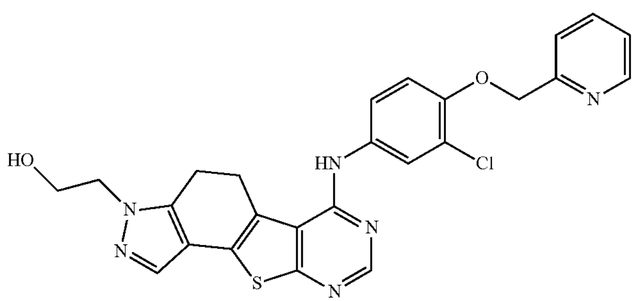 | 2-(6-{[3-chloro-4-(pyridin-2-ylmethoxy)phenyl]amino}-4,5-dihydro-3H-pyrimido[5',4':4,5]thieno[2,3-e]indazol-3-yl)ethanol | 2.41 | 505.1 |

-continued

| Example No | Structure | IUPAC name | LCMS RT (min) | LCMS Ion [M + H]+ |
|---|---|---|---|---|
| 101 | 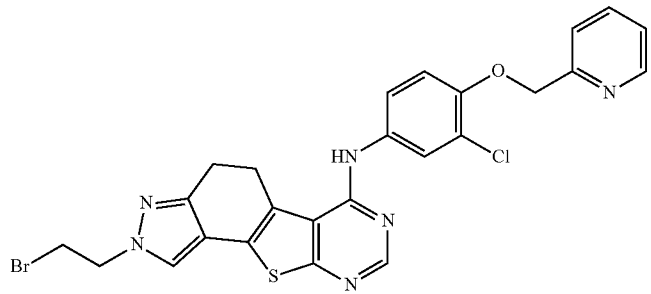 | 2-(2-bromoethyl)-N-[3-chloro-4-(pyridin-2-ylmethoxy)phenyl]-4,5-dihydro-2H-pyrimido[5′,4′:4,5]thieno[2,3-e]indazol-6-amine | 2.89 | 567.4 |
| 102 | 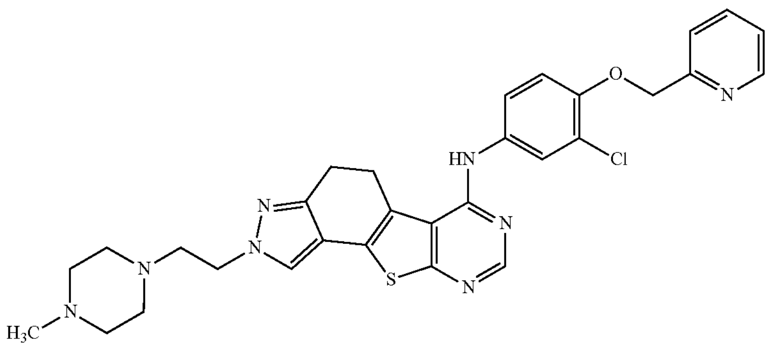 | N-[3-chloro-4-(pyridin-2-ylmethoxy)phenyl]-2-[2-(4-methylpiperazin-1-yl)ethyl]-4,5-dihydro-2H-pyrimido[5′,4′:4,5]thieno[2,3-e]indazol-6-amine | 2.18 | 587.4 |
| 103 | 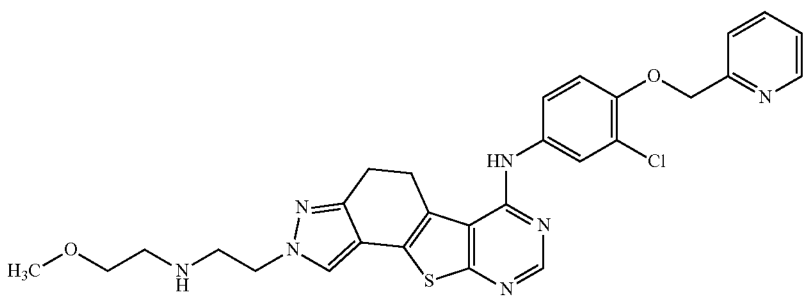 | N-[3-chloro-4-(pyridin-2-ylmethoxy)phenyl]-2-{2-[(2-methoxyethyl)amino]ethyl}-4,5-dihydro-2H-pyrimido[5′,4′:4,5]thieno[2,3-e]indazol-6-amine | 2.14 | 562.3 |

| Example No | Structure | IUPAC name | LCMS RT (min) | LCMS Ion [M + H]+ |
|---|---|---|---|---|
| 104 | 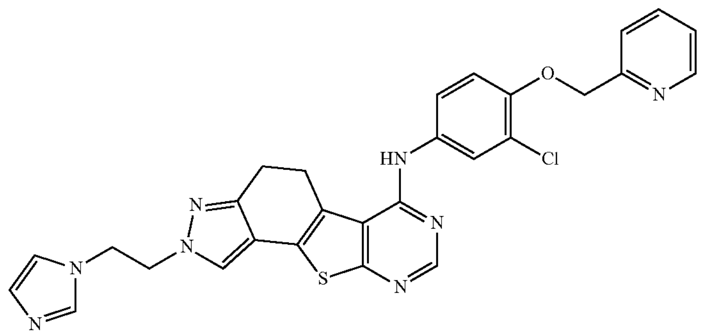 | N-[3-chloro-4-(pyridin-2-ylmethoxy)phenyl]-2-[2-(1H-imidazol-1-yl)ethyl]-4,5-dihydro-2H-pyrimido[5′,4′:4,5]thieno[2,3-e]indazol-6-amine | 2.19 | 555.1 |
| 105 | 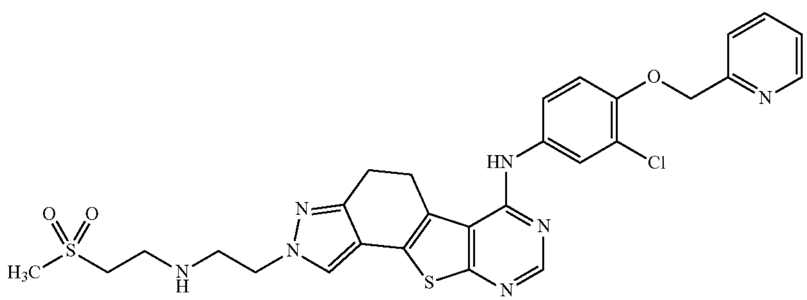 | N-[3-chloro-4-(pyridin-2-ylmethoxy)phenyl]-2-(2-{[2-(methylsulfonyl)ethyl]amino}ethyl)-4,5-dihydro-2H-pyrimido[5′,4′:4,5]thieno[2,3-e]indazol-6-amine | 2.21 | 610.1 |
| 106 | 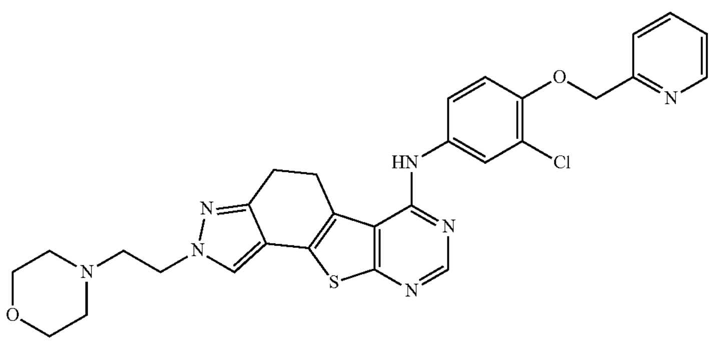 | N-[3-chloro-4-(pyridin-2-ylmethoxy)phenyl]-2-(2-morpholin-4-ylethyl)-4,5-dihydro-2H-pyrimido[5′,4′:4,5]thieno[2,3-e]indazol-6-amine | 2.2 | 574.1 |

| Example No | Structure | IUPAC name | LCMS RT (min) | LCMS Ion [M + H]+ |
|---|---|---|---|---|
| 107 | 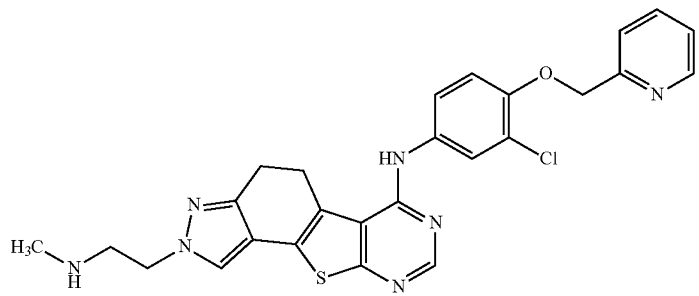 | N-[3-chloro-4-(pyridin-2-ylmethoxy)phenyl]-2-[2-(methylamino)ethyl]-4,5-dihydro-2H-pyrimido[5',4':4,5]thieno[2,3-e]indazol-6-amine | 2.16 | 518.1 |
| 108 | 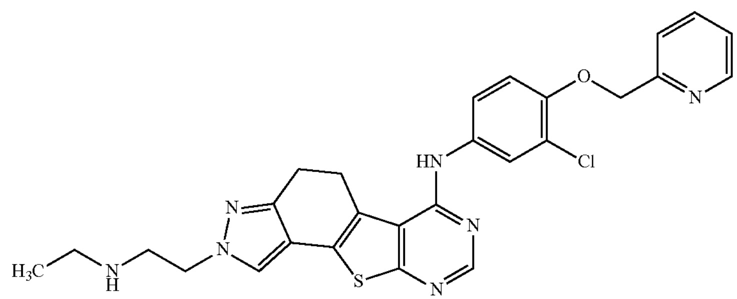 | N-[3-chloro-4-(pyridin-2-ylmethoxy)phenyl]-2-[2-(ethylamino)ethyl]-4,5-dihydro-2H-pyrimido[5',4':4,5]thieno[2,3-e]indazol-6-amine | 2.59 | 532.3 |
| 109 | 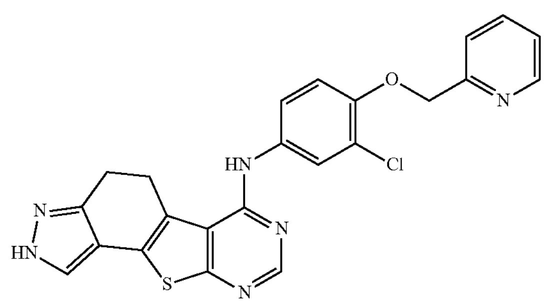 | N-[3-chloro-4-(pyridin-2-ylmethoxy)phenyl]-4,5-dihydro-2H-pyrimido[5',4':4,5]thieno[2,3-e]indazol-6-amine | 2.48 | 461.2 |

| Example No | Structure | IUPAC name | LCMS RT (min) | LCMS Ion [M + H]+ |
|---|---|---|---|---|
| 110 | 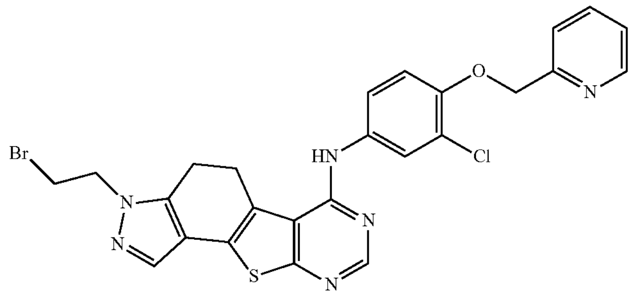 | 3-(2-bromoethyl)-N-[3-chloro-4-(pyridin-2-ylmethoxy)phenyl]-4,5-dihydro-3H-pyrimido[5',4':4,5]thieno[2,3-e]indazol-6-amine | 2.77 | 567 |
| 111 | 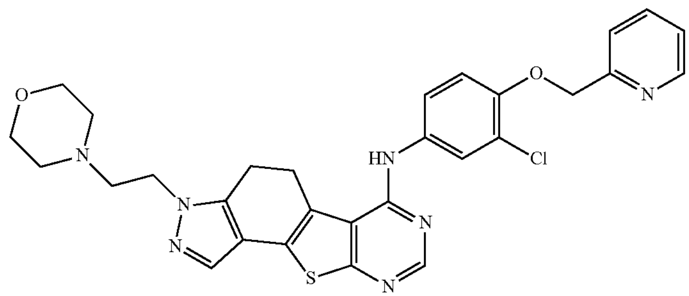 | N-[3-chloro-4-(pyridin-2-ylmethoxy)phenyl]-3-(2-morpholin-4-ylethyl)-4,5-dihydro-3H-pyrimido[5',4':4,5]thieno[2,3-e]indazol-6-amine | 2.21 | 574.1 |
| 112 | 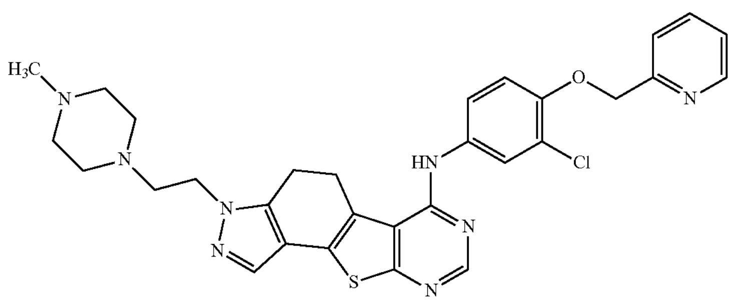 | N-[3-chloro-4-(pyridin-2-ylmethoxy)phenyl]-3-[2-(4-methylpiperazin-1-yl)ethyl]-4,5-dihydro-3H-pyrimido[5',4':4,5]thieno[2,3-e]indazol-6-amine | 2.2 | 587.1 |

-continued

| Example No | Structure | IUPAC name | LCMS RT (min) | LCMS Ion [M + H]+ |
|---|---|---|---|---|
| 113 | 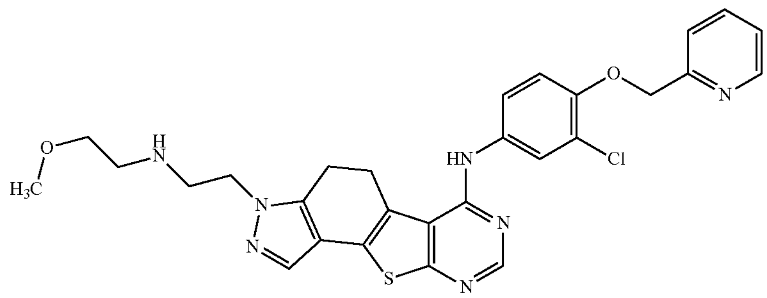 | N-[3-chloro-4-(pyridin-2-ylmethoxy)phenyl]-3-{2-[(2-methoxyethyl)amino]ethyl}-4,5-dihydro-3H-pyrimido[5',4':4,5]thieno[2,3-e]indazol-6-amine | 2.25 | 562.2 |
| 114 | 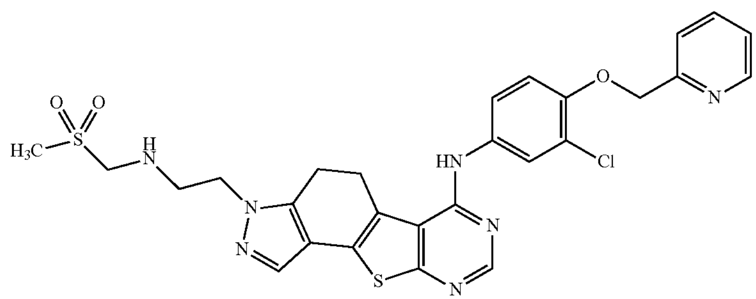 | N-[3-chloro-4-(pyridin-2-ylmethoxy)phenyl]-3-(2-{[2-(methylsulfonyl)ethyl]amino}ethyl)-4,5-dihydro-3H-pyrimido[5',4':4,5]thieno[2,3-e]indazol-6-amine | 2.22 | 610.1 |
| 115 | 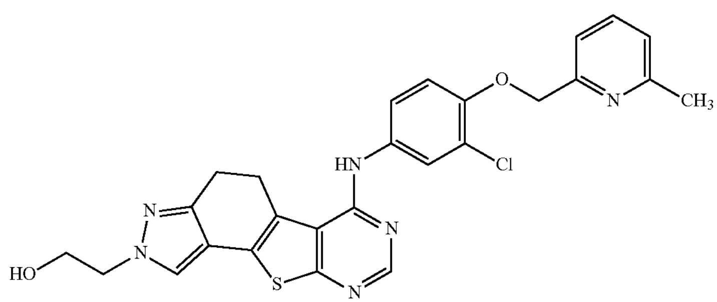 | 2-[6-({3-chloro-4-[(6-methylpyridin-2-yl)methoxy]phenyl}amino)-4,5-dihydro-2H-pyrimido[5',4':4,5]thieno[2,3-e]indazol-2-yl]ethanol | 2.36 | 519.2 |

-continued

| Example No | Structure | IUPAC name | LCMS RT (min) | LCMS Ion [M + H]+ |
|---|---|---|---|---|
| 116 | 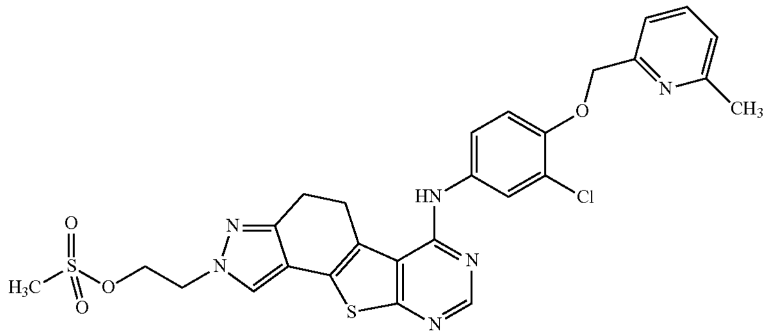 | 2-[6-({3-chloro-4-[(6-methylpyridin-2-yl)methoxy]phenyl}amino)-4,5-dihydro-2H-pyrimido[5',4':4,5]thieno[2,3-e]indazol-2-yl]ethyl methanesulfonate | 2.69 | 597.3 |
| 117 | 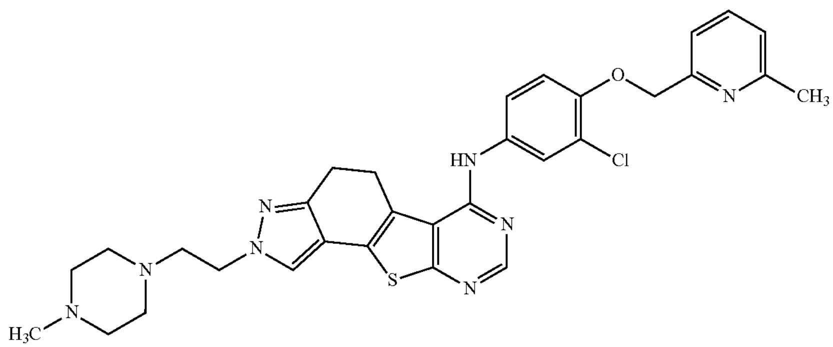 | N-{3-chloro-4-[(6-methylpyridin-2-yl)methoxy]phenyl}-2-[2-(4-methylpiperazin-1-yl)ethyl]-4,5-dihydro-2H-pyrimido[5',4':4,5]thieno[2,3-e]indazol-6-amine | 2.07 | 601.4 |
| 118 | 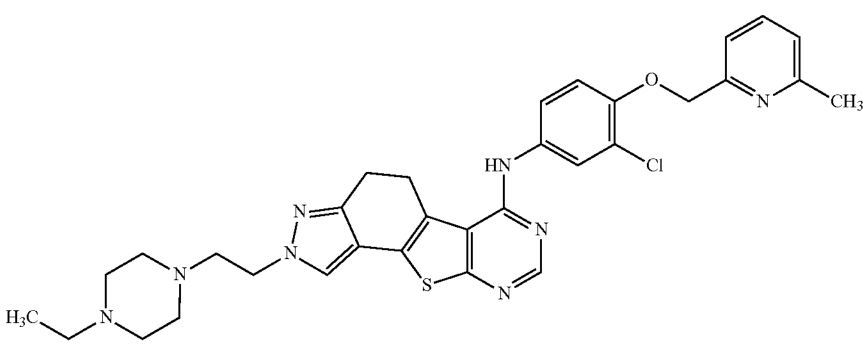 | N-{3-chloro-4-[(6-methylpyridin-2-yl)methoxy]phenyl}-2-[2-(4-ethylpiperazin-1-yl)ethyl]-4,5-dihydro-2H-pyrimido[5',4':4,5]thieno[2,3-e]indazol-6-amine | 2.12 | 615.3 |

| Example No | Structure | IUPAC name | LCMS RT (min) | LCMS Ion [M + H]+ |
|---|---|---|---|---|
| 119 | 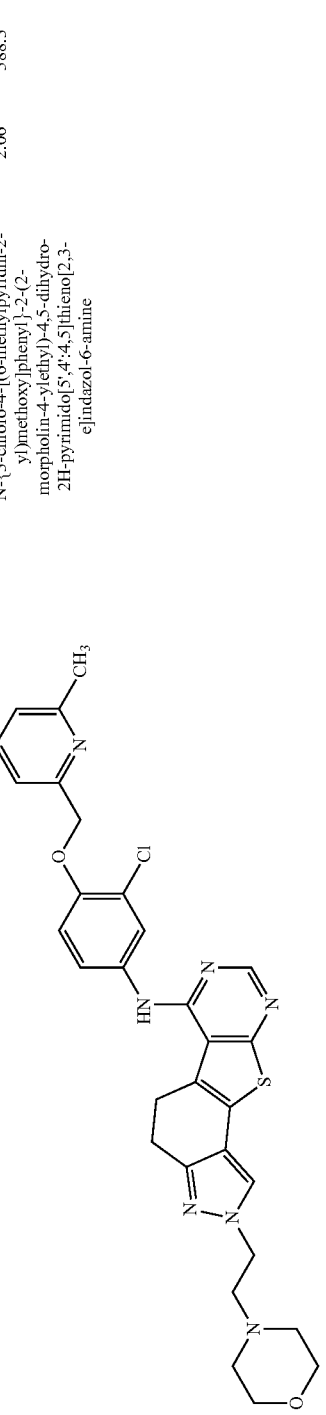 | N-{3-chloro-4-[(6-methylpyridin-2-yl)methoxy]phenyl}-2-(2-morpholin-4-ylethyl)-4,5-dihydro-2H-pyrimido[5',4':4,5]thieno[2,3-e]indazol-6-amine | 2.06 | 588.3 |
| 120 | 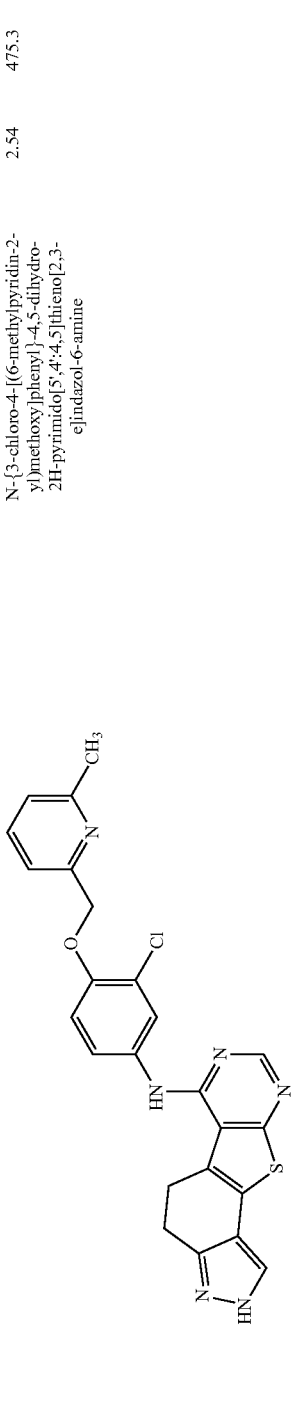 | N-{3-chloro-4-[(6-methylpyridin-2-yl)methoxy]phenyl}-4,5-dihydro-2H-pyrimido[5',4':4,5]thieno[2,3-e]indazol-6-amine | 2.54 | 475.3 |
| 121 | 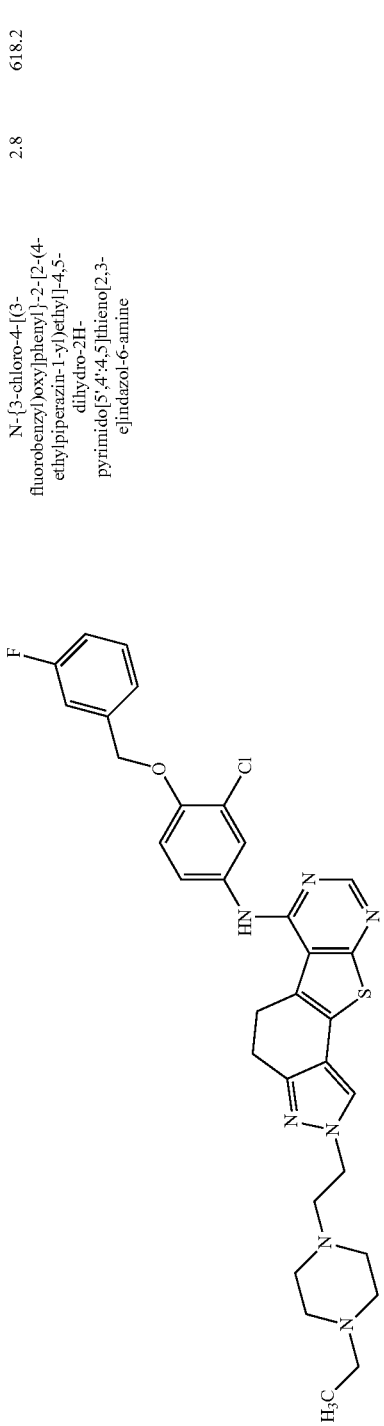 | N-{3-chloro-4-[(3-fluorobenzyl)oxy]phenyl}-2-[2-(4-ethylpiperazin-1-yl)ethyl]-4,5-dihydro-2H-pyrimido[5',4':4,5]thieno[2,3-e]indazol-6-amine | 2.8 | 618.2 |

| Example No | Structure | IUPAC name | LCMS RT (min) | LCMS Ion [M + H]+ |
|---|---|---|---|---|
| 122 | 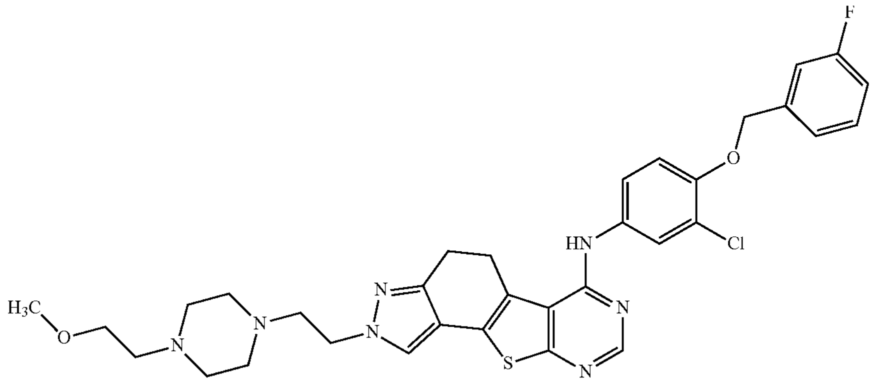 | N-{3-chloro-4-[(3-fluorobenzyl)oxy]phenyl}-2-{2-[4-(2-methoxyethyl)piperazin-1-yl]ethyl}-4,5-dihydro-2H-pyrimido[5',4':4,5]thieno[2,3-e]indazol-6-amine | 2.82 | 648.2 |
| 123 | 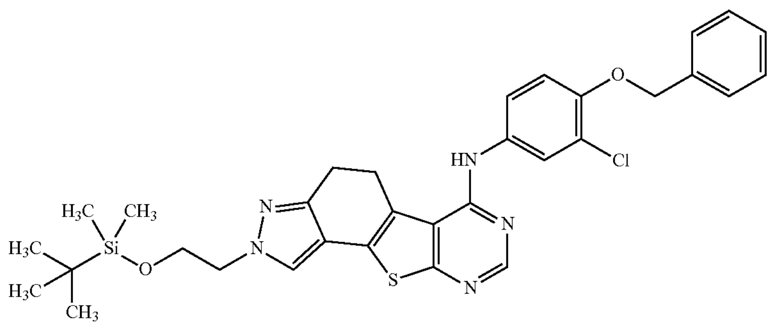 | N-[4-(benzyloxy)-3-chlorophenyl]-2-(2-{[tert-butyl(dimethyl)silyl]oxy}ethyl)-4,5-dihydro-2H-pyrimido[5',4':4,5]thieno[2,3-e]indazol-6-amine | 4.74 | 618.2 |
| 124 | 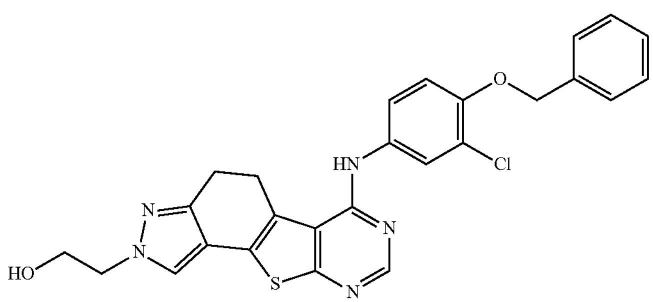 | 2-(6-{[4-(benzyloxy)-3-chlorophenyl]amino}-4,5-dihydro-2H-pyrimido[5',4':4,5]thieno[2,3-e]indazol-2-yl)ethanol | 3.56 | 504.2 |

| Example No | Structure | IUPAC name | LCMS RT (min) | LCMS Ion [M + H]+ |
|---|---|---|---|---|
| 125 | 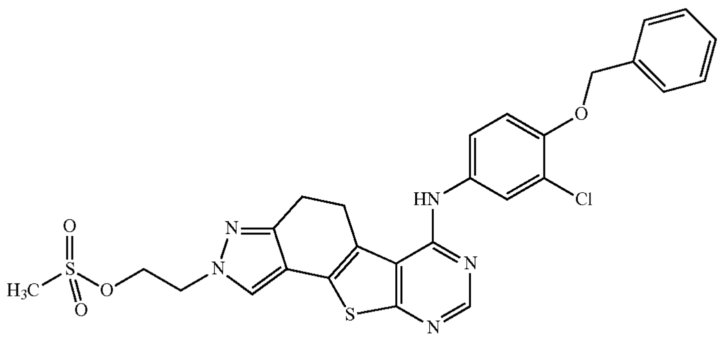 | 2-(6-{[4-(benzyloxy)-3-chlorophenyl]amino}-4,5-dihydro-2H-pyrimido[5',4':4,5]thieno[2,3-e]indazol-2-yl)ethyl methanesulfonate | 3.79 | 582.1 |
| 126 | 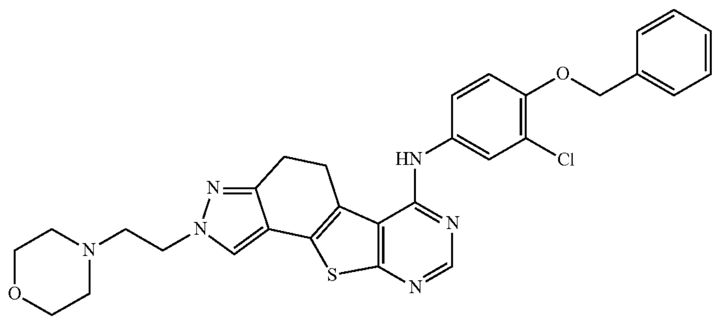 | N-[4-(benzyloxy)-3-chlorophenyl]-2-(2-morpholin-4-ylethyl)-4,5-dihydro-2H-pyrimido[5',4':4,5]thieno[2,3-e]indazol-6-amine | 1.98 | 573.4 |
| 127 | 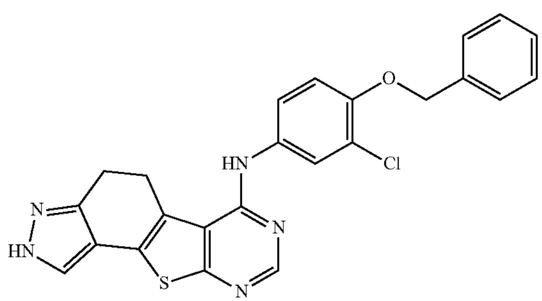 | N-[4-(benzyloxy)-3-chlorophenyl]-4,5-dihydro-2H-pyrimido[5',4':4,5]thieno[2,3-e]indazol-6-amine | 3.4 | 460.2 |

-continued

| Example No | Structure | IUPAC name | LCMS RT (min) | LCMS Ion [M + H]+ |
|---|---|---|---|---|
| 128 | 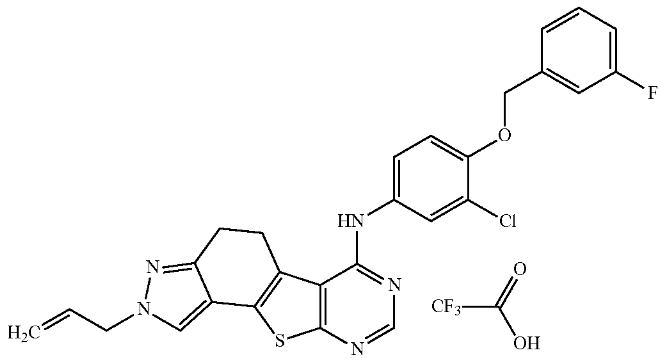 | 2-allyl-N-{3-chloro-4-[(3-fluorobenzyl)oxy]phenyl}-4,5-dihydro-2H-pyrimido[5',4':4,5]thieno[2,3-e]indazol-6-amine trifluoroacetate | 3.83 | 520.1 |
| 129 | 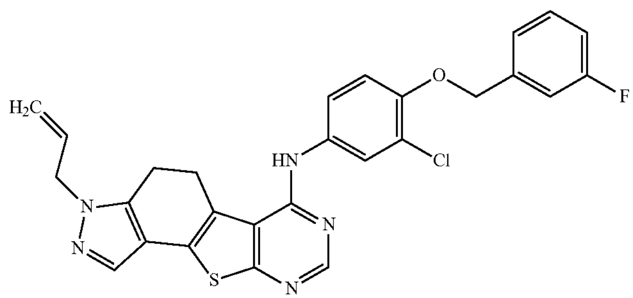 | 3-allyl-N-{3-chloro-4-[(3-fluorobenzyl)oxy]phenyl}-4,5-dihydro-3H-pyrimido[5',4':4,5]thieno[2,3-e]indazol-6-amine trifluoroacetate | 3.74 | 518.1 |
| 130 | 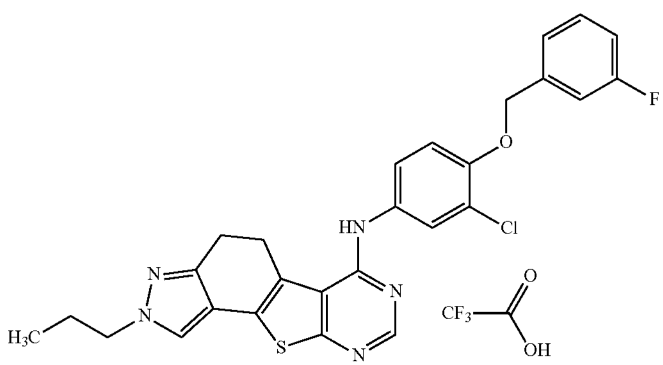 | N-{3-chloro-4-[(3-fluorobenzyl)oxy]phenyl}-2-propyl-4,5-dihydro-2H-pyrimido[5',4':4,5]thieno[2,3-e]indazol-6-amine trifluoroacetate | 3.91 | 522.1 |

| Example No | Structure | IUPAC name | LCMS RT (min) | LCMS Ion [M + H]+ |
|---|---|---|---|---|
| 131 | 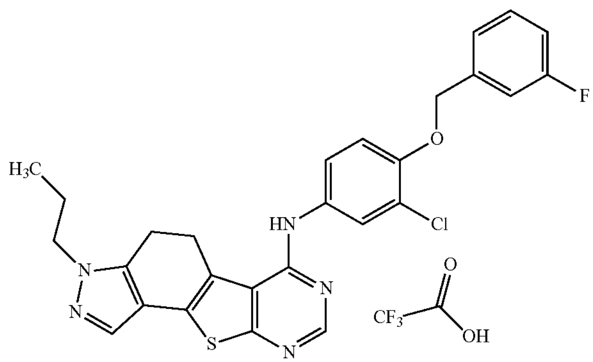 | N-{3-chloro-4-[(3-fluorobenzyl)oxy]phenyl}-3-propyl-4,5-dihydro-3H-pyrimido[5',4':4,5]thieno[2,3-e]indazol-6-amine trifluoroacetate | 3.85 | 522.2 |
| 132 | 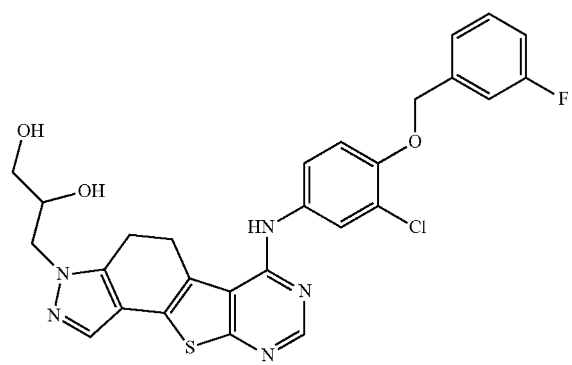 | 3-[6-({3-chloro-4-[(3-fluorobenzyl)oxy]phenyl}amino)-4,5-dihydro-3H-pyrimido[5',4':4,5]thieno[2,3-e]indazol-3-yl]propane-1,2-diol | 3.17 | 553.5 |

| Example No | Structure | IUPAC name | LCMS RT (min) | LCMS Ion [M+H]+ |
|---|---|---|---|---|
| 133 | 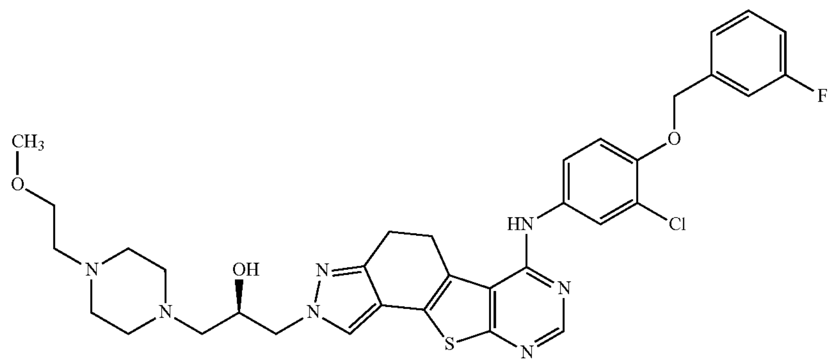 | (2R)-1-[6-({3-chloro-4-[(3-fluorobenzyl)oxy]phenyl}amino)-4,5-dihydro-2H-pyrimido[5',4':4,5]thieno[2,3-e]indazol-2-yl]-3-[4-(2-methoxyethyl)piperazin-1-yl]propan-2-ol | 2.64 | 678.2 |
| 134 | 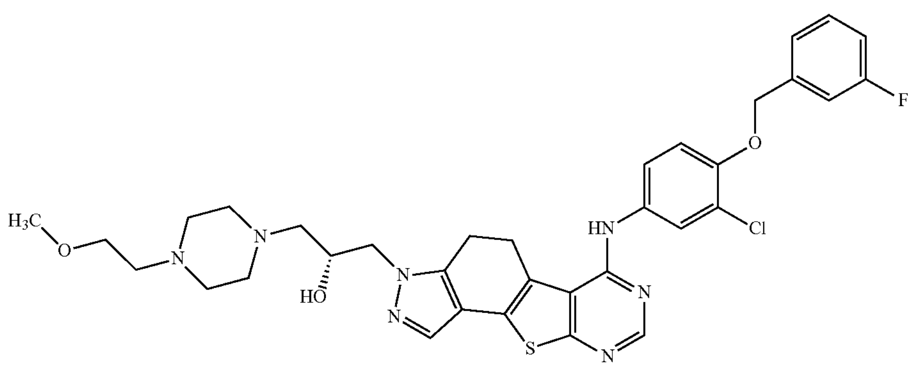 | (2R)-1-[6-({3-chloro-4-[(3-fluorobenzyl)oxy]phenyl}amino)-4,5-dihydro-3H-pyrimido[5',4':4,5]thieno[2,3-e]indazol-3-yl]-3-[4-(2-methoxyethyl)piperazin-1-yl]propan-2-ol | 2.65 | 678.1 |

| Example No | Structure | IUPAC name | LCMS RT (min) | LCMS Ion [M + H]+ |
|---|---|---|---|---|
| 135 | 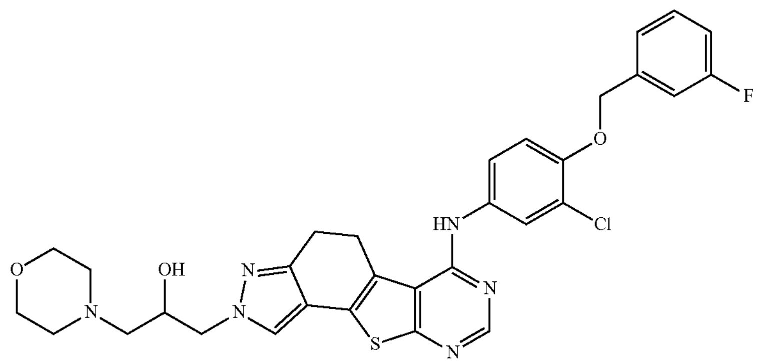 | 1-[6-({3-chloro-4-[(3-fluorobenzyl)oxy]phenyl}amino)-4,5-dihydro-2H-pyrimido[5',4':4,5]thieno[2,3-e]indazol-2-yl]-3-morpholin-4-ylpropan-2-ol | 2.85 | 621.4 |
| 136 | 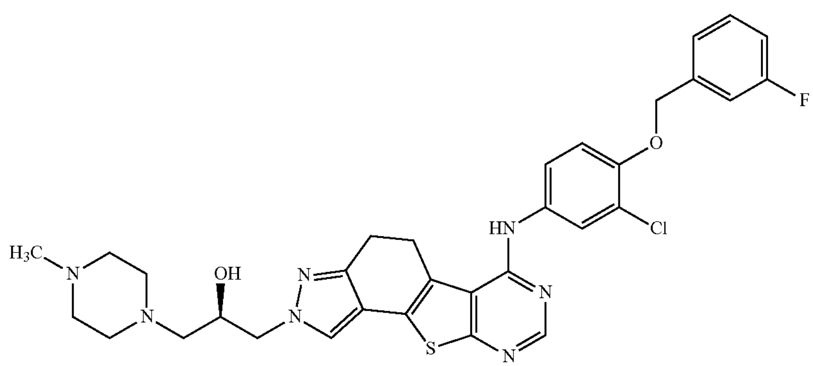 | (2R)-1-[6-({3-chloro-4-[(3-fluorobenzyl)oxy]phenyl}amino)-4,5-dihydro-2H-pyrimido[5',4':4,5]thieno[2,3-e]indazol-2-yl]-3-(4-methylpiperazin-1-yl)propan-2-ol | 2.61 | 634.1 |

| Example No | Structure | IUPAC name | LCMS RT (min) | LCMS Ion [M + H]+ |
|---|---|---|---|---|
| 137 | 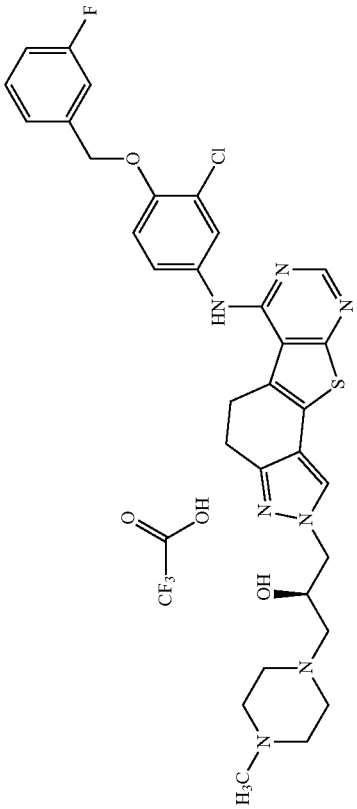 | (2R)-1-[6-({3-chloro-4-[(3-fluorobenzyl)oxy]phenyl}amino)-4,5-dihydro-2H-pyrimido[5',4':4,5]thieno[2,3-e]indazol-2-yl]-3-(4-methylpiperazin-1-yl)propan-2-ol trifluoroacetate (salt) | 2.74 | 634.3 |
| 138 | 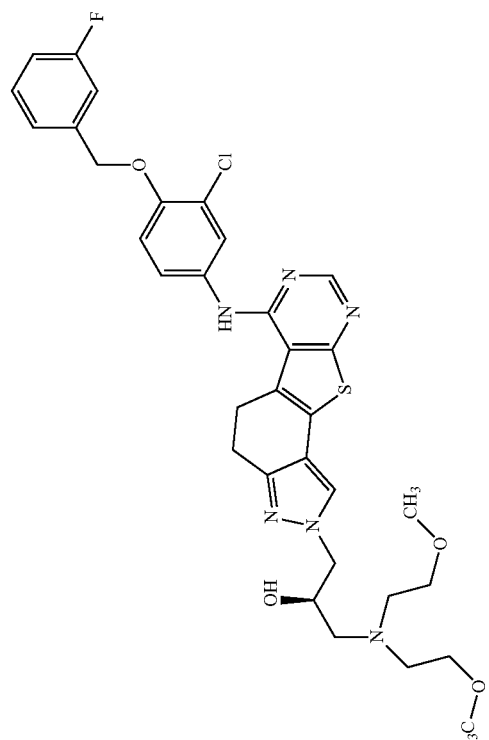 | (2R)-1-[bis(2-methoxyethyl)amino]-3-[6-({3-chloro-4-[(3-fluorobenzyl)oxy]phenyl}amino)-4,5-dihydro-2H-pyrimido[5',4':4,5]thieno[2,3-e]indazol-2-yl]propan-2-ol | 2.85 | 667.1 |

| Example No | Structure | IUPAC name | LCMS RT (min) | LCMS Ion [M + H]+ |
|---|---|---|---|---|
| 139 | 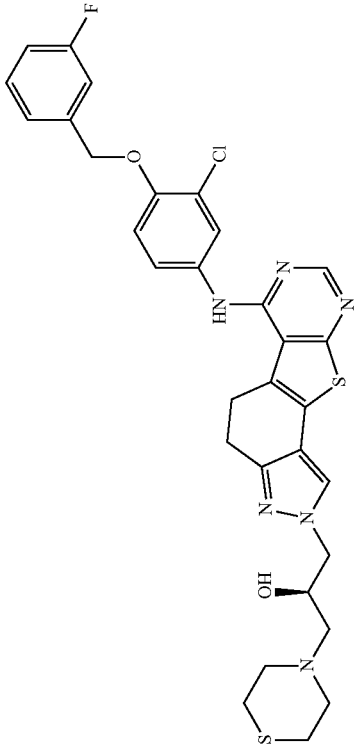 | (2R)-1-[6-({3-chloro-4-[(3-fluorobenzyl)oxy]phenyl}amino)-4,5-dihydro-2H-pyrimido[5',4':4,5]thieno[2,3-e]indazol-2-yl]-3-thiomorpholin-4-ylpropan-2-ol | 2.84 | 637.1 |
| 140 | 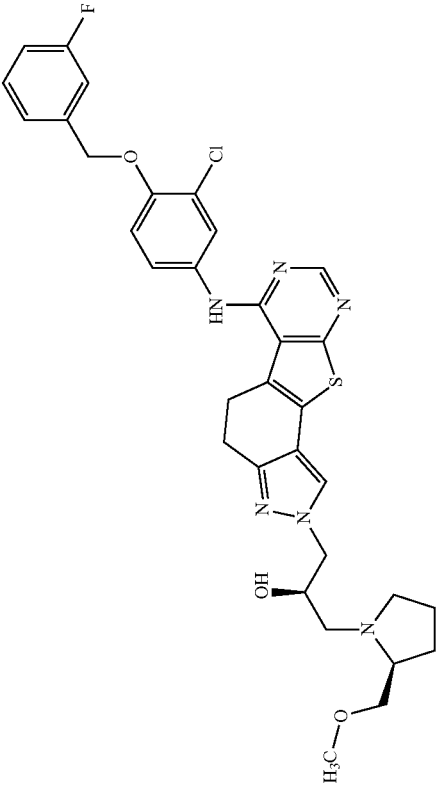 | (2R)-1-[6-({3-chloro-4-[(3-fluorobenzyl)oxy]phenyl}amino)-4,5-dihydro-2H-pyrimido[5',4':4,5]thieno[2,3-e]indazol-2-yl]-3-[(2S)-2-(methoxymethyl)pyrrolidin-1-yl]propan-2-ol | 2.85 | 649.1 |

| Example No | Structure | IUPAC name | LCMS RT (min) | LCMS Ion [M + H]+ |
|---|---|---|---|---|
| 141 | 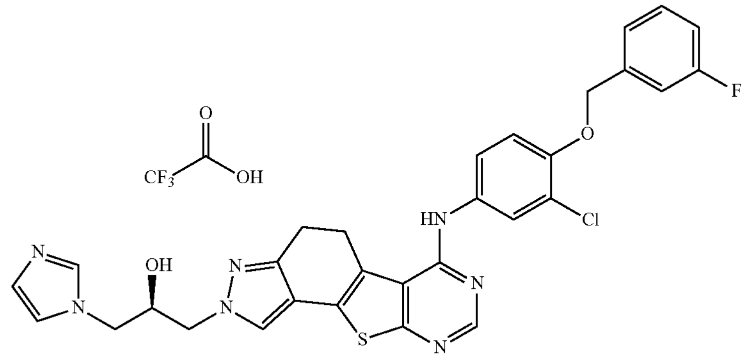 | (2R)-1-[6-({3-chloro-4-[(3-fluorobenzyl)oxy]phenyl}amino)-4,5-dihydro-2H-pyrimido[5',4':4,5]thieno[2,3-e]indazol-2-yl]-3-(1H-imidazol-1-yl)propan-2-ol trifluoroacetate (salt) | 2.78 | 602 |
| 142 | 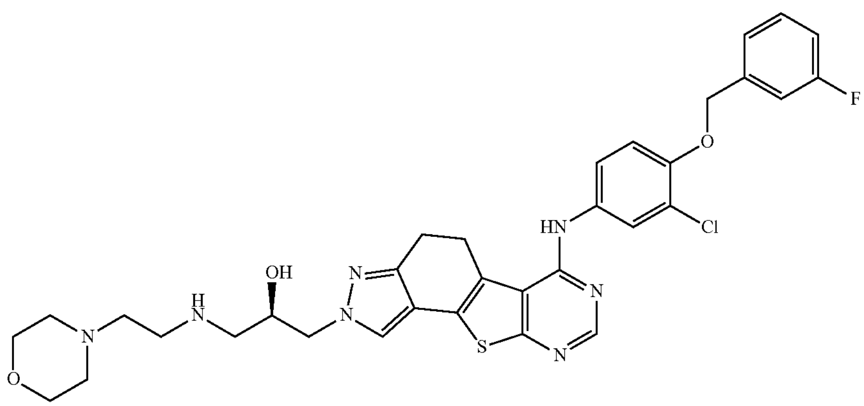 | (2R)-1-[6-({3-chloro-4-[(3-fluorobenzyl)oxy]phenyl}amino)-4,5-dihydro-2H-pyrimido[5',4':4,5]thieno[2,3-e]indazol-2-yl]-3-[(2-morpholin-4-ylethyl)amino]propan-2-ol | 2.96 | 664.2 |

| Example No | Structure | IUPAC name | LCMS RT (min) | LCMS Ion [M + H]+ |
|---|---|---|---|---|
| 143 | 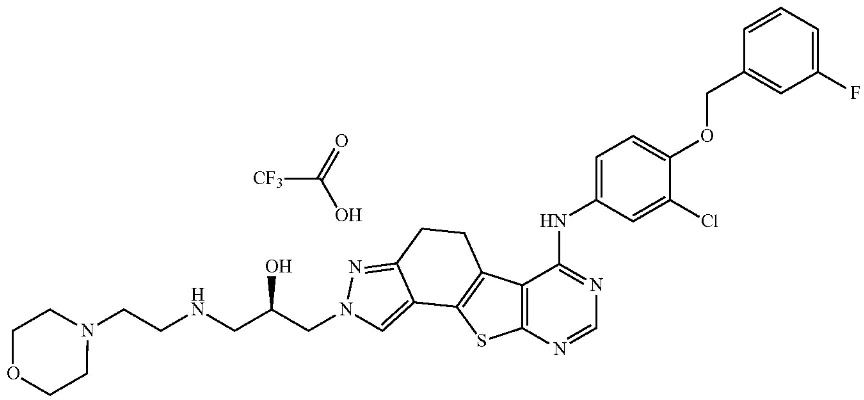 | (2R)-1-[6-({3-chloro-4-[(3-fluorobenzyl)oxy]phenyl}amino)-4,5-dihydro-2H-pyrimido[5',4':4,5]thieno[2,3-e]indazol-2-yl]-3-[(2-morpholin-4-ylethyl)amino]propan-2-ol trifluoroacetate (salt) | 2.56 | 664.1 |
| 144 | 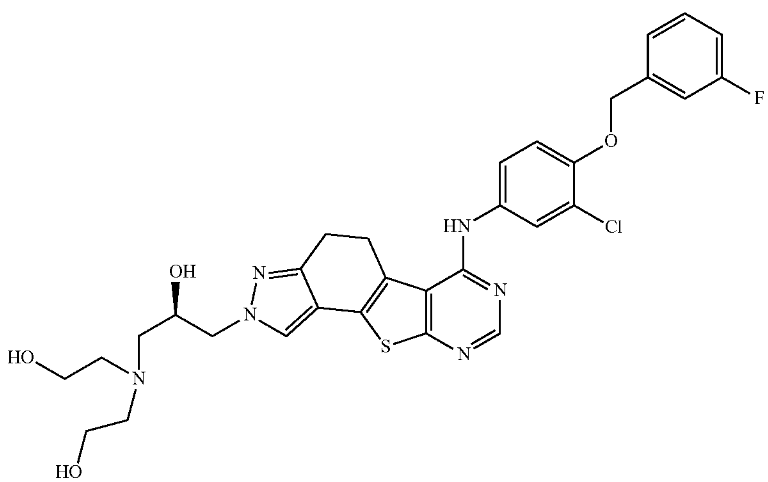 | (2R)-1-[bis(2-hydroxyethyl)amino]-3-[6-({3-chloro-4-[(3-fluorobenzyl)oxy]phenyl}amino)-4,5-dihydro-2H-pyrimido[5',4':4,5]thieno[2,3-e]indazol-2-yl]propan-2-ol | 3.12 | 639.2 |

| Example No | Structure | IUPAC name | LCMS RT (min) | LCMS Ion [M + H]+ |
|---|---|---|---|---|
| 145 | 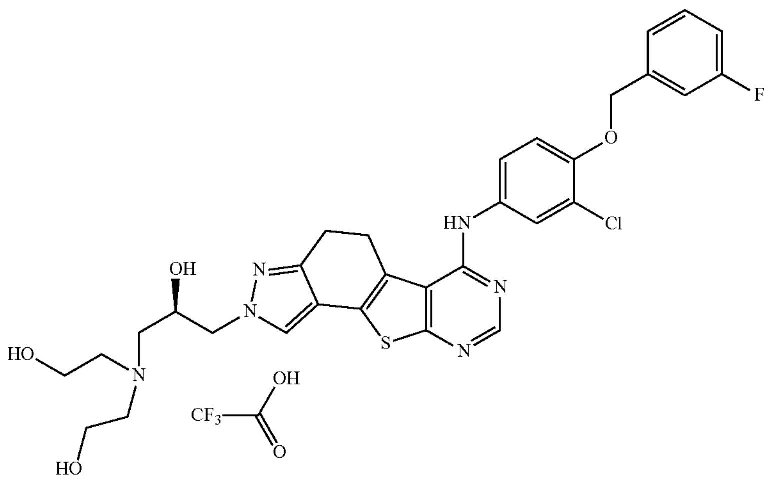 | (2R)-1-[bis(2-hydroxyethyl)amino]-3-[6-({3-chloro-4-[(3-fluorobenzyl)oxy]phenyl}amino)-4,5-dihydro-2H-pyrimido[5',4':4,5]thieno[2,3-e]indazol-2-yl]propan-2-ol trifluoroacetate (salt) | 2.73 | 639.1 |
| 146 | 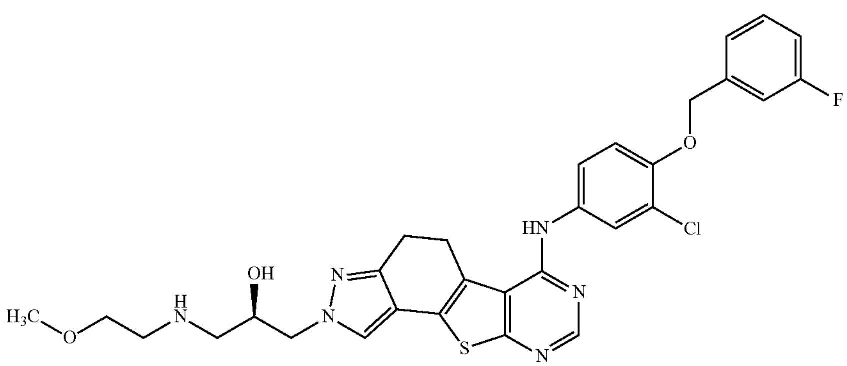 | (2R)-1-[6-({3-chloro-4-[(3-fluorobenzyl)oxy]phenyl}amino)-4,5-dihydro-2H-pyrimido[5',4':4,5]thieno[2,3-e]indazol-2-yl]-3-[(2-methoxyethyl)amino]propan-2-ol | 3.18 | 609.3 |

| Example No | Structure | IUPAC name | LCMS RT (min) | LCMS Ion [M + H]+ |
|---|---|---|---|---|
| 147 | 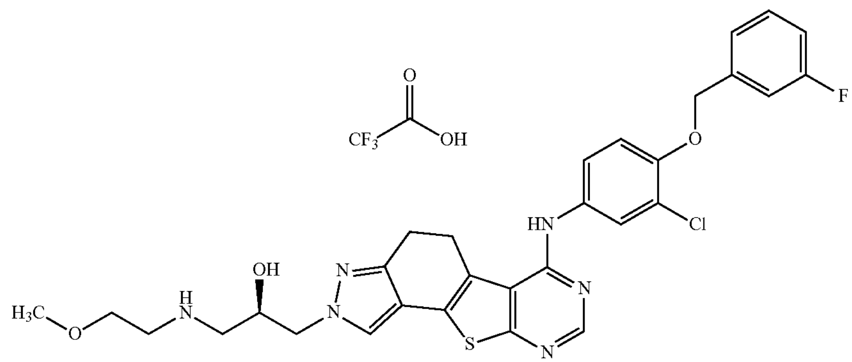 | (2R)-1-[6-({3-chloro-4-[(3-fluorobenzyl)oxy]phenyl}amino)-4,5-dihydro-2H-pyrimido[5',4':4,5]thieno[2,3-e]indazol-2-yl]-3-[(2-methoxyethyl)amino]propan-2-ol trifluoroacetate (salt) | 2.78 | 609.1 |
| 148 | 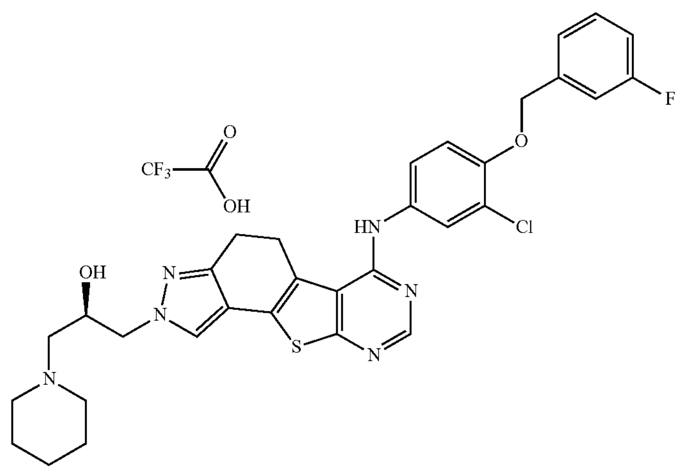 | (2R)-1-[6-({3-chloro-4-[(3-fluorobenzyl)oxy]phenyl}amino)-4,5-dihydro-2H-pyrimido[5',4':4,5]thieno[2,3-e]indazol-2-yl]-3-piperidin-1-ylpropan-2-ol trifluoroacetate (salt) | 2.82 | 619.2 |

-continued

| Example No | Structure | IUPAC name | LCMS RT (min) | LCMS Ion [M + H]+ |
|---|---|---|---|---|
| 149 | 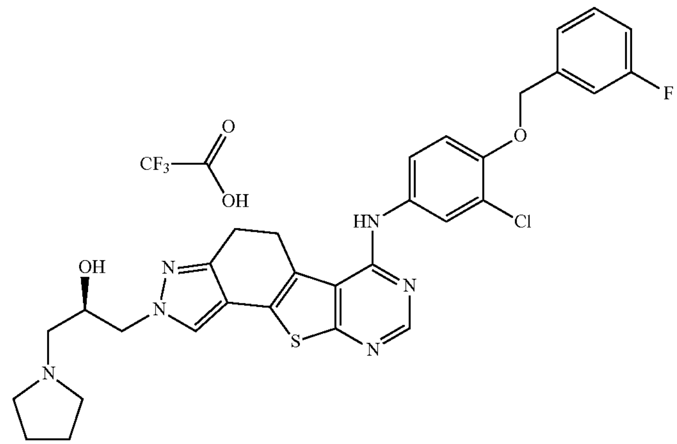 | (2R)-1-[6-({3-chloro-4-[(3-fluorobenzyl)oxy]phenyl}amino)-4,5-dihydro-2H-pyrimido[5',4':4,5]thieno[2,3-e]indazol-2-yl]-3-pyrrolidin-1-ylpropan-2-ol trifluoroacetate (salt) | 2.78 | 605.1 |
| 150 | 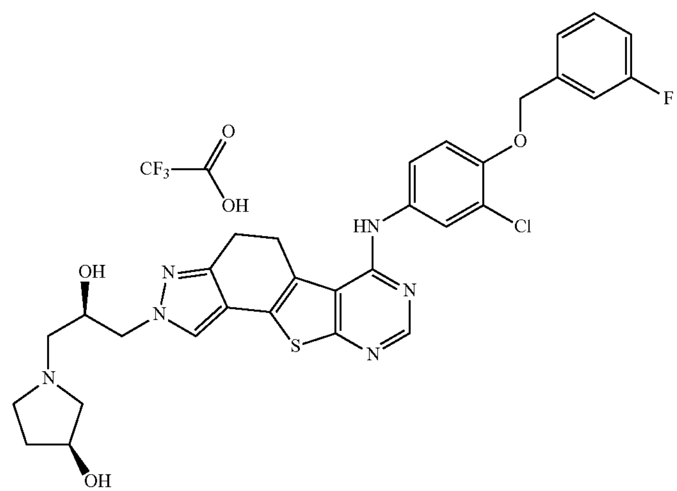 | (3S)-1-{(2R)-3-[6-({3-chloro-4-[(3-fluorobenzyl)oxy]phenyl}amino)-4,5-dihydro-2H-pyrimido[5',4':4,5]thieno[2,3-e]indazol-2-yl]-2-hydroxypropyl}pyrrolidin-3-ol trifluoroacetate (salt) | 2.73 | 621.1 |

-continued

| Example No | Structure | IUPAC name | LCMS RT (min) | LCMS Ion [M + H]+ |
|---|---|---|---|---|
| 151 | 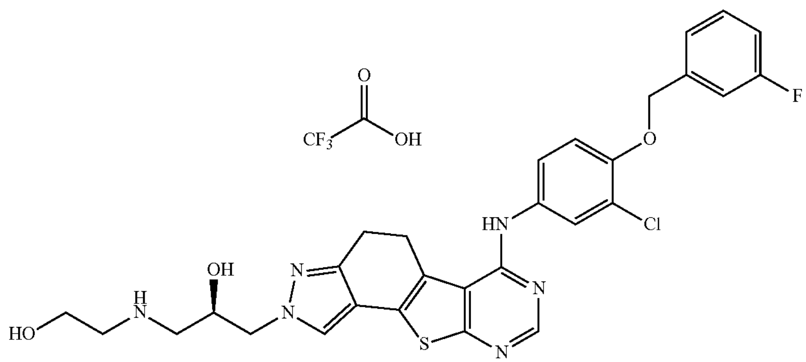 | (2R)-1-[6-({3-chloro-4-[(3-fluorobenzyl)oxy]phenyl}amino)-4,5-dihydro-2H-pyrimido[5',4':4,5]thieno[2,3-e]indazol-2-yl]-3-[(2-hydroxyethyl)amino]propan-2-ol trifluoroacetate (salt) | 2.72 | 595.1 |
| 152 | 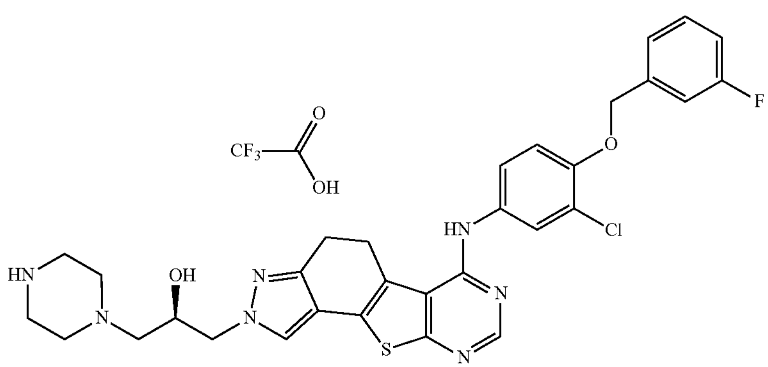 | (2R)-1-[6-({3-chloro-4-[(3-fluorobenzyl)oxy]phenyl}amino)-4,5-dihydro-2H-pyrimido[5',4':4,5]thieno[2,3-e]indazol-2-yl]-3-piperazin-1-ylpropan-2-ol trifluoroacetate (salt) | 2.56 | 620.1 |

| Example No | Structure | IUPAC name | LCMS RT (min) | LCMS Ion [M + H]+ |
|---|---|---|---|---|
| 153 | 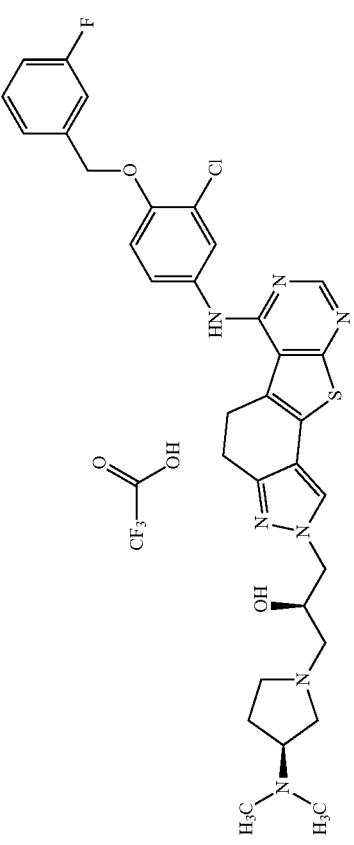 | (2R)-1-[6-({3-chloro-4-[(3-fluorobenzyl)oxy]phenyl}amino)-4,5-dihydro-2H-pyrimido[5',4':4,5]thieno[2,3-e]indazol-2-yl]-3-[(3S)-3-(dimethylamino)pyrrolidin-1-yl]propan-2-ol trifluoroacetate (salt) | 2.49 | 648.1 |
| 154 | 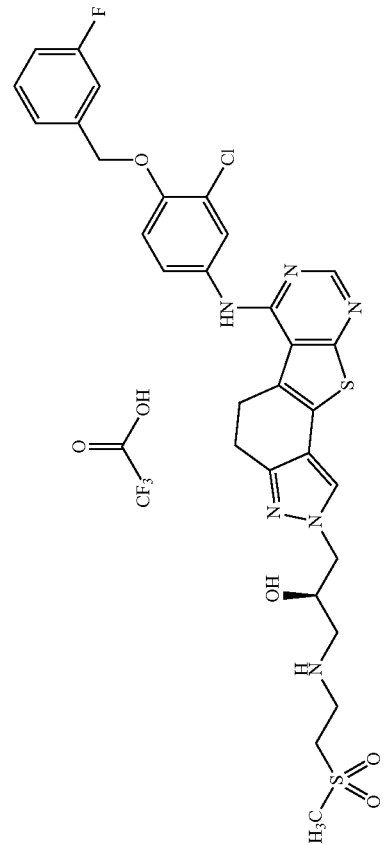 | (2R)-1-[6-({3-chloro-4-[(3-fluorobenzyl)oxy]phenyl}amino)-4,5-dihydro-2H-pyrimido[5',4':4,5]thieno[2,3-e]indazol-2-yl]-3-{[2-(methylsulfonyl)ethyl]amino}propan-2-ol trifluoroacetate (salt) | 2.77 | 657.1 |

| Example No | Structure | IUPAC name | LCMS RT (min) | LCMS Ion [M+H]+ |
|---|---|---|---|---|
| 155 | 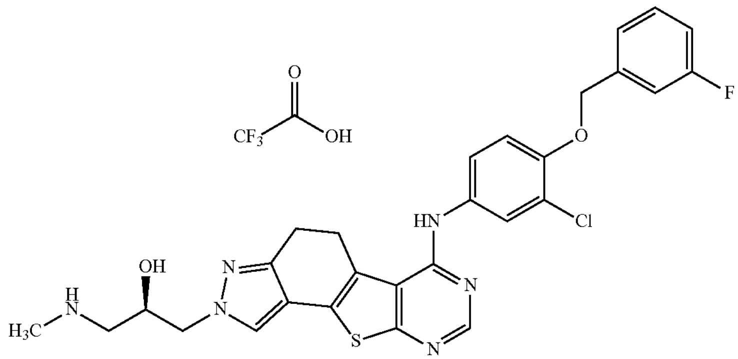 | (2R)-1-[6-({3-chloro-4-[(3-fluorobenzyl)oxy]phenyl}amino)-4,5-dihydro-2H-pyrimido[5′,4′:4,5]thieno[2,3-e]indazol-2-yl]-3-(methylamino)propan-2-ol trifluoroacetate (salt) | 2.74 | 565.1 |
| 156 | 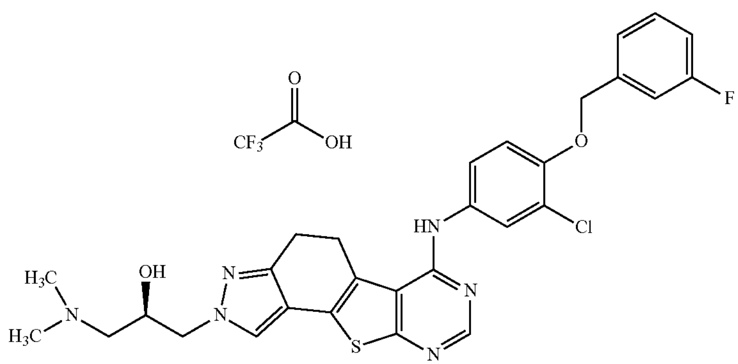 | (2R)-1-[6-({3-chloro-4-[(3-fluorobenzyl)oxy]phenyl}amino)-4,5-dihydro-2H-pyrimido[5′,4′:4,5]thieno[2,3-e]indazol-2-yl]-3-(dimethylamino)propan-2-ol trifluoroacetate (salt) | 2.75 | 579.1 |

| Example No | Structure | IUPAC name | LCMS RT (min) | LCMS Ion [M + H]+ |
|---|---|---|---|---|
| 157 | 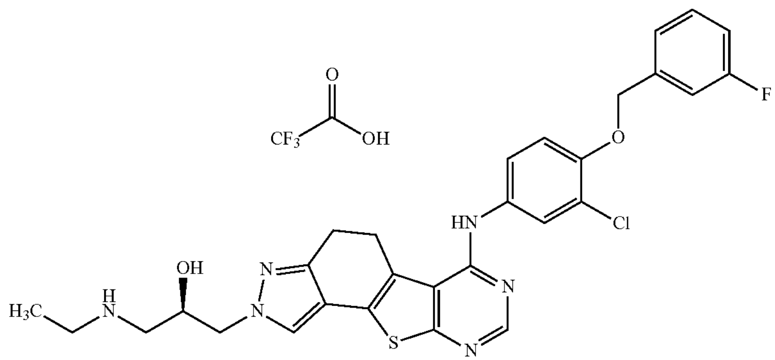 | (2R)-1-[6-({3-chloro-4-[(3-fluorobenzyl)oxy]phenyl}amino)-4,5-dihydro-2H-pyrimido[5',4':4,5]thieno[2,3-e]indazol-2-yl]-3-(ethylamino)propan-2-ol trifluoroacetate (salt) | 2.76 | 579.1 |
| 158 | 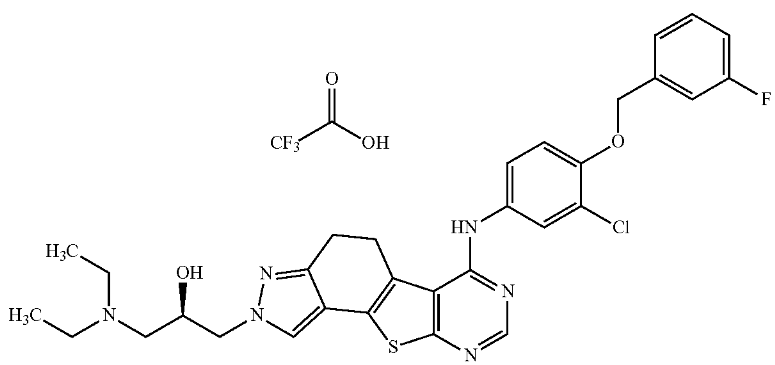 | (2R)-1-[6-({3-chloro-4-[(3-fluorobenzyl)oxy]phenyl}amino)-4,5-dihydro-2H-pyrimido[5',4':4,5]thieno[2,3-e]indazol-2-yl]-3-(diethylamino)propan-2-ol trifluoroacetate (salt) | 2.81 | 607.1 |

| Example No | Structure | IUPAC name | LCMS RT (min) | LCMS Ion [M + H]+ |
|---|---|---|---|---|
| 159 | 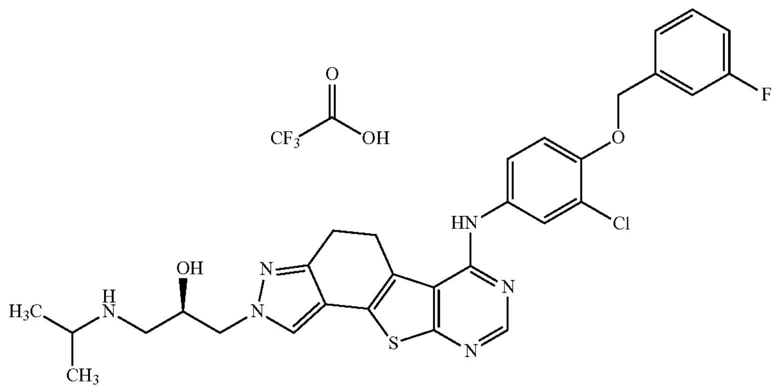 | (2R)-1-[6-({3-chloro-4-[(3-fluorobenzyl)oxy]phenyl}amino)-4,5-dihydro-2H-pyrimido[5',4':4,5]thieno[2,3-e]indazol-2-yl]-3-(isopropylamino)propan-2-ol trifluoroacetate (salt) | 2.8 | 593.1 |
| 160 | 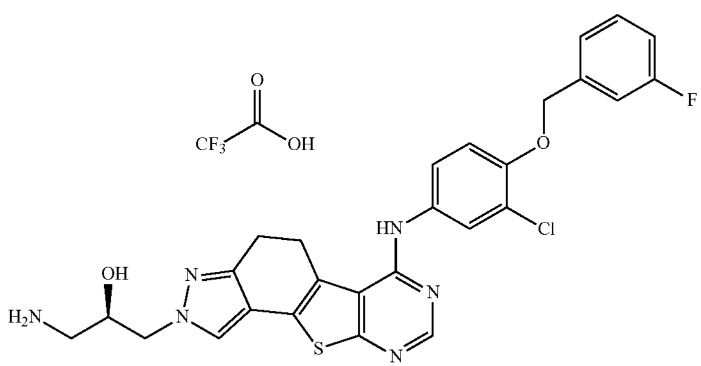 | (2R)-1-amino-3-[6-({3-chloro-4-[(3-fluorobenzyl)oxy]phenyl}amino)-4,5-dihydro-2H-pyrimido[5',4':4,5]thieno[2,3-e]indazol-2-yl]propan-2-ol trifluoroacetate (salt) | 2.72 | 551 |

| Example No | Structure | IUPAC name | LCMS RT (min) | LCMS Ion [M + H]+ |
|---|---|---|---|---|
| 161 | 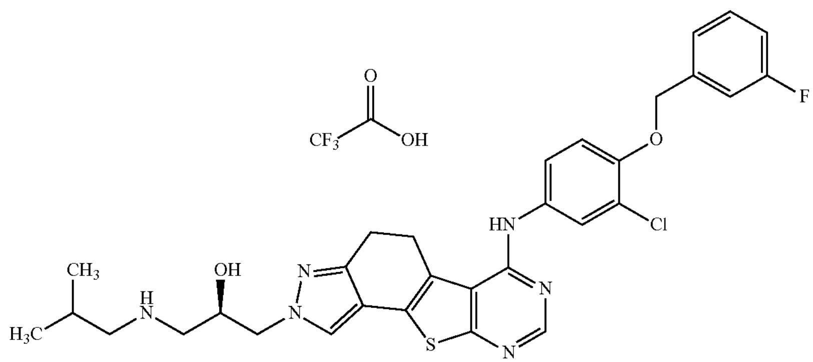 | (2R)-1-[6-({3-chloro-4-[(3-fluorobenzyl)oxy]phenyl}amino)-4,5-dihydro-2H-pyrimido[5',4':4,5]thieno[2,3-e]indazol-2-yl]-3-(isobutylamino)propan-2-ol trifluoroacetate (salt) | 2.87 | 607 |
| 162 | 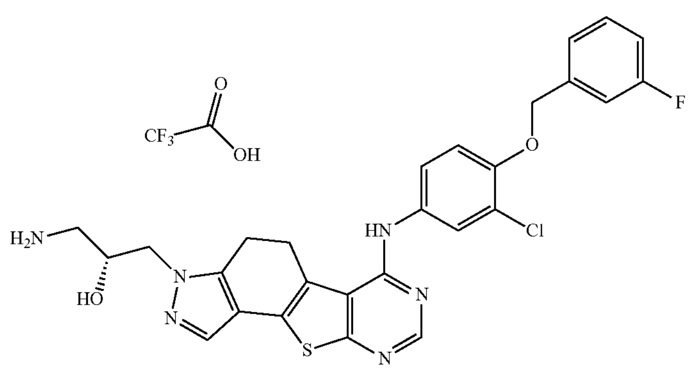 | (2R)-1-amino-3-[6-({3-chloro-4-[(3-fluorobenzyl)oxy]phenyl}amino)-4,5-dihydro-3H-pyrimido[5',4':4,5]thieno[2,3-e]indazol-3-yl]propan-2-ol trifluoroacetate (salt) | 2.71 | 551.1 |

| Example No | Structure | IUPAC name | LCMS RT (min) | LCMS Ion [M + H]+ |
|---|---|---|---|---|
| 163 | 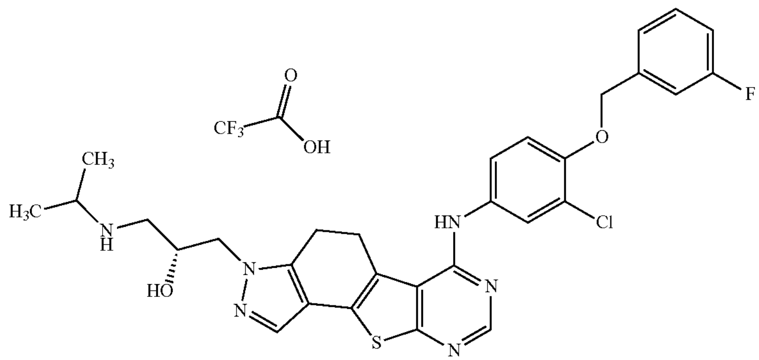 | (2R)-1-[6-({3-chloro-4-[(3-fluorobenzyl)oxy]phenyl}amino)-4,5-dihydro-3H-pyrimido[5',4':4,5]thieno[2,3-e]indazol-3-yl]-3-(isopropylamino)propan-2-ol trifluoroacetate (salt) | 2.79 | 593.1 |
| 164 | 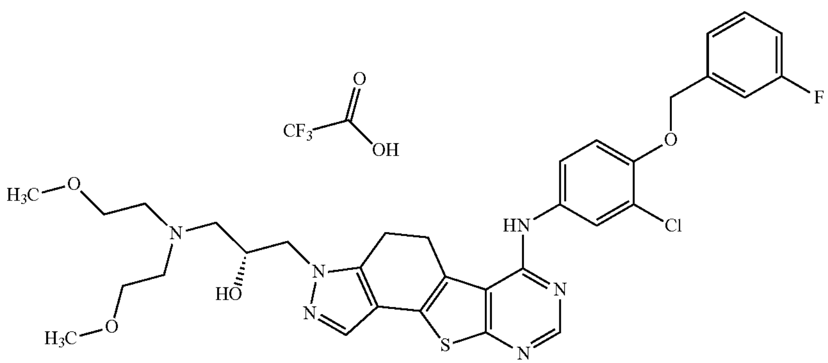 | (2R)-1-[bis(2-methoxyethyl)amino]-3-[6-({3-chloro-4-[(3-fluorobenzyl)oxy]phenyl}amino)-4,5-dihydro-3H-pyrimido[5',4':4,5]thieno[2,3-e]indazol-3-yl]propan-2-ol trifluoroacetate (salt) | 2.94 | 667.2 |

-continued
| Example No | Structure | IUPAC name | LCMS RT (min) | LCMS Ion [M + H]+ |
|---|---|---|---|---|
| 165 | 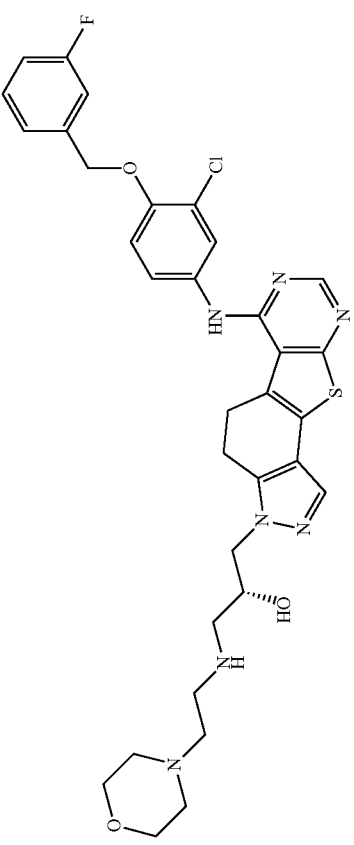 | (2R)-1-[6-({3-chloro-4-[(3-fluorobenzyl)oxy]phenyl}amino)-4,5-dihydro-3H-pyrimido[5',4':4,5]thieno[2,3-e]indazol-3-yl]-3-[(2-morpholin-4-ylethyl)amino]propan-2-ol | 2.96 | 664.3 |
| 166 | 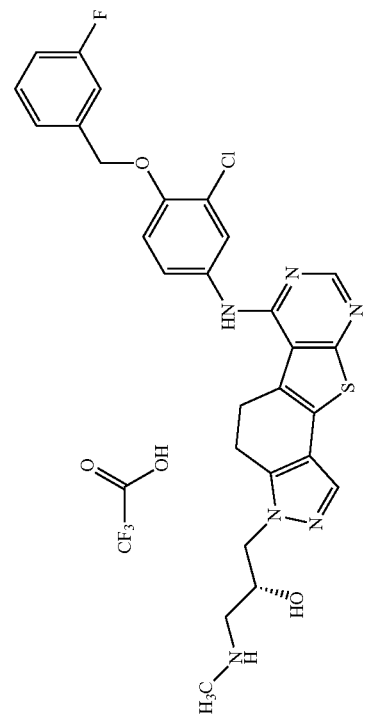 | (2R)-1-[6-({3-chloro-4-[(3-fluorobenzyl)oxy]phenyl}amino)-4,5-dihydro-3H-pyrimido[5',4':4,5]thieno[2,3-e]indazol-3-yl]-3-(methylamino)propan-2-ol trifluoroacetate (salt) | 2.73 | 565.1 |

| Example No | Structure | IUPAC name | LCMS RT (min) | LCMS Ion [M + H]+ |
|---|---|---|---|---|
| 167 | 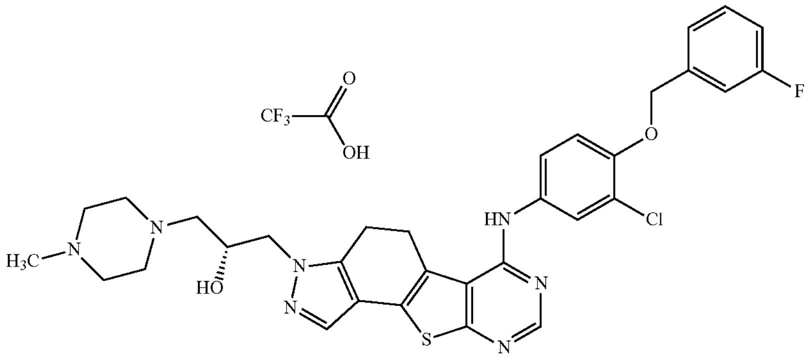 | (2R)-1-[6-({3-chloro-4-[(3-fluorobenzyl)oxy]phenyl}amino)-4,5-dihydro-3H-pyrimido[5′,4′:4,5]thieno[2,3-e]indazol-3-yl]-3-(4-methylpiperazin-1-yl)propan-2-ol trifluoroacetate (salt) | 2.74 | 634.2 |
| 168 | 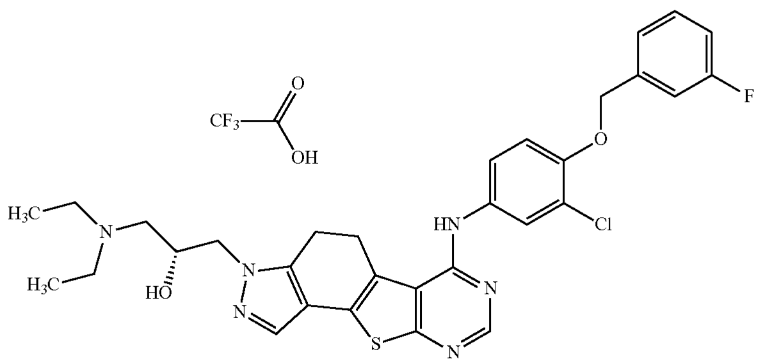 | (2R)-1-[6-({3-chloro-4-[(3-fluorobenzyl)oxy]phenyl}amino)-4,5-dihydro-3H-pyrimido[5′,4′:4,5]thieno[2,3-e]indazol-3-yl]-3-(diethylamino)propan-2-ol trifluoroacetate (salt) | 2.8 | 607.1 |

| Example No | Structure | IUPAC name | LCMS RT (min) | LCMS Ion [M + H]+ |
|---|---|---|---|---|
| 169 | 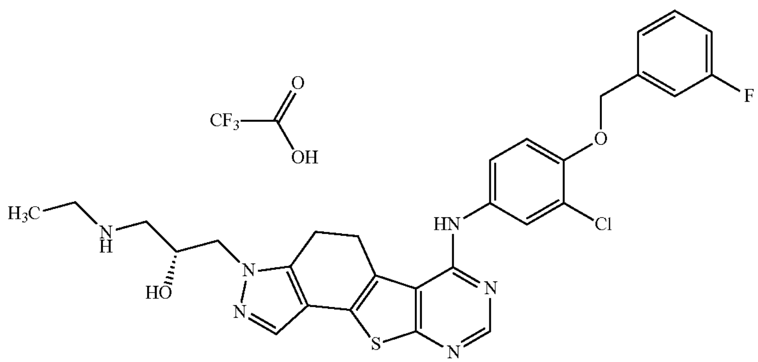 | (2R)-1-[6-({3-chloro-4-[(3-fluorobenzyl)oxy]phenyl}amino)-4,5-dihydro-3H-pyrimido[5′,4′:4,5]thieno[2,3-e]indazol-3-yl]-3-(ethylamino)propan-2-ol trifluoroacetate (salt) | 2.75 | 579.1 |
| 170 | 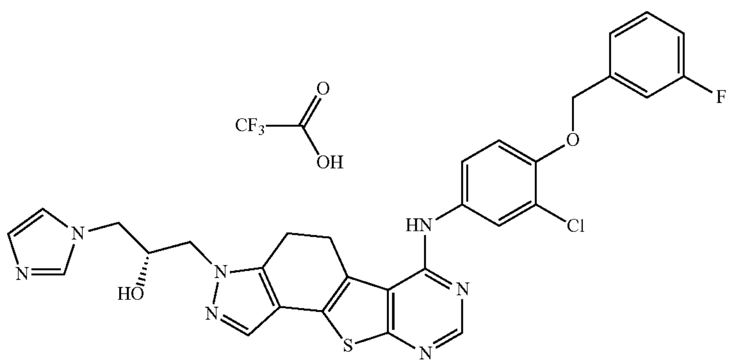 | (2R)-1-[6-({3-chloro-4-[(3-fluorobenzyl)oxy]phenyl}amino)-4,5-dihydro-3H-pyrimido[5′,4′:4,5]thieno[2,3-e]indazol-3-yl]-3-(1H-imidazol-1-yl)propan-2-ol trifluoroacetate (salt) | 2.85 | 602.2 |

| Example No | Structure | IUPAC name | LCMS RT (min) | LCMS Ion [M + H]+ |
|---|---|---|---|---|
| 171 | 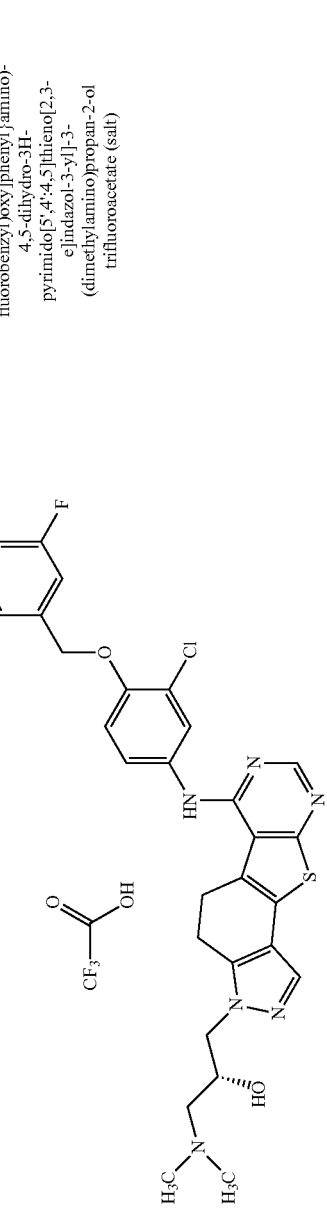 | (2R)-1-[6-({3-chloro-4-[(3-fluorobenzyl)oxy]phenyl}amino)-4,5-dihydro-3H-pyrimido[5',4':4,5]thieno[2,3-e]indazol-3-yl]-3-(dimethylamino)propan-2-ol trifluoroacetate (salt) | 2.74 | 579.1 |
| 172 | 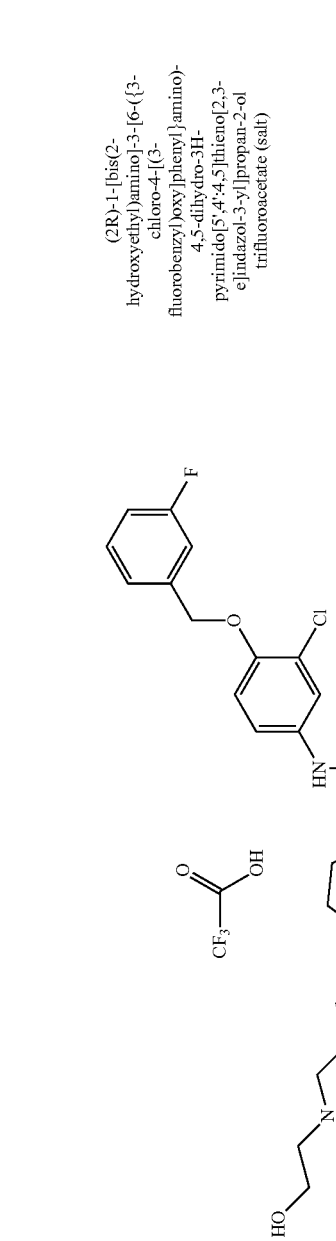 | (2R)-1-[bis(2-hydroxyethyl)amino]-3-[6-({3-chloro-4-[(3-fluorobenzyl)oxy]phenyl}amino)-4,5-dihydro-3H-pyrimido[5',4':4,5]thieno[2,3-e]indazol-3-yl]propan-2-ol trifluoroacetate (salt) | 2.79 | 639.4 |

| Example No | Structure | IUPAC name | LCMS RT (min) | LCMS Ion [M+H]+ |
|---|---|---|---|---|
| 173 | 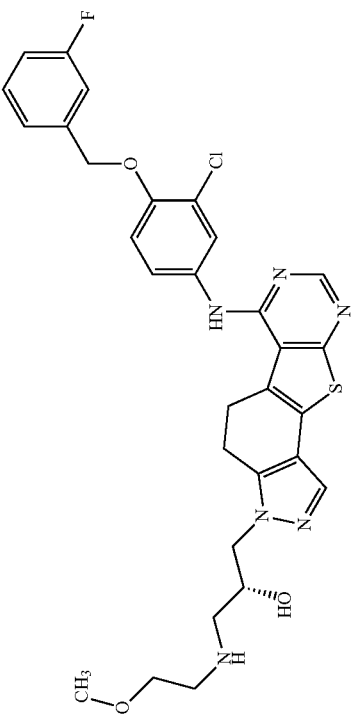 | (2R)-1-[6-({3-chloro-4-[(3-fluorobenzyl)oxy]phenyl}amino)-4,5-dihydro-3H-pyrimido[5',4':4,5]thieno[2,3-e]indazol-3-yl]-3-[(2-methoxyethyl)amino]propan-2-ol trifluoroacetate (salt) | 2.87 | 609.2 |
| 174 | 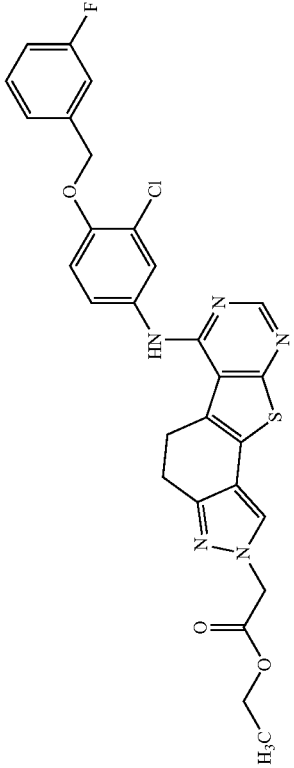 | ethyl [6-({3-chloro-4-[(3-fluorobenzyl)oxy]phenyl}amino)-4,5-dihydro-2H-pyrimido[5',4':4,5]thieno[2,3-e]indazol-2-yl]acetate | 3.78 | 564.1 |
| 175 | 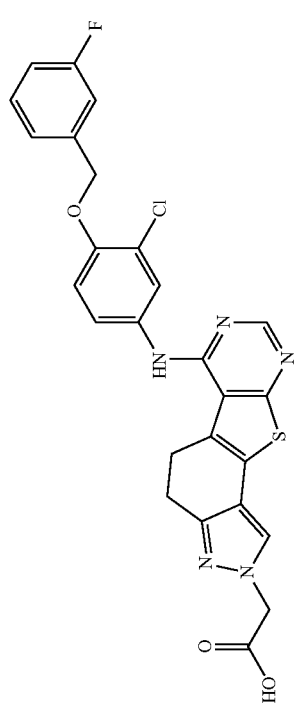 | [6-({3-chloro-4-[(3-fluorobenzyl)oxy]phenyl}amino)-4,5-dihydro-2H-pyrimido[5',4':4,5]thieno[2,3-e]indazol-2-yl]acetic acid | 3.32 | 536.1 |

-continued

| Example No | Structure | IUPAC name | LCMS RT (min) | LCMS Ion [M + H]+ |
|---|---|---|---|---|
| 176 | 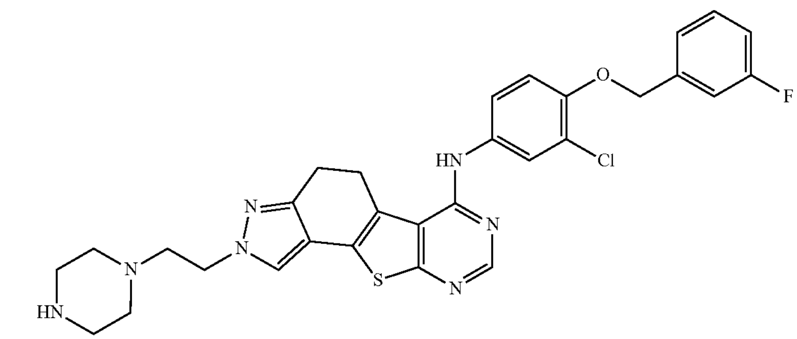 | N-{3-chloro-4-[(3-fluorobenzyl)oxy]phenyl}-2-(2-piperazin-1-ylethyl)-4,5-dihydro-2H-pyrimido[5',4':4,5]thieno[2,3-e]indazol-6-amine | 2.72 | 590.2 |
| 177 | 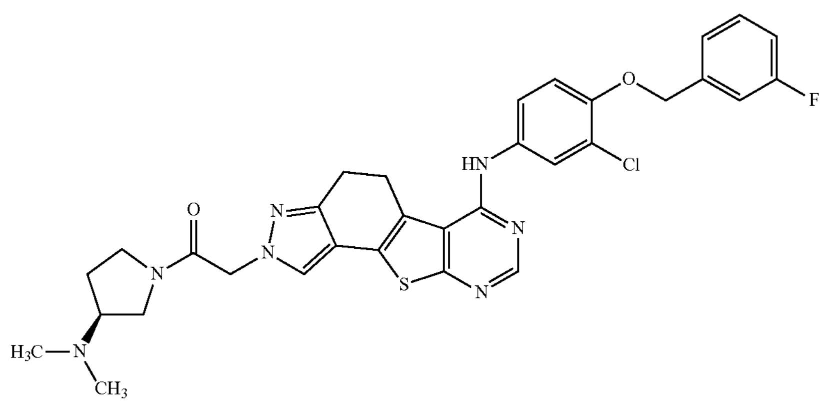 | N-{3-chloro-4-[(3-fluorobenzyl)oxy]phenyl}-2-{2-[(3S)-3-(dimethylamino)pyrrolidin-1-yl]-2-oxoethyl}-4,5-dihydro-2H-pyrimido[5',4':4,5]thieno[2,3-e]indazol-6-amine | 3.8 | 632.2 |
| 178 | 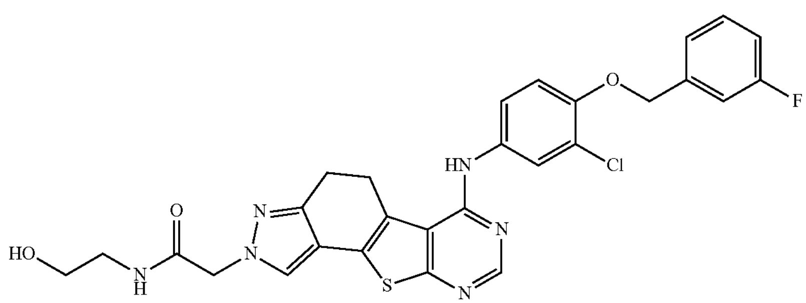 | 2-[6-({3-chloro-4-[(3-fluorobenzyl)oxy]phenyl}amino)-4,5-dihydro-2H-pyrimido[5',4':4,5]thieno[2,3-e]indazol-2-yl]-N-(2-hydroxyethyl)acetamide | 3.18 | 579.1 |

| Example No | Structure | IUPAC name | LCMS RT (min) | LCMS Ion [M + H]+ |
|---|---|---|---|---|
| 179 | 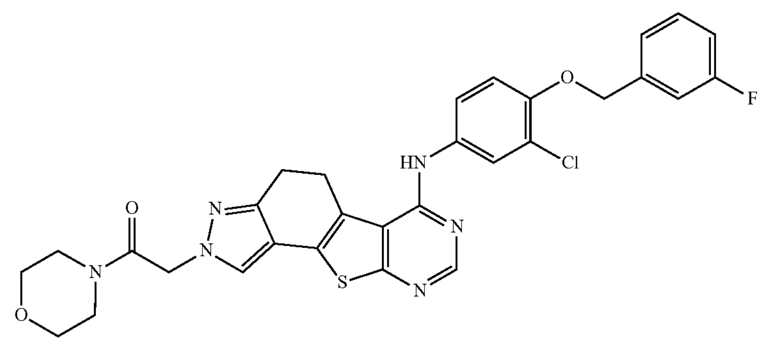 | N-{3-chloro-4-[(3-fluorobenzyl)oxy]phenyl}-2-(2-morpholin-4-yl-2-oxoethyl)-4,5-dihydro-2H-pyrimido[5',4':4,5]thieno[2,3-e]indazol-6-amine | 3.12 | 605.4 |
| 180 | 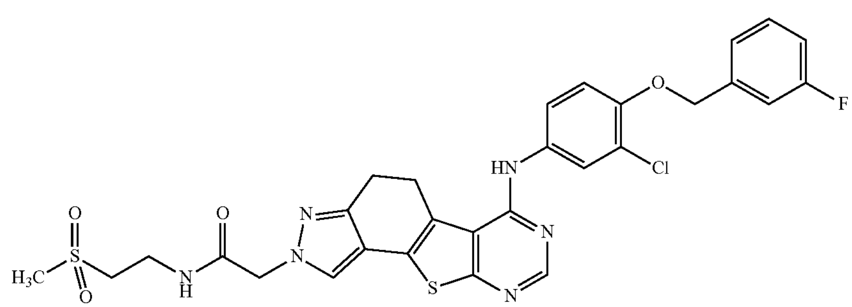 | 2-[6-({3-chloro-4-[(3-fluorobenzyl)oxy]phenyl}amino)-4,5-dihydro-2H-pyrimido[5',4':4,5]thieno[2,3-e]indazol-2-yl]-N-[2-(methylsulfonyl)ethyl]acetamide | 3.21 | 641.1 |

-continued

| Example No | Structure | IUPAC name | LCMS RT (min) | LCMS Ion [M + H]+ |
|---|---|---|---|---|
| 181 | 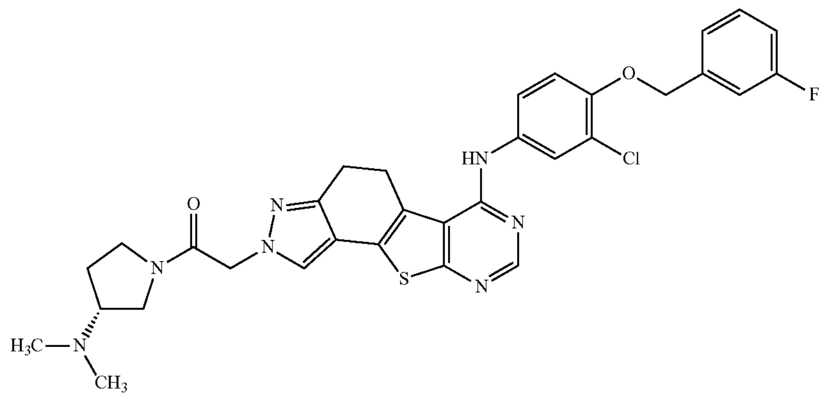 | N-{3-chloro-4-[(3-fluorobenzyl)oxy]phenyl}-2-{2-[3-(dimethylamino)pyrrolidin-1-yl]-2-oxoethyl}-4,5-dihydro-2H-pyrimido[5',4':4,5]thieno[2,3-e]indazol-6-amine | 2.75 | 632.2 |
| 182 | 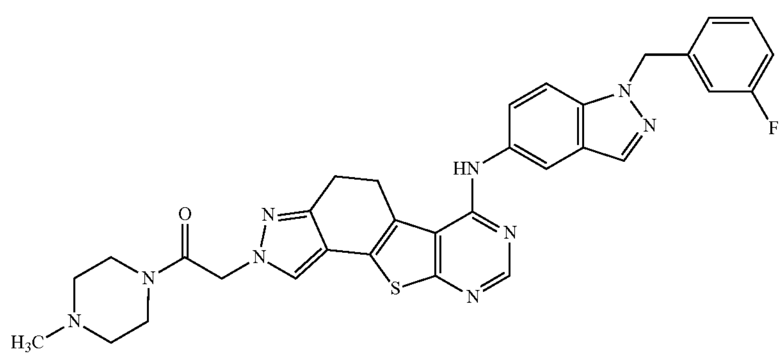 | N-[1-(3-fluorobenzyl)-1H-indazol-5-yl]-2-[2-(4-methylpiperazin-1-yl)-2-oxoethyl]-4,5-dihydro-2H-pyrimido[5',4':4,5]thieno[2,3-e]indazol-6-amine | 2.49 | 608.2 |

| Example No | Structure | IUPAC name | LCMS RT (min) | LCMS Ion [M+H]+ |
|---|---|---|---|---|
| 183 | 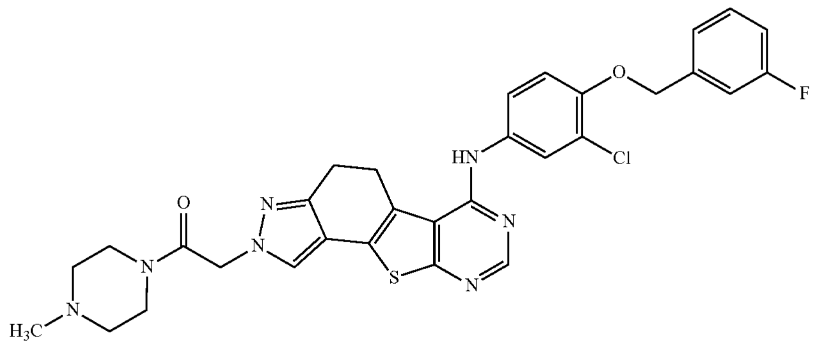 | N-{3-chloro-4-[(3-fluorobenzyl)oxy]phenyl}-2-[2-(4-methylpiperazin-1-yl)-2-oxoethyl]-4,5-dihydro-2H-pyrimido[5',4':4,5]thieno[2,3-e]indazol-6-amine | 3.07 | 618.3 |
| 184 | 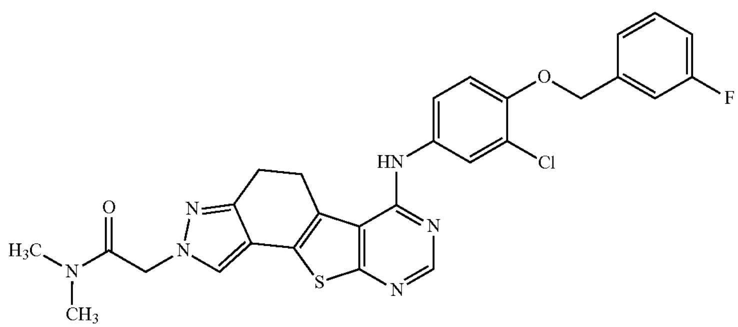 | 2-[6-({3-chloro-4-[(3-fluorobenzyl)oxy]phenyl}amino)-4,5-dihydro-2H-pyrimido[5',4':4,5]thieno[2,3-e]indazol-2-yl]-N,N-dimethylacetamide | 3.45 | 563.3 |

| Example No | Structure | IUPAC name | LCMS RT (min) | LCMS Ion [M + H]+ |
|---|---|---|---|---|
| 185 | 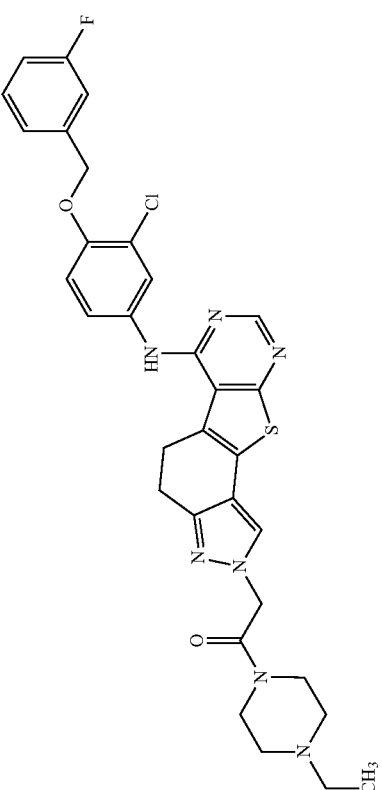 | N-{3-chloro-4-[(3-fluorobenzyl)oxy]phenyl}-2-{2-[4-ethylpiperazin-1-yl)-2-oxoethyl]-4,5-dihydro-2H-pyrimido[5',4':4,5]thieno[2,3-e]indazol-6-amine | 2.77 | 632.2 |
| 186 | 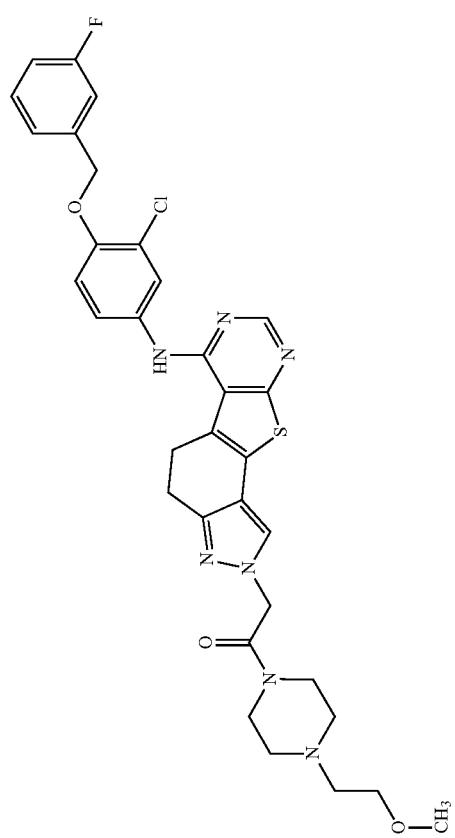 | N-{3-chloro-4-[(3-fluorobenzyl)oxy]phenyl}-2-{2-[4-(2-methoxyethyl)piperazin-1-yl]-2-oxoethyl]-4,5-dihydro-2H-pyrimido[5',4':4,5]thieno[2,3-e]indazol-6-amine | 2.76 | 662.2 |

| Example No | Structure | IUPAC name | LCMS RT (min) | LCMS Ion [M + H]+ |
|---|---|---|---|---|
| 187 | 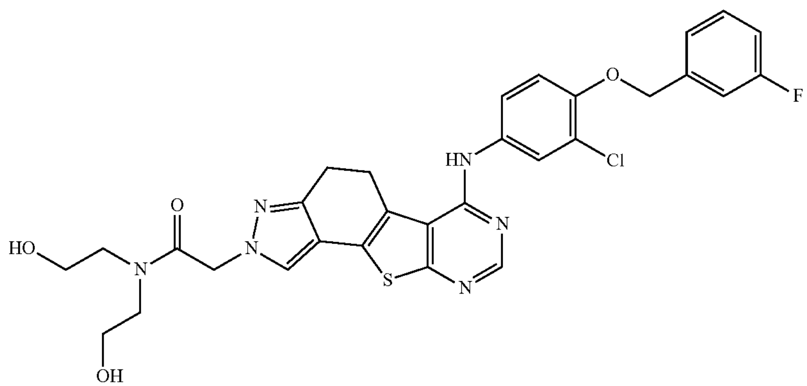 | 2-[6-({3-chloro-4-[(3-fluorobenzyl)oxy]phenyl}amino)-4,5-dihydro-2H-pyrimido[5',4':4,5]thieno[2,3-e]indazol-2-yl]-N,N-bis(2-hydroxyethyl)acetamide | 3.21 | 623.2 |
| 188 | 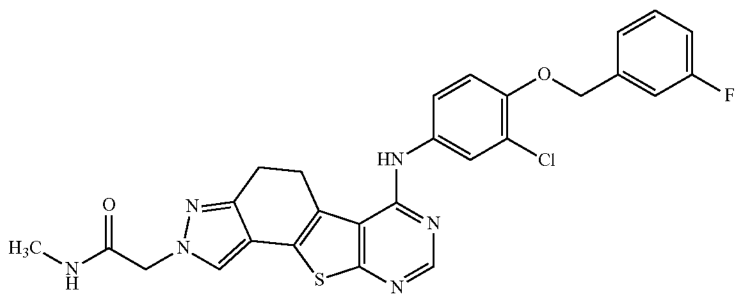 | 2-[6-({3-chloro-4-[(3-fluorobenzyl)oxy]phenyl}amino)-4,5-dihydro-2H-pyrimido[5',4':4,5]thieno[2,3-e]indazol-2-yl]-N-methylacetamide | 3.28 | 549.1 |
| 189 | 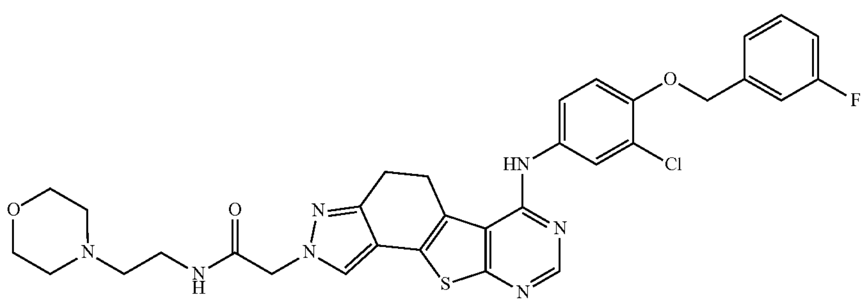 | 2-[6-({3-chloro-4-[(3-fluorobenzyl)oxy]phenyl}amino)-4,5-dihydro-2H-pyrimido[5',4':4,5]thieno[2,3-e]indazol-2-yl]-N-(2-morpholin-4-ylethyl)acetamide | 2.82 | 648.2 |

| Example No | Structure | IUPAC name | LCMS RT (min) | LCMS Ion [M+H]+ |
|---|---|---|---|---|
| 190 | 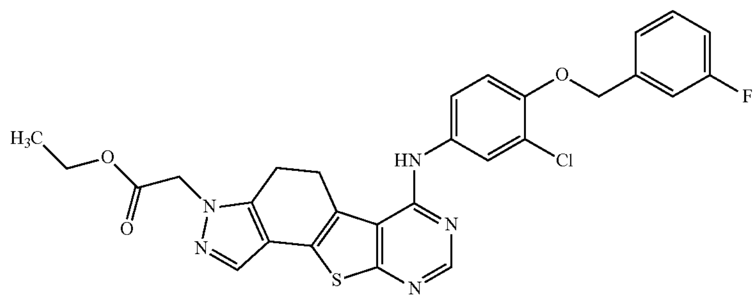 | ethyl [6-({3-chloro-4-[(3-fluorobenzyl)oxy]phenyl}amino)-4,5-dihydro-3H-pyrimido[5',4':4,5]thieno[2,3-e]indazol-3-yl]acetate | 3.74 | 564.3 |
| 191 | 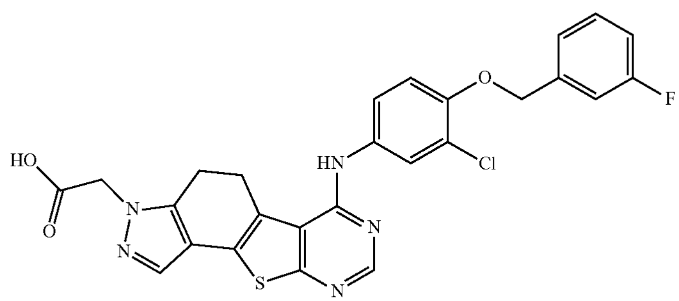 | [6-({3-chloro-4-[(3-fluorobenzyl)oxy]phenyl}amino)-4,5-dihydro-3H-pyrimido[5',4':4,5]thieno[2,3-e]indazol-3-yl]acetic acid | 3.38 | 536.2 |
| 192 | 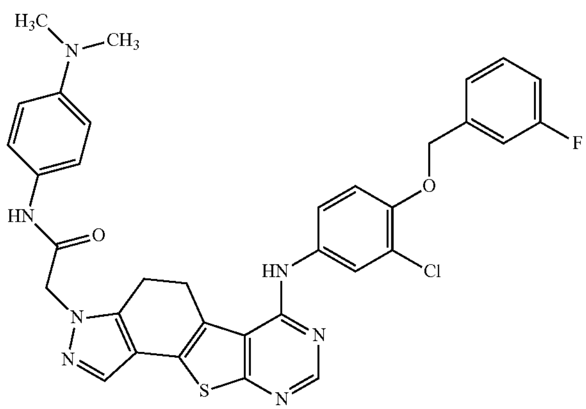 | 2-[6-({3-chloro-4-[(3-fluorobenzyl)oxy]phenyl}amino)-4,5-dihydro-3H-pyrimido[5',4':4,5]thieno[2,3-e]indazol-3-yl]-N-[4-(dimethylamino)phenyl]acetamide | 2.96 | 654.3 |

-continued

| Example No | Structure | IUPAC name | LCMS RT (min) | LCMS Ion [M + H]+ |
|---|---|---|---|---|
| 193 | 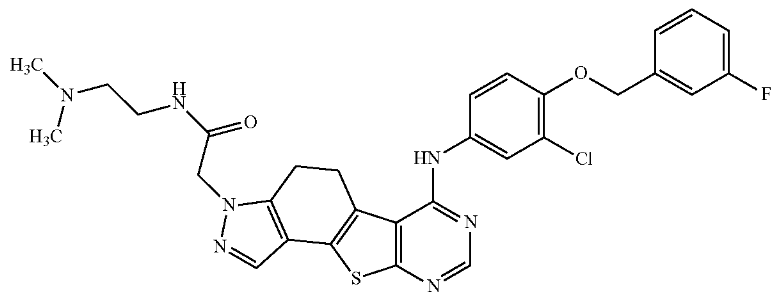 | 2-[6-({3-chloro-4-[(3-fluorobenzyl)oxy]phenyl}amino)-4,5-dihydro-3H-pyrimido[5',4':4,5]thieno[2,3-e]indazol-3-yl]-N-[2-(dimethylamino)ethyl]acetamide | 3.02 | 606.2 |
| 194 | 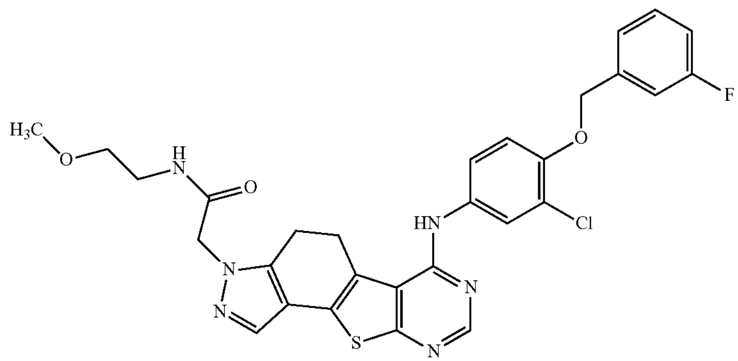 | 2-[6-({3-chloro-4-[(3-fluorobenzyl)oxy]phenyl}amino)-4,5-dihydro-2H-pyrimido[5',4':4,5]thieno[2,3-e]indazol-2-yl]-N-(2-methoxyethyl)acetamide | 3.31 | 593.1 |
| 195 | 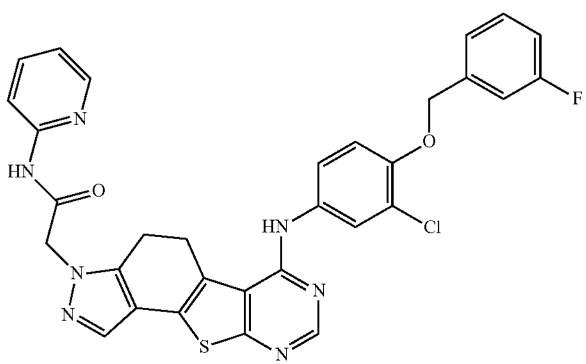 | 2-[6-({3-chloro-4-[(3-fluorobenzyl)oxy]phenyl}amino)-4,5-dihydro-3H-pyrimido[5',4':4,5]thieno[2,3-e]indazol-3-yl]-N-pyridin-2-ylacetamide | 3.47 | 612 |

-continued

| Example No | Structure | IUPAC name | LCMS RT (min) | LCMS Ion [M + H]+ |
|---|---|---|---|---|
| 196 | 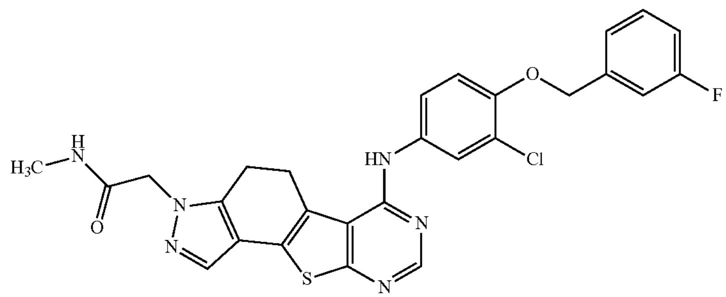 | 2-[6-({3-chloro-4-[(3-fluorobenzyl)oxy]phenyl}amino)-4,5-dihydro-3H-pyrimido[5',4':4,5]thieno[2,3-e]indazol-3-yl]-N-methylacetamide | 3.54 | 549.2 |
| 197 | 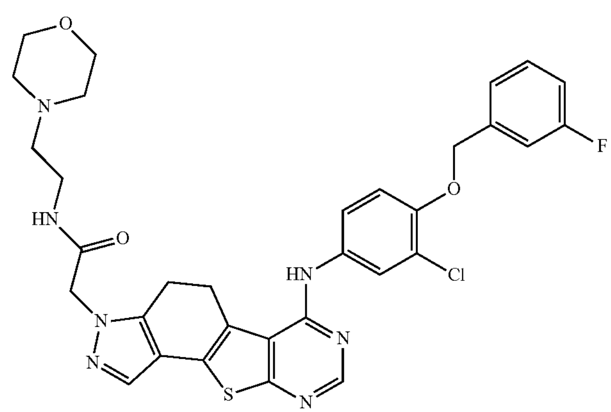 | 2-[6-({3-chloro-4-[(3-fluorobenzyl)oxy]phenyl}amino)-4,5-dihydro-3H-pyrimido[5',4':4,5]thieno[2,3-e]indazol-3-yl]-N-(2-morpholin-4-ylethyl)acetamide | 2.79 | 648.3 |

| Example No | Structure | IUPAC name | LCMS RT (min) | LCMS Ion [M + H]+ |
|---|---|---|---|---|
| 198 | 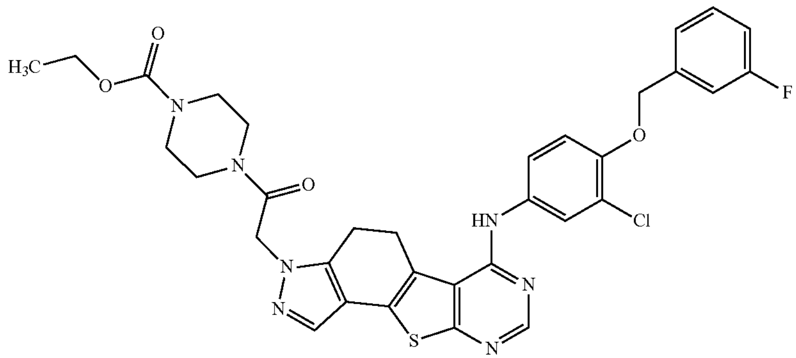 | ethyl 4-[[6-({3-chloro-4-[(3-fluorobenzyl)oxy]phenyl}amino)-4,5-dihydro-3H-pyrimido[5',4':4,5]thieno[2,3-e]indazol-3-yl]acetyl]piperazine-1-carboxylate | 3.59 | 676.2 |
| 199 | 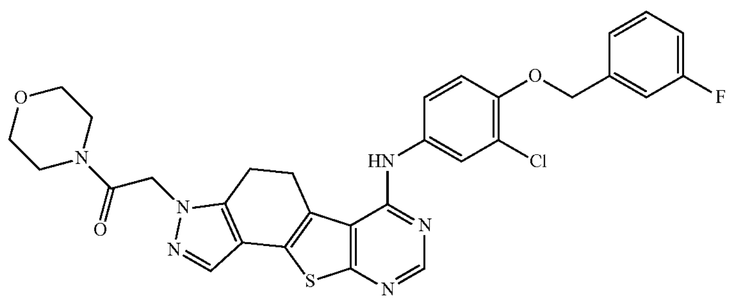 | N-{3-chloro-4-[(3-fluorobenzyl)oxy]phenyl}-3-(2-morpholin-4-yl-2-oxoethyl)-4,5-dihydro-3H-pyrimido[5',4':4,5]thieno[2,3-e]indazol-6-amine | 3.12 | 605.3 |

-continued

| Example No | Structure | IUPAC name | LCMS RT (min) | LCMS Ion [M + H]+ |
|---|---|---|---|---|
| 200 | 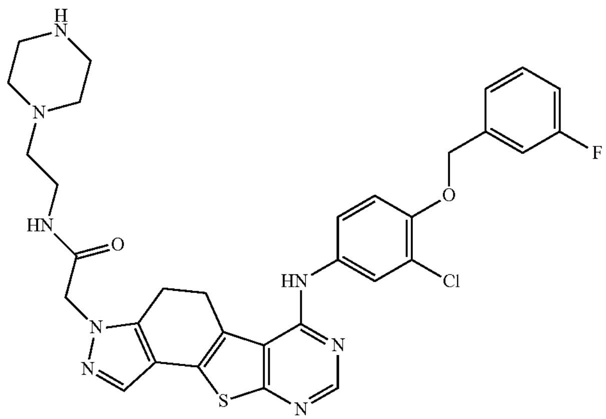 | 2-[6-{3-chloro-4-[(3-fluorobenzyl)oxy]phenyl}amino)-4,5-dihydro-3H-pyrimido[5',4':4,5]thieno[2,3-e]indazol-3-yl]-N-(2-piperazin-1-ylethyl)acetamide | 2.53 | 647.2 |
| 201 | 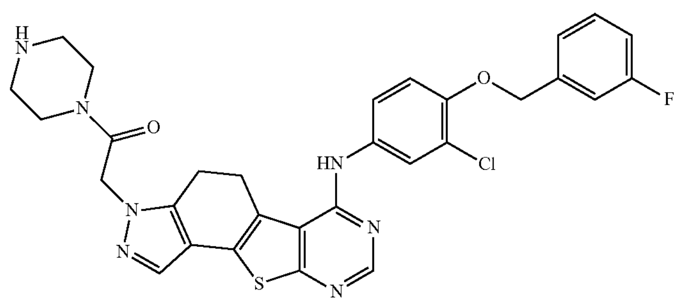 | N-{3-chloro-4-[(3-fluorobenzyl)oxy]phenyl}-3-(2-oxo-2-piperazin-1-ylethyl)-4,5-dihydro-3H-pyrimido[5',4':4,5]thieno[2,3-e]indazol-6-amine | 2.81 | 604.2 |
| 202 | 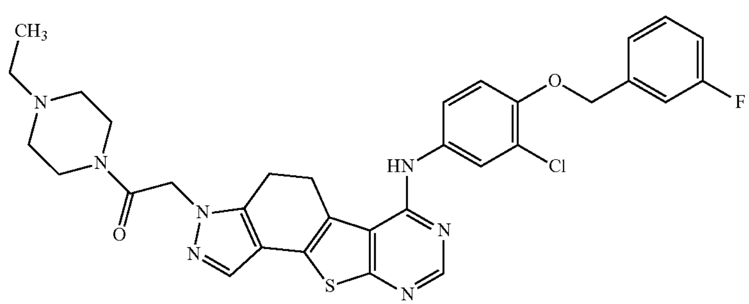 | N-{3-chloro-4-[(3-fluorobenzyl)oxy]phenyl}-3-[2-(4-ethylpiperazin-1-yl)-2-oxoethyl]-4,5-dihydro-3H-pyrimido[5',4':4,5]thieno[2,3-e]indazol-6-amine | 2.8 | 632.3 |

| Example No | Structure | IUPAC name | LCMS RT (min) | LCMS Ion [M + H]+ |
|---|---|---|---|---|
| 203 | 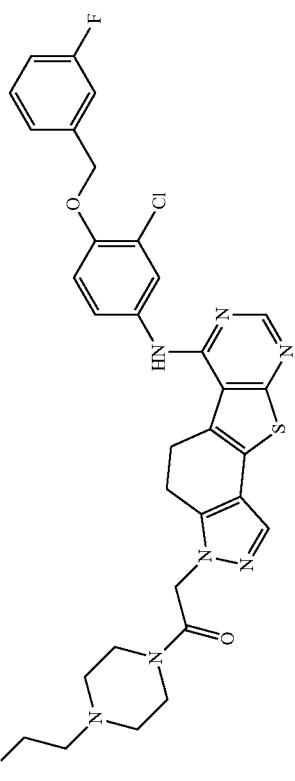 | N-{3-chloro-4-[(3-fluorobenzyl)oxy]phenyl}-3-{2-[4-(2-methoxyethyl)piperazin-1-yl]-2-oxoethyl}-4,5-dihydro-3H-pyrimido[5',4':4,5]thieno[2,3-e]indazol-6-amine | 2.41 | 662.4 |
| 204 | 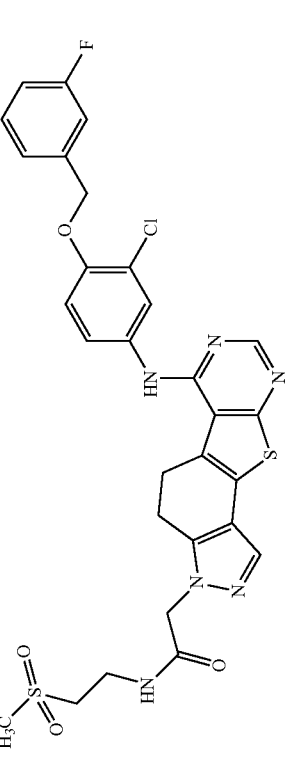 | 2-[6-({3-chloro-4-[(3-fluorobenzyl)oxy]phenyl}amino)-4,5-dihydro-3H-pyrimido[5',4':4,5]thieno[2,3-e]indazol-3-yl]-N-[2-(methylsulfonyl)ethyl]acetamide | 3.54 | 641.2 |
| 205 | 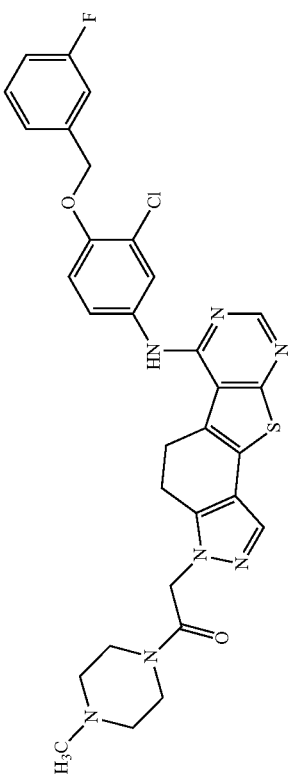 | N-{3-chloro-4-[(3-fluorobenzyl)oxy]phenyl}-3-[2-(4-methylpiperazin-1-yl)-2-oxoethyl]-4,5-dihydro-3H-pyrimido[5',4':4,5]thieno[2,3-e]indazol-6-amine | 2.73 | 618.2 |

| Example No | Structure | IUPAC name | LCMS RT (min) | LCMS Ion [M + H]+ |
|---|---|---|---|---|
| 206 | 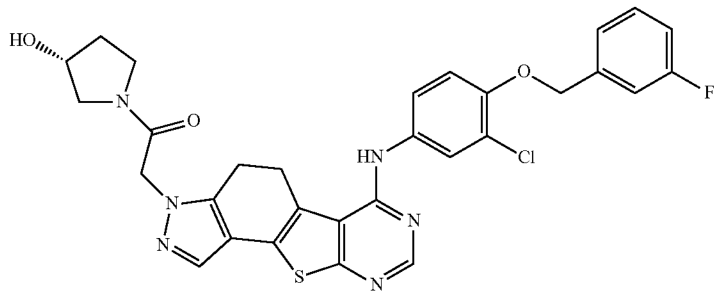 | (3R)-1-[[6-({3-chloro-4-[(3-fluorobenzyl)oxy]phenyl}amino)-4,5-dihydro-3H-pyrimido[5',4':4,5]thieno[2,3-e]indazol-3-yl]acetyl]pyrrolidin-3-ol | 3.17 | 605.2 |
| 207 | 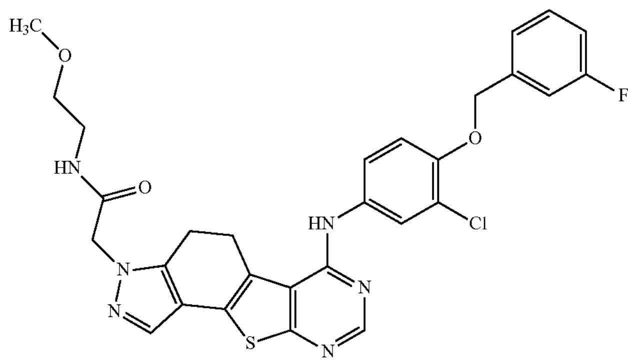 | 2-[6-({3-chloro-4-[(3-fluorobenzyl)oxy]phenyl}amino)-4,5-dihydro-3H-pyrimido[5',4':4,5]thieno[2,3-e]indazol-3-yl]-N-(2-methoxyethyl)acetamide | 3.63 | 593.2 |
| 208 | 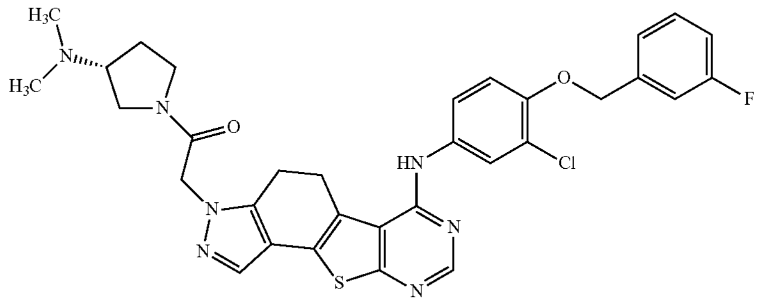 | N-{3-chloro-4-[(3-fluorobenzyl)oxy]phenyl}-3-{2-[(3S)-3-(dimethylamino)pyrrolidin-1-yl]-2-oxoethyl}-4,5-dihydro-3H-pyrimido[5',4':4,5]thieno[2,3-e]indazol-6-amine | 2.8 | 632.3 |

| Example No | Structure | IUPAC name | LCMS RT (min) | LCMS Ion [M + H]+ |
|---|---|---|---|---|
| 209 | 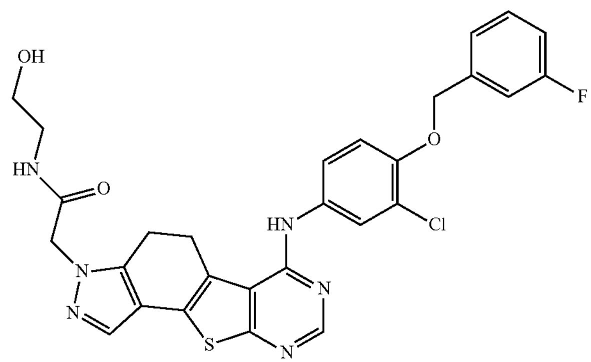 | 2-[6-{[3-chloro-4-[(3-fluorobenzyl)oxy]phenyl}amino)-4,5-dihydro-3H-pyrimido[5',4':4,5]thieno[2,3-e]indazol-3-yl]-N-(2-hydroxyethyl)acetamide | 3.12 | 579.2 |
| 210 | 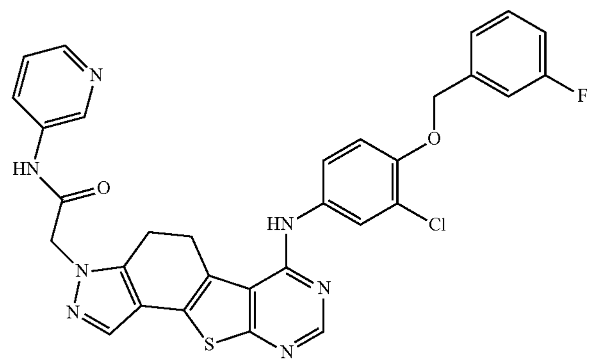 | 2-[6-{[3-chloro-4-[(3-fluorobenzyl)oxy]phenyl}amino)-4,5-dihydro-3H-pyrimido[5',4':4,5]thieno[2,3-e]indazol-3-yl]-N-pyridin-3-ylacetamide | 3.1 | 612.2 |
| 211 | 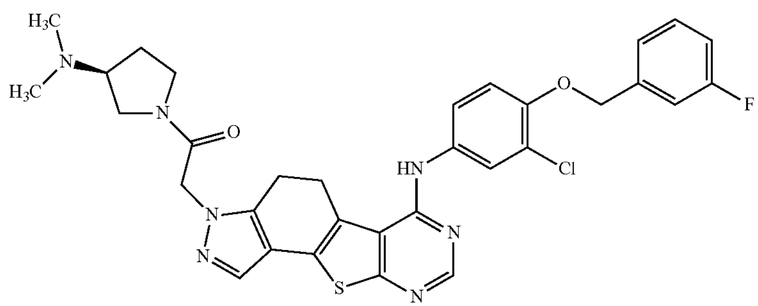 | N-{3-chloro-4-[(3-fluorobenzyl)oxy]phenyl}-3-{2-[(3R)-3-(dimethylamino)pyrrolidin-1-yl]-2-oxoethyl}-4,5-dihydro-3H-pyrimido[5',4':4,5]thieno[2,3-e]indazol-6-amine | 2.79 | 632.3 |

| Example No | Structure | IUPAC name | LCMS RT (min) | LCMS Ion [M + H]+ |
|---|---|---|---|---|
| 212 | 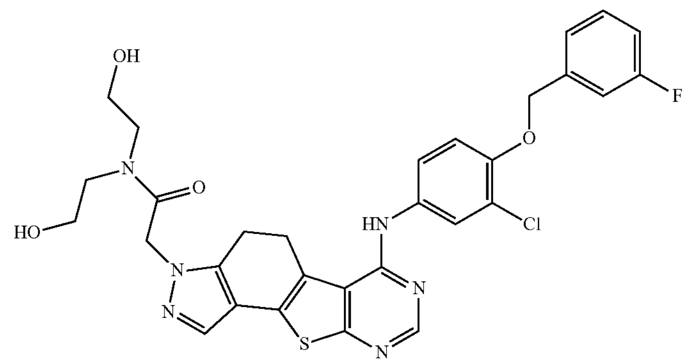 | 2-[6-({3-chloro-4-[(3-fluorobenzyl)oxy]phenyl}amino)-4,5-dihydro-3H-pyrimido[5',4':4,5]thieno[2,3-e]indazol-3-yl]-N,N-bis(2-hydroxyethyl)acetamide | 3.06 | 623.2 |
| 213 | 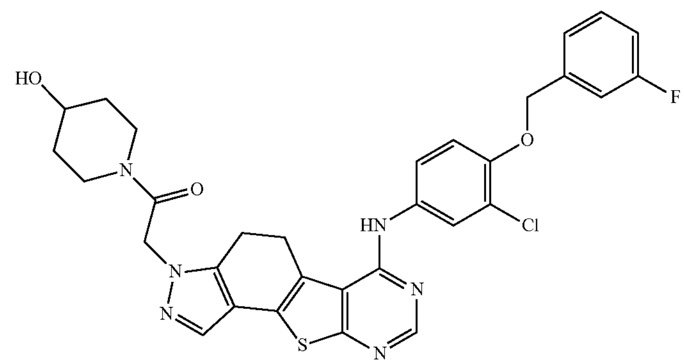 | 1-[[6-({3-chloro-4-[(3-fluorobenzyl)oxy]phenyl}amino)-4,5-dihydro-3H-pyrimido[5',4':4,5]thieno[2,3-e]indazol-3-yl]acetyl]piperidin-4-ol | 3.21 | 619.2 |
| 214 | 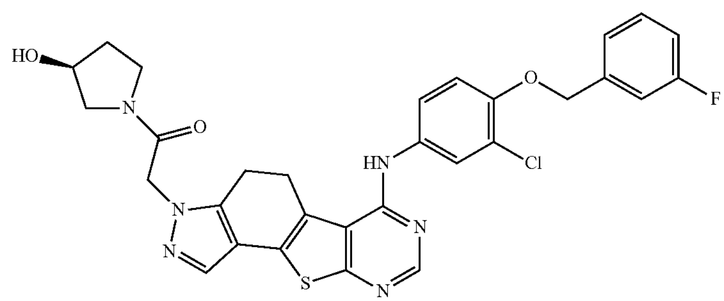 | 1-{[6-({3-chloro-4-[(3-fluorobenzyl)oxy]phenyl}amino)-4,5-dihydro-3H-pyrimido[5',4':4,5]thieno[2,3-e]indazol-3-yl]acetyl}pyrrolidin-3-ol | 3.15 | 605.3 |

| Example No | Structure | IUPAC name | LCMS RT (min) | LCMS Ion [M + H]+ |
|---|---|---|---|---|
| 215 | 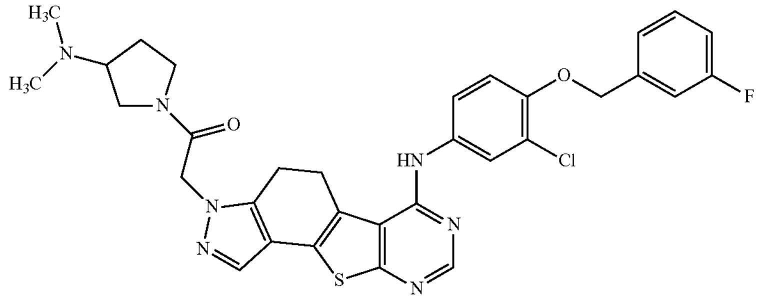 | N-{3-chloro-4-[(3-fluorobenzyl)oxy]phenyl}-3-{2-[3-(dimethylamino)pyrrolidin-1-yl]-2-oxoethyl}-4,5-dihydro-3H-pyrimido[5',4':4,5]thieno[2,3-e]indazol-6-amine | 2.8 | 632.3 |
| 216 | 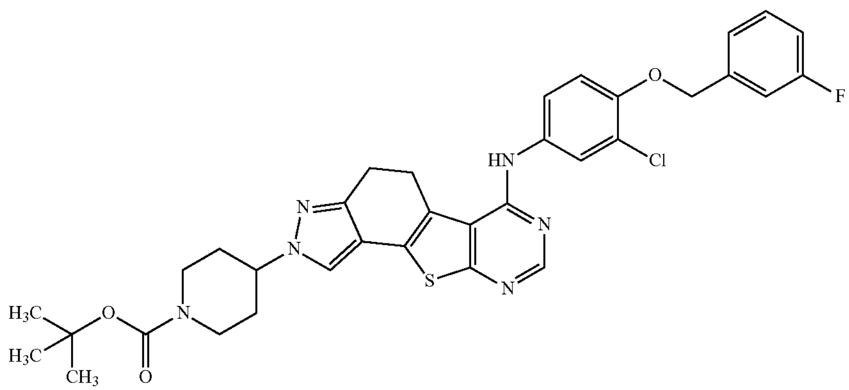 | tert-butyl 4-[6-({3-chloro-4-[(3-fluorobenzyl)oxy]phenyl}amino)-4,5-dihydro-2H-pyrimido[5',4':4,5]thieno[2,3-e]indazol-2-yl]piperidine-1-carboxylate | 4.22 | 661.1 |
| 217 | 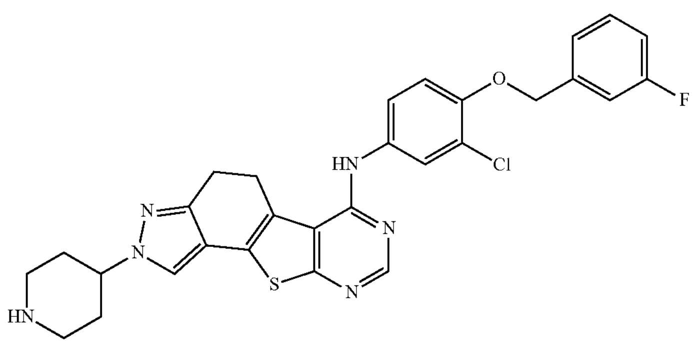 | N-{3-chloro-4-[(3-fluorobenzyl)oxy]phenyl}-2-piperidin-4-yl-4,5-dihydro-2H-pyrimido[5',4':4,5]thieno[2,3-e]indazol-6-amine | 2.83 | 561.2 |

| Example No | Structure | IUPAC name | LCMS RT (min) | LCMS Ion [M + H]+ |
|---|---|---|---|---|
| 218 | 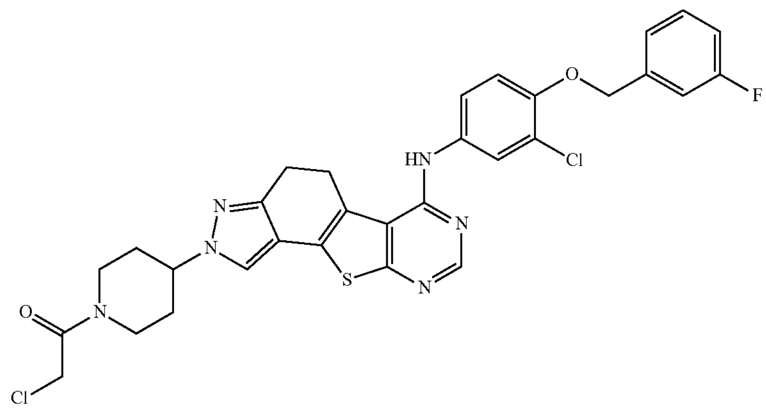 | 2-[1-(chloroacetyl)piperidin-4-yl]-N-{3-chloro-4-[(3-fluorobenzyl)oxy]phenyl}-4,5-dihydro-2H-pyrimido[5',4':4,5]thieno[2,3-e]indazol-6-amine | 3.68 | 637.4 |
| 219 | 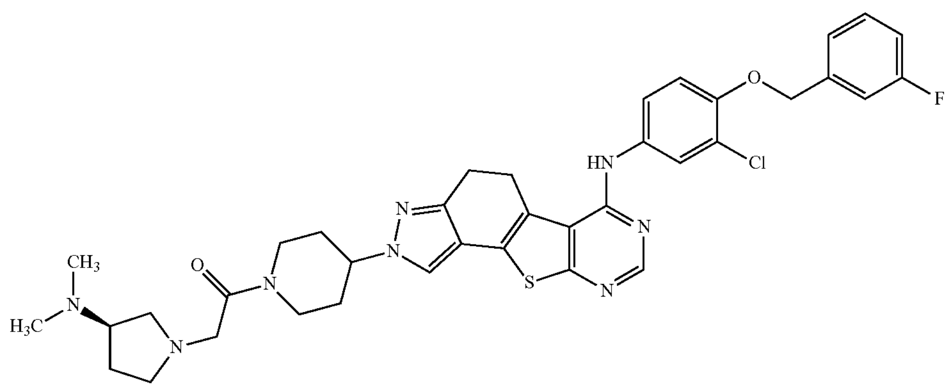 | N-{3-chloro-4-[(3-fluorobenzyl)oxy]phenyl}-2-(4-{[(3R)-3-(dimethylamino)pyrrolidin-1-yl]acetyl}piperidin-4-yl)-4,5-dihydro-2H-pyrimido[5',4':4,5]thieno[2,3-e]indazol-6-amine | 2.62 | 715.2 |

-continued

| Example No | Structure | IUPAC name | LCMS RT (min) | LCMS Ion [M + H]+ |
|---|---|---|---|---|
| 220 | 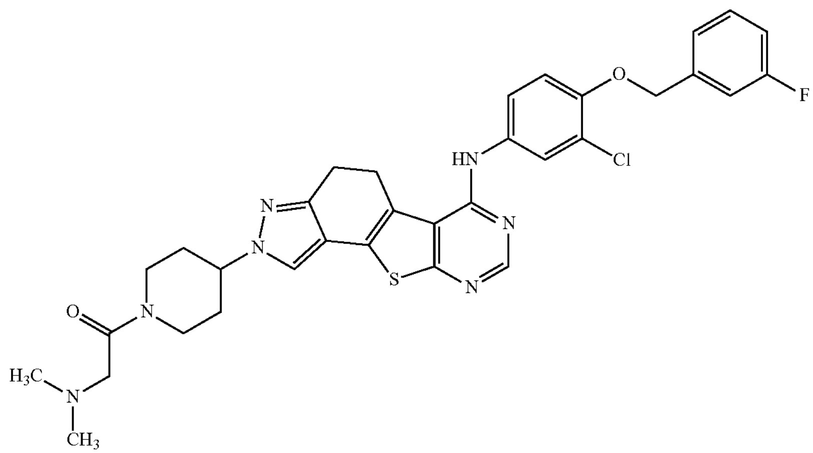 | N-{3-chloro-4-[(3-fluorobenzyl)oxy]phenyl}-2-{1-[(diethylamino)acetyl]piperidin-4-yl}-4,5-dihydro-2H-pyrimido[5',4':4,5]thieno[2,3-e]indazol-6-amine | 2.98 | 674.3 |
| 221 | 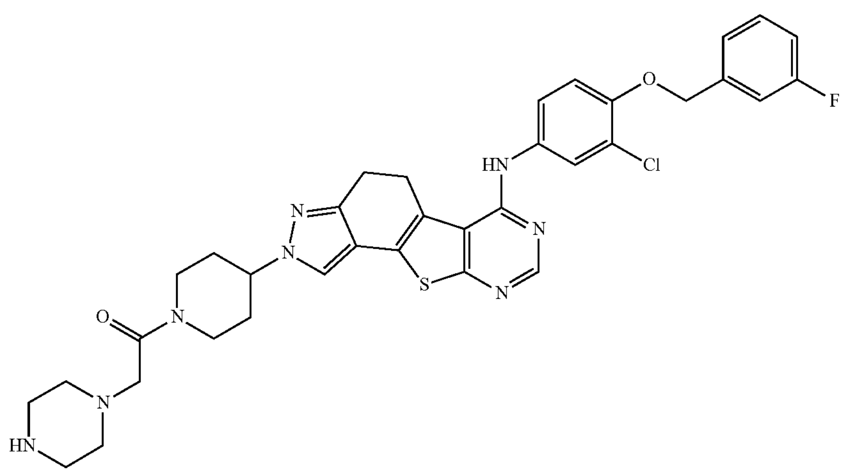 | N-{3-chloro-4-[(3-fluorobenzyl)oxy]phenyl}-2-[1-(piperazin-1-ylacetyl)piperidin-4-yl]-4,5-dihydro-2H-pyrimido[5',4':4,5]thieno[2,3-e]indazol-6-amine | 2.69 | 687.3 |

| Example No | Structure | IUPAC name | LCMS RT (min) | LCMS Ion [M + H]+ |
|---|---|---|---|---|
| 222 | 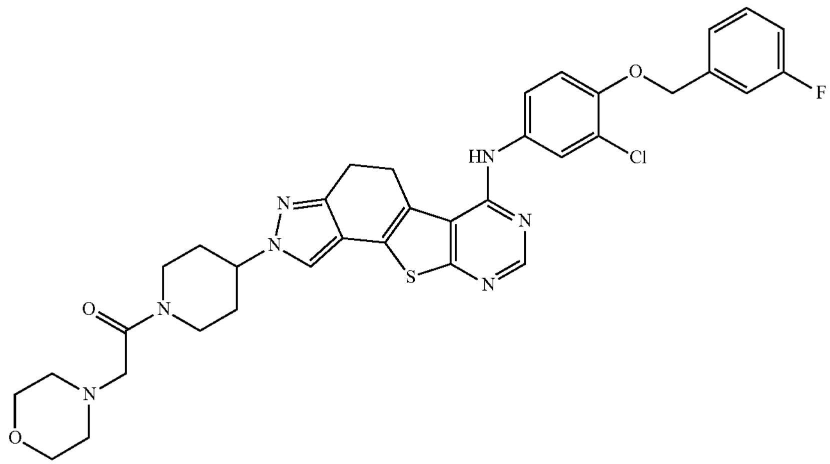 | N-{3-chloro-4-[(3-fluorobenzyl)oxy]phenyl}-2-[1-(morpholin-4-ylacetyl)piperidin-4-yl]-4,5-dihydro-2H-pyrimido[5',4':4,5]thieno[2,3-e]indazol-6-amine | 2.87 | 688.2 |
| 223 | 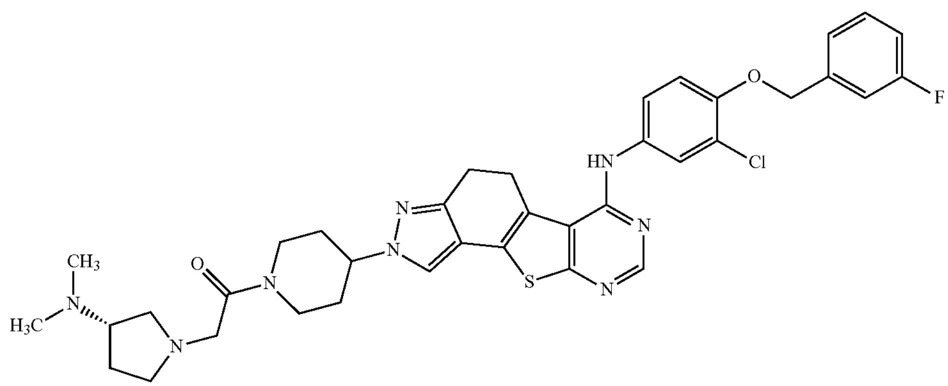 | N-{3-chloro-4-[(3-fluorobenzyl)oxy]phenyl}-2-(1-{[(3S)-3-(dimethylamino)pyrrolidin-1-yl]acetyl}piperidin-4-yl)-4,5-dihydro-2H-pyrimido[5',4':4,5]thieno[2,3-e]indazol-6-amine | 2.64 | 715.2 |

| Example No | Structure | IUPAC name | LCMS RT (min) | LCMS Ion [M + H]+ |
|---|---|---|---|---|
| 224 | 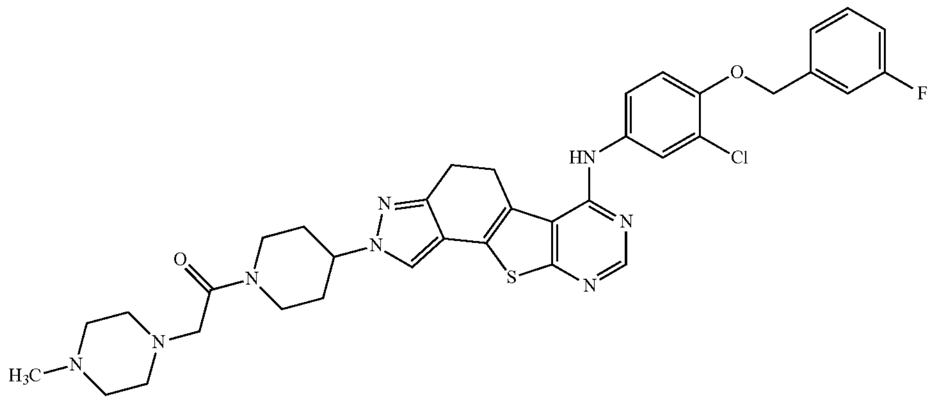 | N-{3-chloro-4-[(3-fluorobenzyl)oxy]phenyl}-2-{1-[(4-methylpiperazin-1-yl)acetyl]piperidin-4-yl}-4,5-dihydro-2H-pyrimido[5',4':4,5]thieno[2,3-e]indazol-6-amine | 2.78 | 701.2 |
| 225 | 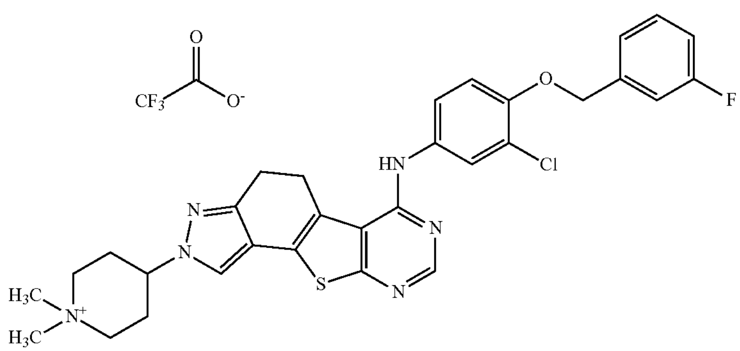 | 4-[6-({3-chloro-4-[(3-fluorobenzyl)oxy]phenyl}amino)-4,5-dihydro-2H-pyrimido[5',4':4,5]thieno[2,3-e]indazol-2-yl]-1,1-dimethylpiperidinium trifluoroacetate | 2.87 | 589.3 |

| Example No | Structure | IUPAC name | LCMS RT (min) | LCMS Ion [M + H]+ |
|---|---|---|---|---|
| 226 | 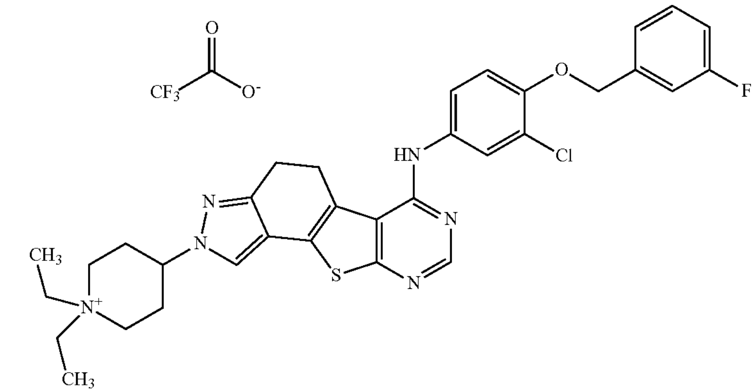 | 4-[6-({3-chloro-4-[(3-fluorobenzyl)oxy]phenyl}amino)-4,5-dihydro-2H-pyrimido[5',4':4,5]thieno[2,3-e]indazol-2-yl]-1,1-diethylpiperidinium trifluoroacetate | 2.9 | 617.3 |
| 227 | 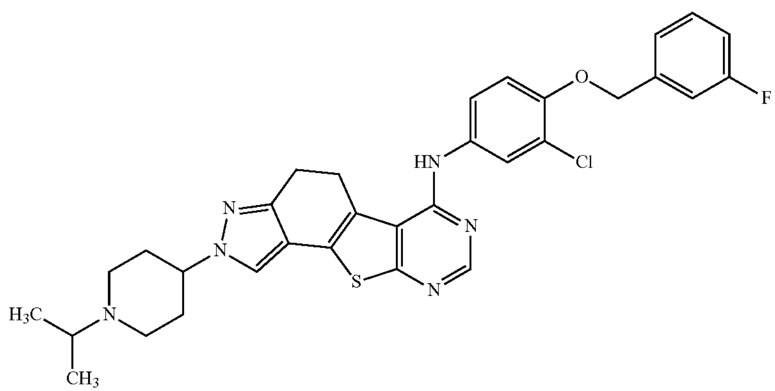 | N-{3-chloro-4-[(3-fluorobenzyl)oxy]phenyl}-2-(1-isopropylpiperidin-4-yl)-4,5-dihydro-2H-pyrimido[5',4':4,5]thieno[2,3-e]indazol-6-amine | 2.87 | 603.2 |

| Example No | Structure | IUPAC name | LCMS RT (min) | LCMS Ion [M + H]+ |
|---|---|---|---|---|
| 228 | 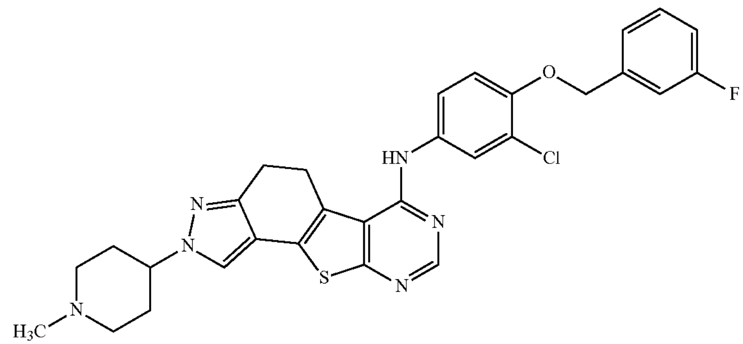 | N-{3-chloro-4-[(3-fluorobenzyl)oxy]phenyl}-2-(1-methylpiperidin-4-yl)-4,5-dihydro-2H-pyrimido[5',4':4,5]thieno[2,3-e]indazol-6-amine | 2.81 | 575.1 |
| 229 | 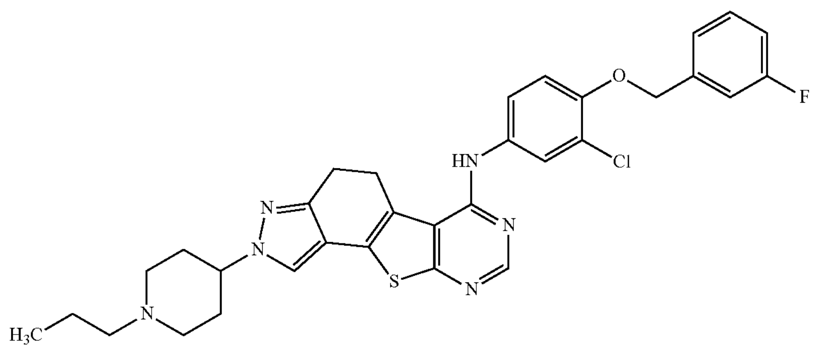 | N-{3-chloro-4-[(3-fluorobenzyl)oxy]phenyl}-2-(1-propylpiperidin-4-yl)-4,5-dihydro-2H-pyrimido[5',4':4,5]thieno[2,3-e]indazol-6-amine | 2.87 | 603.3 |
| 230 | 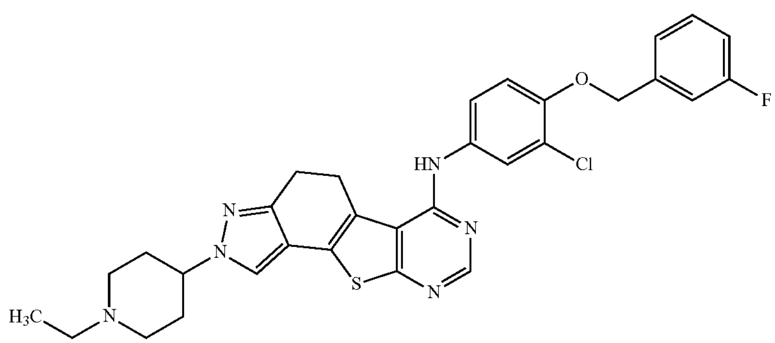 | N-{3-chloro-4-[(3-fluorobenzyl)oxy]phenyl}-2-(1-ethylpiperidin-4-yl)-4,5-dihydro-2H-pyrimido[5',4':4,5]thieno[2,3-e]indazol-6-amine | 2.83 | 589.3 |

| Example No | Structure | IUPAC name | LCMS RT (min) | LCMS Ion [M + H]+ |
|---|---|---|---|---|
| 231 | 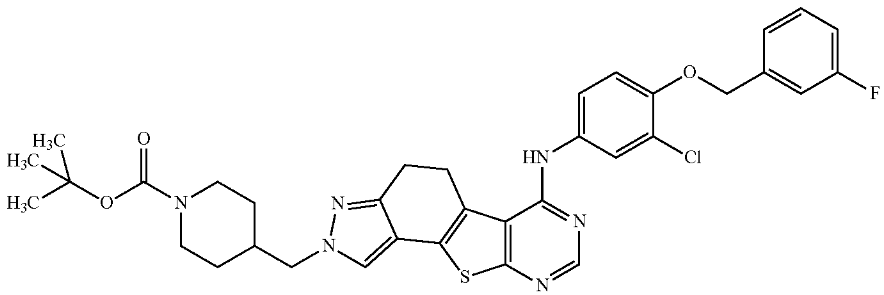 | tert-butyl 4-{[6-({3-chloro-4-[(3-fluorobenzyl)oxy]phenyl}amino)-4,5-dihydro-2H-pyrimido[5',4':4,5]thieno[2,3-e]indazol-2-yl]methyl}piperidine-1-carboxylate | 4.22 | 675.1 |
| 232 | 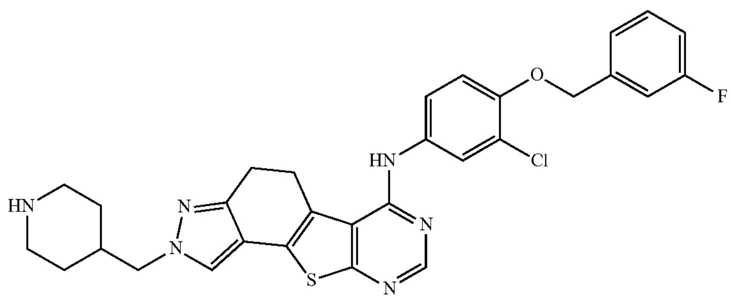 | N-{3-chloro-4-[(3-fluorobenzyl)oxy]phenyl}-2-(piperidin-4-ylmethyl)-4,5-dihydro-2H-pyrimido[5',4':4,5]thieno[2,3-e]indazol-6-amine | 2.89 | 575.3 |
| 233 | 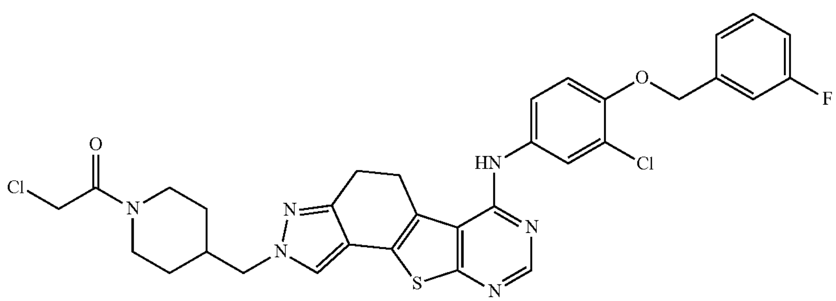 | 2-{[1-(chloroacetyl)piperidin-4-yl]methyl}-N-{3-chloro-4-[(3-fluorobenzyl)oxy]phenyl}-4,5-dihydro-2H-pyrimido[5',4':4,5]thieno[2,3-e]indazol-6-amine trifluoroacetate | 3.31 | 651.4 |

-continued

| Example No | Structure | IUPAC name | LCMS RT (min) | LCMS Ion [M + H]+ |
|---|---|---|---|---|
| 234 | 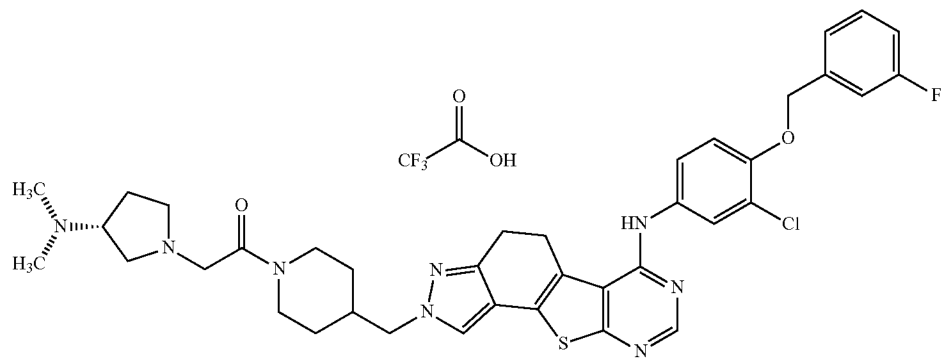 | N-{3-chloro-4-[(3-fluorobenzyl)oxy]phenyl}-2-[(1-{[(3R)-3-(dimethylamino)pyrrolidin-1-yl]acetyl}piperidin-4-yl)methyl]-4,5-dihydro-2H-pyrimido[5',4':4,5]thieno[2,3-e]indazol-6-amine trifluoroacetate | 2.74 | 729.3 |
| 235 | 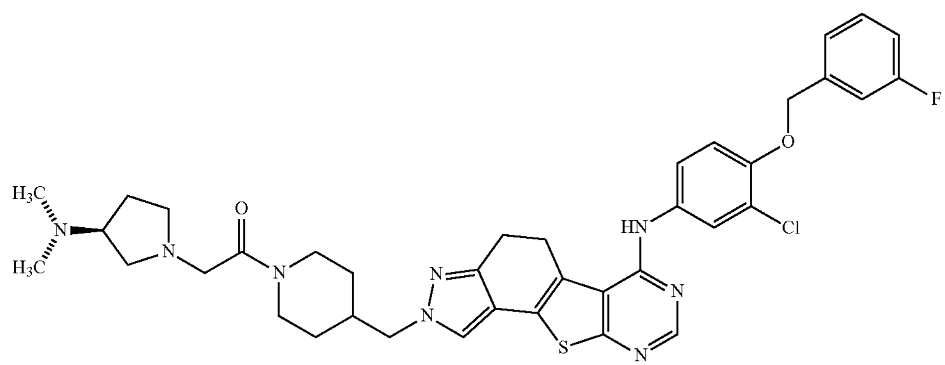 | N-{3-chloro-4-[(3-fluorobenzyl)oxy]phenyl}-2-[(1-{[(3S)-3-(dimethylamino)pyrrolidin-1-yl]acetyl}piperidin-4-yl)methyl]-4,5-dihydro-2H-pyrimido[5',4':4,5]thieno[2,3-e]indazol-6-amine | 3.02 | 729.4 |

| Example No | Structure | IUPAC name | LCMS RT (min) | LCMS Ion [M + H]+ |
|---|---|---|---|---|
| 236 | 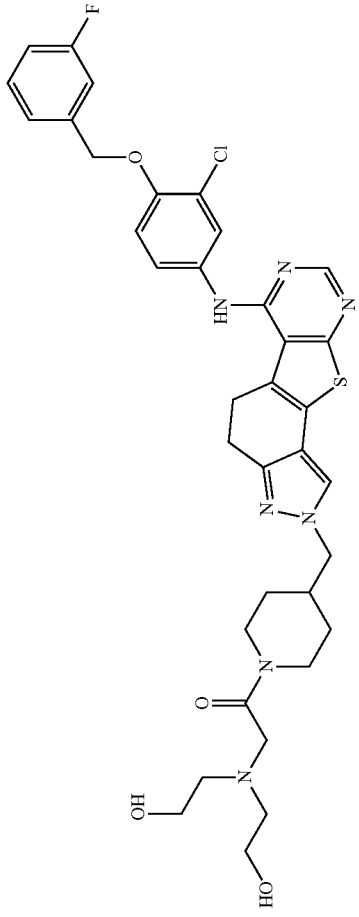 | N-{3-chloro-4-[(3-fluorobenzyl)oxy]phenyl}-2-[(1-methylpiperidin-4-yl)methyl]-4,5-dihydro-2H-pyrimido[5',4':4,5]thieno[2,3-e]indazol-6-amine | 2.84 | 589.2 |
| 237 | 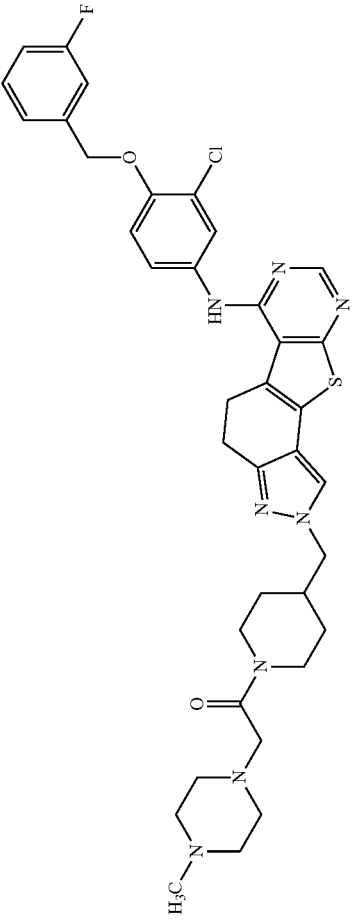 | N-{3-chloro-4-[(3-fluorobenzyl)oxy]phenyl}-2-({1-[(4-methylpiperidin-1-yl)acetyl]piperidin-4-yl}methyl)-4,5-dihydro-2H-pyrimido[5',4':4,5]thieno[2,3-e]indazol-6-amine | 3.16 | 715.4 |

| Example No | Structure | IUPAC name | LCMS RT (min) | LCMS Ion [M + H]+ |
|---|---|---|---|---|
| 238 | 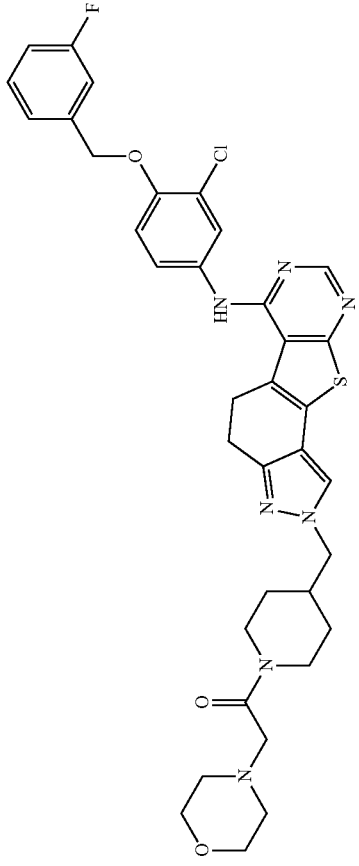 | N-{3-chloro-4-[(3-fluorobenzyl)oxy]phenyl}-2-{[1-(morpholin-4-ylacetyl)piperidin-4-yl]methyl}-4,5-dihydro-2H-pyrimido[5',4':4,5]thieno[2,3-e]indazol-6-amine | 3.25 | 702.4 |
| 239 | 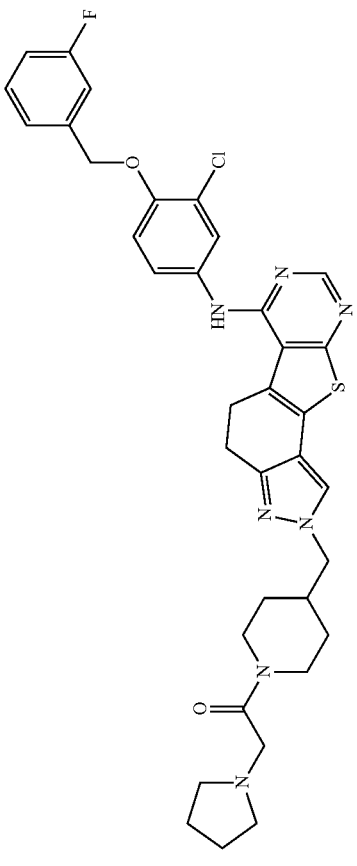 | N-{3-chloro-4-[(3-fluorobenzyl)oxy]phenyl}-2-{[1-(pyrrolidin-1-ylacetyl)piperidin-4-yl]methyl}-4,5-dihydro-2H-pyrimido[5',4':4,5]thieno[2,3-e]indazol-6-amine | 2.87 | 686.2 |

-continued

| Example No | Structure | IUPAC name | LCMS RT (min) | LCMS Ion [M + H]+ |
|---|---|---|---|---|
| 240 | 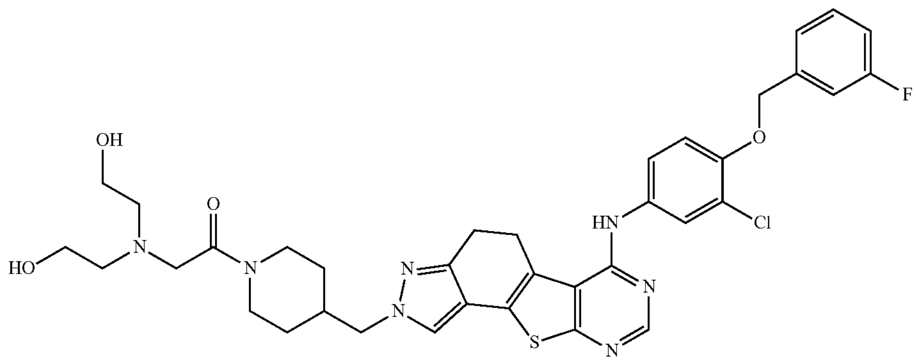 | 2,2'-{[2-(4-{[6-({3-chloro-4-[(3-fluorobenzyl)oxy]phenyl}amino)-4,5-dihydro-2H-pyrimido[5',4':4,5]thieno[2,3-e]indazol-2-yl]methyl}piperidin-1-yl)-2-oxoethyl]imino}diethanol | 2.8 | 720.2 |
| 241 | 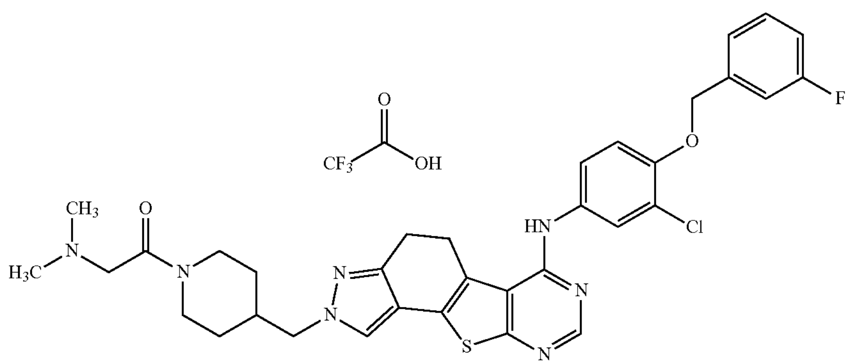 | N-{3-chloro-4-[(3-fluorobenzyl)oxy]phenyl}-2-({1-[(dimethylamino)acetyl]piperidin-4-yl}methyl)-4,5-dihydro-2H-pyrimido[5',4':4,5]thieno[2,3-e]indazol-6-amine trifluoroacetate | 2.84 | 660.2 |

| Example No | Structure | IUPAC name | LCMS RT (min) | LCMS Ion [M + H]+ |
|---|---|---|---|---|
| 242 | 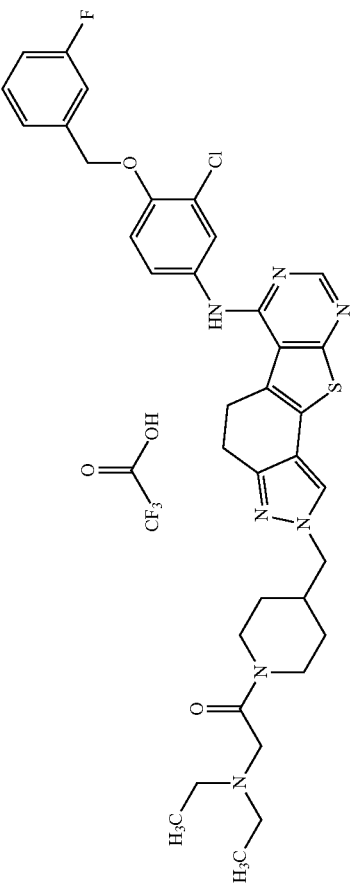 | N-{3-chloro-4-[(3-fluorobenzyl)oxy]phenyl}-2-({1-[(diethylamino)acetyl]piperidin-4-yl}methyl)-4,5-dihydro-2H-pyrimido[5′,4′:4,5]thieno[2,3-e]indazol-6-amine trifluoroacetate | 2.94 | 688.2 |
| 243 | 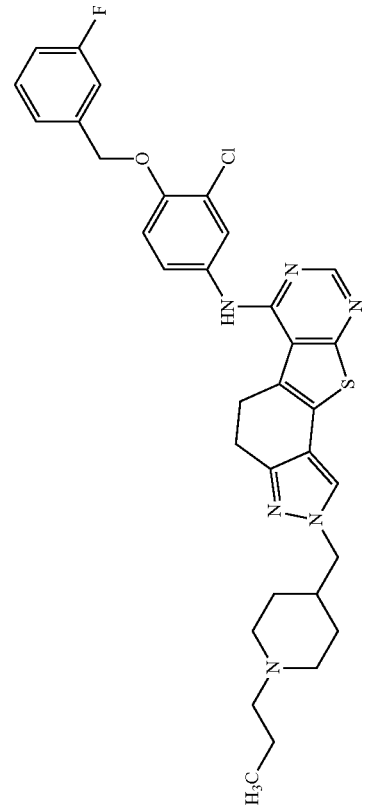 | N-{3-chloro-4-[(3-fluorobenzyl)oxy]phenyl}-2-[(1-propylpiperidin-4-yl)methyl]-4,5-dihydro-2H-pyrimido[5′,4′:4,5]thieno[2,3-e]indazol-6-amine | 2.91 | 617.2 |

| Example No | Structure | IUPAC name | LCMS RT (min) | LCMS Ion [M + H]+ |
|---|---|---|---|---|
| 244 | 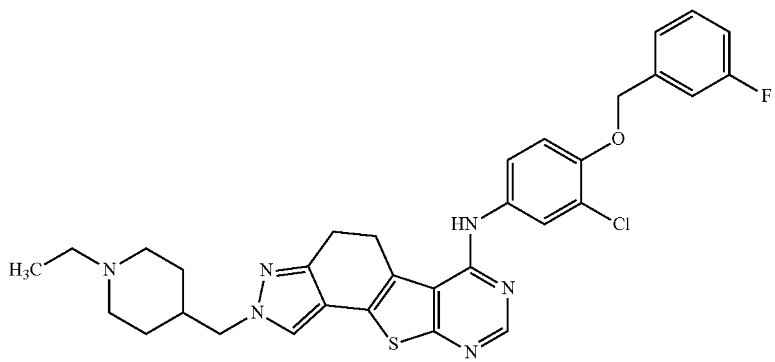 | N-{3-chloro-4-[(3-fluorobenzyl)oxy]phenyl}-2-[(1-ethylpiperidin-4-yl)methyl]-4,5-dihydro-2H-pyrimido[5',4':4,5]thieno[2,3-e]indazol-6-amine | 2.88 | 603.2 |
| 245 | 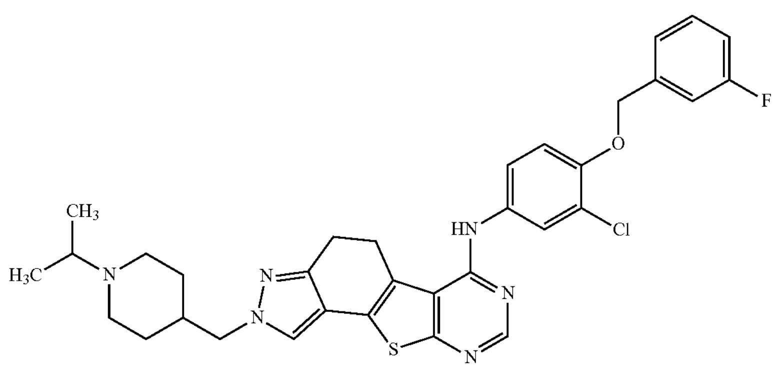 | N-{3-chloro-4-[(3-fluorobenzyl)oxy]phenyl}-2-[(1-isopropylpiperidin-4-yl)methyl]-4,5-dihydro-2H-pyrimido[5',4':4,5]thieno[2,3-e]indazol-6-amine | 2.9 | 617.2 |

-continued
| Example No | Structure | IUPAC name | LCMS RT (min) | LCMS Ion [M + H]+ |
|---|---|---|---|---|
| 246 | 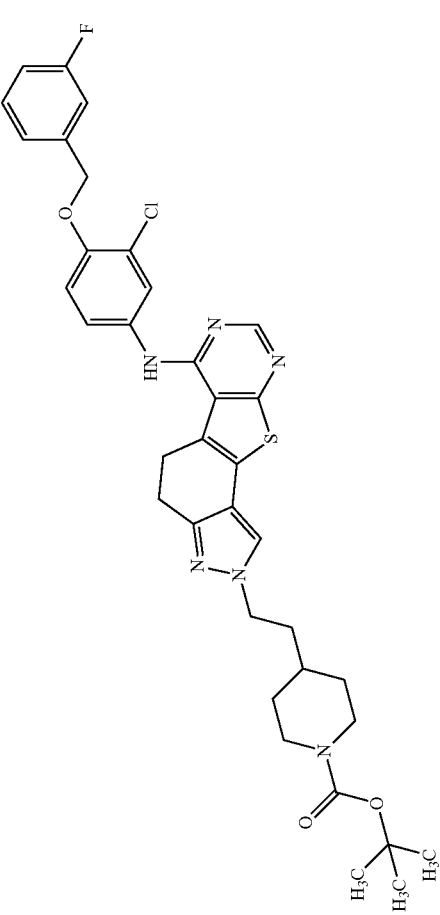 | tert-butyl 4-{2-[6-({3-chloro-4-[(3-fluorobenzyl)oxy]phenyl}amino)-4,5-dihydro-2H-pyrimido[5',4':4,5]thieno[2,3-e]indazol-2-yl]ethyl}piperidine-1-carboxylate | 4.31 | 689.1 |
| 247 | 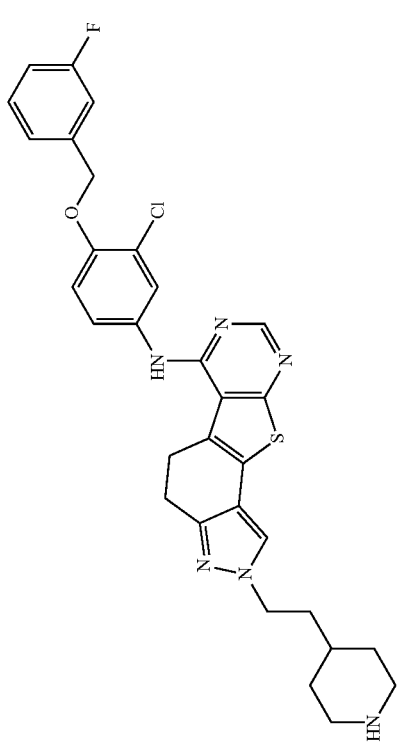 | N-{3-chloro-4-[(3-fluorobenzyl)oxy]phenyl}-2-(2-piperidin-4-ylethyl)-4,5-dihydro-2H-pyrimido[5',4':4,5]thieno[2,3-e]indazol-6-amine | 2.96 | 589.2 |

| Example No | Structure | IUPAC name | LCMS RT (min) | LCMS Ion [M+H]+ |
|---|---|---|---|---|
| 248 | 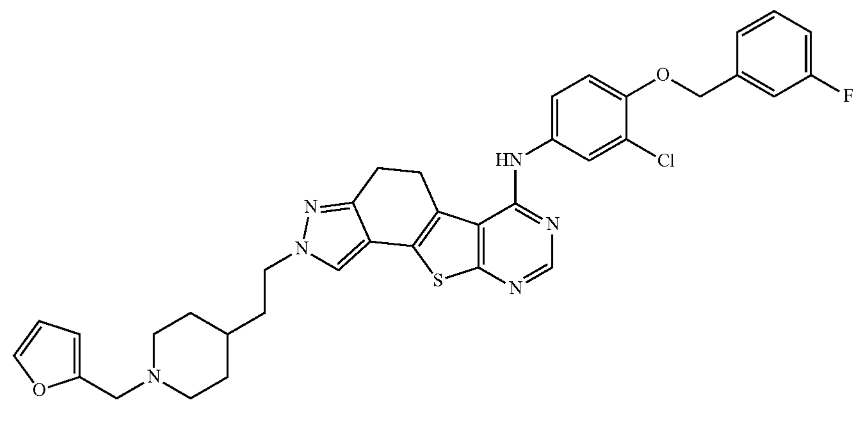 | N-[3-chloro-4-[(3-fluorobenzyl)oxy]phenyl]-2-{2-[1-(2-furylmethyl)piperidin-4-yl]ethyl}-4,5-dihydro-2H-pyrimido[5',4':4,5]thieno[2,3-e]indazol-6-amine | 3.02 | 669.2 |
| 249 | 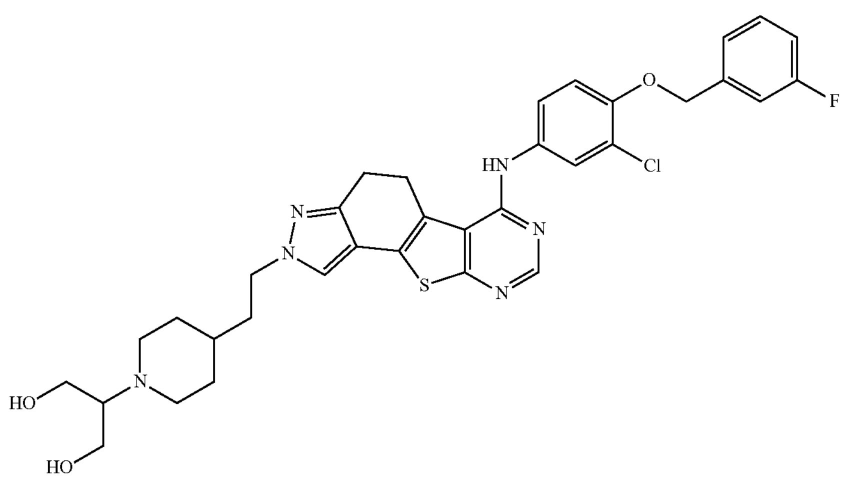 | 2-(4-{2-[6-({3-chloro-4-[(3-fluorobenzyl)oxy]phenyl}amino)-4,5-dihydro-2H-pyrimido[5',4':4,5]thieno[2,3-e]indazol-2-yl]ethyl}piperidin-1-yl)propane-1,3-diol | 2.84 | 663.2 |

| Example No | Structure | IUPAC name | LCMS RT (min) | LCMS Ion [M + H]+ |
|---|---|---|---|---|
| 250 | 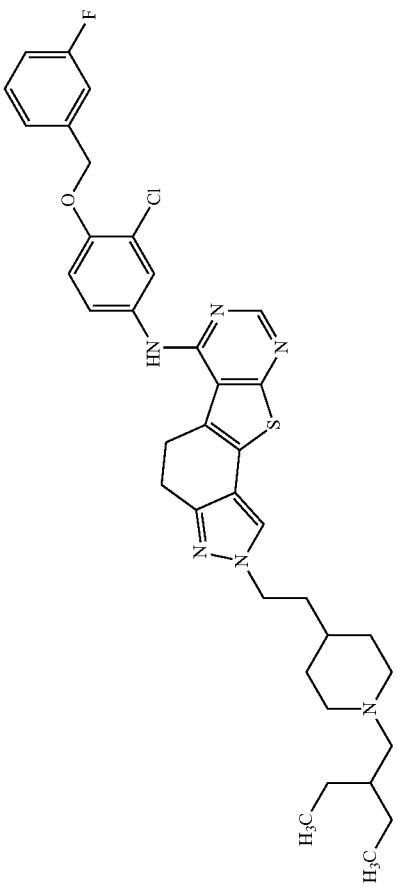 | N-{3-chloro-4-[(3-fluorobenzyl)oxy]phenyl}-2-{2-[1-(2-ethylbutyl)piperidin-4-yl]ethyl}-4,5-dihydro-2H-pyrimido[5',4':4,5]thieno[2,3-e]indazol-6-amine | 3.14 | 673.2 |
| 251 | 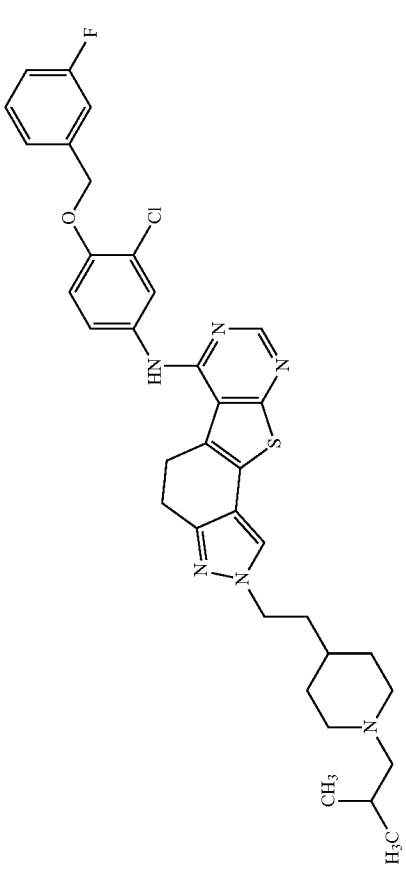 | N-{3-chloro-4-[(3-fluorobenzyl)oxy]phenyl}-2-[2-(1-isobutylpiperidin-4-yl)ethyl]-4,5-dihydro-2H-pyrimido[5',4':4,5]thieno[2,3-e]indazol-6-amine | 3.02 | 645.2 |

| Example No | Structure | IUPAC name | LCMS RT (min) | LCMS Ion [M + H]+ |
|---|---|---|---|---|
| 252 | 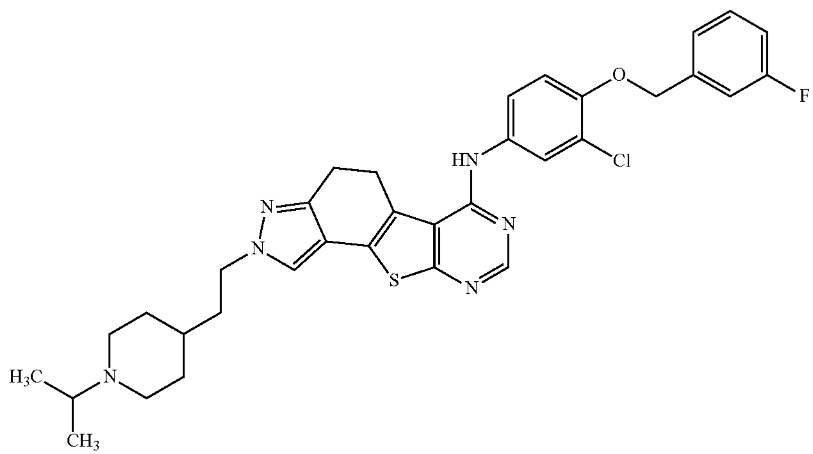 | N-{3-chloro-4-[(3-fluorobenzyl)oxy]phenyl}-2-[2-(1-isopropylpiperidin-4-yl)ethyl]-4,5-dihydro-2H-pyrimido[5',4':4,5]thieno[2,3-e]indazol-6-amine | 2.98 | 631.2 |
| 253 | 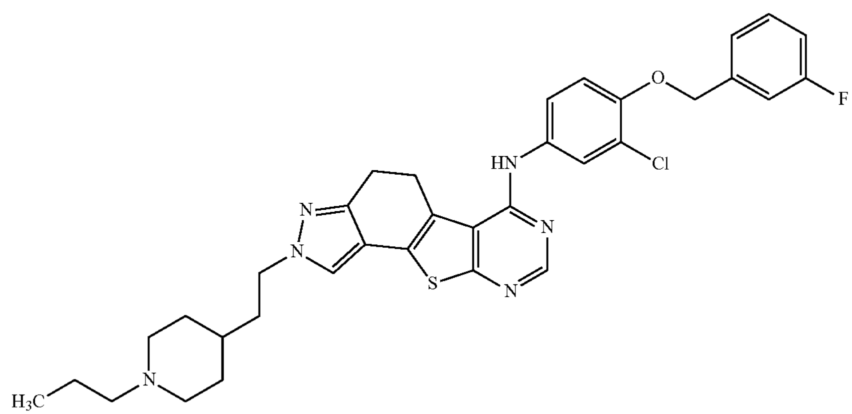 | N-{3-chloro-4-[(3-fluorobenzyl)oxy]phenyl}-2-[2-(1-propylpiperidin-4-yl)ethyl]-4,5-dihydro-2H-pyrimido[5',4':4,5]thieno[2,3-e]indazol-6-amine | 3 | 631.2 |

| Example No | Structure | IUPAC name | LCMS RT (min) | LCMS Ion [M + H]+ |
|---|---|---|---|---|
| 254 | 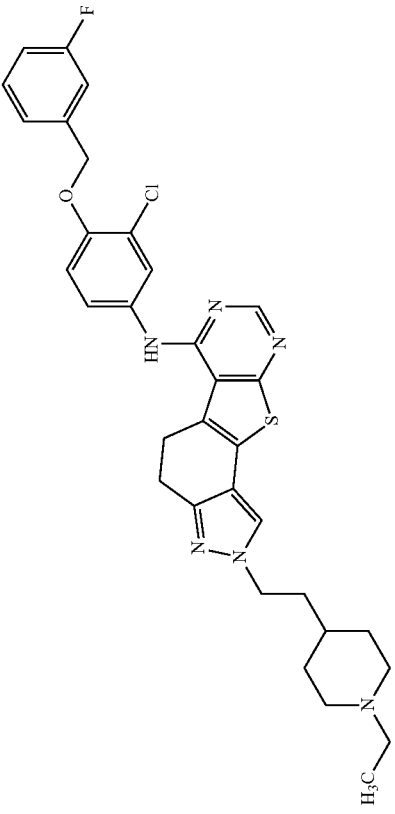 | N-{3-chloro-4-[(3-fluorobenzyl)oxy]phenyl}-2-[2-(1-ethylpiperidin-4-yl)ethyl]-4,5-dihydro-2H-pyrimido[5',4':4,5]thieno[2,3-e]indazol-6-amine | 2.95 | 617.2 |
| 255 | 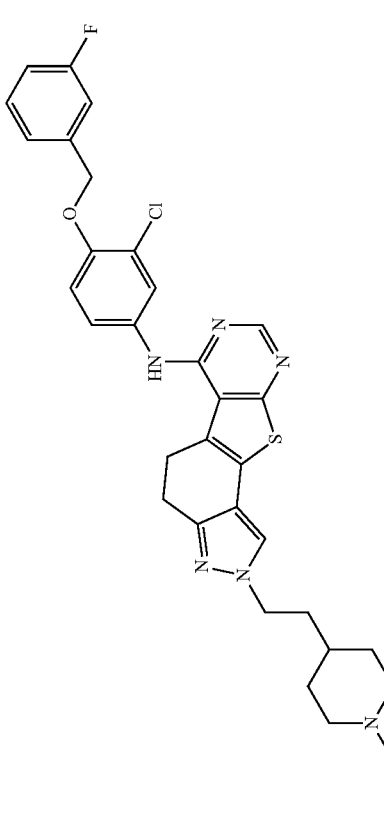 | N-{3-chloro-4-[(3-fluorobenzyl)oxy]phenyl}-2-[2-(1-methylpiperidin-4-yl)ethyl]-4,5-dihydro-2H-pyrimido[5',4':4,5]thieno[2,3-e]indazol-6-amine | 2.87 | 603.2 |

| Example No | Structure | IUPAC name | LCMS RT (min) | LCMS Ion [M + H]+ |
|---|---|---|---|---|
| 256 | 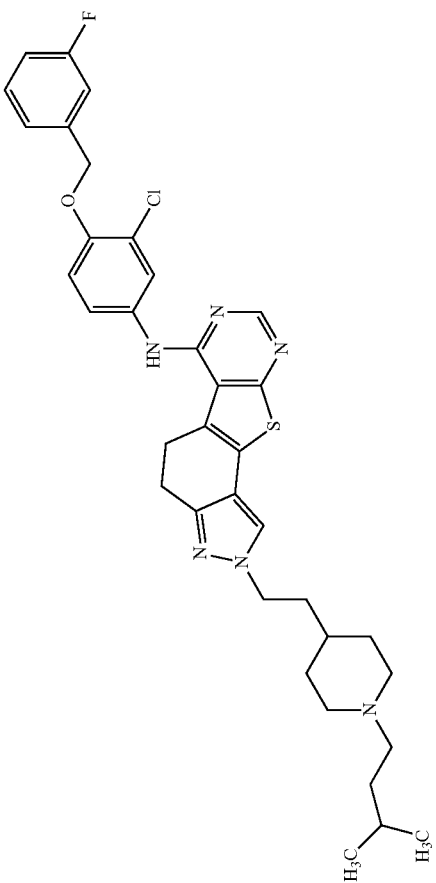 | N-[3-chloro-4-[(3-fluorobenzyl)oxy]phenyl]-2-{2-[1-(3-methylbutyl)piperidin-4-yl]ethyl}-4,5-dihydro-2H-pyrimido[5',4':4,5]thieno[2,3-e]indazol-6-amine | 3.08 | 659.2 |
| 257 | 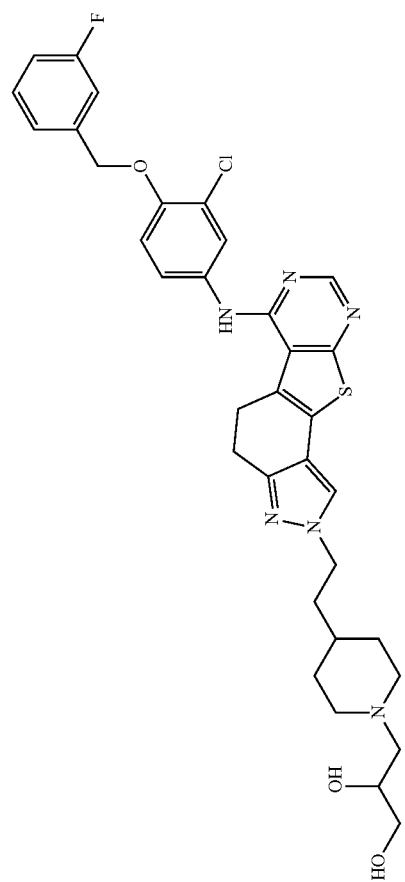 | 3-(4-{2-[6-({3-chloro-4-[(3-fluorobenzyl)oxy]phenyl}amino)-4,5-dihydro-2H-pyrimido[5',4':4,5]thieno[2,3-e]indazol-2-yl]ethyl}piperidin-1-yl)propane-1,2-diol | 2.83 | 663.2 |

-continued
| Example No | Structure | IUPAC name | LCMS RT (min) | LCMS Ion [M + H]+ |
|---|---|---|---|---|
| 258 | 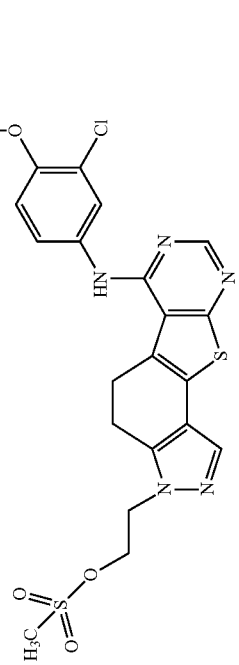 | 2-[6-({3-chloro-4-[(3-fluorobenzyl)oxy]phenyl}amino)-4,5-dihydro-3H-pyrimido[5',4':4,5]thieno[2,3-e]indazol-3-yl]ethyl methanesulfonate | 3.83 | 600.2 |
| 259 | 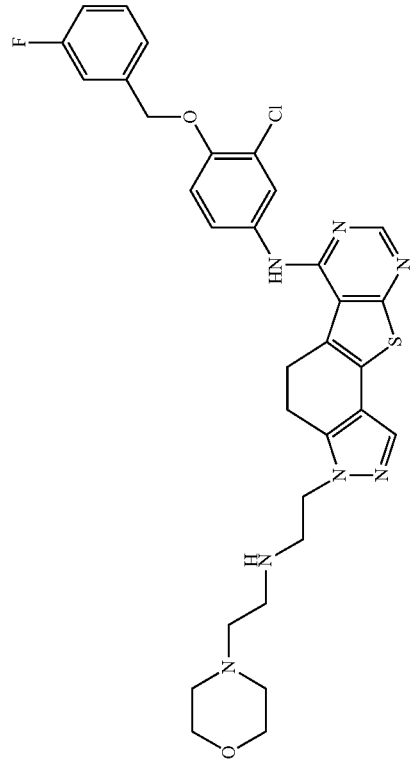 | N-{3-chloro-4-[(3-fluorobenzyl)oxy]phenyl}-3-{2-[(2-morpholin-4-ylethyl)amino]ethyl}-4,5-dihydro-3H-pyrimido[5',4':4,5]thieno[2,3-e]indazol-6-amine | 3.08 | 634.3 |

| Example No | Structure | IUPAC name | LCMS RT (min) | LCMS Ion [M + H]+ |
|---|---|---|---|---|
| 260 | 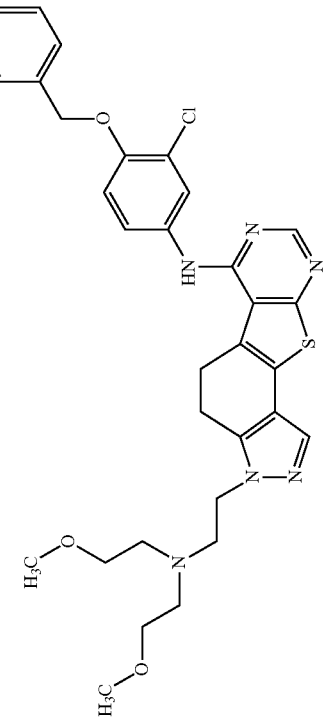 | 3-{2-[bis(2-methoxyethyl)amino]ethyl}-N-{3-chloro-4-[(3-fluorobenzyl)oxy]phenyl}-4,5-dihydro-3H-pyrimido[5',4':4,5]thieno[2,3-e]indazol-6-amine | 3.02 | 637.6 |
| 261 | 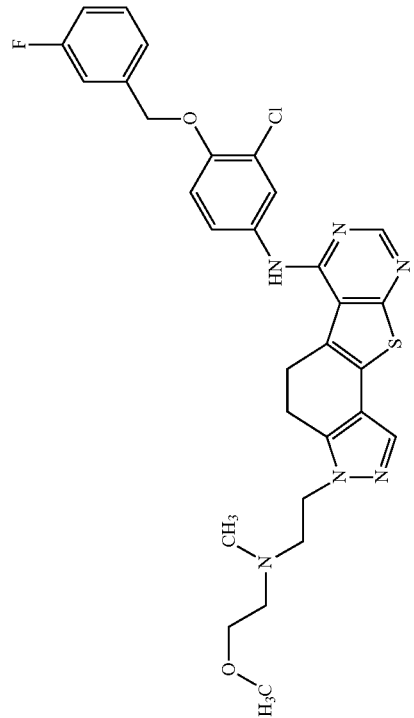 | N-{3-chloro-4-[(3-fluorobenzyl)oxy]phenyl}-3-{2-[(2-methoxyethyl)(methyl)amino]ethyl}-4,5-dihydro-3H-pyrimido[5',4':4,5]thieno[2,3-e]indazol-6-amine | 2.93 | 593.5 |

| Example No | Structure | IUPAC name | LCMS RT (min) | LCMS Ion [M + H]+ |
|---|---|---|---|---|
| 262 | 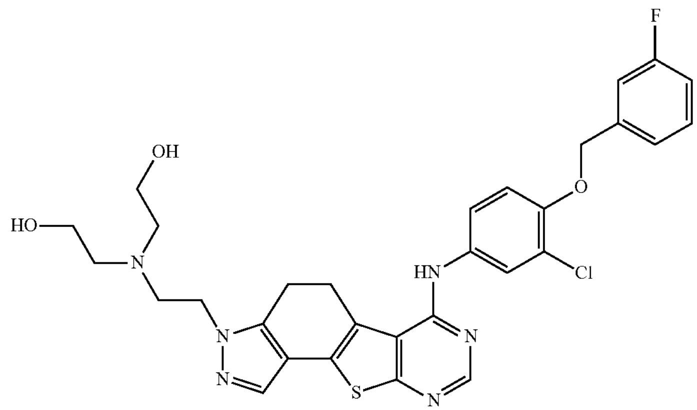 | 2,2'-({2-[6-({3-chloro-4-[(3-fluorobenzyl)oxy]phenyl}amino)-4,5-dihydro-3H-pyrimido[5',4':4,5]thieno[2,3-e]indazol-3-yl]ethyl}iminodiethanol | 2.82 | 609.5 |
| 263 | 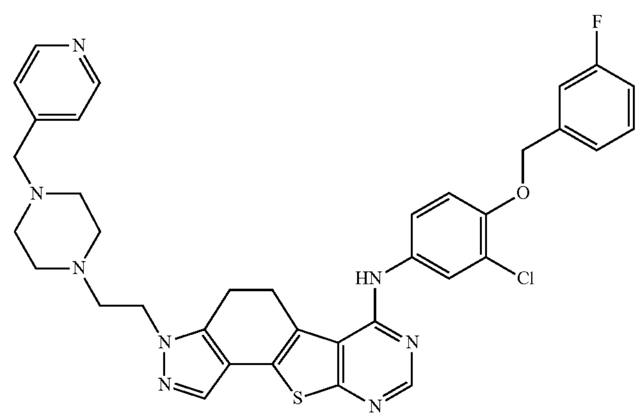 | N-{3-chloro-4-[(3-fluorobenzyl)oxy]phenyl}-3-{2-[4-(pyridin-4-ylmethyl)piperazin-1-yl]ethyl}-4,5-dihydro-3H-pyrimido[5',4':4,5]thieno[2,3-e]indazol-6-amine | 2.62 | 681.6 |

| Example No | Structure | IUPAC name | LCMS RT (min) | LCMS Ion [M + H]+ |
|---|---|---|---|---|
| 264 | 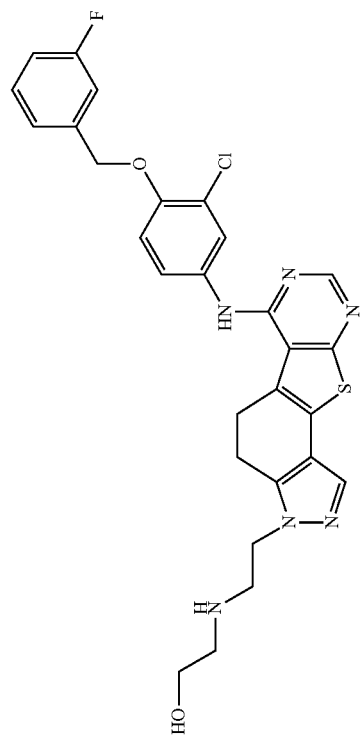 | 2-({2-[6-({3-chloro-4-[(3-fluorobenzyl)oxy]phenyl}amino)-4,5-dihydro-3H-pyrimido[5',4':4,5]thieno[2,3-e]indazol-3-yl]ethyl}amino)ethanol | 3.19 | 565.3 |
| 265 | 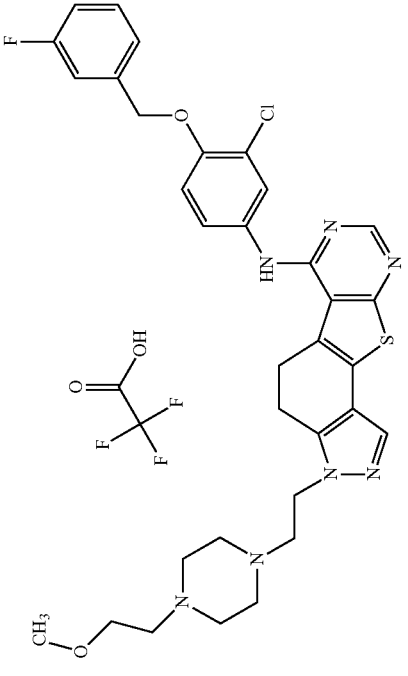 | N-{3-chloro-4-[(3-fluorobenzyl)oxy]phenyl}-3-{2-[4-(2-methoxyethyl)piperazin-1-yl]ethyl}-4,5-dihydro-3H-pyrimido[5',4':4,5]thieno[2,3-e]indazol-6-amine trifluoroacetate | 2.82 | 648.6 |

| Example No | Structure | IUPAC name | LCMS RT (min) | LCMS Ion [M + H]+ |
|---|---|---|---|---|
| 266 | 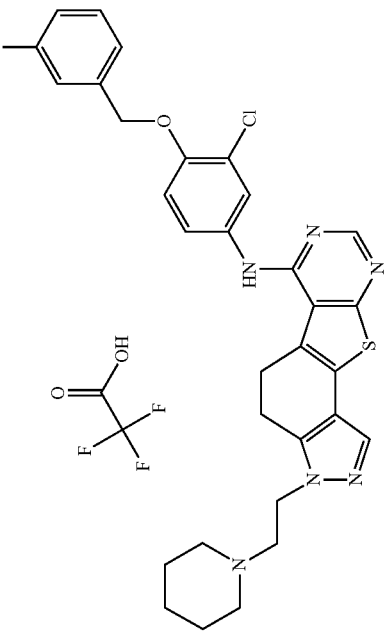 | N-{3-chloro-4-[(3-fluorobenzyl)oxy]phenyl}-3-(2-piperazin-1-ylethyl)-4,5-dihydro-3H-pyrimido[5',4':4,5]thieno[2,3-e]indazol-6-amine trifluoroacetate | 2.93 | 589.6 |
| 267 | 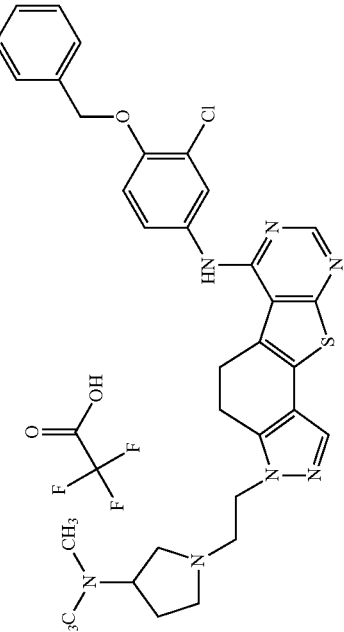 | N-{3-chloro-4-[(3-fluorobenzyl)oxy]phenyl}-3-{2-[3-(dimethylamino)pyrrolidin-1-yl]ethyl}-4,5-dihydro-3H-pyrimido[5',4':4,5]thieno[2,3-e]indazol-6-amine trifluoroacetate | 2.62 | 618.5 |

-continued

| Example No | Structure | IUPAC name | LCMS RT (min) | LCMS Ion [M + H]+ |
|---|---|---|---|---|
| 268 | 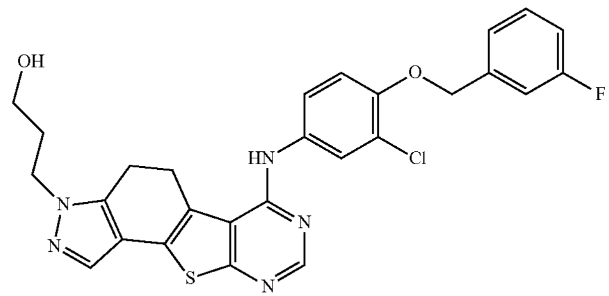 | 3-[6-({3-chloro-4-[(3-fluorobenzyl)oxy]phenyl}amino)-4,5-dihydro-3H-pyrimido[5',4':4,5]thieno[2,3-e]indazol-3-yl]propan-1-ol | 3.65 | 536.3 |
| 269 | 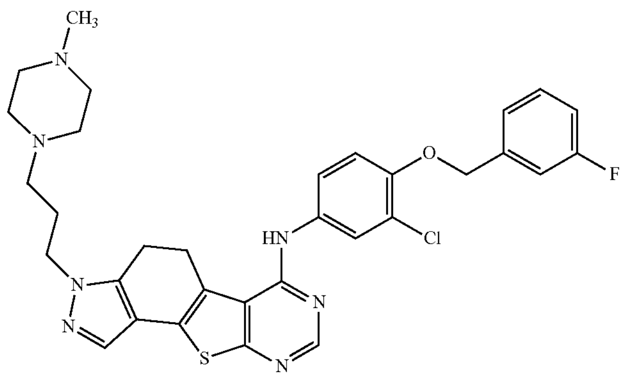 | N-{3-chloro-4-[(3-fluorobenzyl)oxy]phenyl}-3-[3-(4-methylpiperazin-1-yl)propyl]-4,5-dihydro-3H-pyrimido[5',4':4,5]thieno[2,3-e]indazol-6-amine | 2.73 | 618.2 |
| 270 | 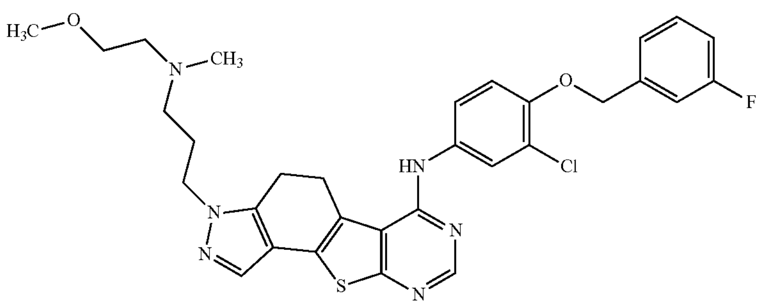 | N-{3-chloro-4-[(3-fluorobenzyl)oxy]phenyl}-3-{3-[(2-methoxyethyl)(methyl)amino]propyl}-4,5-dihydro-3H-pyrimido[5',4':4,5]thieno[2,3-e]indazol-6-amine | 2.9 | 607.4 |

-continued

| Example No | Structure | IUPAC name | LCMS RT (min) | LCMS Ion [M + H]+ |
|---|---|---|---|---|
| 271 | 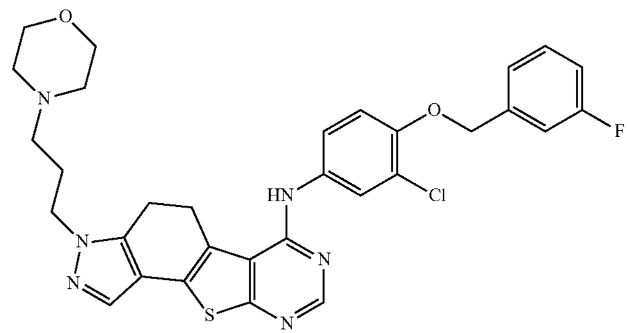 | N-{3-chloro-4-[(3-fluorobenzyl)oxy]phenyl}-3-(3-morpholin-4-ylpropyl)-4,5-dihydro-3H-pyrimido[5',4':4,5]thieno[2,3-e]indazol-6-amine | 2.93 | 605.2 |
| 272 | 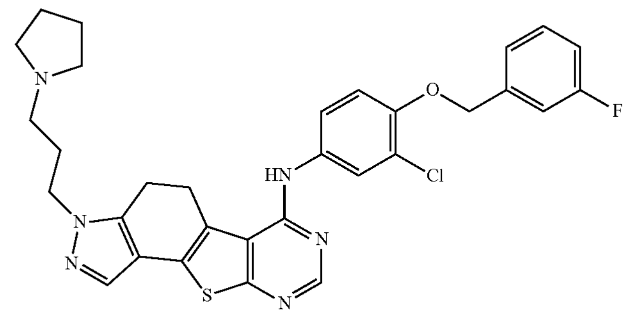 | N-{3-chloro-4-[(3-fluorobenzyl)oxy]phenyl}-3-(3-pyrrolidin-1-ylpropyl)-4,5-dihydro-3H-pyrimido[5',4':4,5]thieno[2,3-e]indazol-6-amine | 2.89 | 589.4 |
| 273 | 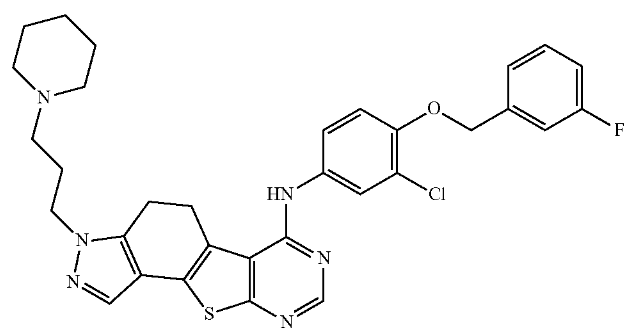 | N-{3-chloro-4-[(3-fluorobenzyl)oxy]phenyl}-3-(3-piperazin-1-ylpropyl)-4,5-dihydro-3H-pyrimido[5',4':4,5]thieno[2,3-e]indazol-6-amine | 2.94 | 603.3 |

-continued

| Example No | Structure | IUPAC name | LCMS RT (min) | LCMS Ion [M + H]+ |
|---|---|---|---|---|
| 275 | 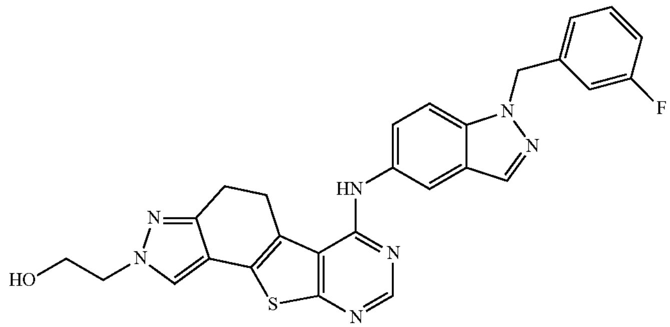 | 2-(6-{[1-(3-fluorobenzyl)-1H-indazol-5-yl]amino}-4,5-dihydro-2H-pyrimido[5',4':4,5]thieno[2,3-e]indazol-2-yl)ethanol | 2.83 | 512.3 |
| 276 | 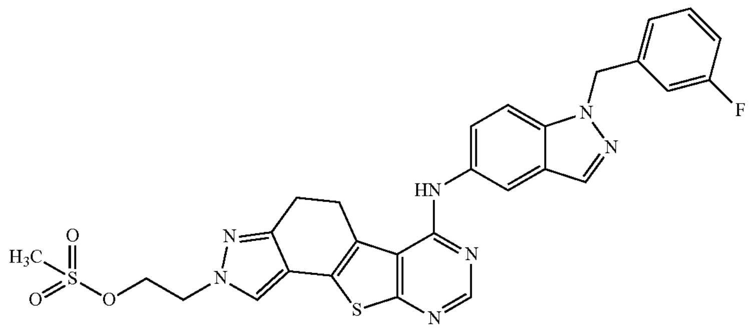 | 2-(6-{[1-(3-fluorobenzyl)-1H-indazol-5-yl]amino}-4,5-dihydro-2H-pyrimido[5',4':4,5]thieno[2,3-e]indazol-2-yl)ethyl methanesulfonate | 2.93 | 590.4 |
| 277 | 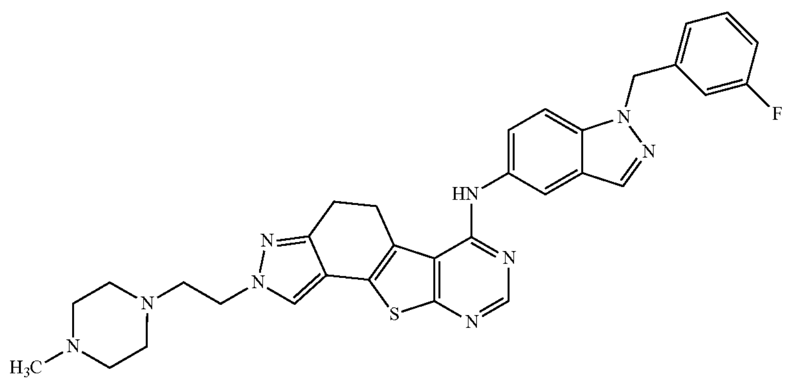 | N-[1-(3-fluorobenzyl)-1H-indazol-5-yl]-2-[2-(4-methylpiperazin-1-yl)ethyl]-4,5-dihydro-2H-pyrimido[5',4':4,5]thieno[2,3-e]indazol-6-amine | 2.82 | 594.3 |

| Example No | Structure | IUPAC name | LCMS RT (min) | LCMS Ion [M + H]+ |
|---|---|---|---|---|
| 278 | 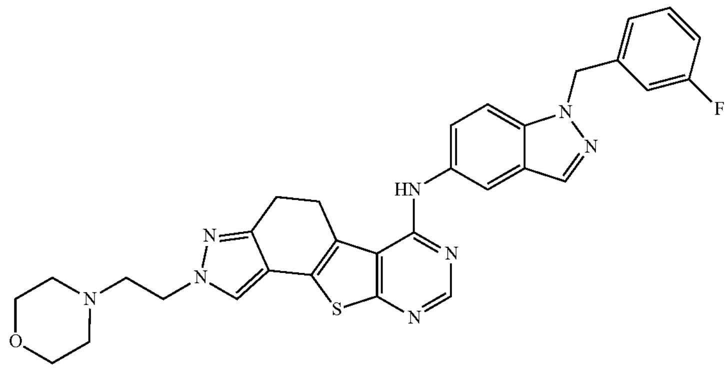 | N-[1-(3-fluorobenzyl)-1H-indazol-5-yl]-2-(2-morpholin-4-ylethyl)-4,5-dihydro-2H-pyrimido[5',4':4,5]thieno[2,3-e]indazol-6-amine | 2.49 | 581.5 |
| 279 | 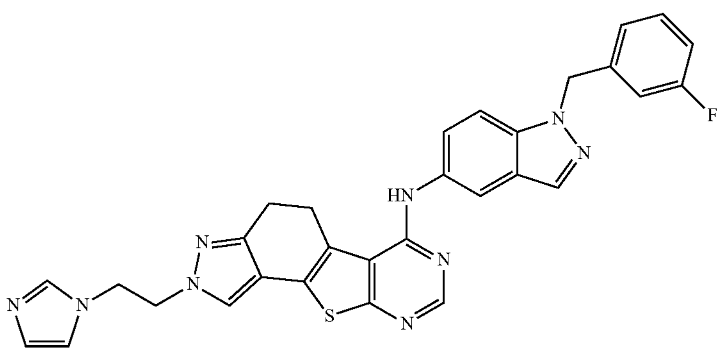 | N-[1-(3-fluorobenzyl)-1H-indazol-5-yl]-2-[2-(1H-imidazol-1-yl)ethyl]-4,5-dihydro-2H-pyrimido[5',4':4,5]thieno[2,3-e]indazol-6-amine | 2.48 | 562.4 |

| Example No | Structure | IUPAC name | LCMS RT (min) | LCMS Ion [M + H]+ |
|---|---|---|---|---|
| 280 | 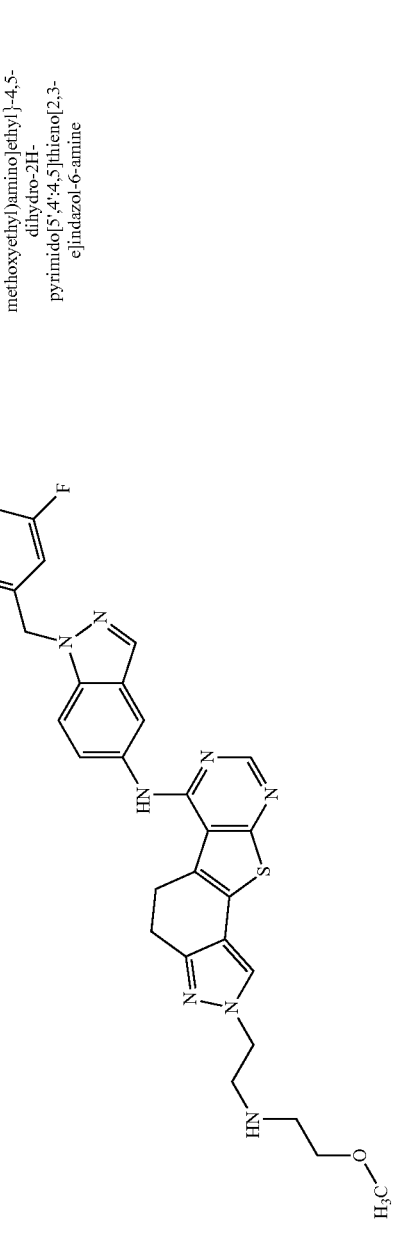 | N-[1-(3-fluorobenzyl)-1H-indazol-5-yl]-2-{2-[(2-methoxyethyl)amino]ethyl}-4,5-dihydro-2H-pyrimido[5',4':4,5]thieno[2,3-e]indazol-6-amine | 2.52 | 569.4 |
| 281 | 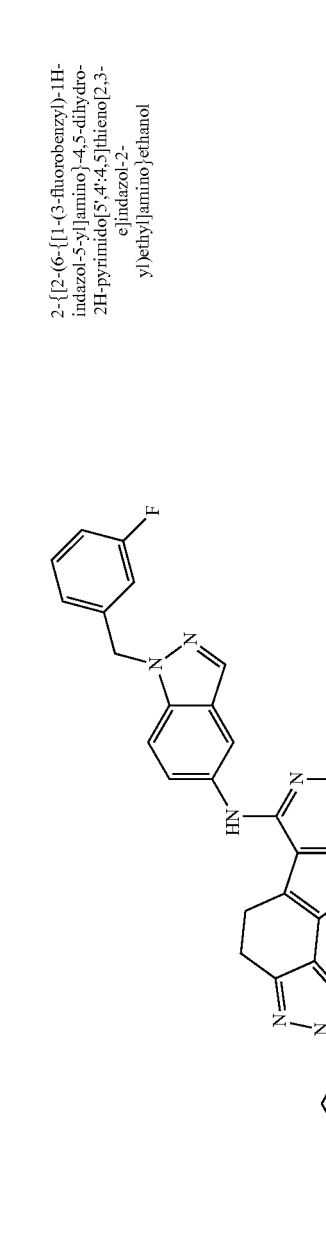 | 2-{[2-(6-{[1-(3-fluorobenzyl)-1H-indazol-5-yl]amino}-4,5-dihydro-2H-pyrimido[5',4':4,5]thieno[2,3-e]indazol-2-yl)ethyl]amino}ethanol | 2.45 | 555.4 |

-continued

| Example No | Structure | IUPAC name | LCMS RT (min) | LCMS Ion [M + H]+ |
|---|---|---|---|---|
| 282 | 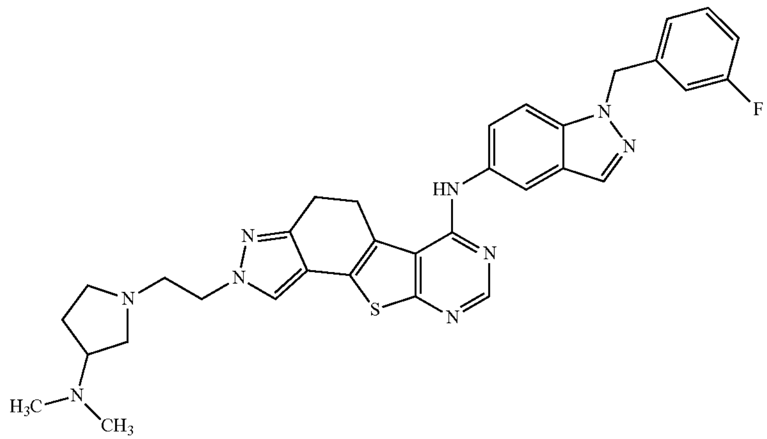 | 2-{2-[3-(dimethyl)aminopyrrolidin-1-yl]ethyl}-N-[1-(3-fluorobenzyl)-1H-indazol-5-yl]-4,5-dihydro-2H-pyrimido[5',4':4,5]thieno[2,3-e]indazol-6-amine | 2.3 | 608.4 |
| 283 | 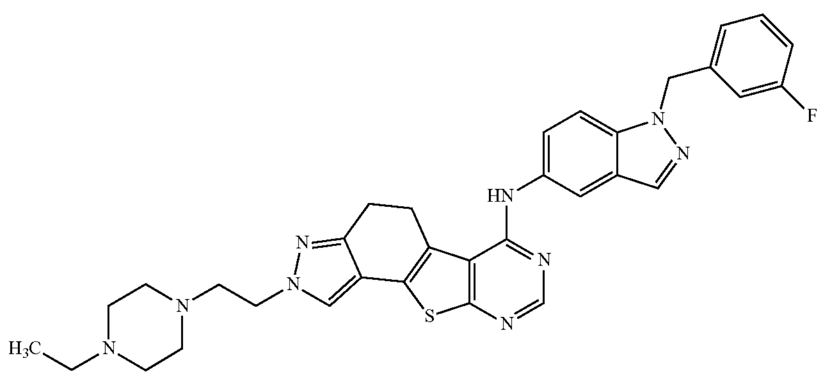 | 2-[2-(4-ethylpiperazin-1-yl)ethyl]-N-[1-(3-fluorobenzyl)-1H-indazol-5-yl]-4,5-dihydro-2H-pyrimido[5',4':4,5]thieno[2,3-e]indazol-6-amine | 2.43 | 608.3 |

| Example No | Structure | IUPAC name | LCMS RT (min) | LCMS Ion [M + H]+ |
|---|---|---|---|---|
| 284 | 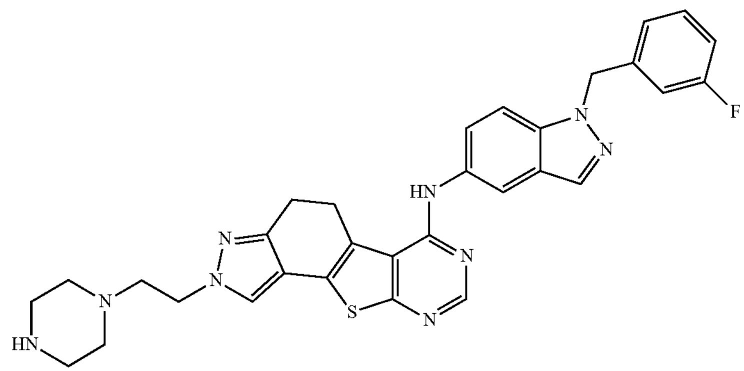 | N-[1-(3-fluorobenzyl)-1H-indazol-5-yl]-2-(2-piperazin-1-ylethyl)-4,5-dihydro-2H-pyrimido[5',4':4,5]thieno[2,3-e]indazol-6-amine | 1.97 | 580.3 |
| 285 | 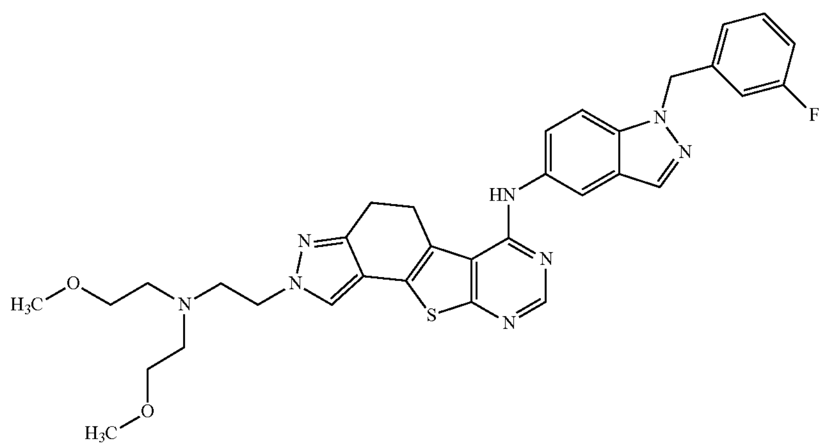 | 2-{2-[bis(2-methoxyethyl)amino]ethyl}-N-[1-(3-fluorobenzyl)-1H-indazol-5-yl]-4,5-dihydro-2H-pyrimido[5',4':4,5]thieno[2,3-e]indazol-6-amine | 2.65 | 627.5 |

| Example No | Structure | IUPAC name | LCMS RT (min) | LCMS Ion [M + H]+ |
|---|---|---|---|---|
| 286 | 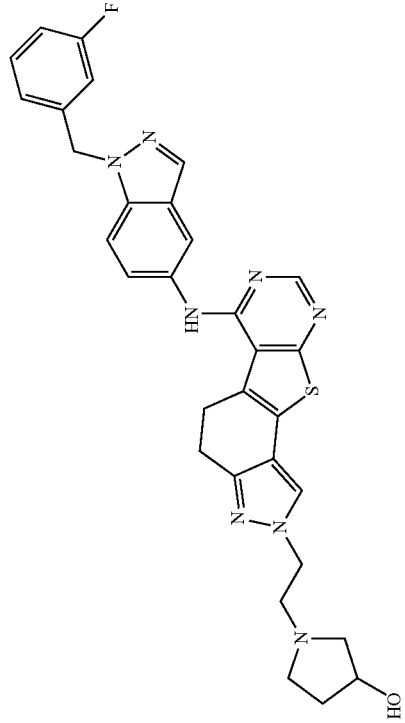 | 1-[2-(6-{[1-(3-fluorobenzyl)-1H-indazol-5-yl]amino}-4,5-dihydro-2H-pyrimido[5',4':4,5]thieno[2,3-e]indazol-2-yl)ethyl]pyrrolidin-3-ol | 2.41 | 581.3 |
| 287 | 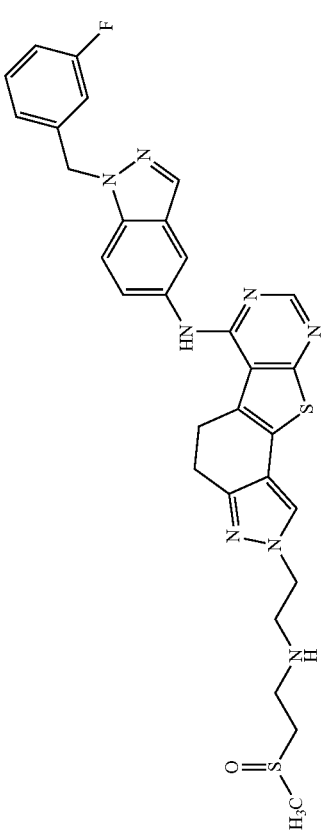 | N-[1-(3-fluorobenzyl)-1H-indazol-5-yl]-2-{2-(methylsulfonyl)ethyl]amino]ethyl}-4,5-dihydro-2H-pyrimido[5',4':4,5]thieno[2,3-e]indazol-6-amine | 2.51 | 617.4 |

-continued

| Example No | Structure | IUPAC name | LCMS RT (min) | LCMS Ion [M + H]+ |
|---|---|---|---|---|
| 288 | 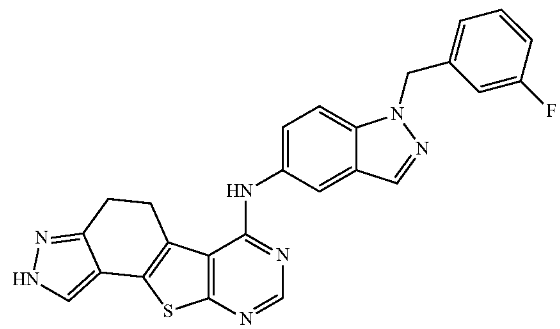 | N-[1-(3-fluorobenzyl)-1H-indazol-5-yl]-4,5-dihydro-2H-pyrimido[5',4':4,5]thieno[2,3-e]indazol-6-amine | 2.91 | 468.4 |
| 289 | 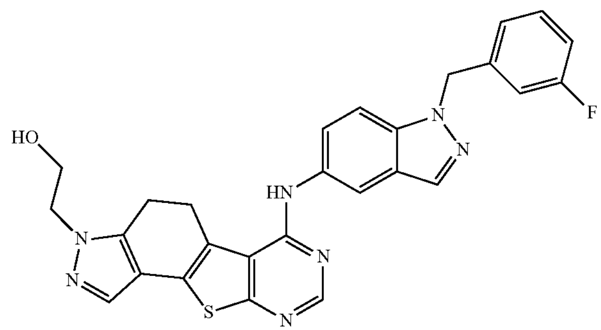 | 2-(6-{[1-(3-fluorobenzyl)-1H-indazol-5-yl]amino}-4,5-dihydro-3H-pyrimido[5',4':4,5]thieno[2,3-e]indazol-3-yl)ethanol | 3.16 | 512.4 |
| 290 | 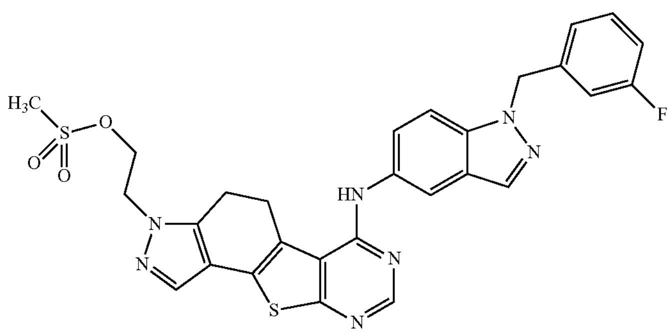 | 2-(6-{[1-(3-fluorobenzyl)-1H-indazol-5-yl]amino}-4,5-dihydro-3H-pyrimido[5',4':4,5]thieno[2,3-e]indazol-3-yl)ethyl methanesulfonate | 2.76 | 590.4 |

| Example No | Structure | IUPAC name | LCMS RT (min) | LCMS Ion [M + H]+ |
|---|---|---|---|---|
| 291 | 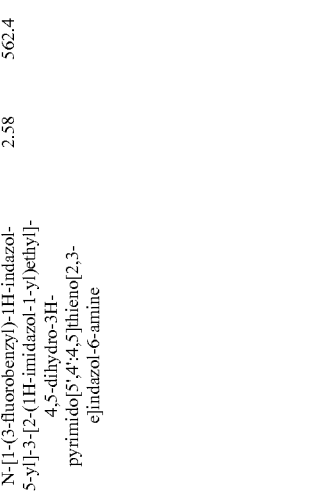 | N-[1-(3-fluorobenzyl)-1H-indazol-5-yl]-3-[2-(1H-imidazol-1-yl)ethyl]-4,5-dihydro-3H-pyrimido[5',4':4,5]thieno[2,3-e]indazol-6-amine | 2.58 | 562.4 |
| 292 | 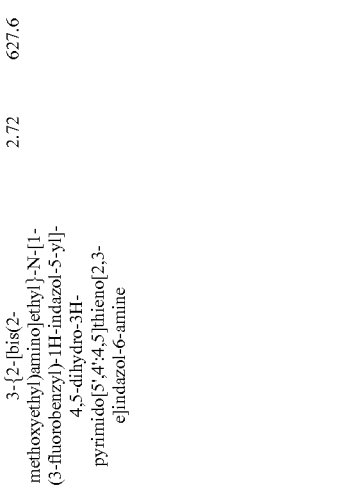 | 3-{2-[bis(2-methoxyethyl)amino]ethyl}-N-[1-(3-fluorobenzyl)-1H-indazol-5-yl]-4,5-dihydro-3H-pyrimido[5',4':4,5]thieno[2,3-e]indazol-6-amine | 2.72 | 627.6 |
| 293 | 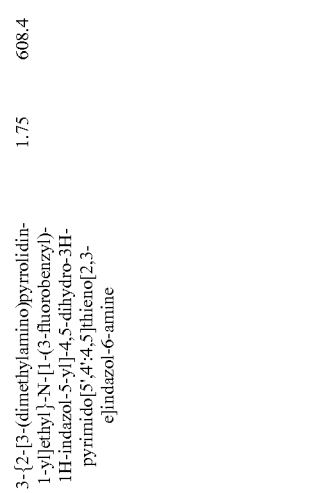 | 3-{2-[3-(dimethylamino)pyrrolidin-1-yl]ethyl}-N-[1-(3-fluorobenzyl)-1H-indazol-5-yl]-4,5-dihydro-3H-pyrimido[5',4':4,5]thieno[2,3-e]indazol-6-amine | 1.75 | 608.4 |

-continued

| Example No | Structure | IUPAC name | LCMS RT (min) | LCMS Ion [M + H]+ |
|---|---|---|---|---|
| 294 | 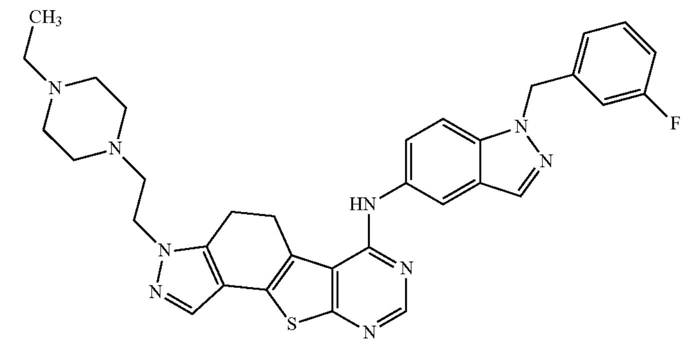 | 3-[2-(4-ethylpiperazin-1-yl)ethyl]-N-[1-(3-fluorobenzyl)-1H-indazol-5-yl]-4,5-dihydro-3H-pyrimido[5',4':4,5]thieno[2,3-e]indazol-6-amine | 2.32 | 608.4 |
| 295 | 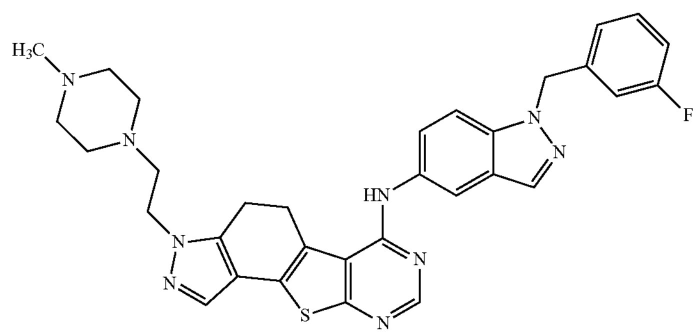 | 3-[2-(4-methylpiperazin-1-yl)ethyl]-N-[1-(3-fluorobenzyl)-1H-indazol-5-yl]-4,5-dihydro-3H-pyrimido[5',4':4,5]thieno[2,3-e]indazol-6-amine | 2.34 | 594.3 |
| 296 | 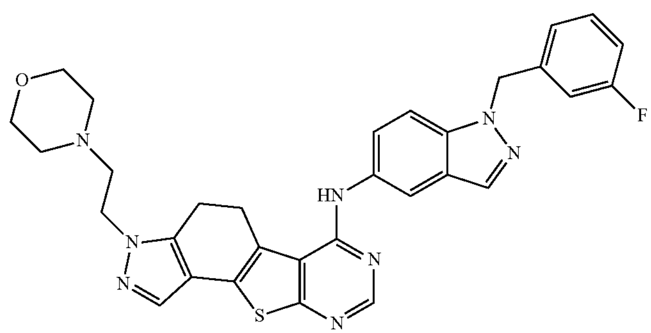 | N-[1-(3-fluorobenzyl)-1H-indazol-5-yl]-3-(2-morpholin-4-ylethyl)-4,5-dihydro-3H-pyrimido[5',4':4,5]thieno[2,3-e]indazol-6-amine | 2.5 | 581.5 |

| Example No | Structure | IUPAC name | LCMS RT (min) | LCMS Ion [M + H]+ |
|---|---|---|---|---|
| 297 | 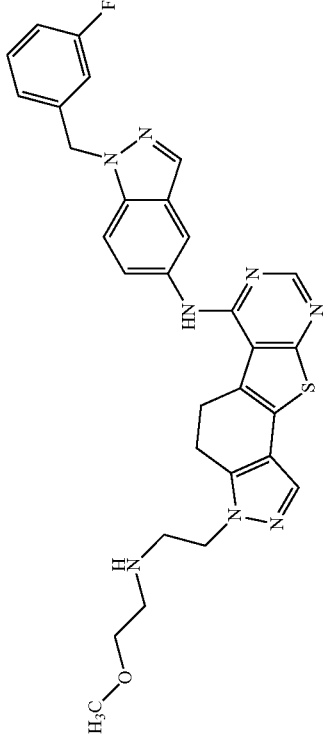 | N-[1-(3-fluorobenzyl)-1H-indazol-5-yl]-3-{2-[(2-methoxyethyl)amino]ethyl}-4,5-dihydro-3H-pyrimido[5',4':4,5]thieno[2,3-e]indazol-6-amine | 2.34 | 569.5 |
| 298 | 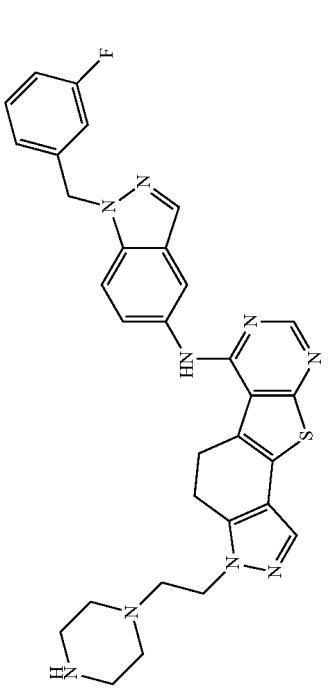 | N-[1-(3-fluorobenzyl)-1H-indazol-5-yl]-3-(2-piperazin-1-ylethyl)-4,5-dihydro-3H-pyrimido[5',4':4,5]thieno[2,3-e]indazol-6-amine | 2.55 | 580.3 |
| 299 | 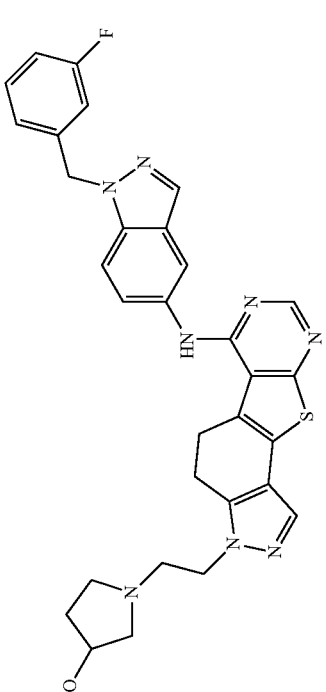 | 1-[2-(6-{[1-(3-fluorobenzyl)-1H-indazol-5-yl]amino}-4,5-dihydro-3H-pyrimido[5',4':4,5]thieno[2,3-e]indazol-3-yl)ethyl]pyrrolidin-3-ol | 2.44 | 581.3 |

-continued

| Example No | Structure | IUPAC name | LCMS RT (min) | LCMS Ion [M + H]+ |
|---|---|---|---|---|
| 300 | 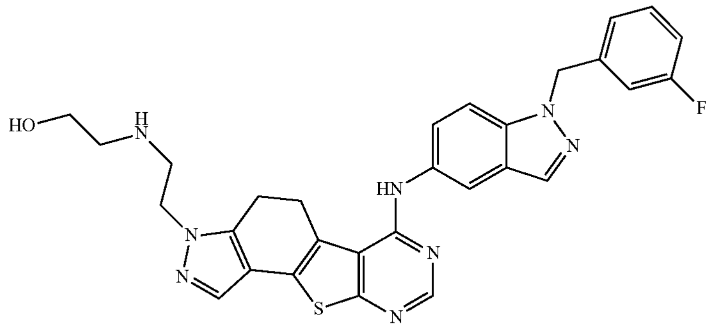 | 2-{[2-(6-{[1-(3-fluorobenzyl)-1H-indazol-5-yl]amino}-4,5-dihydro-3H-pyrimido[5',4':4,5]thieno[2,3-e]indazol-3-yl)ethyl]amino}ethanol | 2.13 | 555.3 |
| 302 | 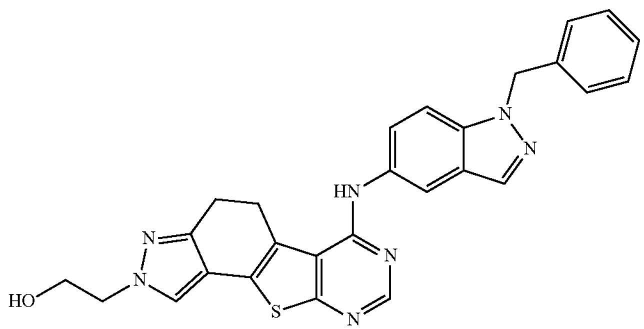 | 2-{6-[(1-benzyl-1H-indazol-5-yl)amino]-4,5-dihydro-2H-pyrimido[5',4':4,5]thieno[2,3-e]indazol-2-yl}ethanol | 2.77 | 494.5 |
| 303 | 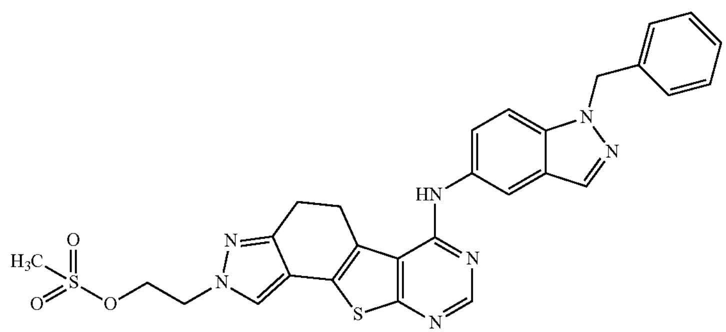 | 2-{6-[(1-benzyl-1H-indazol-5-yl)amino]-4,5-dihydro-2H-pyrimido[5',4':4,5]thieno[2,3-e]indazol-2-yl}ethyl methanesulfonate | 3.44 | 572.3 |

| Example No | Structure | IUPAC name | LCMS RT (min) | LCMS Ion [M + H]+ |
|---|---|---|---|---|
| 304 | 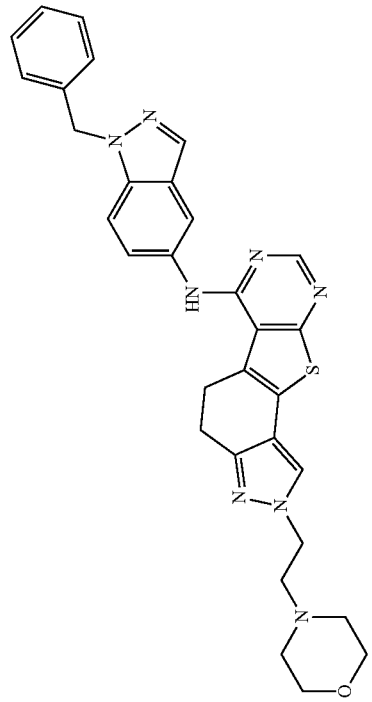 | N-(1-benzyl-1H-indazol-5-yl)-2-(2-morpholin-4-ylethyl)-4,5-dihydro-2H-pyrimido[5',4':4,5]thieno[2,3-e]indazol-6-amine | 2.4 | 563.3 |
| 305 | 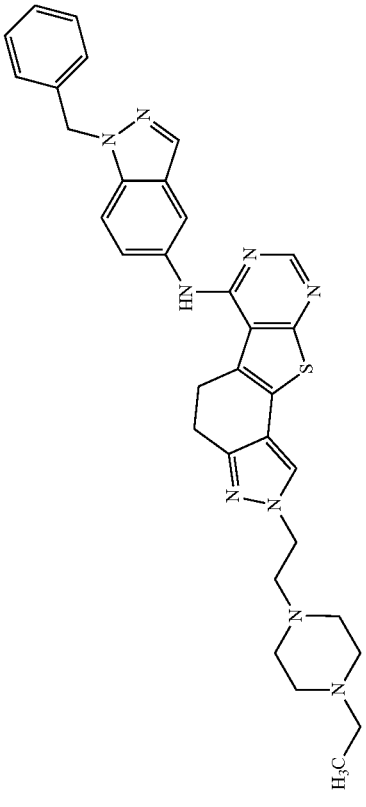 | N-(1-benzyl-1H-indazol-5-yl)-2-[2-(4-ethylpiperazin-1-yl)ethyl]-4,5-dihydro-2H-pyrimido[5',4':4,5]thieno[2,3-e]indazol-6-amine | 2.5 | 590.3 |

-continued

| Example No | Structure | IUPAC name | LCMS RT (min) | LCMS Ion [M + H]+ |
|---|---|---|---|---|
| 306 | 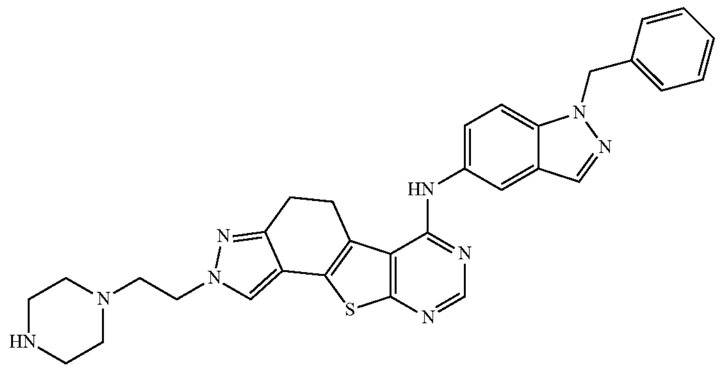 | N-(1-benzyl-1H-indazol-5-yl)-2-(2-piperazin-1-ylethyl)-4,5-dihydro-2H-pyrimido[5',4':4,5]thieno[2,3-e]indazol-6-amine | 2.22 | 562.3 |
| 307 | 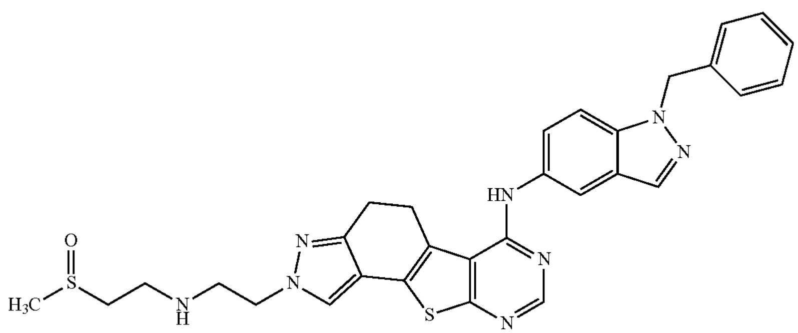 | N-(1-benzyl-1H-indazol-5-yl)-2-(2-{[2-(methylsulfonyl)ethyl]amino}ethyl)-4,5-dihydro-2H-pyrimido[5',4':4,5]thieno[2,3-e]indazol-6-amine | 2.41 | 599.3 |

| Example No | Structure | IUPAC name | LCMS RT (min) | LCMS Ion [M + H]+ |
|---|---|---|---|---|
| 308 | 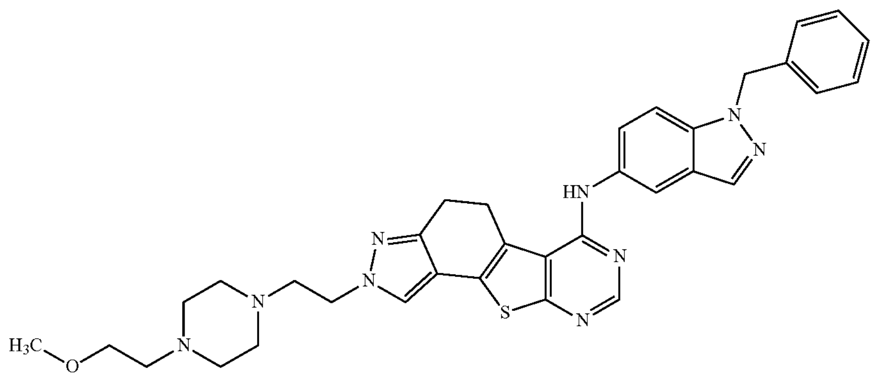 | N-(1-benzyl-1H-indazol-5-yl)-2-{2-[4-(2-methoxyethyl)piperazin-1-yl]ethyl}-4,5-dihydro-2H-pyrimido[5',4':4,5]thieno[2,3-e]indazol-6-amine | 2.55 | 620.3 |
| 309 | 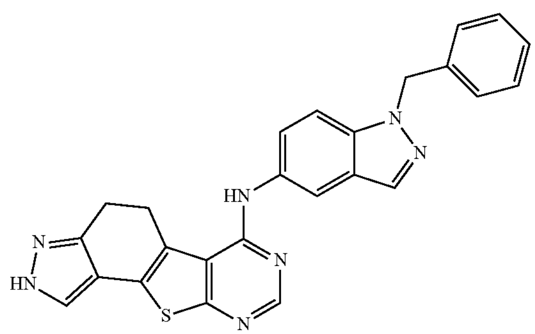 | N-(1-benzyl-1H-indazol-5-yl)-4,5-dihydro-2H-pyrimido[5',4':4,5]thieno[2,3-e]indazol-6-amine | 2.81 | 450.3 |
| 310 | 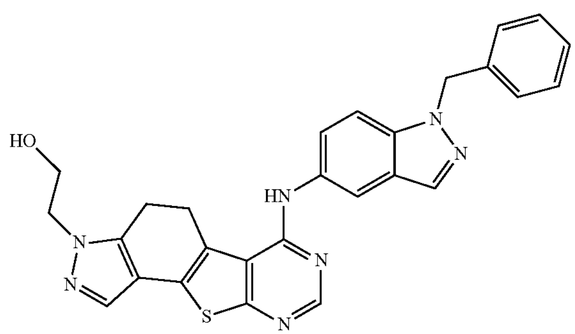 | 2-{6-[(1-benzyl-1H-indazol-5-yl)amino]-4,5-dihydro-3H-pyrimido[5',4':4,5]thieno[2,3-e]indazol-3-yl}ethanol | 2.64 | 494.4 |

| Example No | Structure | IUPAC name | LCMS RT (min) | LCMS Ion [M + H]+ |
|---|---|---|---|---|
| 311 | 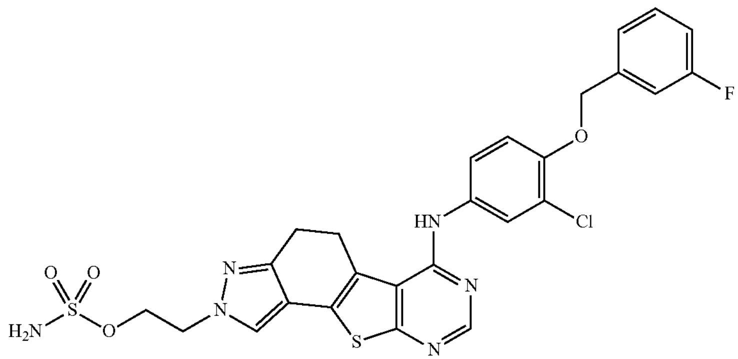 | 2-[6-({3-chloro-4-[(3-fluorobenzyl)oxy]phenyl}amino)-4,5-dihydro-2H-pyrimido[5',4':4,5]thieno[2,3-e]indazol-2-yl]ethyl sulfamate | 3.45 | 601.2 |
| 312 | 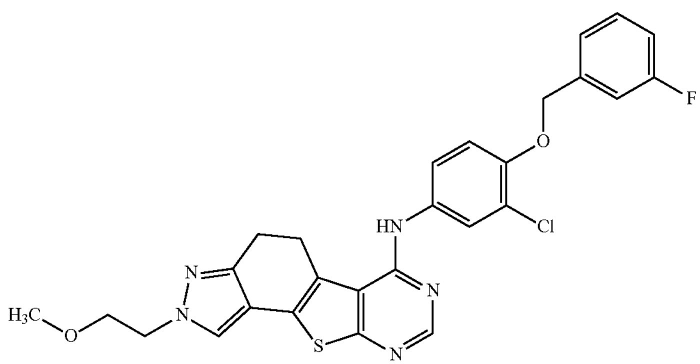 | N-{3-chloro-4-[(3-fluorobenzyl)oxy]phenyl}-2-(2-methoxyethyl)-4,5-dihydro-2H-pyrimido[5',4':4,5]thieno[2,3-e]indazol-6-amine | 3.32 | 536.3 |

| Example No | Structure | IUPAC name | LCMS RT (min) | LCMS Ion [M + H]+ |
|---|---|---|---|---|
| 314 | 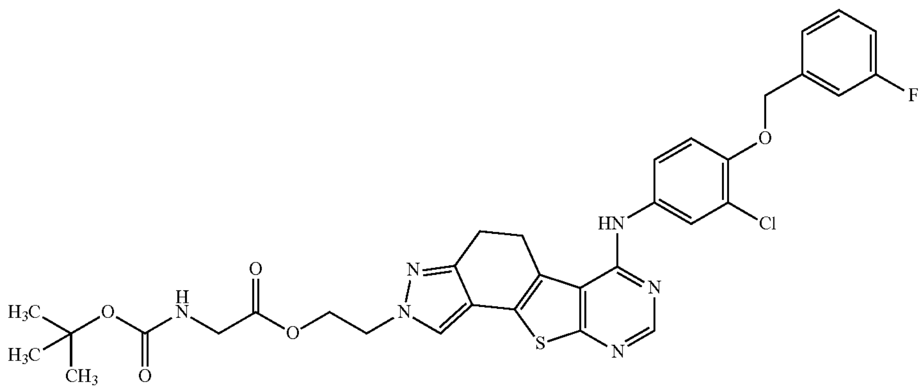 | 2-[6-({3-chloro-4-[(3-fluorobenzyl)oxy]phenyl}amino)-4,5-dihydro-2H-pyrimido[5',4':4,5]thieno[2,3-e]indazol-2-yl]ethyl N-(tert-butoxycarbonyl)glycinate | 3.84 | 679.3 |
| 315 | 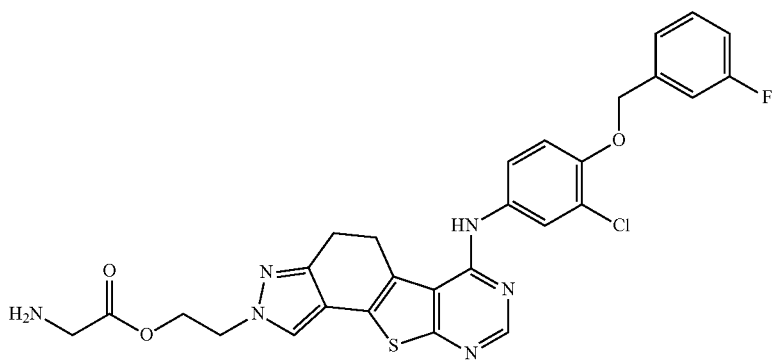 | 2-[6-({3-chloro-4-[(3-fluorobenzyl)oxy]phenyl}amino)-4,5-dihydro-2H-pyrimido[5',4':4,5]thieno[2,3-e]indazol-2-yl]ethyl glycinate | 2.85 | 579.1 |
| 316 | 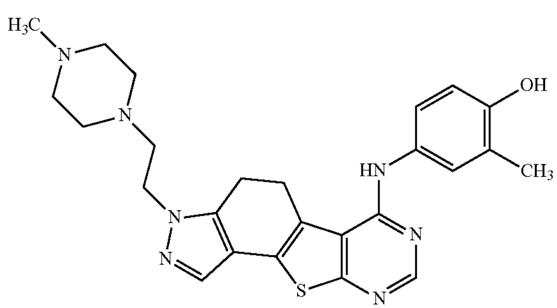 | 2-methyl-4-({3-[2-(4-methylpiperazin-1-yl)ethyl]-4,5-dihydro-3H-pyrimido[5',4':4,5]thieno[2,3-e]indazol-6-yl}amino)phenol | 1.89 | 477.2 |

| Example No | Structure | IUPAC name | LCMS RT (min) | LCMS Ion [M + H]+ |
|---|---|---|---|---|
| 317 | 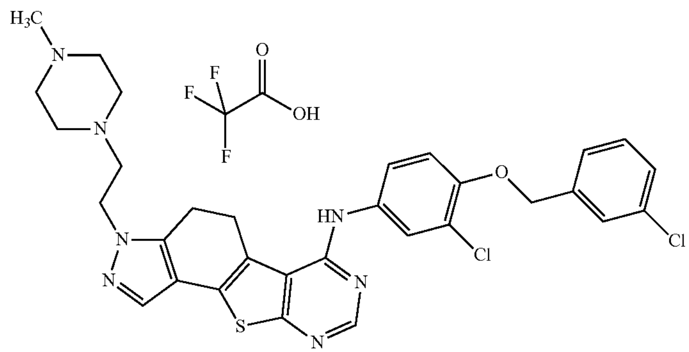 | N-{3-chloro-4-[(3-chlorobenzyl)oxy]phenyl}-3-[2-(4-methylpiperazin-1-yl)ethyl]-4,5-dihydro-3H-pyrimido[5',4':4,5]thieno[2,3-e]indazol-6-amine trifluoroacetate | 2.78 | 622.2 |
| 318 | 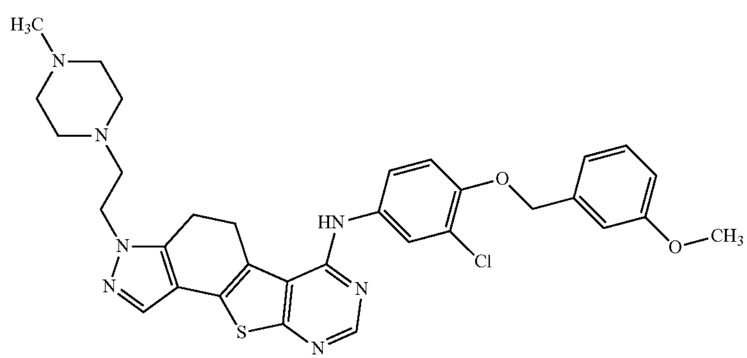 | N-{3-chloro-4-[(3-methoxybenzyl)oxy]phenyl}-3-[2-(4-methylpiperazin-1-yl)ethyl]-4,5-dihydro-3H-pyrimido[5',4':4,5]thieno[2,3-e]indazol-6-amine | 2.7 | 618.2 |

| Example No | Structure | IUPAC name | LCMS RT (min) | LCMS Ion [M + H]+ |
|---|---|---|---|---|
| 319 | 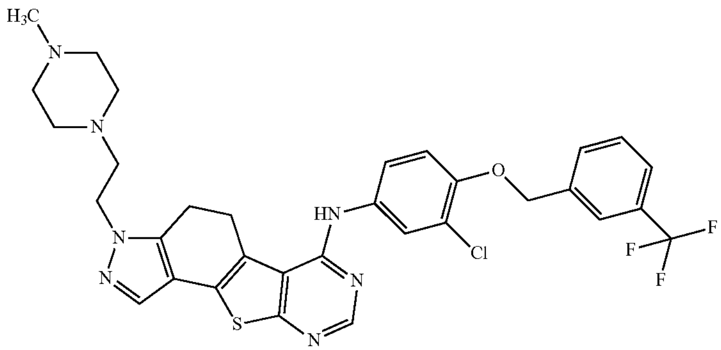 | N-(3-chloro-4-{[3-(trifluoromethyl)benzyl]oxy}phenyl)-3-[2-(4-methylpiperazin-1-yl)ethyl]-4,5-dihydro-3H-pyrimido[5',4':4,5]thieno[2,3-e]indazol-6-amine | 2.88 | 656.1 |
| 320 | 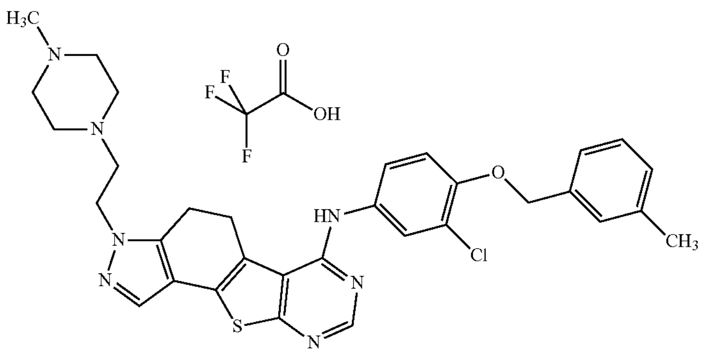 | N-{3-chloro-4-[(3-methylbenzyl)oxy]phenyl}-3-[2-(4-methylpiperazin-1-yl)ethyl]-4,5-dihydro-3H-pyrimido[5',4':4,5]thieno[2,3-e]indazol-6-amine trifluoroacetate | 3.19 | 602.3 |
| 322 | 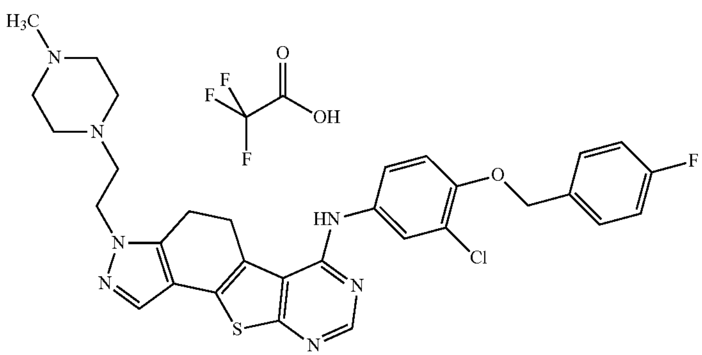 | N-{3-chloro-4-[(4-fluorobenzyl)oxy]phenyl}-3-[2-(4-methylpiperazin-1-yl)ethyl]-4,5-dihydro-3H-pyrimido[5',4':4,5]thieno[2,3-e]indazol-6-amine trifluoroacetate | 3.14 | 604.3 |

| Example No | Structure | IUPAC name | LCMS RT (min) | LCMS Ion [M+H]+ |
|---|---|---|---|---|
| 323 | 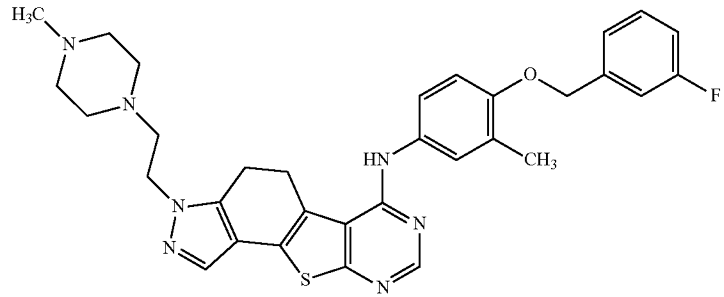 | N-{4-[(3-fluorobenzyl)oxy]-3-methylphenyl}-3-[2-(4-methylpiperazin-1-yl)ethyl]-4,5-dihydro-3H-pyrimido[5',4':4,5]thieno[2,3-e]indazol-6-amine | 2.73 | 585.3 |
| 324 | 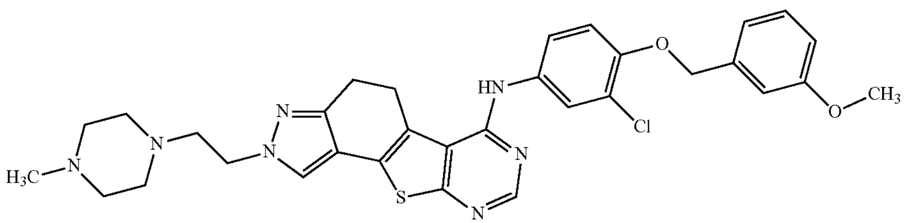 | N-{3-chloro-4-[(3-methoxybenzyl)oxy]phenyl}-2-[2-(4-methylpiperazin-1-yl)ethyl]-4,5-dihydro-2H-pyrimido[5',4':4,5]thieno[2,3-e]indazol-6-amine | 2.69 | 618.1 |
| 325 | 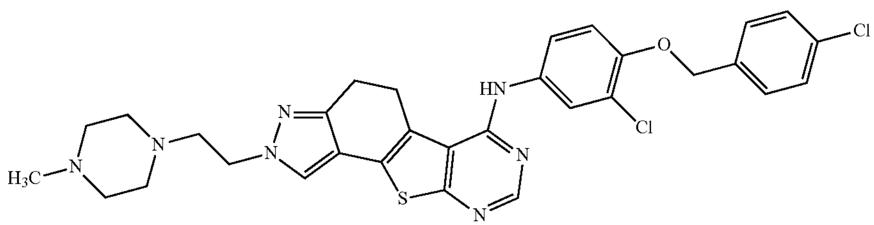 | N-{3-chloro-4-[(4-chlorobenzyl)oxy]phenyl}-3-[2-(4-methylpiperazin-1-yl)ethyl]-4,5-dihydro-3H-pyrimido[5',4':4,5]thieno[2,3-e]indazol-6-amine | 2.83 | 622.1 |
| 326 | 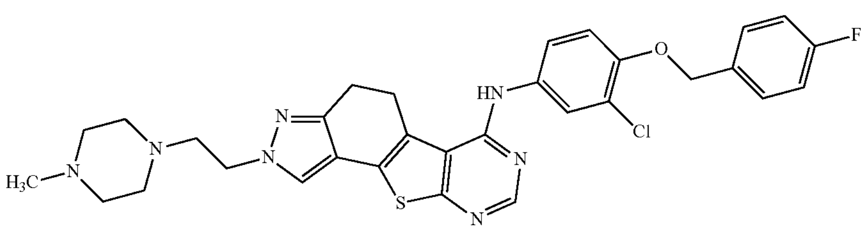 | N-{3-chloro-4-[(4-fluorobenzyl)oxy]phenyl}-2-[2-(4-methylpiperazin-1-yl)ethyl]-4,5-dihydro-2H-pyrimido[5',4':4,5]thieno[2,3-e]indazol-6-amine | 2.75 | 605.1 |

-continued

| Example No | Structure | IUPAC name | LCMS RT (min) | LCMS Ion [M + H]+ |
|---|---|---|---|---|
| 327 | 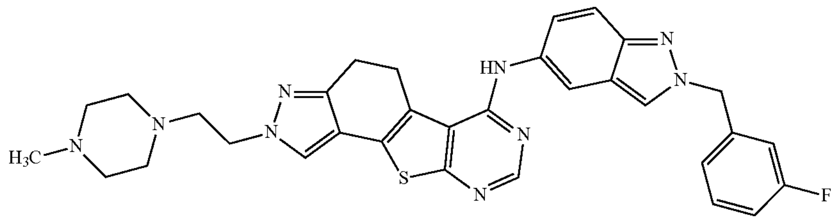 | N-[2-(3-fluorobenzyl)-2H-indazol-5-yl]-2-[2-(4-methylpiperazin-1-yl)ethyl]-4,5-dihydro-2H-pyrimido[5',4':4,5]thieno[2,3-e]indazol-6-amine | 2.31 | 595.2 |
| 328 | 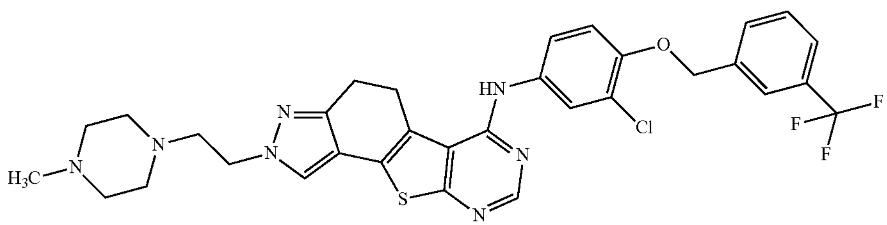 | N-(3-chloro-4-{[3-(trifluoromethyl)benzyl]oxy}phenyl)-2-[2-(4-methylpiperazin-1-yl)ethyl]-4,5-dihydro-2H-pyrimido[5',4':4,5]thieno[2,3-e]indazol-6-amine | 2.88 | 656.1 |
| 329 | 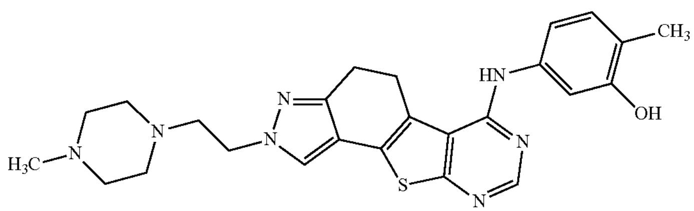 | 2-methyl-5-({2-[2-(4-methylpiperazin-1-yl)ethyl]-4,5-dihydro-2H-pyrimido[5',4':4,5]thieno[2,3-e]indazol-6-yl}amino)phenol | 2.14 | 477.4 |
| 330 | 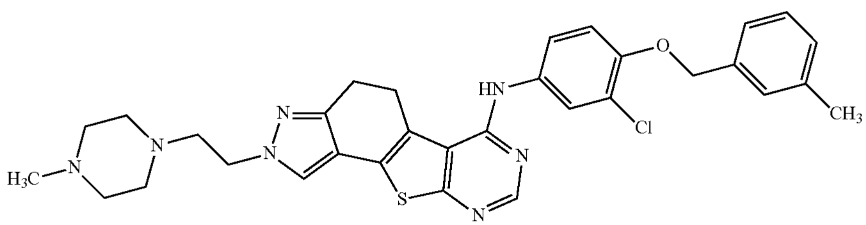 | N-{3-chloro-4-[(3-methylbenzyl)oxy]phenyl}-2-[2-(4-methylpiperazin-1-yl)ethyl]-4,5-dihydro-2H-pyrimido[5',4':4,5]thieno[2,3-e]indazol-6-amine | 2.78 | 601.2 |

-continued

| Example No | Structure | IUPAC name | LCMS RT (min) | LCMS Ion [M + H]+ |
|---|---|---|---|---|
| 331 | 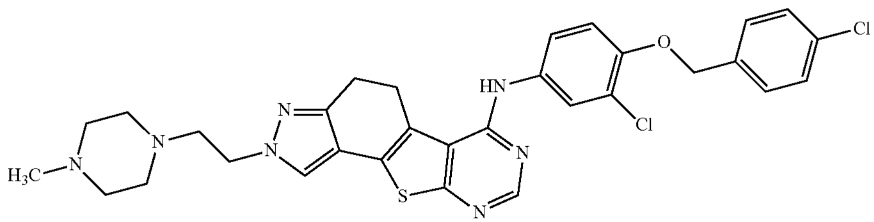 | N-{3-chloro-4-[(4-chlorobenzyl)oxy]phenyl}-2-[2-(4-methylpiperazin-1-yl)ethyl]-4,5-dihydro-2H-pyrimido[5',4':4,5]thieno[2,3-e]indazol-6-amine | 2.96 | 622.3 |
| 332 | 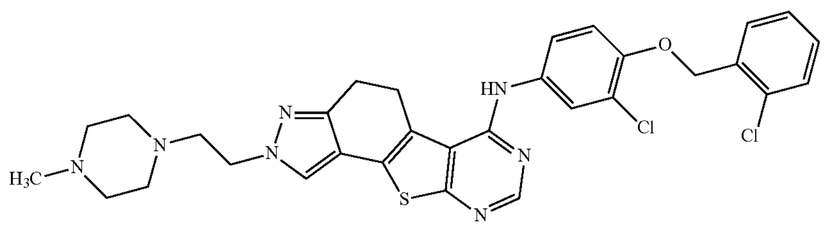 | N-{3-chloro-4-[(2-chlorobenzyl)oxy]phenyl}-2-[2-(4-methylpiperazin-1-yl)ethyl]-4,5-dihydro-2H-pyrimido[5',4':4,5]thieno[2,3-e]indazol-6-amine | 2.84 | 622 |
| 333 | 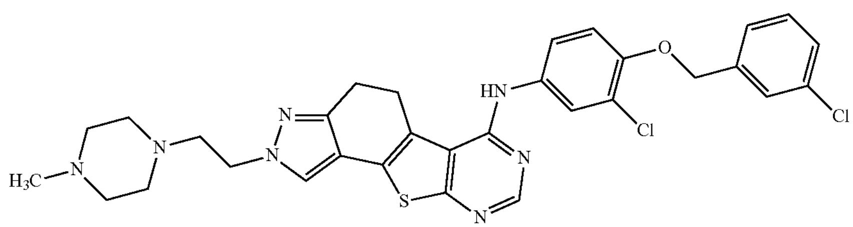 | N-{3-chloro-4-[(3-chlorobenzyl)oxy]phenyl}-2-[2-(4-methylpiperazin-1-yl)ethyl]-4,5-dihydro-2H-pyrimido[5',4':4,5]thieno[2,3-e]indazol-6-amine | 2.84 | 622 |
| 334 | 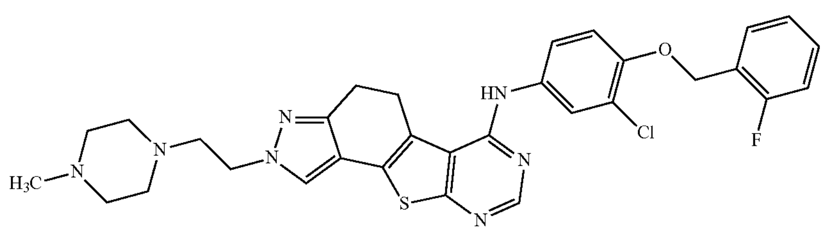 | N-{3-chloro-4-[(2-fluorobenzyl)oxy]phenyl}-2-[2-(4-methylpiperazin-1-yl)ethyl]-4,5-dihydro-2H-pyrimido[5',4':4,5]thieno[2,3-e]indazol-6-amine | 2.71 | 606.1 |

| Example No | Structure | IUPAC name | LCMS RT (min) | LCMS Ion [M + H]+ |
|---|---|---|---|---|
| 335 | 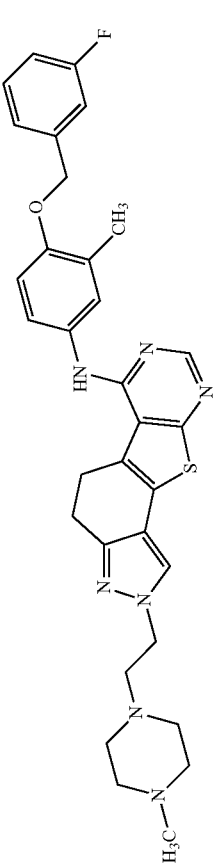 | N-{4-[(3-fluorobenzyl)oxy]-3-methylphenyl}-2-[2-(4-methylpiperazin-1-yl)ethyl]-4,5-dihydro-2H-pyrimido[5',4':4,5]thieno[2,3-e]indazol-6-amine | 2.76 | 585.4 |
| 336 | 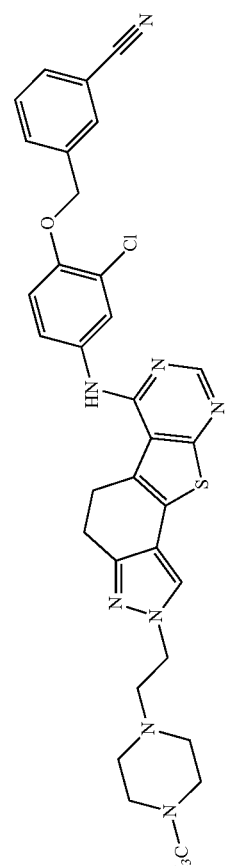 | 3-{[2-chloro-4-({2-[2-(4-methylpiperazin-1-yl)ethyl]-4,5-dihydro-2H-pyrimido[5',4':4,5]thieno[2,3-e]indazol-6-yl}amino)phenoxy]methyl}benzonitrile | 2.59 | 613 |
| 337 | 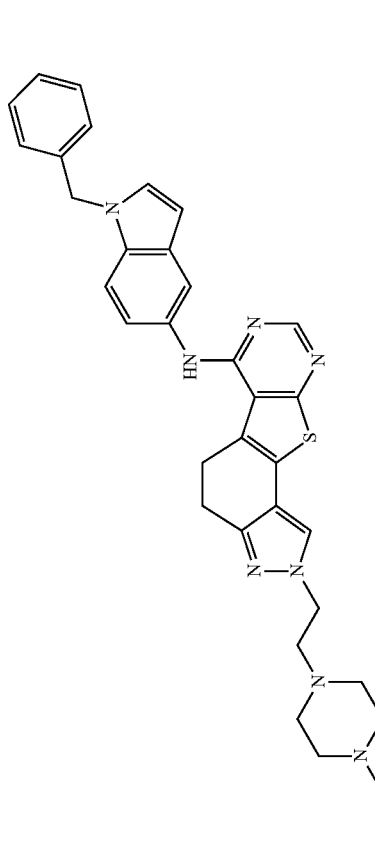 | N-(1-benzyl-1H-indol-5-yl)-2-[2-(4-methylpiperazin-1-yl)ethyl]-4,5-dihydro-2H-pyrimido[5',4':4,5]thieno[2,3-e]indazol-6-amine | 2.92 | 575.7 |

| Example No | Structure | IUPAC name | LCMS RT (min) | LCMS Ion [M + H]+ |
|---|---|---|---|---|
| 338 | 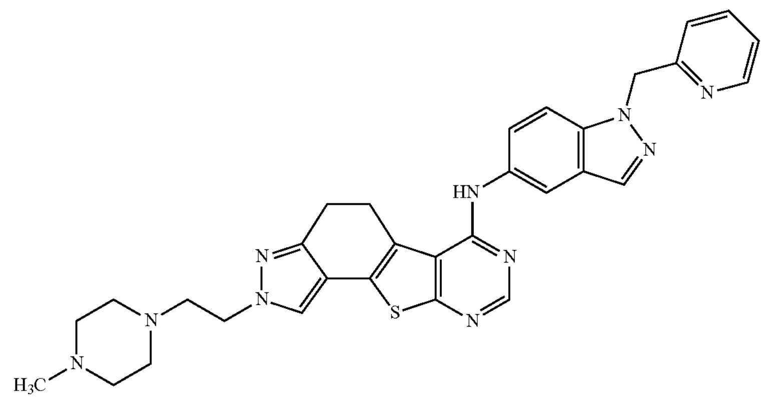 | 2-[2-(4-methylpiperazin-1-yl)ethyl]-N-[1-(pyridin-2-ylmethyl)-1H-indazol-5-yl]-4,5-dihydro-2H-pyrimido[5',4':4,5]thieno[2,3-e]indazol-6-amine | 2.67 | 577.7 |
| 340 | 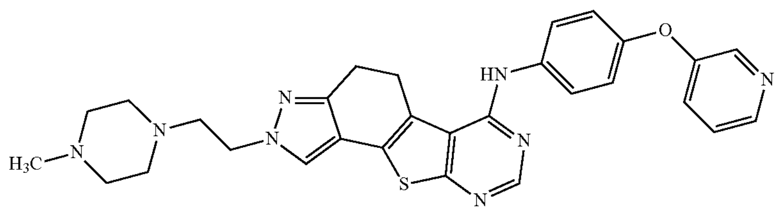 | 2-[2-(4-methylpiperazin-1-yl)ethyl]-N-[4-(pyridin-3-yloxy)phenyl]-4,5-dihydro-2H-pyrimido[5',4':4,5]thieno[2,3-e]indazol-6-amine | 1.96 | 540.2 |
| 341 | 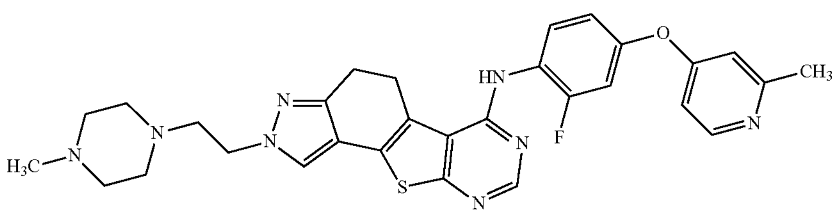 | N-{2-fluoro-4-[(2-methylpyridin-4-yl)oxy]phenyl}-2-[2-(4-methylpiperazin-1-yl)ethyl]-4,5-dihydro-2H-pyrimido[5',4':4,5]thieno[2,3-e]indazol-6-amine | 1.89 | 572.2 |
| 342 | 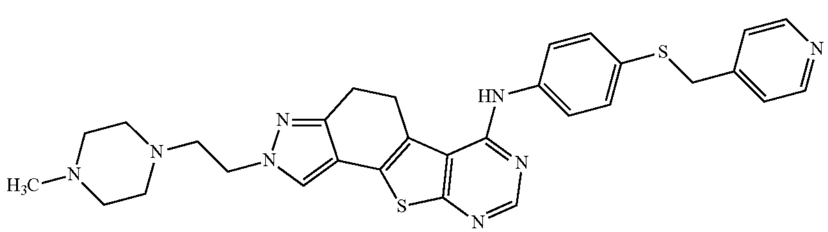 | 2-[2-(4-methylpiperazin-1-yl)ethyl]-N-{4-[(pyridin-4-ylmethyl)thio]phenyl}-4,5-dihydro-2H-pyrimido[5',4':4,5]thieno[2,3-e]indazol-6-amine | 2.02 | 570.3 |

-continued

| Example No | Structure | IUPAC name | LCMS RT (min) | LCMS Ion [M + H]+ |
|---|---|---|---|---|
| 343 | 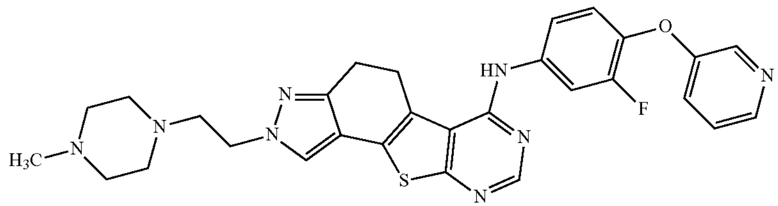 | N-[3-fluoro-4-(pyridin-3-yloxy)phenyl]-2-[2-(4-methylpiperazin-1-yl)ethyl]-4,5-dihydro-2H-pyrimido[5',4':4,5]thieno[2,3-e]indazol-6-amine | 2.12 | 558.2 |
| 344 | 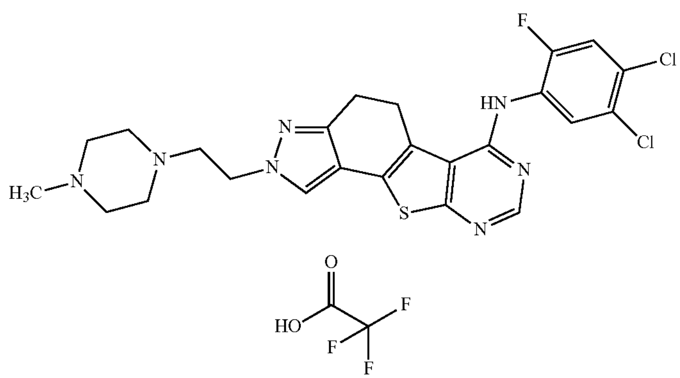 | N-(4,5-dichloro-2-fluorophenyl)-2-[2-(4-methylpiperazin-1-yl)ethyl]-4,5-dihydro-2H-pyrimido[5',4':4,5]thieno[2,3-e]indazol-6-amine trifluoroacetate | 2.61 | 534 |

-continued

| Example No | Structure | IUPAC name | LCMS RT (min) | LCMS Ion [M + H]+ |
|---|---|---|---|---|
| 347 | 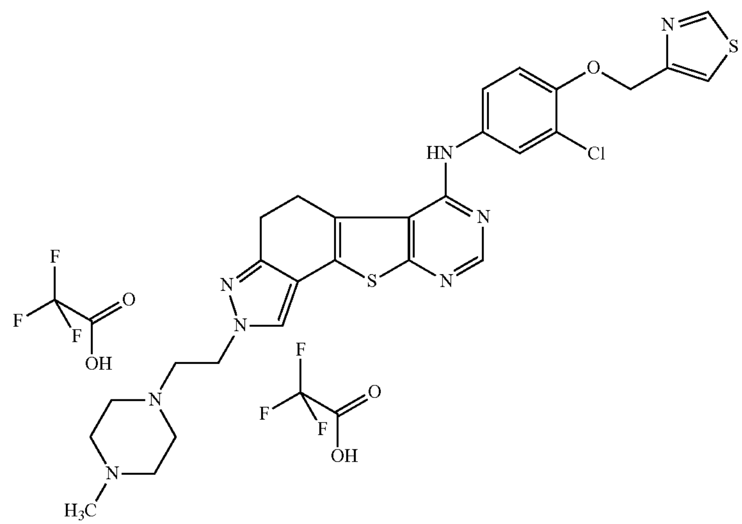 | N-[3-chloro-4-(1,3-thiazol-4-ylmethoxy)phenyl]-2-[2-(4-methylpiperazin-1-yl)ethyl]-4,5-dihydro-2H-pyrimido[5',4':4,5]thieno[2,3-e]indazol-6-amine bis(trifluoroacetate) | 2.44 | 593.1 |
| 348 | 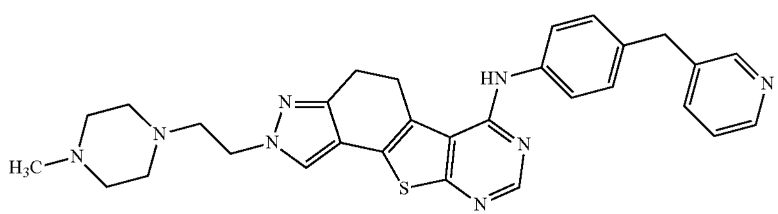 | 2-[2-(4-methylpiperazin-1-yl)ethyl]-N-[4-(pyridin-3-ylmethyl)phenyl]-4,5-dihydro-2H-pyrimido[5',4':4,5]thieno[2,3-e]indazol-6-amine | 1.85 | 538.3 |

| Example No | Structure | IUPAC name | LCMS RT (min) | LCMS Ion [M + H]+ |
|---|---|---|---|---|
| 350 | 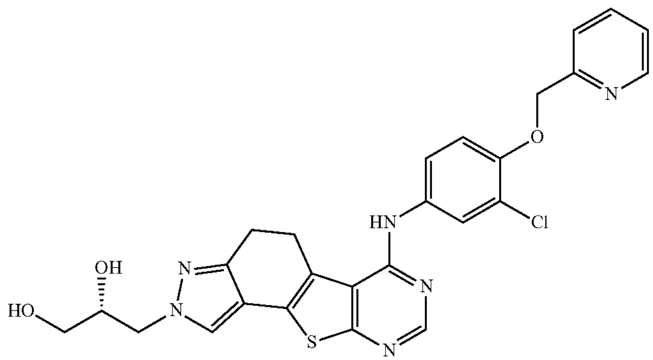 | 3-(6-{[3-chloro-4-(pyridin-2-ylmethoxy)phenyl]amino}-4,5-dihydro-2H-pyrimido[5',4':4,5]thieno[2,3-e]indazol-2-yl)propane-1,2-diol | 2.21 | 535.3 |
| 351 | 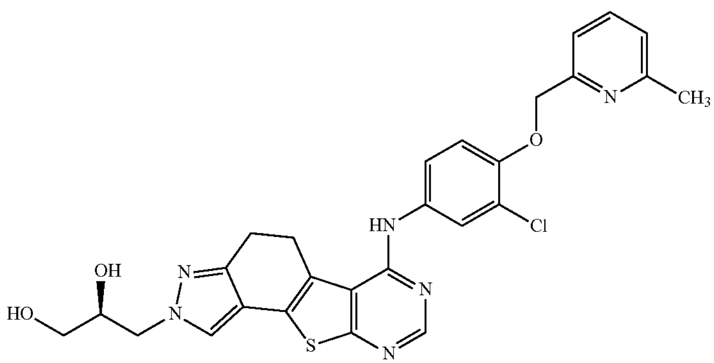 | (2S)-3-(6-{[3-chloro-4-(pyridin-2-ylmethoxy)phenyl]amino}-4,5-dihydro-2H-pyrimido[5',4':4,5]thieno[2,3-e]indazol-2-yl)propane-1,2-diol | 2.37 | 535.1 |

| Example No | Structure | IUPAC name | LCMS RT (min) | LCMS Ion [M + H]+ |
|---|---|---|---|---|
| 352 | 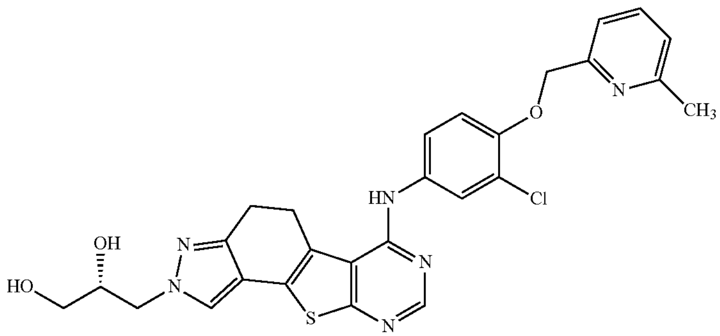 | (2R)-3-{6-[(3-chloro-4-[(6-methylpyridin-2-yl)methoxy]phenyl}amino)-4,5-dihydro-2H-pyrimido[5',4':4,5]thieno[2,3-e]indazol-2-yl]propane-1,2-diol | 2.15 | 549.1 |
| 353 | 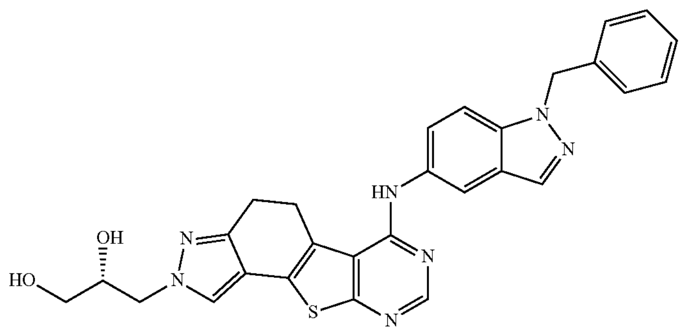 | (2R)-3-{6-[(1-benzyl-1H-indazol-5-yl)amino]-4,5-dihydro-2H-pyrimido[5',4':4,5]thieno[2,3-e]indazol-2-yl}propane-1,2-diol | 2.75 | 524.5 |
| 354 | 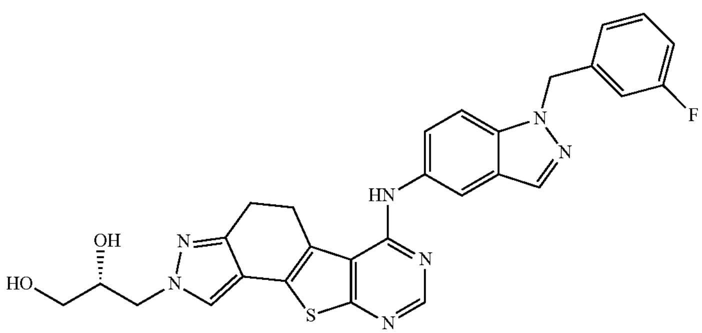 | (2R)-3-(6-{[1-(3-fluorobenzyl)-1H-indazol-5-yl]amino}-4,5-dihydro-2H-pyrimido[5',4':4,5]thieno[2,3-e]indazol-2-yl)propane-1,2-diol | 2.76 | 542.5 |

-continued

| Example No | Structure | IUPAC name | LCMS RT (min) | LCMS Ion [M + H]+ |
|---|---|---|---|---|
| 355 | 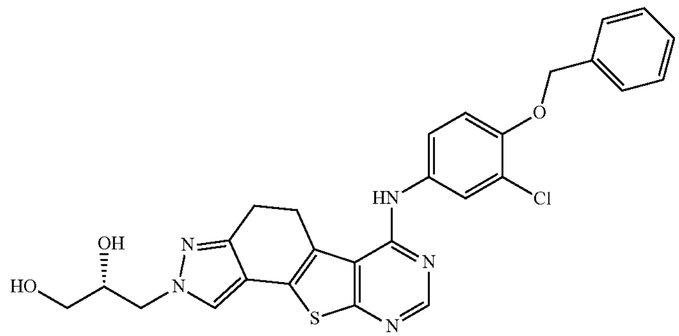 | (2R)-3-(6-{[4-(benzyloxy)-3-chlorophenyl]amino}-4,5-dihydro-2H-pyrimido[5',4':4,5]thieno[2,3-e]indazol-2-yl)propane-1,2-diol | 3.29 | 534.2 |
| 356 | 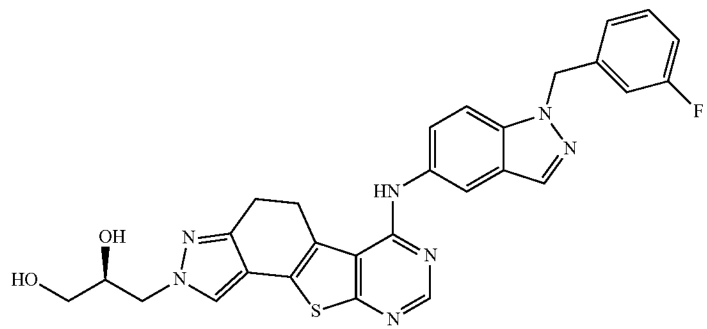 | (2S)-3-(6-{[1-(3-fluorobenzyl)-1H-indazol-5-yl]amino}-4,5-dihydro-2H-pyrimido[5',4':4,5]thieno[2,3-e]indazol-2-yl)propane-1,2-diol | 2.76 | 542.5 |
| 357 | 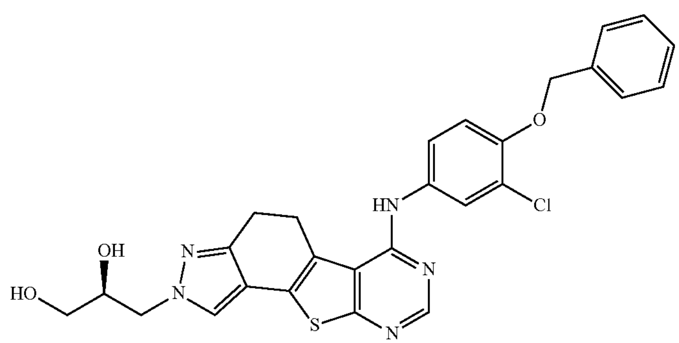 | (2S)-3-(6-{[4-(benzyloxy)-3-chlorophenyl]amino}-4,5-dihydro-2H-pyrimido[5',4':4,5]thieno[2,3-e]indazol-2-yl)propane-1,2-diol | 3.38 | 534.3 |

| Example No | Structure | IUPAC name | LCMS RT (min) | LCMS Ion [M + H]+ |
|---|---|---|---|---|
| 358 | 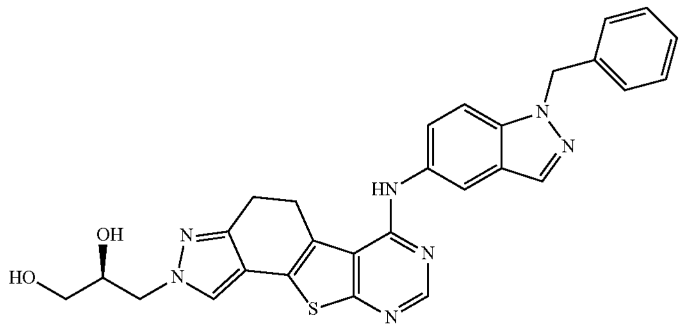 | (2S)-3-{6-[(1-benzyl-1H-indazol-5-yl)amino]-4,5-dihydro-2H-pyrimido[5',4':4,5]thieno[2,3-e]indazol-2-yl}propane-1,2-diol | 3.01 | 524.4 |
| 359 | 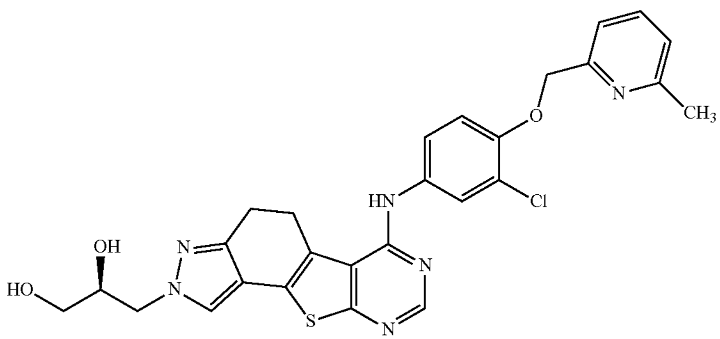 | (2S)-3-[6-({3-chloro-4-[(6-methylpyridin-2-yl)methoxy]phenyl}amino)-4,5-dihydro-2H-pyrimido[5',4':4,5]thieno[2,3-e]indazol-2-yl]propane-1,2-diol | 2.23 | 549.2 |
| 360 | 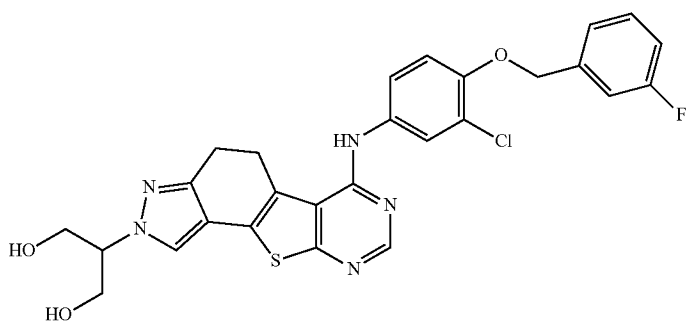 | 2-[6-({3-chloro-4-[(3-fluorobenzyl)oxy]phenyl}amino)-4,5-dihydro-2H-pyrimido[5',4':4,5]thieno[2,3-e]indazol-2-yl]propane-1,3-diol | 3.17 | 552.2 |

| Example No | Structure | IUPAC name | LCMS RT (min) | LCMS Ion [M + H]+ |
|---|---|---|---|---|
| 361 | 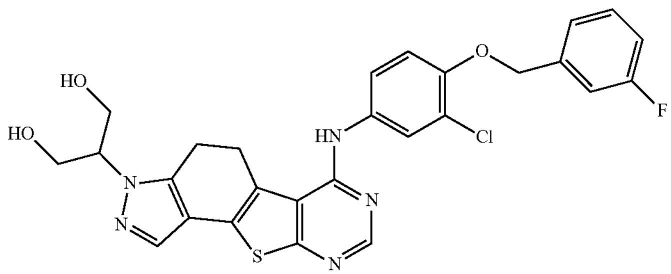 | 2-[6-({3-chloro-4-[(3-fluorobenzyl)oxy]phenyl}amino)-4,5-dihydro-2H-pyrimido[5',4':4,5]thieno[2,3-e]indazol-3-yl]propane-1,3-diol | 3.1 | 552.3 |
| 362 | 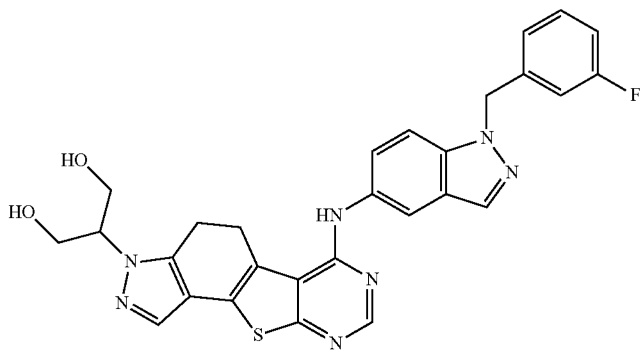 | 2-(6-{[1-(3-fluorobenzyl)-1H-indazol-5-yl]amino}-4,5-dihydro-3H-pyrimido[5',4':4,5]thieno[2,3-e]indazol-3-yl)propane-1,3-diol | 2.71 | 542.3 |
| 363 | 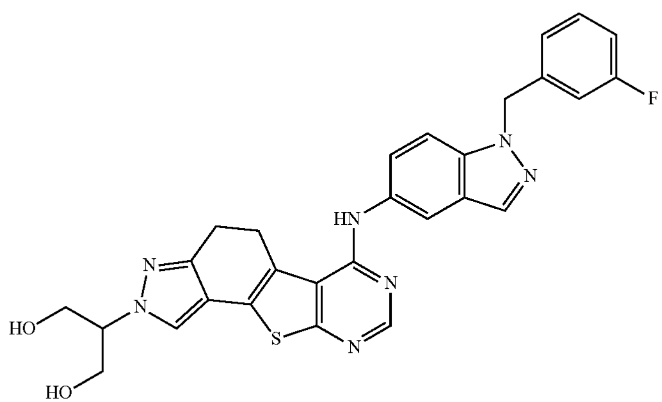 | 2-(6-{[1-(3-fluorobenzyl)-1H-indazol-5-yl]amino}-2H-pyrimido[5',4':4,5]thieno[2,3-e]indazol-2-yl)propane-1,3-diol | 2.7 | 542.3 |

B. EVALUATION OF PHYSIOLOGICAL ACTIVITY

The utility of the compounds of the present invention can be demonstrated, for example, by their activity in vitro in the in vitro tumor cell proliferation assay described below. The link between activity in tumor cell proliferation assays in vitro and anti-tumor activity in the clinical setting has been very well established in the art. For example, the therapeutic utility of taxol (Silvestrini et al. *Stem Cells* 1993, 11(6), 528-35), taxotere (Bissery et al. *Anti Cancer Drugs* 1995, 6(3), 339), and topoisomerase inhibitors (Edelman et al. *Cancer Chemother. Pharmacol.* 1996, 37(5), 385-93) were demonstrated with the use of in vitro tumor proliferation assays.

Compounds and compositions described herein exhibit anti-proliferative activity with $IC_{50} \leq 50$ μM in either of the following specified cell lines and are thus useful to prevent or treat the disorders associated with hyper-proliferation. The following assay is one of the methods by which compound activity relating to treatment of the disorders identified herein can be determined.

In vitro Tumor Cell Proliferation Assay

The tumor cell proliferation assay used to test the compounds of the present invention involves a readout called Cell Titer-Glow® Luminescent Cell Viability Assay developed by Promega® (Cunningham, B A "A Growing Issue: Cell Proliferation Assays, Modern kits ease quantification of cell growth" *The Scientist* 2001, 15(13), 26, and Crouch, S P et al., "The use of ATP bioluminescence as a measure of cell proliferation and cytotoxicity" *Journal of Immunological Methods* 1993, 160, 81-88), that measures inhibition of cell proliferation. Generation of a luminescent signal corresponds to the amount of ATP present, which is directly proportional to the number of metabolically active (proliferating) cells.

A431cells (human epidermoid carcinoma, ATCC #HTB-20) and BT474 (human breast carcinoma, ATCC #CRL-1555) were plated at a density of $2.5 \times 10^3$ cells/well in 96 well black-clear bottom tissue culture plates in RPMI media with 10% Fetal Bovine Serum and incubated at 37° C. Twenty-four hours later, test compounds are added at a final concentration range from as high 100 μm to as low 64 pM depend on the activities of the tested compounds in serial dilutions at a final DMSO concentration of 0.1%. Cells were incubated for 72 hours at 37° C. in complete growth media after addition of the test compound. After 72 hours of drug exposure, the plates were equilibrated to room temperature for approximately 30 min. Then, using a Promega Cell Titer Glo Luminescent® assay kit, lysis buffer containing 100 microliters of the enzyme luciferase and its substrate, luciferin mixture, was added to each well. The plates were mixed for 2 min on orbital shaker to ensure cell lysis and incubated for 10 min at room temperature to stabilize luminescence signal. The samples were read on VICTOR 2 using Luminescence protocol, and analyzed with Analyze5 software to generate $IC_{50}$ values. Representative compounds of this invention showed inhibition of tumor cell proliferation in this assay.

For determination of $IC_{50}$'s, a linear regression analysis can be used to determine drug concentration which results in a 50% inhibition of cell proliferation using this assay format. The anti-proliferative activities of selective sets of compounds are listed below. In A431 cells, Examples 1-17, 19-38, 40-45, 47, 49-51, 53, 54, 56-70, 73-78, 80, 82-85, 87, 88, 90-97, 99, 100, 102, 105, 107, 110, 112, 114, 120-122, 127, 132, 153, 173, 176, 177, 179, 181-186, 201, 202, 205, 206, 208, 210, 211, 213, 214, 215, 217, 219, 220, 222-224, 226-230, 232, 235-258, 266, 267, 269, 272, 273, 275-286, 288-292, 295-300, 302, 305, 309, 310, 314, 315, 317-320, 322-336, 344, 350, 351, 353-358, 360, 362, and 363 have $IC_{50}$'s $\leq 5$ μM; whereas examples 6, 18, 39, 46, 48, 52, 55, 71, 72, 79, 81, 86, 89, 98, 101, 103, 104, 106, 108, 109, 111, 113, 115-119, 123-126, 128-131, 133-172, 174, 175, 178, 180, 187-200, 203, 204, 207, 209, 212, 216, 218, 221, 225, 231, 234, 246, 247, 259-265, 268, 270, 271, 287, 293, 294, 304, 307, 308, 311-312, 316, 338, 340-343, 347, 348, 352, 359, and 361 have $IC_{50}$'s $\leq 50$ μM. In BT474 cells, examples 1, 2, 7, 8, 15, 20, 39, 43-45, 47-46, 49, 53, 54, 56-71, 73-80, 82-87, 95, 96, 98-115, 121, 122, 124-129, 131-157, 165-174, 176-190, 193-215, 217-224, 226-230, 232, 233, 235-245, 247-258, 261-273, 275-300, 302-311, 311, 314, 315, 317, 322, 323, 331-338, 345-363 have $IC_{50}$'s $\leq 1$ μM, whereas examples 3-6, 9-14, 16, 17, 19-38, 40-43, 46, 48, 50, 52, 55, 81, 88, 90-94, 97, 116-120, 123, 130, 158-164, 175, 192, 225, 231, 234, 246, 259, 260, 312, 318-320, 324-330, 340-344 have $IC_{50}$'s $\leq 5$ μM; whereas examples 18, 51, 72, 81, 89, 191, 216, and 316 have $IC_{50}$'s $\leq 50$ μM.

C. OPERATIVE EXAMPLES RELATING TO PHARMACEUTICAL COMPOSITIONS

The compounds according to the invention can be converted into pharmaceutical preparations as follows:

Tablet

Composition:

100 mg of the compound of Example 1, 50 mg of lactose (monohydrate), 50 mg of maize starch (native), 10 mg of polyvinylpyrrolidone (PVP 25) (from BASF®, Ludwigshafen, Germany) and 2 mg of magnesium stearate.

Tablet weight 212 mg, diameter 8 mm, curvature radius 12 mm.

Preparation:

The mixture of active component, lactose and starch is granulated with a 5% solution (m/m) of the PVP in water. After drying, the granules are mixed with magnesium stearate for 5 min. This mixture is moulded using a customary tablet press (tablet format, see above). The moulding force applied is typically 15 kN.

Suspension for Oral Administration

Composition:

1000 mg of the compound of Example 1, 1000 mg of ethanol (96%), 400 mg of Rhodigel (xanthan gum from FMC®, Pennsylvania, USA) and 99 g of water.

A single dose of 100 mg of the compound according to the invention is provided by 10 mL of oral suspension.

Preparation:

The Rhodigel is suspended in ethanol and the active component is added to the suspension. The water is added with stirring. Stirring is continued for about 6 h until the swelling of the Rhodigel is complete.

The invention claimed is:
1. A compound of formula

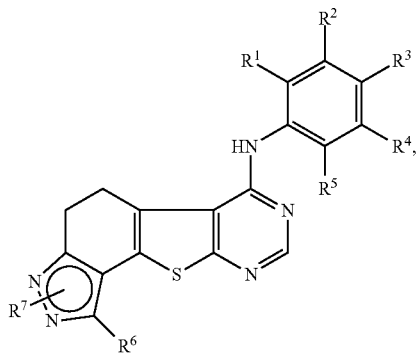

(I)

wherein
$R^1$ is selected from the group consisting of hydrogen, alkyl, and halo;
$R^2$ is selected from the group consisting of hydrogen, alkyl, hydroxy, cyano, and halo;
$R^3$ is selected from the group consisting of hydrogen, alkyl, halo, hydroxy, alkoxy, trifluoromethoxy, benzyloxy, pyridoxy, pyridylmethyl, pyridylmethoxy, pyridylmethylthio, thiazolylmethoxy, and N-morpholinyl, wherein benzyloxy, pyridoxy and pyridylmethoxy can optionally be substituted with 0, 1 or 2 substituents independently selected from the group consisting of halo, alkyl, alkoxy, and trifluoromethyl or
$R^2$ and $R^3$, together with the carbon atoms to which they are attached, form a pyrazole ring, wherein said pyrazole ring can optionally be substituted with 0, 1 or 2 substituents independently selected from the group consisting of alkyl, benzyl, halogenated benzyl, pyridylmethyl, pyridylmethoxy, and halogenated pyridylmethoxy;
$R^4$ is selected from the group consisting of hydrogen, alkyl, hydroxy, cyano, and halo;
$R^5$ is selected from the group consisting of hydrogen, alkyl, and halo;
$R^6$ is selected from the group consisting of hydrogen, and alkyl;
$R^7$ is selected from the group consisting of hydrogen, and alkyl, or
$R^7$ is a heterocycle selected from the group consisting of pyrrolidinyl, morpholinyl, piperidinyl, and piperazinyl, or
$R^7$ is piperidinyl, wherein said piperidinyl is substituted with 1, 2 or 3 independently selected substituents $R^{7-3}$, wherein
$R^{7-3}$ is alkyl, wherein said alkyl can optionally be substituted with 0, 1, or 2 substituents independently selected from the group consisting of halo, oxo, amino, alkylamino, piperazinyl, N-methylpiperazinyl, morpholinyl, and alkylaminopyrrolidinyl, or
$R^7$ is alkyl selected from the group consisting of methyl, ethyl, n-propyl, i-propyl, n-butyl, i-butyl and t-butyl, wherein said alkyl is substituted with 1, 2 or 3 independently selected substituents $R^{7-1}$,
wherein $R^{7-1}$ is selected from the group consisting of halo, oxo, hydroxy, alkoxy, hydroxycarbonyl, alkoxycarbonyl, pyridylaminocarbonyl, alkylsulfonyloxy, aminosulfonyloxy, aminoalkylcarbonyloxy, alkyl-C(O) NHCH$_2$C(O)O—*, and amino, or $R^{7-1}$ is alkylamino, wherein said alkylamino can optionally be substituted with 0, 1 or 2 substituents independently selected from the group consisting of hydroxy, alkoxy, amino, alkylamino, alkylsulfonyl, alkylsulfenyl, pyrrolidinyl, morpholinyl, piperidinyl, and piperazinyl, or
$R^{7-1}$ is alkenylamino, wherein said alkenylamino can optionally be substituted with 0, 1 or 2 substituents independently selected from the group consisting of oxo, hydroxy, alkoxy, amino, alkylamino, alkylsulfonyl, N-pyrrolidinyl, N-morpholinyl, N-piperidinyl, and N-piperazinyl, or
$R^{7-1}$ is a heterocycle selected from the group consisting of pyrrolidinyl, imidazolidinyl, imidazolyl, pyrazolyl, morpholinyl, piperidinyl, piperazinyl, and thiomorpholinyl, wherein said heterocycle can optionally be substituted with 0, 1 or 2 substituents independently selected from the group consisting of halo, hydroxy, alkoxy, amino, alkylamino, hydroxyalkyl, alkoxyalkyl, carboxyl, alkoxycarbonyl, N-pyrrolidinyl, N-piperidinyl, N-piperazinyl, pyrazinyl, benzyl, and pyridylmethyl, or
$R^{7-1}$ is a heterocycle selected from the group consisting of piperidinyl, wherein said heterocycle is substituted with 1 alkyl, wherein said alkyl can optionally be substituted with 0, 1 or 2 substituents independently selected from the group consisting of halo, hydroxy, oxo, alkylamino, hydroxyalkylamino, pyrrolidinyl, alkylaminopyrrolidinyl, piperazinyl, N-methylpiperazinyl, morpholinyl, furyl, or
$R^7$ is alkenyl selected from the group consisting of allyl, prop-1-enyl, 2-methyl-prop-1-enyl, but-1-enyl, but-2-enyl, but-3-enyl, pent-1-enyl, pent-2-enyl, pent-3-enyl, pent-4-enyl, wherein said alkenyl is substituted with 1, 2 or 3 independently selected substituents $R^{7-2}$,
wherein $R^{7-2}$ is oxo, or
wherein $R^{7-2}$ is alkylamino, wherein said alkylamino can optionally be substituted with 0, 1 or 2 substituents independently selected from the group consisting of oxo, hydroxy, alkoxy, amino, and alkylamino;
or a pharmaceutically acceptable salt thereof.
2. The compound of claim 1, wherein
$R^1$ is hydrogen;
$R^2$ is selected from the group consisting of hydrogen, and halo;
$R^3$ is selected from the group consisting of halo, benzyloxy, and pyridylmethoxy, wherein benzyloxy, and pyridylmethoxy can optionally be substituted with 0, 1 or 2 substituents independently selected from the group consisting of halo, and alkyl, or
$R^2$ and $R^3$, together with the carbon atoms to which they are attached, form a pyrazole ring, wherein said pyrazole ring can optionally be substituted with 0, 1 or 2 substituents independently selected from the group consisting of benzyl, and halogenated benzyl;
$R^4$ is selected from the group consisting of hydrogen, and halo;
$R^5$ is hydrogen;
$R^6$ is hydrogen;
$R^7$ is hydrogen, or
$R^7$ is piperidinyl, wherein said piperidinyl is substituted with 1, 2 or 3 independently selected substituents $R^{7-3}$, wherein
$R^{7-3}$ is alkyl, wherein said alkyl can optionally be substituted with 0, 1, or 2 substituents independently selected from the group consisting of halo, oxo, amino, alkylamino, piperazinyl, N-methylpiperazinyl, morpholinyl, and alkylaminopyrrolidinyl, or R⁷ is alkyl selected from the group consisting of methyl, ethyl, n-propyl, and i-propyl, wherein said alkyl is substituted with 1, 2 or 3 independently selected substituents $R^{7-1}$, wherein $R^{7-1}$ is selected from the group consisting of oxo, hydroxy, alkoxy, hydroxycarbonyl, alkoxycarbonyl, alkylsulfonyloxy, aminosulfonyloxy, aminoalkylcarbonyloxy, alkyl-C(O)NHCH₂C(O)O—*, and amino, or $R^{7-1}$ is alkylamino, wherein said alkylamino can optionally be substituted with 0, 1 or 2 substituents independently selected from the group consisting of hydroxy, alkoxy, amino, alkylamino, alkylsulfonyl, pyrrolidinyl, morpholinyl, piperidinyl, and piperazinyl, or $R^{7-1}$ is a heterocycle selected from the group consisting of pyrrolidinyl, imidazolidinyl, imidazolyl, pyrazolyl, morpholinyl, piperidinyl, and piperazinyl, wherein said heterocycle can optionally be substituted with 0, 1 or 2 substituents independently selected from the group consisting of hydroxy, alkoxy, amino, alkylamino, hydroxyalkyl, alkoxyalkyl, carboxyl, and alkoxycarbonyl, or $R^{7-1}$ is a heterocycle selected from the group consisting of piperidinyl, wherein said heterocycle is substituted with 1 alkyl, wherein said alkyl can optionally be substituted with 0, 1 or 2 substituents independently selected from the group consisting of hydroxy, oxo, alkylamino, or hydroxyalkylamino, or a pharmaceutically acceptable salt thereof.

3. The compound of claim 1, wherein $R^1$ is hydrogen;

$R^2$ is selected from the group consisting of hydrogen, and halo;

$R^3$ is selected from the group consisting of benzyloxy, and pyridylmethoxy, wherein benzyloxy, and pyridylmethoxy can optionally be substituted with 0, 1 or 2 substituents independently selected from the group consisting of halo, and alkyl, or $R^2$ and $R^3$, together with the carbon atoms to which they are attached, form a pyrazole ring, wherein said pyrazole ring can optionally be substituted with 0, 1 or 2 substituents independently selected from the group consisting of benzyl, and halogenated benzyl;

$R^4$ is hydrogen;

$R^5$ is hydrogen;

$R^6$ is hydrogen;

$R^7$ is hydrogen, or $R^7$ is alkyl selected from the group consisting of methyl, ethyl, n-propyl, and i-propyl, wherein said alkyl is substituted with 1, 2 or 3 independently selected substituents $R^{7-1}$, wherein $R^{7-1}$ is selected from the group consisting of oxo, hydroxy, alkoxy, hydroxycarbonyl, alkoxycarbonyl, alkylsulfonyloxy, aminosulfonyloxy, aminoalkylcarbonyloxy, alkyl-C(O)NHCH₂C(O)O—*, and amino, or $R^{7-1}$ is alkylamino, wherein said alkylamino can optionally be substituted with 0, 1 or 2 substituents independently selected from the group consisting of hydroxy, alkoxy, amino, alkylamino, alkylsulfonyl, pyrrolidinyl, morpholinyl, piperidinyl, and piperazinyl, or $R^{7-1}$ is a heterocycle selected from the group consisting of morpholinyl, piperidinyl, and piperazinyl, wherein said heterocycle can optionally be substituted with 0, 1 or 2 substituents independently selected from the group consisting of hydroxy, alkoxy, amino, alkylamino, hydroxyalkyl, alkoxyalkyl, carboxyl, and alkoxycarbonyl, or $R^{7-1}$ is a heterocycle selected from the group consisting of piperidinyl, wherein said heterocycle is substituted with 1 alkyl, wherein said alkyl can optionally be substituted with 0, 1 or 2 substituents independently selected from the group consisting of hydroxy, oxo, alkylamino, or hydroxyalkylamino, or pharmaceutically acceptable salt thereof.

4. The compound of claim 1, wherein $R^2$ and $R^3$, together with the carbon atoms to which they are attached, form a pyrazole ring, wherein said pyrazole ring is substituted with 1 substituent m-fluorobenzyl or m-chlorobenzyl.

5. The compound of claim 1, wherein $R^1$, $R^2$, and $R^5$ are hydrogen, $R^3$ is fluoro and $R^4$ is chloro.

6. The compound of claim 1, wherein $R^1$, $R^2$, $R^4$, and $R^5$ are hydrogen, and $R^3$ is 3-fluorobenzyloxy.

7. A process for preparing the compounds of the formula (I), wherein a compound of formula (8)

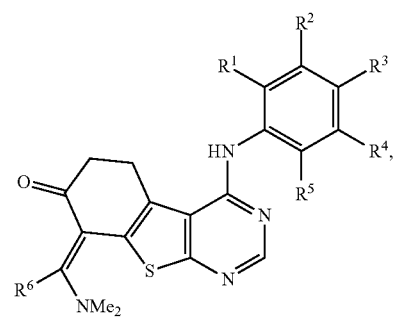

(8)

wherein $R^1$ to $R^6$ have the meaning indicated in claim 1, is reacted with a compound of formula

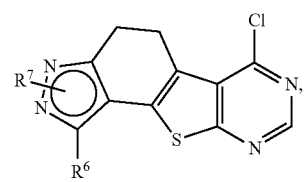

wherein $R^7$ has the meaning indicated in claim 1, or a compound of formula

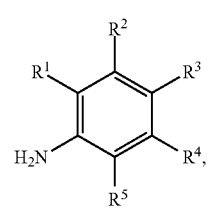

wherein $R^6$ and $R^7$ have the meaning indicated in claim 1, is reacted with a compound of formula (20)

(20)

wherein $R^1$ to $R^5$ have the meaning indicated in claim 1.

8. A pharmaceutical composition comprising a compound according to claim 1.

9. A pharmaceutical composition comprising a compound according to claim 1 in combination with at least one pharmaceutically acceptable excipient.

10. A process for preparing a pharmaceutical composition, comprising combining at least one compound of claim 1 with at least one pharmaceutically acceptable excipient, mixing the combination and bringing the combination into a suitable administration form.

11. A method of treating human epidermoid carcinoma or human breast carcinoma in a mammal, comprising administering to the mammal in need thereof an effective amount of a compound according to claim 1.

12. A compound of formula (8)

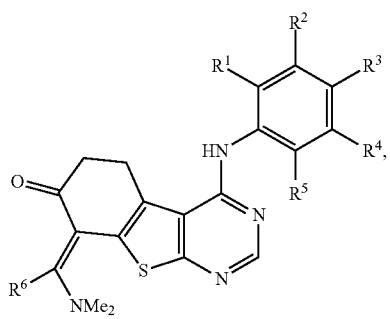

(8)

wherein
$R^1$ is selected from the group consisting of hydrogen, alkyl, and halo;
$R^2$ is selected from the group consisting of hydrogen, alkyl, hydroxy, cyano, and halo;
$R^3$ is selected from the group consisting of hydrogen, alkyl, halo, hydroxy, alkoxy, trifluoromethoxy, benzyloxy, pyridoxy, pyridylmethyl, pyridylmethoxy, pyridylmethylthio, thiazolylmethoxy, and N-morpholinyl, wherein benzyloxy, pyridoxy and pyridylmethoxy can optionally be substituted with 0, 1 or 2 substituents independently selected from the group consisting of halo, alkyl, alkoxy, and trifluoromethyl or
$R^2$ and $R^3$, together with the carbon atoms to which they are attached, form a pyrazole ring, wherein said pyrazole ring can optionally be substituted with 0, 1 or 2 substituents independently selected from the group consisting of alkyl, benzyl, halogenated benzyl, pyridylmethyl, pyridylmethoxy, and halogenated pyridylmethoxy;
$R^4$ is selected from the group consisting of hydrogen, alkyl, hydroxy, cyano, and halo;
$R^5$ is selected from the group consisting of hydrogen, alkyl, and halo;
$R^6$ is selected from the group consisting of hydrogen, and alkyl; and
$R^7$ is selected from the group consisting of hydrogen, and alkyl, or
$R^7$ is a heterocycle selected from the group consisting of pyrrolidinyl, morpholinyl, piperidinyl, and piperazinyl, or
$R^7$ is piperidinyl, wherein said piperidinyl is substituted with 1, 2 or 3 independently selected substituents $R^{7-3}$, wherein $R^{7-3}$ is alkyl, wherein said alkyl can optionally be substituted with 0, 1, or 2 substituents independently selected from the group consisting of halo, oxo, amino, alkylamino, piperazinyl, N-methylpiperazinyl, morpholinyl, and alkylaminopyrrolidinyl, or
$R^7$ is alkyl selected from the group consisting of methyl, ethyl, n-propyl, i-propyl, n-butyl, i-butyl and t-butyl, wherein said alkyl is substituted with 1, 2 or 3 independently selected substituents $R^{7-1}$,
wherein $R^{7-1}$ is selected from the group consisting of halo, oxo, hydroxy, alkoxy, hydroxycarbonyl, alkoxycarbonyl, pyridylaminocarbonyl, alkylsulfonyloxy, aminosulfonyloxy, aminoalkylcarbonyloxy, alkyl-C(O)NHCH$_2$C(O)O—*, and amino, or
$R^{7-1}$ is alkylamino, wherein said alkylamino can optionally be substituted with 0, 1 or 2 substituents independently selected from the group consisting of hydroxy, alkoxy, amino, alkylamino, alkylsulfonyl, alkylsulfenyl, pyrrolidinyl, morpholinyl, piperidinyl, and piperazinyl, or
$R^{7-1}$ is alkenylamino, wherein said alkenylamino can optionally be substituted with 0, 1 or 2 substituents independently selected from the group consisting of oxo, hydroxy, alkoxy, amino, alkylamino, alkylsulfonyl, N-pyrrolidinyl, N-morpholinyl, N-piperidinyl, and N-piperazinyl, or
$R^{7-1}$ is a heterocycle selected from the group consisting of pyrrolidinyl, imidazolidinyl, imidazolyl, pyrazolyl, morpholinyl, piperidinyl, piperazinyl, and thiomorpholinyl, wherein said heterocycle can optionally be substituted with 0, 1 or 2 substituents independently selected from the group consisting of halo, hydroxy, alkoxy, amino, alkylamino, hydroxyalkyl, alkoxyalkyl, carboxyl, alkoxycarbonyl, N-pyrrolidinyl, N-piperidinyl, N-piperazinyl, pyrazinyl, benzyl, and pyridylmethyl, or
$R^{7-1}$ is a heterocycle selected from the group consisting of piperidinyl, wherein said heterocycle is substituted with 1 alkyl, wherein said alkyl can optionally be substituted with 0, 1 or 2 substituents independently selected from the group consisting of halo, hydroxy, oxo, alkylamino, hydroxyalkylamino, pyrrolidinyl, alkylaminopyrrolidinyl, piperazinyl, N-methylpiperazinyl, morpholinyl, furyl, or
$R^7$ is alkenyl selected from the group consisting of allyl, prop-1-enyl, 2-methyl-prop-1-enyl, but-1-enyl, but-2-enyl, but-3-enyl, pent-1-enyl, pent-2-enyl, pent-3-enyl, pent-4-enyl, wherein said alkenyl is substituted with 1, 2 or 3 independently selected substituents $R^{7-2}$,
wherein $R^{7-2}$ is oxo, or
wherein $R^{7-2}$ is alkylamino, wherein said alkylamino can optionally be substituted with 0, 1 or 2 substituents independently selected from the group consisting of oxo, hydroxy, alkoxy, amino, and alkylamino.

13. A packaged pharmaceutical composition comprising a container comprising the pharmaceutical composition of claim 8 and instructions for using the pharmaceutical composition to treat human epidermoid carcinoma or human breast carcinoma in a mammal.

* * * * *